US010533200B2

(12) United States Patent
Voss et al.

(10) Patent No.: US 10,533,200 B2
(45) Date of Patent: Jan. 14, 2020

(54) **METHOD FOR THE PRODUCTION OF FINE CHEMICALS USING A *CORYNEBACTERIUM* SECRETING MODIFIED α-1,6-GLUCOSIDASES**

(71) Applicant: Evonik Degussa GmbH, Essen (DE)

(72) Inventors: Kornelia Voss, Halle (DE); Michaela Voss, Steinhagen (DE); Georg Thierbach, Bielefeld (DE)

(73) Assignee: Evonik Degussa GmbH, Essen (DE)

( * ) Notice: Subject to any disclaimer, the term of this patent is extended or adjusted under 35 U.S.C. 154(b) by 5 days.

(21) Appl. No.: 16/007,523

(22) Filed: Jun. 13, 2018

(65) Prior Publication Data
US 2018/0363014 A1  Dec. 20, 2018

(30) Foreign Application Priority Data

Jun. 14, 2017  (EP) .................................. 17175992

(51) Int. Cl.

| C12P 13/06 | (2006.01) |
|---|---|
| C12P 19/02 | (2006.01) |
| C12P 19/14 | (2006.01) |
| C12P 19/30 | (2006.01) |
| C12P 19/38 | (2006.01) |
| C12P 25/00 | (2006.01) |
| C12N 1/20 | (2006.01) |
| C12N 9/44 | (2006.01) |
| C12P 13/04 | (2006.01) |
| C12N 15/77 | (2006.01) |
| C12P 13/08 | (2006.01) |

(52) U.S. Cl.
CPC ................ *C12P 13/06* (2013.01); *C12N 1/20* (2013.01); *C12N 9/2451* (2013.01); *C12N 15/77* (2013.01); *C12P 13/04* (2013.01); *C12P 13/08* (2013.01); *C12P 19/02* (2013.01); *C12P 19/14* (2013.01); *C12P 19/30* (2013.01); *C12P 19/38* (2013.01); *C12P 25/00* (2013.01); *C12Y 302/0101* (2013.01); *C07K 2319/10* (2013.01); C12Y 302/01033 (2013.01)

(58) Field of Classification Search
CPC ........ C12N 9/2451; C12N 15/77; C12N 1/20; C12P 13/06; C07K 2319/10; C12Y 302/0101; C12Y 302/01033
See application file for complete search history.

(56) References Cited

U.S. PATENT DOCUMENTS

| 4,956,471 A | 9/1990 | Ito et al. |
| 5,279,744 A | 1/1994 | Itoh et al. |
| 5,431,933 A | 7/1995 | Binder et al. |
| 8,044,191 B2 | 10/2011 | Kroger et al. |
| 8,071,365 B2 | 12/2011 | Kroger et al. |
| 8,637,295 B1 | 1/2014 | Claes et al. |
| 9,074,229 B2 | 7/2015 | Reth et al. |
| 2004/0171160 A1 | 9/2004 | Pompejus et al. |
| 2009/0246836 A1 | 10/2009 | Kroger et al. |
| 2010/0240131 A1 | 9/2010 | Pompejus et al. |

FOREIGN PATENT DOCUMENTS

| EP | 1 375 664 | 1/2004 |
| EP | 1 748 077 | 1/2007 |
| EP | 2 241 632 | 10/2010 |
| EP | 2 787 082 | 10/2014 |
| EP | 3 130 671 | 2/2017 |
| WO | WO 99/27124 | 6/1999 |
| WO | WO 02/40679 | 5/2002 |
| WO | WO 03/040373 | 5/2003 |
| WO | WO 2004/018645 | 3/2004 |
| WO | WO 2004/069996 | 8/2004 |
| WO | WO 2005/100583 | 10/2005 |
| WO | WO 2008/033001 | 3/2008 |
| WO | WO 2008/049782 | 5/2008 |
| WO | WO 2014/093312 | 6/2014 |
| WO | WO 2015/061289 | 4/2015 |

OTHER PUBLICATIONS

Breitinger, K.J., "Effiziente Stärkeverwertung von *Corynebacterium glutamicum* für das Wachstum und die Produktion von organischen Säuren und Aminosäuren," Dissertation/Ph.D. Thesis Ulm University (2013) with English abstract attached.
Schäfer, et al., "High-Frequency Conjugal Plasmid Transfer from Gram-Negative *Escherichia coli* to Various Gram-Positive Coryneform Bacteria," *Journal of Bacteriology* 172(3):1663-1666 (Mar. 1990).
Schäfer, et al., "Small mobilizable multi-purpose cloning vectors derived from the *Escherichia coli* plasmids pK18 and pK19: selection of defined deletions in the chromosome of *Corynebacterium glutamicum*," *Gene* 145(1):69-73 (Jul. 1994).
Teramoto, et al., "High yield secretion of heterologous proteins in *Corynebacterium glutamicum* using its own Tat-type signal sequence," *Appl. Microbiol. Biotechnol.* 91(3):677-687 (Aug. 2011).
Thierbach, et al., "Transformation of spheroplasts and protoplasts of *Corynebacterium glutamicum*," *Appl. Microbiol. Biotechnol.* 29(4):356-362 (Oct. 1988).
Watanabe, et al., "Scanning the *Corynebacterium glutamicum* R genome for high-efficiency signal sequences," *Microbiology* 155:741-750 (2009).
Whiting, et al., "Metabolism of polysaccharides by the *Streptococcus mutans* dexB gene product," *Journal of General Microbiology* 139:2019-2026 (1993).
Yim, et al.,"High-level secretory production of recombinant single-chain variable fragment (scFv) in *Corynebacterium glutamicum*," *Appl. Microbiol. Biotechnol.*98(1):273-284 (Jan. 2014).

(Continued)

*Primary Examiner* — Kagnew H Gebreyesus
(74) *Attorney, Agent, or Firm* — Law Office of Michael A. Sanzo, LLC

(57) ABSTRACT

The present invention relates to polynucleotides encoding novel fusion polypeptides essentially composed of a signal peptide for membrane translocation and a polypeptide providing α-1,6-glucosidase activity and to bacteria containing said polynucleotides. The invention further relates to methods for producing fine chemicals using media containing isomaltose and/or panose as carbon source.

18 Claims, 6 Drawing Sheets

Specification includes a Sequence Listing.

(56) References Cited

OTHER PUBLICATIONS

GenBank accession No. AY008307.1, submitted Sep. 28, 2000.
GenBank accession No. FJ386389, submitted Oct. 15, 2008.
GenBank accession No. FJ386390, submitted Oct. 15, 2008.
GenBank accession No. FJ437239, submitted Nov. 4, 2008.
GenBank accession No. NC_001139-Tag-YGR287C, submitted Dec. 12, 2009.
Gen Bank accession No. NC_003450-Tag-NCg10801, submitted Jan. 21, 2005.
GenBank accession No. NC_003450-Tag-NCg112176, submitted Jan. 21, 2005.
GenBank accession No. NC_003450-Tag-NCg112177, submitted Jan. 21, 2005.
GenBank accession No. NC_006958-1-Tag-RS04205, submitted Jan. 21, 2004.
GenBank accession No. WP_003858344, submitted Aug. 10, 2005.
GenBank accession BAF53923-Tag-CGR0949, submitted Aug. 10, 2005.
GenBank accession No. NC009342-Tag-RS04950, submitted Aug. 10, 2005.
European Search Report and Search Opinion for corresponding application EP 17 17 5992 dated Jul. 20, 2017.
Amarakone, et al., "Conversion of Oligosaccharides Formed during Starch Hydrolysis by a Dual Enzyme System," *J. Jpn. Soc. Starch Sci.* 31(1):1-7 (1984).
Billman-Jacobe, et al., "Expression and Secretion of Heterologous Proteases by *Corynebacterium glutamicum*," *Applied and Environmental Microbiology* 61(4)1610-1613 (Apr. 1995).
Blombach, et al., "Acetohydroxacid Synthase, a Novel Target for Improvement of L-Lysine Production by *Corynebacterium glutamicum*," *Applied and Environmental Microbiology* 75(2):419-427 (Jan. 2009).
Brurberg, et al., "Comparative studies of chitinases A and B from *Serratia marcescens*," *Microbiology* 142:1581-1589 (1996).
Cohen, et al., "Human Epidermal Growth Factor: Isolation and Chemical and Biological Properties," *Proc. Nat. Acad. Sci. USA* 72(4):1317-1321 (Apr. 1975).
De Boer, et al., "The *tac* promoter: A functional hybrid derived from the *trp* and *lac* promoters," *Proc. Natl. Acad. Sci. USA* 80(1):21-25 (Jan. 1983).
Deng, et al., "Similarities and differences in the biochemical and enzymological properties of the four isomaltases from *Saccharomyces cerevisiae*," *FEBS Open Bio* 4:200-212 (2012).
Dunican, et al., "High Frequency Transformation of Whole Cells of Amino Acid Producing Coiyneform Bacteria Using High Voltage Electrporation," *Bio/Technology* 7:1067-1070 (Oct. 1989).
Eikmanns, "Identification, Sequence Analysis, and Expression of a *Corynebacterium glutamicum* Gene Cluster Encoding the Three Glycolytic Enzymes Glyceraldehyde-3-Phosphate Dehydrogenase, 3-Phosphoglycerate Kinase, and Triosephosphate Isomerase," *Journal of Bacteriology* 174(19):6076-6086 (Oct. 1992).
Fath, et al., "Multiparameter RNA and Codon Optimization: A Standardized Tool to Assess and Enhance Autologous Mammalian Gene Expression," *PlosOne* 6(3):e17596 (Mar. 2011).
Fincan, et al., "Production, purification, and characterization of thermostable α-amylase from thermophilic *Geobacillus stearothermophilus*," *Starch* 66:182-189 (2014).
Freudl, "Beyond amino acids: Use of the *Corynebacterium glutamicum* cell factory for the secretion of heterologous proteins," *Journal of Biotechnology* 258(2)101-109 (Sep. 2017).
Hemmerich, et al., "Use of a Sec signal peptide library from *Bacillus subtilis* for the optimization of cutinase secretion in *Corynebacterium glutamicum*," *Microb. Cell Fact.* 15(1):208 (Dec. 2016).
Hyeon, et al., "Production of minicellulosomes for the enhanced hydrolysis of cellulosic substrates by recombinant *Corynebacterium glutamicum*," *Enzyme and Microbial Technology* 48(4-5):371-377 (Apr. 2011).

Iwai, et al., "Molecular Cloning and Expression of an Isomalto-Dextranase Gene from *Arthobacter globiformis* T6," *Journal of Bacteriology* 176(24):7730-7734 (Dec. 1994).
Kendall, et al., "*Aequorea victoria* bioluminescence moves into am exciting new era," *Trends in Biotechnology* 16(5):216-224 (Dec. 1998).
Kikuchi, et al., "Production of *Chryseobacterium proteolyticum* protein-glutaminase using the twin-arginine translocation pathway in *Corynebacterium glutamicum*," *Appl. Microbiol. biotechnol.* 78(1):67-74 (Feb. 2008).
Kikuchi, et al., "Functional Analysis of the Twin-Arginine Translocation Pathway in *Corynebacterium glutamicum* ATCC 13869," *Applied and Environmental Microbiology* 72(11):7183-7192 (Nov. 2006).
Kim, et al., "Bi-functional cellulases complexes displayed on the cell surface of *Corynebacterium glutamicum* increase hydrolysis of lignocelluloses at elevated temperature," *Enzyme and Microbial Technology* 66:67-73 (Nov. 2014).
Kornacker, et al., "Molecular characterization of *pulA* and its product, pullulanase, a secreted enzyme of *Klebsiella pneumoniae* UNF5023," *Molecular Microbiology* 4(1):73-85 (Jan. 1990).
Li, et al., "Pyruvate production in *Candida glabrata*: manipulation and optimization of physiological function," *Critical Reviews in Biotechnology* 36(1):1-10 (2016).
Liebl, et al., Expression, Secretion, and Processing of Staphylococcal Nuclease by *Corynebacterium glutamicum* 174(6):1854-1861 (Mar. 1992).
Matano, et al., "*Corynebacterium glutamicum* possesses β-N-acetylglucosaminidase," *BCM Microbiology* 16:177 (2016).
Meissner, et al., "Comparative analysis of twin-arginine (Tat)-dependent protein secretion of a heterologous model protein (GFP) in three differnt Gram-positive bacteria," *Appl. Microbiol. biotechnol.* 76(3):633-642 (Sep. 2007).
Morinaga, et al., "Expression of *Escherichia coli* promoters in *Brevibacterium lactofermentum* using the shuttle vector pEB003," *Journal of Biotechnology* 5(4):305-312 (May 1987).
Natale, et al., "Sec- and Tat-mediated protein secretion across the bacterial cytoplasmic membrane: Distinct translocases and mechanisms," *Biochemica et Biophysica Acta* 1778(9):1735-1756 (Sep. 2008).
Pasternack, et al., "Bacterial pro-transglutaminase from *Streptoverticillium mobaraense* Purification, characterisation and sequence of the zymogen," *EJB* 257570-576 (Jun. 1998).
Patek, et al., "*Corynebacterium glutamicum* promoters: a practical approach," *Microbial Biotechnology* 6:103-117 (2013).
Peters-Wendisch, et al., "Pyruvate Carboxylase is a Major Bottleneck for Glutamate and Lysine Production by *Corynebacterium glutamicum*," *J. Mol. Microbiol. biotechnol.* 3(2):295-300 (2001).
Pokusaeva, et al., "Characterization of Two Novel α-Glucosidases from *Bifidobacterium breve* UCC2003," *Applied and Environmental Microbiology* 75(4):1135-1143 (Feb. 2009).
Pokusaeva, et al., "Carbohydrate metabolism in Bifidobacteria," *Genes Nutr* 6:285-306 (2011).
Rossol, et al., "The *Corynebacterium glutamicum aceD* Gene Encodes a C-S Lyase with α,β-Elimination Activity That Degrades Aminoethylcysteine," *Journal of Bacteriology* 174(9):2968-2977 (May 1992).
Ruan, et al., "Improving the electro-transformation efficiency of *Corynebacterium glutamicum* by weakening its cell wall and increasing the cytoplasmic membrane fluidity," *Biotechnol. Lett.* 37(12):2445-2452 (published online Sep. 2015).
Salim, et al., "Heterologous Expression of the *Mycobacterium tuberculosis* Gene Encoding Antigen 85A in *Corynebacterium glutamicum*," *Applied and Environmental Microbiology* 63(11):4392-4400 (Nov. 1997).
Scheele, et al., "Secretory production of an FAD cofactor-containing cytosolic enzyme (sorbitol-xylitol oxidase from *Streptomyces coelicolor*) using the twin-arginine translocation (Tat) pathway of *Corynebacterium glutamicum*," *Microbial Biotechnology* 6(2):202-206 (Nov. 2011).

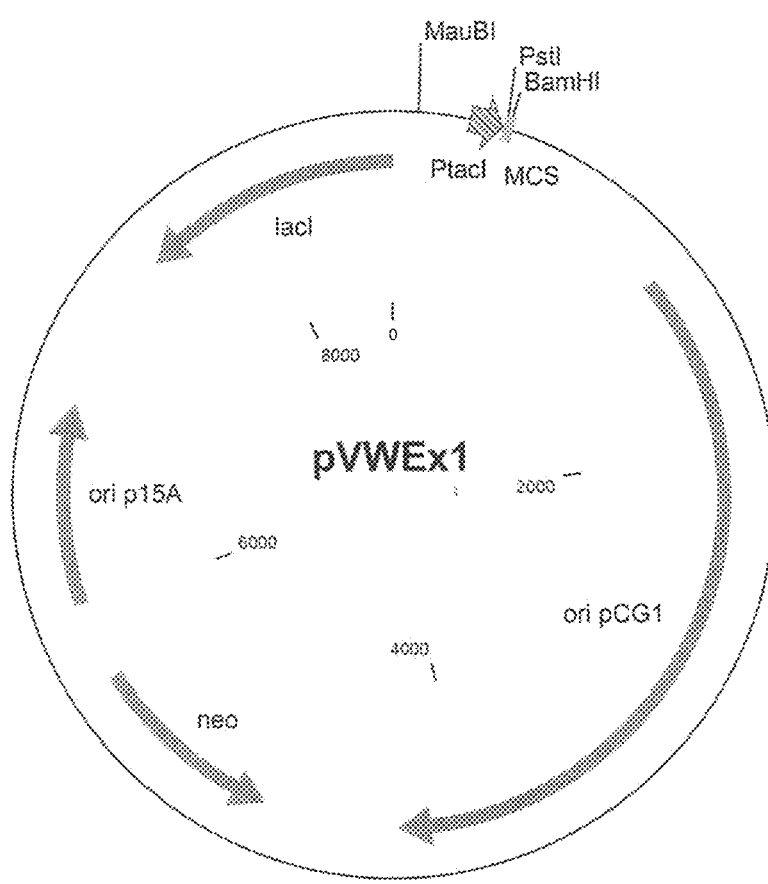
Figure 1: Map of plasmid pVWEx1.

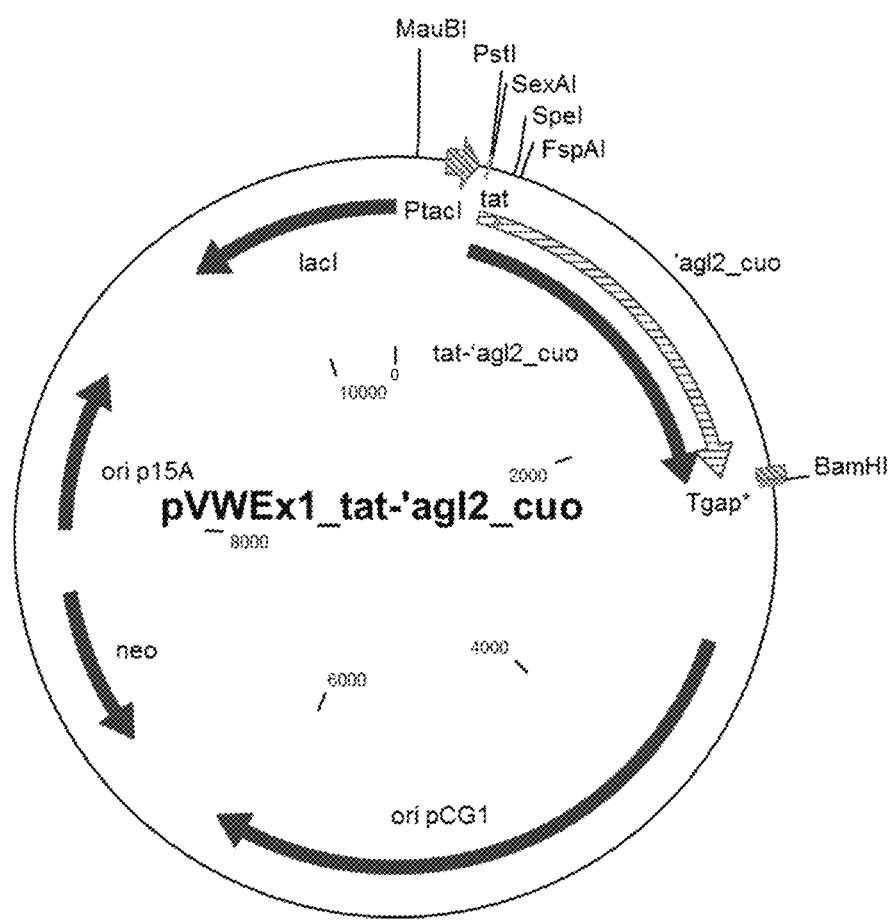
Figure 2: Map of plasmid pVWEx1_tat-'agl2_cuo.

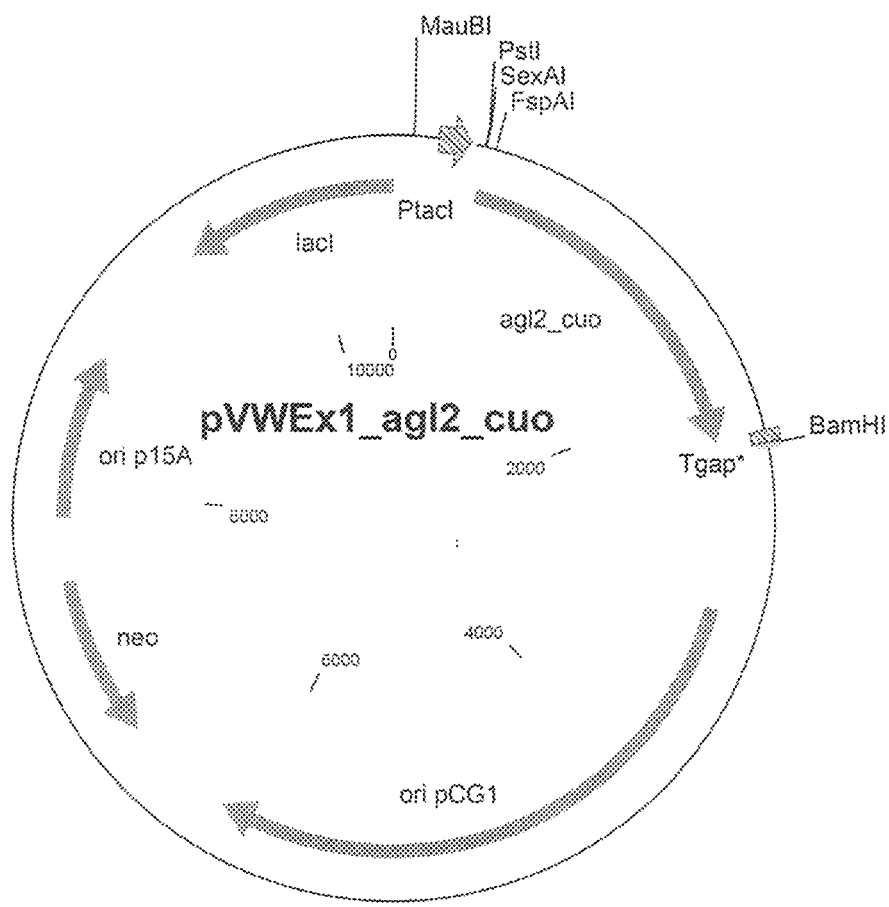
Figure 3: Map of plasmid pVWEx1_agl2_cuo.

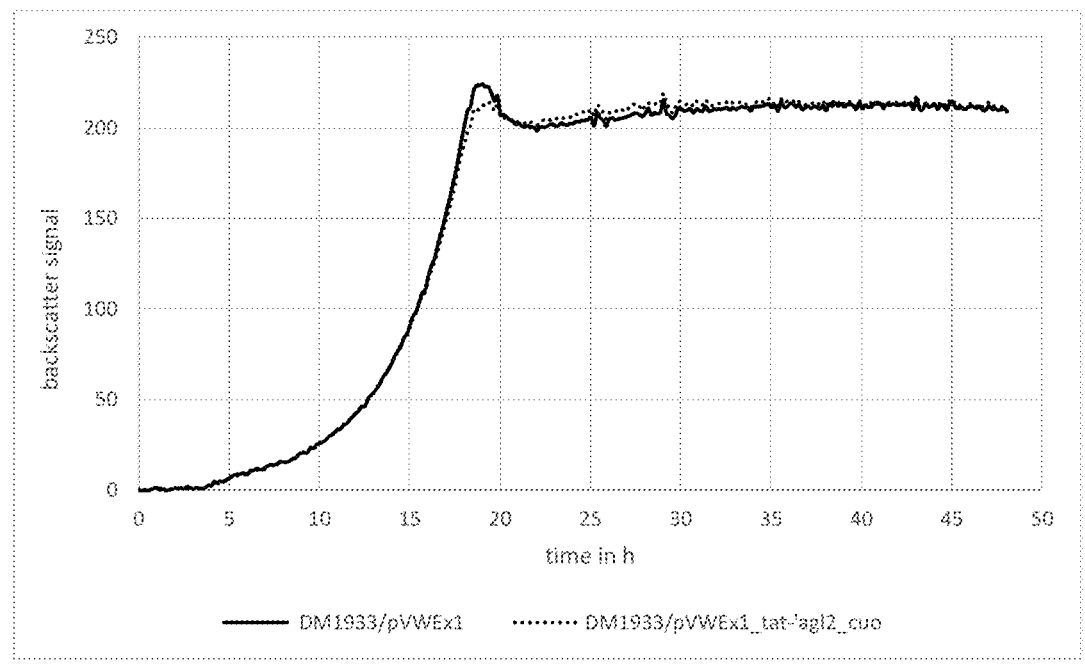
Figure 4: Growth rate of strains DM1933/pVWEx1 and DM1933/pVWEx1_tat-'agl2_cuo using glucose as carbon source.

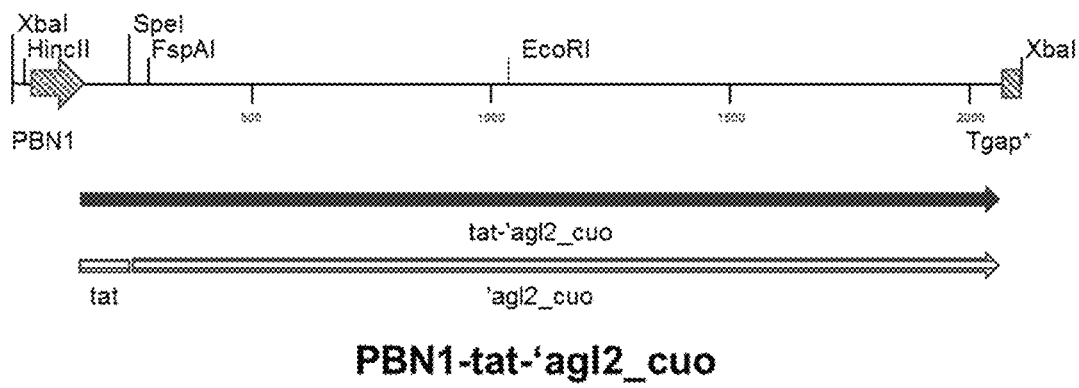
Figure 5: Map of expression unit PBN1-tat-'agl2_cuo.
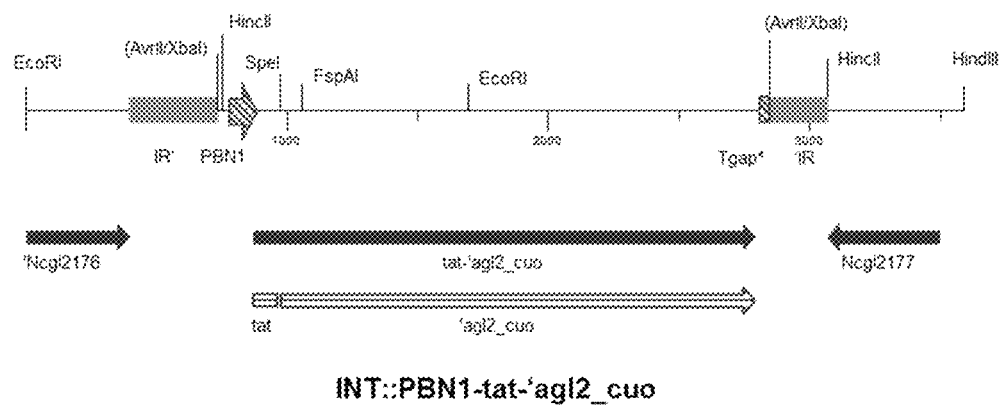
Figure 6: Map of the INT::PBN1-tat-'agl2_cuo unit.

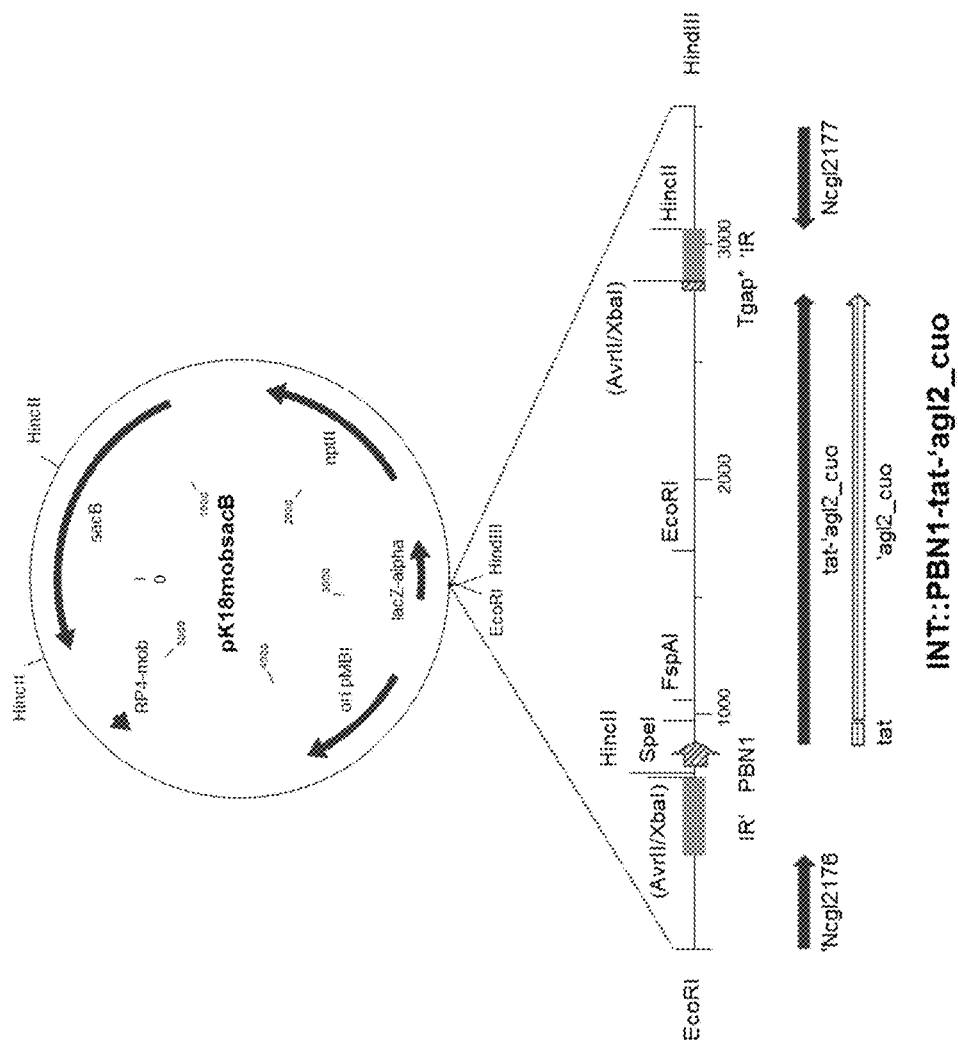
Figure 7: Map of plasmid pK18mobsacB_INT::PBN1-tat-'agl2_cuo consisting of the pK18mobsacB unit and the PBN1-tat-'agl2_cuo unit.

SEQUENCE LISTING

```
<160> NUMBER OF SEQ ID NOS: 72

<210> SEQ ID NO 1
<211> LENGTH: 843
<212> TYPE: DNA
<213> ORGANISM: Corynebacterium glutamicum ATCC13032
<220> FEATURE:
<221> NAME/KEY: CDS
<222> LOCATION: (1)..(840)
<223> OTHER INFORMATION: cg0955
<220> FEATURE:
<221> NAME/KEY: misc_signal
<222> LOCATION: (1)..(99)
<223> OTHER INFORMATION: 5' sequence of cg0955 encoding Tat-signal
      peptide of Cg0955
<220> FEATURE:
<221> NAME/KEY: misc_feature
<222> LOCATION: (1)..(101)
<223> OTHER INFORMATION: 5' sequence of cg0955
<220> FEATURE:
<221> NAME/KEY: misc_feature
<222> LOCATION: (102)..(102)
<223> OTHER INFORMATION: nucleobase cytosine
<220> FEATURE:
<221> NAME/KEY: misc_feature
```

<222> LOCATION: (841)..(843)
<223> OTHER INFORMATION: stop codon

<400> SEQUENCE: 1

```
atg caa ata aac cgc cga ggc ttc tta aaa gcc acc aca gga ctt gcc    48
Met Gln Ile Asn Arg Arg Gly Phe Leu Lys Ala Thr Thr Gly Leu Ala
1               5                   10                  15 act atc ggc gct gcc agc atg ttt atg cca aag gcc aac gcc ctt gga    96
Thr Ile Gly Ala Ala Ser Met Phe Met Pro Lys Ala Asn Ala Leu Gly
            20                  25                  30 gca atc aag ggc acc gtc atc gac tac gca gca ggc gtc ccc agc gca   144
Ala Ile Lys Gly Thr Val Ile Asp Tyr Ala Ala Gly Val Pro Ser Ala
        35                  40                  45 gca tcc att aaa aat gca ggg cac ctt gga gct gtc cgt tac gtg tca   192
Ala Ser Ile Lys Asn Ala Gly His Leu Gly Ala Val Arg Tyr Val Ser
    50                  55                  60 cag cga cgc ccc ggc act gaa tcc tgg atg atc ggc aag cca gtc aca   240
Gln Arg Arg Pro Gly Thr Glu Ser Trp Met Ile Gly Lys Pro Val Thr
65                  70                  75                  80 ctg gca gaa acc cga gct ttt gaa caa aac ggc ctc aaa acc gca tcc   288
Leu Ala Glu Thr Arg Ala Phe Glu Gln Asn Gly Leu Lys Thr Ala Ser
                85                  90                  95 gtc tat caa tac gga aag gca gag acc gcc gat tgg aag aac ggc gcc   336
Val Tyr Gln Tyr Gly Lys Ala Glu Thr Ala Asp Trp Lys Asn Gly Ala
            100                 105                 110 gca gga gcg gca acc cac gct cca cag gca att gcg ctt cac gtg gca   384
Ala Gly Ala Ala Thr His Ala Pro Gln Ala Ile Ala Leu His Val Ala
        115                 120                 125 gct ggt ggc cct aaa aat cgc ccc atc tac gtg gcg atc gac gac aac   432
Ala Gly Gly Pro Lys Asn Arg Pro Ile Tyr Val Ala Ile Asp Asp Asn
    130                 135                 140 cca agc tgg tct gaa tac acc aat cag att cgc ccc tac ctc cag gca   480
Pro Ser Trp Ser Glu Tyr Thr Asn Gln Ile Arg Pro Tyr Leu Gln Ala
145                 150                 155                 160 ttc aat gtt gcg ctg tcc gct gcc ggc tac cag tta ggt gtc tac ggc   528
Phe Asn Val Ala Leu Ser Ala Ala Gly Tyr Gln Leu Gly Val Tyr Gly
                165                 170                 175 aac tac aac gtc att aat tgg gct atc gcc gac ggc ttg gga gaa ttc   576
Asn Tyr Asn Val Ile Asn Trp Ala Ile Ala Asp Gly Leu Gly Glu Phe
            180                 185                 190 ttc tgg atg cac aac tgg gga tca gaa gga aag atc cac cca cgc acc   624
Phe Trp Met His Asn Trp Gly Ser Glu Gly Lys Ile His Pro Arg Thr
        195                 200                 205 acc atc cac cag atc cgc att gat aag gac acc ctc gac gga gtc ggc   672
Thr Ile His Gln Ile Arg Ile Asp Lys Asp Thr Leu Asp Gly Val Gly
    210                 215                 220 atc gac atg aac aat gtc tat gca gac gac tgg ggt cag tgg acc cca   720
Ile Asp Met Asn Asn Val Tyr Ala Asp Asp Trp Gly Gln Trp Thr Pro
225                 230                 235                 240 ggc aac gcg gtt gac gat gcc atc ccc acc att cct gga aac tcc aac   768
Gly Asn Ala Val Asp Asp Ala Ile Pro Thr Ile Pro Gly Asn Ser Asn
                245                 250                 255 acg gga aca ggt act gga att gat gct gac acc atc aac caa gta atc   816
Thr Gly Thr Gly Thr Gly Ile Asp Ala Asp Thr Ile Asn Gln Val Ile
            260                 265                 270 aag att ctt ggc acc cta tct agc taa                               843
Lys Ile Leu Gly Thr Leu Ser Ser
        275                 280
```

<210> SEQ ID NO 2

-continued

```
<211> LENGTH: 280
<212> TYPE: PRT
<213> ORGANISM: Corynebacterium glutamicum ATCC13032

<400> SEQUENCE: 2

Met Gln Ile Asn Arg Arg Gly Phe Leu Lys Ala Thr Thr Gly Leu Ala
1               5                   10                  15

Thr Ile Gly Ala Ala Ser Met Phe Met Pro Lys Ala Asn Ala Leu Gly
            20                  25                  30

Ala Ile Lys Gly Thr Val Ile Asp Tyr Ala Ala Gly Val Pro Ser Ala
        35                  40                  45

Ala Ser Ile Lys Asn Ala Gly His Leu Gly Ala Val Arg Tyr Val Ser
    50                  55                  60

Gln Arg Arg Pro Gly Thr Glu Ser Trp Met Ile Gly Lys Pro Val Thr
65                  70                  75                  80

Leu Ala Glu Thr Arg Ala Phe Glu Gln Asn Gly Leu Lys Thr Ala Ser
                85                  90                  95

Val Tyr Gln Tyr Gly Lys Ala Glu Thr Ala Asp Trp Lys Asn Gly Ala
            100                 105                 110

Ala Gly Ala Ala Thr His Ala Pro Gln Ala Ile Ala Leu His Val Ala
        115                 120                 125

Ala Gly Gly Pro Lys Asn Arg Pro Ile Tyr Val Ala Ile Asp Asp Asn
    130                 135                 140

Pro Ser Trp Ser Glu Tyr Thr Asn Gln Ile Arg Pro Tyr Leu Gln Ala
145                 150                 155                 160

Phe Asn Val Ala Leu Ser Ala Ala Gly Tyr Gln Leu Gly Val Tyr Gly
                165                 170                 175

Asn Tyr Asn Val Ile Asn Trp Ala Ile Ala Asp Gly Leu Gly Glu Phe
            180                 185                 190

Phe Trp Met His Asn Trp Gly Ser Glu Gly Lys Ile His Pro Arg Thr
        195                 200                 205

Thr Ile His Gln Ile Arg Ile Asp Lys Asp Thr Leu Asp Gly Val Gly
    210                 215                 220

Ile Asp Met Asn Asn Val Tyr Ala Asp Asp Trp Gly Gln Trp Thr Pro
225                 230                 235                 240

Gly Asn Ala Val Asp Asp Ala Ile Pro Thr Ile Pro Gly Asn Ser Asn
                245                 250                 255

Thr Gly Thr Gly Thr Gly Ile Asp Ala Asp Thr Ile Asn Gln Val Ile
            260                 265                 270

Lys Ile Leu Gly Thr Leu Ser Ser
        275                 280

<210> SEQ ID NO 3
<211> LENGTH: 843
<212> TYPE: DNA
<213> ORGANISM: Corynebacterium glutamicum R
<220> FEATURE:
<221> NAME/KEY: CDS
<222> LOCATION: (1)..(840)
<223> OTHER INFORMATION: cgR0949
<220> FEATURE:
<221> NAME/KEY: misc_signal
<222> LOCATION: (1)..(99)
<223> OTHER INFORMATION: 5' sequence of cgR0949 encoding Tat-signal
      peptide of CgR0949
<220> FEATURE:
<221> NAME/KEY: misc_feature
<222> LOCATION: (1)..(101)
<223> OTHER INFORMATION: 5' sequence of cgR0949
<220> FEATURE:
```

```
<221> NAME/KEY: misc_feature
<222> LOCATION: (102)..(102)
<223> OTHER INFORMATION: nucleobase cytosine
<220> FEATURE:
<221> NAME/KEY: misc_feature
<222> LOCATION: (841)..(843)
<223> OTHER INFORMATION: stop codon

<400> SEQUENCE: 3
```

| | | | | | | | | | | | | | | | | |
|---|---|---|---|---|---|---|---|---|---|---|---|---|---|---|---|---|
| atg | caa | ata | aac | cgc | cga | ggc | ttc | tta | aaa | gcc | acc | gca | gga | ctt | gcc | 48 |
| Met | Gln | Ile | Asn | Arg | Arg | Gly | Phe | Leu | Lys | Ala | Thr | Ala | Gly | Leu | Ala | |
| 1 | | | | 5 | | | | | 10 | | | | | 15 | | |
| act | atc | ggc | gct | gcc | agc | atg | ttt | atg | cca | aag | gcc | aac | gcc | ctt | gga | 96 |
| Thr | Ile | Gly | Ala | Ala | Ser | Met | Phe | Met | Pro | Lys | Ala | Asn | Ala | Leu | Gly | |
| | | | 20 | | | | | 25 | | | | | 30 | | | |
| gca | atc | aag | ggc | acc | gtc | atc | gac | tac | gca | gca | ggc | gtc | ccc | agc | gca | 144 |
| Ala | Ile | Lys | Gly | Thr | Val | Ile | Asp | Tyr | Ala | Ala | Gly | Val | Pro | Ser | Ala | |
| | | 35 | | | | | 40 | | | | | 45 | | | | |
| gca | tcc | att | aaa | aat | gca | ggg | cac | ctt | gga | gct | gtc | cgt | tac | gtg | tca | 192 |
| Ala | Ser | Ile | Lys | Asn | Ala | Gly | His | Leu | Gly | Ala | Val | Arg | Tyr | Val | Ser | |
| | 50 | | | | | 55 | | | | | 60 | | | | | |
| cag | cga | cgc | ccc | ggc | act | gaa | tcc | tgg | atg | atc | ggc | aag | cca | gtc | aca | 240 |
| Gln | Arg | Arg | Pro | Gly | Thr | Glu | Ser | Trp | Met | Ile | Gly | Lys | Pro | Val | Thr | |
| 65 | | | | | 70 | | | | | 75 | | | | | 80 | |
| ctg | gca | gaa | acc | cga | tct | ttt | gaa | caa | aac | ggc | ctc | aaa | acc | gca | tcc | 288 |
| Leu | Ala | Glu | Thr | Arg | Ser | Phe | Glu | Gln | Asn | Gly | Leu | Lys | Thr | Ala | Ser | |
| | | | | 85 | | | | | 90 | | | | | 95 | | |
| gtt | tat | caa | tac | gga | aag | gca | gag | acc | gcc | gat | tgg | aag | aac | ggc | gcc | 336 |
| Val | Tyr | Gln | Tyr | Gly | Lys | Ala | Glu | Thr | Ala | Asp | Trp | Lys | Asn | Gly | Ala | |
| | | | 100 | | | | | 105 | | | | | 110 | | | |
| gca | gga | gcg | gca | acc | cac | gct | cca | cag | gca | att | gcg | ctt | cac | gtg | gca | 384 |
| Ala | Gly | Ala | Ala | Thr | His | Ala | Pro | Gln | Ala | Ile | Ala | Leu | His | Val | Ala | |
| | | 115 | | | | | 120 | | | | | 125 | | | | |
| gct | ggt | ggc | cct | aaa | aat | cgc | ccc | atc | tac | gtg | gcg | atc | gac | gac | aac | 432 |
| Ala | Gly | Gly | Pro | Lys | Asn | Arg | Pro | Ile | Tyr | Val | Ala | Ile | Asp | Asp | Asn | |
| | 130 | | | | | 135 | | | | | 140 | | | | | |
| cca | agc | tgg | tct | gaa | tac | acc | aat | cag | att | cgc | cct | tac | ctc | cag | gca | 480 |
| Pro | Ser | Trp | Ser | Glu | Tyr | Thr | Asn | Gln | Ile | Arg | Pro | Tyr | Leu | Gln | Ala | |
| 145 | | | | | 150 | | | | | 155 | | | | | 160 | |
| ttc | aat | gtt | gcg | ctg | tcc | gct | gcc | ggc | tac | cag | tta | ggt | gtg | tac | ggc | 528 |
| Phe | Asn | Val | Ala | Leu | Ser | Ala | Ala | Gly | Tyr | Gln | Leu | Gly | Val | Tyr | Gly | |
| | | | | 165 | | | | | 170 | | | | | 175 | | |
| aac | tac | aac | gtc | att | gat | tgg | gct | atc | gcc | gac | ggc | ctt | gga | gaa | ttc | 576 |
| Asn | Tyr | Asn | Val | Ile | Asp | Trp | Ala | Ile | Ala | Asp | Gly | Leu | Gly | Glu | Phe | |
| | | | 180 | | | | | 185 | | | | | 190 | | | |
| ttc | tgg | atg | cac | aac | tgg | gga | tca | gaa | gga | aag | atc | cac | cca | cgc | acc | 624 |
| Phe | Trp | Met | His | Asn | Trp | Gly | Ser | Glu | Gly | Lys | Ile | His | Pro | Arg | Thr | |
| | | 195 | | | | | 200 | | | | | 205 | | | | |
| acc | atc | cac | cag | atc | cgc | att | gat | aaa | gac | aac | ctc | gag | ggt | gtt | ggc | 672 |
| Thr | Ile | His | Gln | Ile | Arg | Ile | Asp | Lys | Asp | Asn | Leu | Glu | Gly | Val | Gly | |
| | 210 | | | | | 215 | | | | | 220 | | | | | |
| att | gac | atg | aac | aat | gtc | tat | gca | gac | gac | tgg | ggc | cag | tgg | acc | cca | 720 |
| Ile | Asp | Met | Asn | Asn | Val | Tyr | Ala | Asp | Asp | Trp | Gly | Gln | Trp | Thr | Pro | |
| 225 | | | | | 230 | | | | | 235 | | | | | 240 | |
| gac | aat | gcg | gtt | gac | gat | gtc | ttc | ccc | acc | att | ccc | gga | aac | tcc | aac | 768 |
| Asp | Asn | Ala | Val | Asp | Asp | Val | Phe | Pro | Thr | Ile | Pro | Gly | Asn | Ser | Asn | |
| | | | | 245 | | | | | 250 | | | | | 255 | | |
| acg | gga | aca | ggt | act | gga | att | gat | gct | gac | acc | atc | aac | caa | gta | atc | 816 |
| Thr | Gly | Thr | Gly | Thr | Gly | Ile | Asp | Ala | Asp | Thr | Ile | Asn | Gln | Val | Ile | |
| | | | 260 | | | | | 265 | | | | | 270 | | | |
| aag | att | ctt | ggc | acc | ctg | tct | agc | taa | | | | | | | | 843 |

```
Lys Ile Leu Gly Thr Leu Ser Ser
        275                 280

<210> SEQ ID NO 4
<211> LENGTH: 280
<212> TYPE: PRT
<213> ORGANISM: Corynebacterium glutamicum R

<400> SEQUENCE: 4

Met Gln Ile Asn Arg Arg Gly Phe Leu Lys Ala Thr Ala Gly Leu Ala
1               5                   10                  15

Thr Ile Gly Ala Ala Ser Met Phe Met Pro Lys Ala Asn Ala Leu Gly
            20                  25                  30

Ala Ile Lys Gly Thr Val Ile Asp Tyr Ala Ala Gly Val Pro Ser Ala
        35                  40                  45

Ala Ser Ile Lys Asn Ala Gly His Leu Gly Ala Val Arg Tyr Val Ser
    50                  55                  60

Gln Arg Arg Pro Gly Thr Glu Ser Trp Met Ile Gly Lys Pro Val Thr
65                  70                  75                  80

Leu Ala Glu Thr Arg Ser Phe Glu Gln Asn Gly Leu Lys Thr Ala Ser
                85                  90                  95

Val Tyr Gln Tyr Gly Lys Ala Glu Thr Ala Asp Trp Lys Asn Gly Ala
            100                 105                 110

Ala Gly Ala Ala Thr His Ala Pro Gln Ala Ile Ala Leu His Val Ala
        115                 120                 125

Ala Gly Gly Pro Lys Asn Arg Pro Ile Tyr Val Ala Ile Asp Asp Asn
    130                 135                 140

Pro Ser Trp Ser Glu Tyr Thr Asn Gln Ile Arg Pro Tyr Leu Gln Ala
145                 150                 155                 160

Phe Asn Val Ala Leu Ser Ala Ala Gly Tyr Gln Leu Gly Val Tyr Gly
                165                 170                 175

Asn Tyr Asn Val Ile Asp Trp Ala Ile Ala Asp Gly Leu Gly Glu Phe
            180                 185                 190

Phe Trp Met His Asn Trp Gly Ser Glu Gly Lys Ile His Pro Arg Thr
        195                 200                 205

Thr Ile His Gln Ile Arg Ile Asp Lys Asp Asn Leu Glu Gly Val Gly
    210                 215                 220

Ile Asp Met Asn Asn Val Tyr Ala Asp Trp Gly Gln Trp Thr Pro
225                 230                 235                 240

Asp Asn Ala Val Asp Asp Val Phe Pro Thr Ile Pro Gly Asn Ser Asn
                245                 250                 255

Thr Gly Thr Gly Thr Gly Ile Asp Ala Asp Thr Ile Asn Gln Val Ile
            260                 265                 270

Lys Ile Leu Gly Thr Leu Ser Ser
        275                 280

<210> SEQ ID NO 5
<211> LENGTH: 1815
<212> TYPE: DNA
<213> ORGANISM: Bifidobacterium breve UCC2003
<220> FEATURE:
<221> NAME/KEY: CDS
<222> LOCATION: (1)..(1812)
<223> OTHER INFORMATION: agl2
<220> FEATURE:
<221> NAME/KEY: misc_feature
<222> LOCATION: (4)..(1812)
<223> OTHER INFORMATION: 'agl2
<220> FEATURE:
```

<221> NAME/KEY: misc_feature
<222> LOCATION: (1813)..(1815)
<223> OTHER INFORMATION: stop codon

<400> SEQUENCE: 5

| | | | | | | | | | | | | | | | | |
|---|---|---|---|---|---|---|---|---|---|---|---|---|---|---|---|---|
| atg | acc | tct | ttc | aac | cgt | gaa | ccc | ctg | ccc | gac | gcc | gtc | cgc | acg | aat | 48 |
| Met | Thr | Ser | Phe | Asn | Arg | Glu | Pro | Leu | Pro | Asp | Ala | Val | Arg | Thr | Asn | |
| 1 | | | | 5 | | | | | 10 | | | | | 15 | | |
| ggc | gcc | acg | ccc | aac | ccg | tgg | tgg | tcg | aat | gcg | gtg | gtg | tac | cag | atc | 96 |
| Gly | Ala | Thr | Pro | Asn | Pro | Trp | Trp | Ser | Asn | Ala | Val | Val | Tyr | Gln | Ile | |
| | | 20 | | | | | 25 | | | | | 30 | | | | |
| tac | ccg | cgg | tcg | ttc | cag | gac | acg | aac | ggc | gac | ggt | ctc | ggc | gac | ctg | 144 |
| Tyr | Pro | Arg | Ser | Phe | Gln | Asp | Thr | Asn | Gly | Asp | Gly | Leu | Gly | Asp | Leu | |
| | | 35 | | | | | 40 | | | | | 45 | | | | |
| aag | ggc | atc | acc | tcc | cgc | ctc | gac | tat | ctc | gcc | gac | ctc | ggc | gtg | gat | 192 |
| Lys | Gly | Ile | Thr | Ser | Arg | Leu | Asp | Tyr | Leu | Ala | Asp | Leu | Gly | Val | Asp | |
| 50 | | | | | 55 | | | | | 60 | | | | | | |
| gtg | ctc | tgg | ctc | tcc | ccg | gtc | tac | agg | tcc | ccg | caa | gac | gac | aac | ggc | 240 |
| Val | Leu | Trp | Leu | Ser | Pro | Val | Tyr | Arg | Ser | Pro | Gln | Asp | Asp | Asn | Gly | |
| 65 | | | | | 70 | | | | | 75 | | | | | 80 | |
| tac | gac | atc | tcc | gac | tac | cgg | gat | atc | gac | ccg | ctg | ttc | ggc | acg | ctc | 288 |
| Tyr | Asp | Ile | Ser | Asp | Tyr | Arg | Asp | Ile | Asp | Pro | Leu | Phe | Gly | Thr | Leu | |
| | | | | 85 | | | | | 90 | | | | | 95 | | |
| gac | gac | atg | gac | gag | ctg | ctc | gcc | gaa | gcg | cac | aag | cgc | ggc | ctc | aag | 336 |
| Asp | Asp | Met | Asp | Glu | Leu | Leu | Ala | Glu | Ala | His | Lys | Arg | Gly | Leu | Lys | |
| | | | 100 | | | | | 105 | | | | | 110 | | | |
| atc | gtg | atg | gac | ctg | gtg | gtc | aac | cac | acc | tcc | gac | gag | cac | gcg | tgg | 384 |
| Ile | Val | Met | Asp | Leu | Val | Val | Asn | His | Thr | Ser | Asp | Glu | His | Ala | Trp | |
| | | | 115 | | | | | 120 | | | | | 125 | | | |
| ttc | gag | gcg | tcg | aag | gac | aag | gac | gac | ccg | cac | gcc | gac | tgg | tac | tgg | 432 |
| Phe | Glu | Ala | Ser | Lys | Asp | Lys | Asp | Asp | Pro | His | Ala | Asp | Trp | Tyr | Trp | |
| | 130 | | | | | 135 | | | | | 140 | | | | | |
| tgg | cgt | ccc | gcc | cgc | ccc | ggc | cac | gag | ccg | ggc | acg | ccc | ggc | gcc | gag | 480 |
| Trp | Arg | Pro | Ala | Arg | Pro | Gly | His | Glu | Pro | Gly | Thr | Pro | Gly | Ala | Glu | |
| 145 | | | | | 150 | | | | | 155 | | | | | 160 | |
| ccg | aat | cag | tgg | ggc | tcc | tac | ttc | ggc | ggt | tcc | gca | tgg | gag | tac | agc | 528 |
| Pro | Asn | Gln | Trp | Gly | Ser | Tyr | Phe | Gly | Gly | Ser | Ala | Trp | Glu | Tyr | Ser | |
| | | | | 165 | | | | | 170 | | | | | 175 | | |
| ccg | gag | cgc | ggc | gag | tac | tac | ctg | cac | cag | ttc | tcg | aag | aag | cag | cct | 576 |
| Pro | Glu | Arg | Gly | Glu | Tyr | Tyr | Leu | His | Gln | Phe | Ser | Lys | Lys | Gln | Pro | |
| | | | 180 | | | | | 185 | | | | | 190 | | | |
| gat | ctc | aac | tgg | gag | aac | ccg | gcc | gtg | cgc | cgc | gcg | gtg | tac | gac | atg | 624 |
| Asp | Leu | Asn | Trp | Glu | Asn | Pro | Ala | Val | Arg | Arg | Ala | Val | Tyr | Asp | Met | |
| | | | 195 | | | | | 200 | | | | | 205 | | | |
| atg | aac | tgg | tgg | ctc | gat | cgc | ggc | atc | gac | ggc | ttc | cgt | atg | gat | gtc | 672 |
| Met | Asn | Trp | Trp | Leu | Asp | Arg | Gly | Ile | Asp | Gly | Phe | Arg | Met | Asp | Val | |
| | 210 | | | | | 215 | | | | | 220 | | | | | |
| atc | acc | ctg | atc | tcc | aag | cgc | acc | gac | ccc | aac | ggc | agg | ctc | ccc | ggc | 720 |
| Ile | Thr | Leu | Ile | Ser | Lys | Arg | Thr | Asp | Pro | Asn | Gly | Arg | Leu | Pro | Gly | |
| 225 | | | | | 230 | | | | | 235 | | | | | 240 | |
| gag | acc | ggt | tcc | gag | ctc | cag | gac | ctg | ccg | gtg | ggg | gag | gag | ggc | tac | 768 |
| Glu | Thr | Gly | Ser | Glu | Leu | Gln | Asp | Leu | Pro | Val | Gly | Glu | Glu | Gly | Tyr | |
| | | | | 245 | | | | | 250 | | | | | 255 | | |
| tcc | agc | ccg | aac | ccg | ttc | tgc | gcc | gac | ggt | ccg | cgt | cag | gac | gag | ttc | 816 |
| Ser | Ser | Pro | Asn | Pro | Phe | Cys | Ala | Asp | Gly | Pro | Arg | Gln | Asp | Glu | Phe | |
| | | | 260 | | | | | 265 | | | | | 270 | | | |
| ctc | gcc | gag | atg | cgc | cgc | gag | gtg | ttc | gac | ggg | cgt | gac | ggc | ttc | ctc | 864 |
| Leu | Ala | Glu | Met | Arg | Arg | Glu | Val | Phe | Asp | Gly | Arg | Asp | Gly | Phe | Leu | |
| | | 275 | | | | | 280 | | | | | 285 | | | | |
| acc | gtc | ggc | gag | gca | ccc | ggc | atc | acc | gcc | gaa | cgc | aac | gag | cac | atc | 912 |

|  |  |  |  |  |  |  |  |  |  |  |  |  |
|---|---|---|---|---|---|---|---|---|---|---|---|---|
| Thr | Val | Gly | Glu | Ala | Pro | Gly | Ile | Thr | Ala | Glu | Arg | Asn | Glu | His | Ile |
| | 290 | | | | 295 | | | | 300 | | | | | | |

```
acc gac ccc gcc aac ggc gaa ctc gac atg ctc ttc ctg ttc gaa cac      960
Thr Asp Pro Ala Asn Gly Glu Leu Asp Met Leu Phe Leu Phe Glu His
305                 310                 315                 320 atg ggc gtc gac caa acc ccc gaa tcg aaa tgg gac gac aaa cca tgg     1008
Met Gly Val Asp Gln Thr Pro Glu Ser Lys Trp Asp Asp Lys Pro Trp
                325                 330                 335 acg ccg gcc gac ctc gaa acc aag ctt gcc gaa caa cag gac gcc atc     1056
Thr Pro Ala Asp Leu Glu Thr Lys Leu Ala Glu Gln Gln Asp Ala Ile
            340                 345                 350 gcc cga cgc ggc tgg gcc agc ctg ttc ctc gac aac cac gac cag ccg     1104
Ala Arg Arg Gly Trp Ala Ser Leu Phe Leu Asp Asn His Asp Gln Pro
        355                 360                 365 cgt gtc gtc tcc cgt tgg ggc gac gac acc agc aag acc ggc cgc atc     1152
Arg Val Val Ser Arg Trp Gly Asp Asp Thr Ser Lys Thr Gly Arg Ile
    370                 375                 380 cgc tcc gcc aag gcg ctc gcg ctg ctg ctg cac atg cac cgc ggc acc     1200
Arg Ser Ala Lys Ala Leu Ala Leu Leu Leu His Met His Arg Gly Thr
385                 390                 395                 400 ccg tac gtc tac cag ggc gag gag ctc ggc atg acc aat gcg cac ttc     1248
Pro Tyr Val Tyr Gln Gly Glu Glu Leu Gly Met Thr Asn Ala His Phe
                405                 410                 415 acc tcg ctc gac cag tac cgc gac ctc gaa tcc atc aac gcc tac cat     1296
Thr Ser Leu Asp Gln Tyr Arg Asp Leu Glu Ser Ile Asn Ala Tyr His
            420                 425                 430 caa cgc gtc gag gaa acc ggg ata cgg aca tcg gag acc atg atg cga     1344
Gln Arg Val Glu Glu Thr Gly Ile Arg Thr Ser Glu Thr Met Met Arg
        435                 440                 445 tcc ctc gcc cga tac ggc agg gac aac gcg cgc acc ccg atg caa tgg     1392
Ser Leu Ala Arg Tyr Gly Arg Asp Asn Ala Arg Thr Pro Met Gln Trp
    450                 455                 460 gac gac tcc acc tac gcc ggc ttc acc atg ccc gac gcc ccg gtc gaa     1440
Asp Asp Ser Thr Tyr Ala Gly Phe Thr Met Pro Asp Ala Pro Val Glu
465                 470                 475                 480 ccc tgg atc gcc gtc aac ccg aac cac acg gag atc aac gcc gcc gac     1488
Pro Trp Ile Ala Val Asn Pro Asn His Thr Glu Ile Asn Ala Ala Asp
                485                 490                 495 gag acc gac gac ccc gac tcc gtg tac tcg ttc cac aaa cgg ctc atc     1536
Glu Thr Asp Asp Pro Asp Ser Val Tyr Ser Phe His Lys Arg Leu Ile
            500                 505                 510 gcc ctg cgc cac acc gac ccc gtg gtc gcc gcc ggc gac tac cga cgc     1584
Ala Leu Arg His Thr Asp Pro Val Val Ala Ala Gly Asp Tyr Arg Arg
        515                 520                 525 gtg gaa acc gga aac gac cgg atc atc gcc ttc acc aga acc ctc gac     1632
Val Glu Thr Gly Asn Asp Arg Ile Ile Ala Phe Thr Arg Thr Leu Asp
    530                 535                 540 gag cga acc atc ctc acc gtc atc aac ctc tcg ccc aca cag gcc gca     1680
Glu Arg Thr Ile Leu Thr Val Ile Asn Leu Ser Pro Thr Gln Ala Ala
545                 550                 555                 560 ccg gcc gga gaa ctg gaa acg atg ccc gac ggc acg atc ctc atc gcc     1728
Pro Ala Gly Glu Leu Glu Thr Met Pro Asp Gly Thr Ile Leu Ile Ala
                565                 570                 575 aac acg gac gat ccc gta gga aac ctg aaa acc acg gga aca ctc gga     1776
Asn Thr Asp Asp Pro Val Gly Asn Leu Lys Thr Thr Gly Thr Leu Gly
            580                 585                 590 cca tgg gag gcg ttc gcc atg gaa acc gat ccg gaa taa                 1815
Pro Trp Glu Ala Phe Ala Met Glu Thr Asp Pro Glu
        595                 600
```

```
<210> SEQ ID NO 6
<211> LENGTH: 604
<212> TYPE: PRT
<213> ORGANISM: Bifidobacterium breve UCC2003

<400> SEQUENCE: 6

Met Thr Ser Phe Asn Arg Glu Pro Leu Pro Asp Ala Val Arg Thr Asn
1               5                   10                  15

Gly Ala Thr Pro Asn Pro Trp Trp Ser Asn Ala Val Val Tyr Gln Ile
            20                  25                  30

Tyr Pro Arg Ser Phe Gln Asp Thr Asn Gly Asp Gly Leu Gly Asp Leu
        35                  40                  45

Lys Gly Ile Thr Ser Arg Leu Asp Tyr Leu Ala Asp Leu Gly Val Asp
    50                  55                  60

Val Leu Trp Leu Ser Pro Val Tyr Arg Ser Pro Gln Asp Asp Asn Gly
65                  70                  75                  80

Tyr Asp Ile Ser Asp Tyr Arg Asp Ile Asp Pro Leu Phe Gly Thr Leu
                85                  90                  95

Asp Asp Met Asp Glu Leu Leu Ala Glu Ala His Lys Arg Gly Leu Lys
            100                 105                 110

Ile Val Met Asp Leu Val Val Asn His Thr Ser Asp Glu His Ala Trp
        115                 120                 125

Phe Glu Ala Ser Lys Asp Lys Asp Pro His Ala Asp Trp Tyr Trp
    130                 135                 140

Trp Arg Pro Ala Arg Pro Gly His Glu Pro Gly Thr Pro Gly Ala Glu
145                 150                 155                 160

Pro Asn Gln Trp Gly Ser Tyr Phe Gly Gly Ser Ala Trp Glu Tyr Ser
                165                 170                 175

Pro Glu Arg Gly Glu Tyr Tyr Leu His Gln Phe Ser Lys Lys Gln Pro
            180                 185                 190

Asp Leu Asn Trp Glu Asn Pro Ala Val Arg Arg Ala Val Tyr Asp Met
        195                 200                 205

Met Asn Trp Trp Leu Asp Arg Gly Ile Asp Gly Phe Arg Met Asp Val
    210                 215                 220

Ile Thr Leu Ile Ser Lys Arg Thr Asp Pro Asn Gly Arg Leu Pro Gly
225                 230                 235                 240

Glu Thr Gly Ser Glu Leu Gln Asp Leu Pro Val Gly Glu Gly Tyr
                245                 250                 255

Ser Ser Pro Asn Pro Phe Cys Ala Asp Gly Pro Arg Gln Asp Glu Phe
            260                 265                 270

Leu Ala Glu Met Arg Arg Glu Val Phe Asp Gly Arg Asp Gly Phe Leu
        275                 280                 285

Thr Val Gly Glu Ala Pro Gly Ile Thr Ala Glu Arg Asn Glu His Ile
    290                 295                 300

Thr Asp Pro Ala Asn Gly Glu Leu Asp Met Leu Phe Leu Phe Glu His
305                 310                 315                 320

Met Gly Val Asp Gln Thr Pro Glu Ser Lys Trp Asp Lys Pro Trp
                325                 330                 335

Thr Pro Ala Asp Leu Glu Thr Lys Leu Ala Glu Gln Gln Asp Ala Ile
            340                 345                 350

Ala Arg Arg Gly Trp Ala Ser Leu Phe Leu Asp Asn His Asp Gln Pro
        355                 360                 365

Arg Val Val Ser Arg Trp Gly Asp Asp Thr Ser Lys Thr Gly Arg Ile
    370                 375                 380
```

```
Arg Ser Ala Lys Ala Leu Ala Leu Leu Leu His Met His Arg Gly Thr
385                 390                 395                 400

Pro Tyr Val Tyr Gln Gly Glu Glu Leu Gly Met Thr Asn Ala His Phe
            405                 410                 415

Thr Ser Leu Asp Gln Tyr Arg Asp Leu Glu Ser Ile Asn Ala Tyr His
            420                 425                 430

Gln Arg Val Glu Glu Thr Gly Ile Arg Thr Ser Glu Thr Met Met Arg
        435                 440                 445

Ser Leu Ala Arg Tyr Gly Arg Asp Asn Ala Arg Thr Pro Met Gln Trp
    450                 455                 460

Asp Asp Ser Thr Tyr Ala Gly Phe Thr Met Pro Asp Ala Pro Val Glu
465                 470                 475                 480

Pro Trp Ile Ala Val Asn Pro Asn His Thr Glu Ile Asn Ala Ala Asp
            485                 490                 495

Glu Thr Asp Asp Pro Asp Ser Val Tyr Ser Phe His Lys Arg Leu Ile
            500                 505                 510

Ala Leu Arg His Thr Asp Pro Val Ala Ala Gly Asp Tyr Arg Arg
        515                 520                 525

Val Glu Thr Gly Asn Asp Arg Ile Ile Ala Phe Thr Arg Thr Leu Asp
    530                 535                 540

Glu Arg Thr Ile Leu Thr Val Ile Asn Leu Ser Pro Thr Gln Ala Ala
545                 550                 555                 560

Pro Ala Gly Glu Leu Glu Thr Met Pro Asp Gly Thr Ile Leu Ile Ala
            565                 570                 575

Asn Thr Asp Asp Pro Val Gly Asn Leu Lys Thr Thr Gly Thr Leu Gly
            580                 585                 590

Pro Trp Glu Ala Phe Ala Met Glu Thr Asp Pro Glu
        595                 600

<210> SEQ ID NO 7
<211> LENGTH: 1824
<212> TYPE: DNA
<213> ORGANISM: Bifidobacterium breve UCC2003
<220> FEATURE:
<221> NAME/KEY: CDS
<222> LOCATION: (1)..(1821)
<223> OTHER INFORMATION: agl1
<220> FEATURE:
<221> NAME/KEY: misc_feature
<222> LOCATION: (1822)..(1824)
<223> OTHER INFORMATION: stop codon

<400> SEQUENCE: 7 atg atg act act ttc aac cgc gca ata att ccc gac gcc atc cgc acc     48
Met Met Thr Thr Phe Asn Arg Ala Ile Ile Pro Asp Ala Ile Arg Thr
1               5                   10                  15 aac ggc gcc acc ccc aat ccg tgg tgg tcc aac gcg gtg gtc tat cag     96
Asn Gly Ala Thr Pro Asn Pro Trp Trp Ser Asn Ala Val Val Tyr Gln
            20                  25                  30 att tac ccg cgt tct ttc caa gac acg aac ggc gat gga ttc ggc gat    144
Ile Tyr Pro Arg Ser Phe Gln Asp Thr Asn Gly Asp Gly Phe Gly Asp
        35                  40                  45 ctt aag ggc atc acg tcg cgt ctt gat tac tta gct gat ctt ggc gtg    192
Leu Lys Gly Ile Thr Ser Arg Leu Asp Tyr Leu Ala Asp Leu Gly Val
    50                  55                  60 gat gtg ctg tgg ctc tcc ccg gtc tat aag tcc ccg caa gac gac aac    240
Asp Val Leu Trp Leu Ser Pro Val Tyr Lys Ser Pro Gln Asp Asp Asn
65                  70                  75                  80
```

-continued

| | | |
|---|---|---|
| ggc tat gac atc tct gac tat cag gac atc gac ccg ctg ttc ggc acg<br>Gly Tyr Asp Ile Ser Asp Tyr Gln Asp Ile Asp Pro Leu Phe Gly Thr<br>85 90 95 | | 288 |
| ctc gac gat atg gac gag ctg ctg gcc gaa gcg cat aag cgt ggg ctc<br>Leu Asp Asp Met Asp Glu Leu Leu Ala Glu Ala His Lys Arg Gly Leu<br>100 105 110 | | 336 |
| aaa gtc gtg atg gat ttg gtg gtc aat cac acc tcc gat gag cat gcc<br>Lys Val Val Met Asp Leu Val Val Asn His Thr Ser Asp Glu His Ala<br>115 120 125 | | 384 |
| tgg ttt gag gcg tcc aag aac aag gac gac gag cat gcc gat tgg tat<br>Trp Phe Glu Ala Ser Lys Asn Lys Asp Asp Glu His Ala Asp Trp Tyr<br>130 135 140 | | 432 |
| tgg tgg cgt ccg gct cgt ccc ggc acc acg ccc ggc gag ccc ggc tcc<br>Trp Trp Arg Pro Ala Arg Pro Gly Thr Thr Pro Gly Glu Pro Gly Ser<br>145 150 155 160 | | 480 |
| gag ccc aat cag tgg ggc tcc tac ttt ggc ggt tcc gca tgg gaa tat<br>Glu Pro Asn Gln Trp Gly Ser Tyr Phe Gly Gly Ser Ala Trp Glu Tyr<br>165 170 175 | | 528 |
| tgc ccc gag cgt ggt gag tac tat ctc cac cag ttc tcg aag aag cag<br>Cys Pro Glu Arg Gly Glu Tyr Tyr Leu His Gln Phe Ser Lys Lys Gln<br>180 185 190 | | 576 |
| ccc gat ctg aac tgg gag aac ccg gcc gtg cgc cga gcc gtg tac gac<br>Pro Asp Leu Asn Trp Glu Asn Pro Ala Val Arg Arg Ala Val Tyr Asp<br>195 200 205 | | 624 |
| atg atg aac tgg tgg ctt gac cga ggc atc gac ggc ttc cgc atg gat<br>Met Met Asn Trp Trp Leu Asp Arg Gly Ile Asp Gly Phe Arg Met Asp<br>210 215 220 | | 672 |
| gtc atc acc ctg atc tcc aag cgt acg gat gca aac ggc agg ctg ccc<br>Val Ile Thr Leu Ile Ser Lys Arg Thr Asp Ala Asn Gly Arg Leu Pro<br>225 230 235 240 | | 720 |
| ggc gag tac ggt tcc gag ctg gac gat ctg cct gtg ggc gag gaa ggc<br>Gly Glu Tyr Gly Ser Glu Leu Asp Asp Leu Pro Val Gly Glu Glu Gly<br>245 250 255 | | 768 |
| tat tcc aat ccc aac ccg ttc tgt gcc gat ggg ccg cgc caa gac gag<br>Tyr Ser Asn Pro Asn Pro Phe Cys Ala Asp Gly Pro Arg Gln Asp Glu<br>260 265 270 | | 816 |
| ttc ttg aag gaa atg cgt cgt gaa gtc ttt gcc gga cgc gag gga ttc<br>Phe Leu Lys Glu Met Arg Arg Glu Val Phe Ala Gly Arg Glu Gly Phe<br>275 280 285 | | 864 |
| ctc acc gtg ggc gag gct ccc ggc atc aca cct gtg cgc aac gaa cac<br>Leu Thr Val Gly Glu Ala Pro Gly Ile Thr Pro Val Arg Asn Glu His<br>290 295 300 | | 912 |
| atc acc aat ccg gcc aat ggg gag ctg gat atg ctg ttc ctg ttc gat<br>Ile Thr Asn Pro Ala Asn Gly Glu Leu Asp Met Leu Phe Leu Phe Asp<br>305 310 315 320 | | 960 |
| cat gtc gat ttt gat tgt gat ggc gtc aag tgg aag cct ctg ccg ctc<br>His Val Asp Phe Asp Cys Asp Gly Val Lys Trp Lys Pro Leu Pro Leu<br>325 330 335 | | 1008 |
| gat ttg ccg gga ttc aag cgg atc atg gcc gga tat cag act gct gtg<br>Asp Leu Pro Gly Phe Lys Arg Ile Met Ala Gly Tyr Gln Thr Ala Val<br>340 345 350 | | 1056 |
| gag aac gtg ggc tgg gca agc ttg ttc act ggt aac cac gat cag cca<br>Glu Asn Val Gly Trp Ala Ser Leu Phe Thr Gly Asn His Asp Gln Pro<br>355 360 365 | | 1104 |
| cgt gtg gtc tct cgt tgg ggc gat gac tcc tcg gag gaa tcc cgc gtg<br>Arg Val Val Ser Arg Trp Gly Asp Asp Ser Ser Glu Glu Ser Arg Val<br>370 375 380 | | 1152 |
| cgc tcg gcc aaa gcg ctt ggc ctg atg ttg cac atg cat cgc ggc act<br>Arg Ser Ala Lys Ala Leu Gly Leu Met Leu His Met His Arg Gly Thr<br>385 390 395 400 | | 1200 |

```
ccg tac gta tat cag ggt gag gag ctg ggc atg acc aat gct cac ttc      1248
Pro Tyr Val Tyr Gln Gly Glu Glu Leu Gly Met Thr Asn Ala His Phe
                405                 410                 415 acc agc ctc gat cag tac cgc gac ctt gaa tcc ctc aat gcc tat cgt      1296
Thr Ser Leu Asp Gln Tyr Arg Asp Leu Glu Ser Leu Asn Ala Tyr Arg
            420                 425                 430 cag agg gtc gag gaa gcc aag gtg caa tcg ccg gaa tcg atg ttg gcg      1344
Gln Arg Val Glu Glu Ala Lys Val Gln Ser Pro Glu Ser Met Leu Ala
        435                 440                 445 ggt atc gcc gcg cgc ggt cgc gac aat tcg cgt acc cca atg caa tgg      1392
Gly Ile Ala Ala Arg Gly Arg Asp Asn Ser Arg Thr Pro Met Gln Trp
    450                 455                 460 gat ggt tct gcc tat gca ggt ttc acc gca ccg gat gca gcg acg gag      1440
Asp Gly Ser Ala Tyr Ala Gly Phe Thr Ala Pro Asp Ala Ala Thr Glu
465                 470                 475                 480 ccg tgg att tcc gtc aac ccg aat cat gct gaa atc aat gcg gcc ggc      1488
Pro Trp Ile Ser Val Asn Pro Asn His Ala Glu Ile Asn Ala Ala Gly
                485                 490                 495 gaa ttt gac gat cct gac tcg gtg tat gcc ttc tac aag aag ctc atc      1536
Glu Phe Asp Asp Pro Asp Ser Val Tyr Ala Phe Tyr Lys Lys Leu Ile
            500                 505                 510 gcc ttg cgc cac aac agt tcg att gtg gcg gct ggc gag tgg cag ctg      1584
Ala Leu Arg His Asn Ser Ser Ile Val Ala Ala Gly Glu Trp Gln Leu
        515                 520                 525 att gat gcg gat gac gcg cat gta tat gcg ttc acc cgc acg ctt ggc      1632
Ile Asp Ala Asp Asp Ala His Val Tyr Ala Phe Thr Arg Thr Leu Gly
    530                 535                 540 aac gag cga ttg ctg gtt gtg gtt aac ctg tcc ggc cga acc gtc gac      1680
Asn Glu Arg Leu Leu Val Val Val Asn Leu Ser Gly Arg Thr Val Asp
545                 550                 555                 560 ttg ccg cgt gaa tcc acc gag ctg att gcc ggc ggc gtc act gag cca      1728
Leu Pro Arg Glu Ser Thr Glu Leu Ile Ala Gly Gly Val Thr Glu Pro
                565                 570                 575 gat atc att ctc tcc acg tac gac gcc cct cac act gtg gtc tcc ctc      1776
Asp Ile Ile Leu Ser Thr Tyr Asp Ala Pro His Thr Val Val Ser Leu
            580                 585                 590 gcc aac cgt gag ctt gac ccg tgg gag gct gct gcc gtc cag ctg taa      1824
Ala Asn Arg Glu Leu Asp Pro Trp Glu Ala Ala Ala Val Gln Leu
        595                 600                 605

<210> SEQ ID NO 8
<211> LENGTH: 607
<212> TYPE: PRT
<213> ORGANISM: Bifidobacterium breve UCC2003

<400> SEQUENCE: 8

Met Met Thr Thr Phe Asn Arg Ala Ile Ile Pro Asp Ala Ile Arg Thr
1               5                   10                  15

Asn Gly Ala Thr Pro Asn Pro Trp Trp Ser Asn Ala Val Val Tyr Gln
            20                  25                  30

Ile Tyr Pro Arg Ser Phe Gln Asp Thr Asn Gly Asp Gly Phe Gly Asp
        35                  40                  45

Leu Lys Gly Ile Thr Ser Arg Leu Asp Tyr Leu Ala Asp Leu Gly Val
    50                  55                  60

Asp Val Leu Trp Leu Ser Pro Val Tyr Lys Ser Pro Gln Asp Asp Asn
65                  70                  75                  80

Gly Tyr Asp Ile Ser Asp Tyr Gln Asp Ile Asp Pro Leu Phe Gly Thr
                85                  90                  95
```

-continued

Leu Asp Asp Met Asp Glu Leu Leu Ala Glu Ala His Lys Arg Gly Leu
            100                 105                 110

Lys Val Val Met Asp Leu Val Val Asn His Thr Ser Asp Glu His Ala
        115                 120                 125

Trp Phe Glu Ala Ser Lys Asn Lys Asp Asp Glu His Ala Asp Trp Tyr
    130                 135                 140

Trp Trp Arg Pro Ala Arg Pro Gly Thr Thr Pro Gly Glu Pro Gly Ser
145                 150                 155                 160

Glu Pro Asn Gln Trp Gly Ser Tyr Phe Gly Gly Ser Ala Trp Glu Tyr
                165                 170                 175

Cys Pro Glu Arg Gly Glu Tyr Tyr Leu His Gln Phe Ser Lys Lys Gln
            180                 185                 190

Pro Asp Leu Asn Trp Glu Asn Pro Ala Val Arg Arg Ala Val Tyr Asp
        195                 200                 205

Met Met Asn Trp Trp Leu Asp Arg Gly Ile Asp Gly Phe Arg Met Asp
    210                 215                 220

Val Ile Thr Leu Ile Ser Lys Arg Thr Asp Ala Asn Gly Arg Leu Pro
225                 230                 235                 240

Gly Glu Tyr Gly Ser Glu Leu Asp Asp Leu Pro Val Gly Glu Glu Gly
                245                 250                 255

Tyr Ser Asn Pro Asn Pro Phe Cys Ala Asp Gly Pro Arg Gln Asp Glu
            260                 265                 270

Phe Leu Lys Glu Met Arg Arg Glu Val Phe Ala Gly Arg Glu Gly Phe
        275                 280                 285

Leu Thr Val Gly Glu Ala Pro Gly Ile Thr Pro Val Arg Asn Glu His
    290                 295                 300

Ile Thr Asn Pro Ala Asn Gly Glu Leu Asp Met Leu Phe Leu Phe Asp
305                 310                 315                 320

His Val Asp Phe Asp Cys Asp Gly Val Lys Trp Lys Pro Leu Pro Leu
                325                 330                 335

Asp Leu Pro Gly Phe Lys Arg Ile Met Ala Gly Tyr Gln Thr Ala Val
            340                 345                 350

Glu Asn Val Gly Trp Ala Ser Leu Phe Thr Gly Asn His Asp Gln Pro
        355                 360                 365

Arg Val Val Ser Arg Trp Gly Asp Asp Ser Ser Glu Glu Ser Arg Val
    370                 375                 380

Arg Ser Ala Lys Ala Leu Gly Leu Met Leu His Met His Arg Gly Thr
385                 390                 395                 400

Pro Tyr Val Tyr Gln Gly Glu Glu Leu Gly Met Thr Asn Ala His Phe
                405                 410                 415

Thr Ser Leu Asp Gln Tyr Arg Asp Leu Glu Ser Leu Asn Ala Tyr Arg
            420                 425                 430

Gln Arg Val Glu Glu Ala Lys Val Gln Ser Pro Glu Ser Met Leu Ala
        435                 440                 445

Gly Ile Ala Ala Arg Gly Arg Asp Asn Ser Arg Thr Pro Met Gln Trp
    450                 455                 460

Asp Gly Ser Ala Tyr Ala Gly Phe Thr Ala Pro Asp Ala Ala Thr Glu
465                 470                 475                 480

Pro Trp Ile Ser Val Asn Pro Asn His Ala Glu Ile Asn Ala Ala Gly
                485                 490                 495

Glu Phe Asp Asp Pro Asp Ser Val Tyr Ala Phe Tyr Lys Lys Leu Ile
            500                 505                 510

Ala Leu Arg His Asn Ser Ser Ile Val Ala Ala Gly Glu Trp Gln Leu

```
                515                 520                 525
Ile Asp Ala Asp Ala His Val Tyr Ala Phe Thr Arg Thr Leu Gly
        530                 535                 540

Asn Glu Arg Leu Leu Val Val Val Asn Leu Ser Gly Arg Thr Val Asp
545                 550                 555                 560

Leu Pro Arg Glu Ser Thr Glu Leu Ile Ala Gly Gly Val Thr Glu Pro
                565                 570                 575

Asp Ile Ile Leu Ser Thr Tyr Asp Ala Pro His Thr Val Ser Leu
        580                 585                 590

Ala Asn Arg Glu Leu Asp Pro Trp Glu Ala Ala Ala Val Gln Leu
        595                 600                 605

<210> SEQ ID NO 9
<211> LENGTH: 1920
<212> TYPE: DNA
<213> ORGANISM: artificial sequence
<220> FEATURE:
<223> OTHER INFORMATION: gene fusion tat-'agl2_cuo
<220> FEATURE:
<221> NAME/KEY: CDS
<222> LOCATION: (1)..(1917)
<223> OTHER INFORMATION: sequence coding for fusion polypeptide
      Tat-'Agl2
<220> FEATURE:
<221> NAME/KEY: misc_signal
<222> LOCATION: (1)..(99)
<223> OTHER INFORMATION: 5' sequence of cg0955 encoding Tat-signal
      peptide of Cg0955
<220> FEATURE:
<221> NAME/KEY: misc_feature
<222> LOCATION: (1)..(101)
<223> OTHER INFORMATION: 5' sequence of cg0955
<220> FEATURE:
<221> NAME/KEY: misc_feature
<222> LOCATION: (102)..(102)
<223> OTHER INFORMATION: nucleobase guanine
<220> FEATURE:
<221> NAME/KEY: misc_feature
<222> LOCATION: (103)..(108)
<223> OTHER INFORMATION: SpeI restriction site
<220> FEATURE:
<221> NAME/KEY: misc_feature
<222> LOCATION: (109)..(1917)
<223> OTHER INFORMATION: 'agl2_cuo
<220> FEATURE:
<221> NAME/KEY: misc_feature
<222> LOCATION: (1918)..(1920)
<223> OTHER INFORMATION: stop codon

<400> SEQUENCE: 9 atg caa ata aac cgc cga ggc ttc tta aaa gcc acc aca gga ctt gcc    48
Met Gln Ile Asn Arg Arg Gly Phe Leu Lys Ala Thr Thr Gly Leu Ala
1               5                   10                  15 act atc ggc gct gcc agc atg ttt atg cca aag gcc aac gcc ctt gga    96
Thr Ile Gly Ala Ala Ser Met Phe Met Pro Lys Ala Asn Ala Leu Gly
            20                  25                  30 gca atg act agt acc tcc ttc aac cgc gaa cca ctg cca gat gca gtg   144
Ala Met Thr Ser Thr Ser Phe Asn Arg Glu Pro Leu Pro Asp Ala Val
        35                  40                  45 cgc acc aac ggt gca acc cca aac cca tgg tgg tcc aac gca gtg gtg   192
Arg Thr Asn Gly Ala Thr Pro Asn Pro Trp Trp Ser Asn Ala Val Val
    50                  55                  60 tac cag atc tac cca cgc tcc ttc cag gat acc aac ggc gac ggc ctg   240
Tyr Gln Ile Tyr Pro Arg Ser Phe Gln Asp Thr Asn Gly Asp Gly Leu
65                  70                  75                  80 ggc gat ctg aag ggc atc acc tcc cgc ttg gat tac ctg gca gat ctg   288
Gly Asp Leu Lys Gly Ile Thr Ser Arg Leu Asp Tyr Leu Ala Asp Leu
```

-continued

|  |  | 85 |  |  | 90 |  |  | 95 |  |  |
|---|---|---|---|---|---|---|---|---|---|---|

```
ggc gtg gat gtg ctg tgg ctg tcc cca gtg tac cgc tcc cca cag gat      336
Gly Val Asp Val Leu Trp Leu Ser Pro Val Tyr Arg Ser Pro Gln Asp
            100                 105                 110 gat aac ggc tac gat atc tcc gat tac cgc gat atc gat cca ctg ttc      384
Asp Asn Gly Tyr Asp Ile Ser Asp Tyr Arg Asp Ile Asp Pro Leu Phe
                115                 120                 125 ggc acc ctg gat gat atg gat gaa ctg ctg gca gag gca cac aag cgt      432
Gly Thr Leu Asp Asp Met Asp Glu Leu Leu Ala Glu Ala His Lys Arg
    130                 135                 140 ggc ctg aag atc gtg atg gat ctg gtg gtg aac cac acc tcc gat gaa      480
Gly Leu Lys Ile Val Met Asp Leu Val Val Asn His Thr Ser Asp Glu
145                 150                 155                 160 cac gca tgg ttc gaa gca tcc aag gat aag gat gat cca cac gca gat      528
His Ala Trp Phe Glu Ala Ser Lys Asp Lys Asp Asp Pro His Ala Asp
                165                 170                 175 tgg tac tgg tgg cgt cca gca cgc cca ggc cac gaa cca ggc acc cca      576
Trp Tyr Trp Trp Arg Pro Ala Arg Pro Gly His Glu Pro Gly Thr Pro
            180                 185                 190 ggc gca gaa cca aac cag tgg ggc tcc tac ttc ggt ggc tcc gca tgg      624
Gly Ala Glu Pro Asn Gln Trp Gly Ser Tyr Phe Gly Gly Ser Ala Trp
        195                 200                 205 gaa tac tcc cca gaa cgc ggt gaa tac tac ctg cac cag ttc tcc aag      672
Glu Tyr Ser Pro Glu Arg Gly Glu Tyr Tyr Leu His Gln Phe Ser Lys
    210                 215                 220 aag cag cca gat ctc aac tgg gaa aac cca gca gtg cgt cgc gca gtg      720
Lys Gln Pro Asp Leu Asn Trp Glu Asn Pro Ala Val Arg Arg Ala Val
225                 230                 235                 240 tac gat atg atg aac tgg tgg ttg gat cgc ggt atc gat ggc ttc cgc      768
Tyr Asp Met Met Asn Trp Trp Leu Asp Arg Gly Ile Asp Gly Phe Arg
                245                 250                 255 atg gat gtg atc acc ctg atc tcc aag cgc acc gat cca aac ggt cgc      816
Met Asp Val Ile Thr Leu Ile Ser Lys Arg Thr Asp Pro Asn Gly Arg
            260                 265                 270 ctg cca ggt gaa acc ggc tcc gaa ctc cag gat ctg cca gtg ggc gaa      864
Leu Pro Gly Glu Thr Gly Ser Glu Leu Gln Asp Leu Pro Val Gly Glu
        275                 280                 285 gaa ggc tac tcc tcc cca aac cct ttc tgc gca gat ggc cct cgc cag      912
Glu Gly Tyr Ser Ser Pro Asn Pro Phe Cys Ala Asp Gly Pro Arg Gln
    290                 295                 300 gat gaa ttc ctg gca gaa atg cgt cgc gaa gtt ttc gat ggc cgt gat      960
Asp Glu Phe Leu Ala Glu Met Arg Arg Glu Val Phe Asp Gly Arg Asp
305                 310                 315                 320 ggc ttc ctg acc gtg ggc gaa gca cca ggc atc acc gca gaa cgc aac     1008
Gly Phe Leu Thr Val Gly Glu Ala Pro Gly Ile Thr Ala Glu Arg Asn
                325                 330                 335 gaa cac atc acc gat cca gca aac ggc gaa ctg gat atg ctg ttc ctg     1056
Glu His Ile Thr Asp Pro Ala Asn Gly Glu Leu Asp Met Leu Phe Leu
            340                 345                 350 ttc gaa cac atg ggc gtg gat cag acc cca gaa tcc aag tgg gat gat     1104
Phe Glu His Met Gly Val Asp Gln Thr Pro Glu Ser Lys Trp Asp Asp
        355                 360                 365 aag cca tgg acc cca gca gat ctg gaa acc aag ctg gca gaa cag cag     1152
Lys Pro Trp Thr Pro Ala Asp Leu Glu Thr Lys Leu Ala Glu Gln Gln
    370                 375                 380 gat gca atc gca cgc cgt ggc tgg gcc tcc ctg ttc ctg gat aac cac     1200
Asp Ala Ile Ala Arg Arg Gly Trp Ala Ser Leu Phe Leu Asp Asn His
385                 390                 395                 400 gat cag cca cgc gtg gtg tcc cgc tgg ggt gat gat acc tcc aag acc     1248
```

```
Asp Gln Pro Arg Val Val Ser Arg Trp Gly Asp Thr Ser Lys Thr
                405                 410                 415 ggt cgc atc cgc tcc gca aag gca ctg gca ctg ctg ctg cac atg cac      1296
Gly Arg Ile Arg Ser Ala Lys Ala Leu Ala Leu Leu Leu His Met His
        420                 425                 430 cgt ggc acc cca tac gtg tac cag ggc gaa gaa ctg ggc atg acc aac      1344
Arg Gly Thr Pro Tyr Val Tyr Gln Gly Glu Glu Leu Gly Met Thr Asn
    435                 440                 445 gca cac ttc acc tcc ctg gat cag tac cgc gat ctg gaa tcc atc aac      1392
Ala His Phe Thr Ser Leu Asp Gln Tyr Arg Asp Leu Glu Ser Ile Asn
450                 455                 460 gca tac cac caa cgc gtg gaa gaa acc ggc atc cgc acc tcc gaa acc      1440
Ala Tyr His Gln Arg Val Glu Glu Thr Gly Ile Arg Thr Ser Glu Thr
465                 470                 475                 480 atg atg cgc tcc ctg gca cgc tac ggt cgc gat aac gca cgc acc cca      1488
Met Met Arg Ser Leu Ala Arg Tyr Gly Arg Asp Asn Ala Arg Thr Pro
                485                 490                 495 atg cag tgg gat gat tcc acc tac gca ggc ttc acc atg cca gat gcc      1536
Met Gln Trp Asp Asp Ser Thr Tyr Ala Gly Phe Thr Met Pro Asp Ala
            500                 505                 510 cca gtg gaa cca tgg atc gca gtg aac cca aac cac acc gaa atc aac      1584
Pro Val Glu Pro Trp Ile Ala Val Asn Pro Asn His Thr Glu Ile Asn
        515                 520                 525 gca gca gat gaa acc gat gat cca gat tcc gtg tac tcc ttc cac aag      1632
Ala Ala Asp Glu Thr Asp Asp Pro Asp Ser Val Tyr Ser Phe His Lys
    530                 535                 540 cgc ctg atc gca ctg cgc cac acc gat cca gtg gtg gca gca ggc gat      1680
Arg Leu Ile Ala Leu Arg His Thr Asp Pro Val Val Ala Ala Gly Asp
545                 550                 555                 560 tac cgt cgc gtg gaa acc ggc aac gat cgc atc att gca ttc acc cgc      1728
Tyr Arg Arg Val Glu Thr Gly Asn Asp Arg Ile Ile Ala Phe Thr Arg
                565                 570                 575 acc ctg gac gaa cgc acc atc ctg acc gtg atc aac ctg tcc cca acc      1776
Thr Leu Asp Glu Arg Thr Ile Leu Thr Val Ile Asn Leu Ser Pro Thr
            580                 585                 590 cag gca gca cca gca ggc gaa ctg gaa acc atg cca gac ggc acc atc      1824
Gln Ala Ala Pro Ala Gly Glu Leu Glu Thr Met Pro Asp Gly Thr Ile
        595                 600                 605 ttg atc gca aac acc gat gac cca gtg ggc aac ctc aag acc acc ggc      1872
Leu Ile Ala Asn Thr Asp Asp Pro Val Gly Asn Leu Lys Thr Thr Gly
    610                 615                 620 acc ctg ggt cca tgg gaa gca ttc gca atg gaa acc gat cca gaa taa      1920
Thr Leu Gly Pro Trp Glu Ala Phe Ala Met Glu Thr Asp Pro Glu
625                 630                 635

<210> SEQ ID NO 10
<211> LENGTH: 639
<212> TYPE: PRT
<213> ORGANISM: artificial sequence
<220> FEATURE:
<223> OTHER INFORMATION: Synthetic Construct

<400> SEQUENCE: 10

Met Gln Ile Asn Arg Arg Gly Phe Leu Lys Ala Thr Thr Gly Leu Ala
1               5                   10                  15

Thr Ile Gly Ala Ala Ser Met Phe Met Pro Lys Ala Asn Ala Leu Gly
            20                  25                  30

Ala Met Thr Ser Thr Ser Phe Asn Arg Glu Pro Leu Pro Asp Ala Val
        35                  40                  45

Arg Thr Asn Gly Ala Thr Pro Asn Pro Trp Trp Ser Asn Ala Val Val
```

```
            50                  55                  60
Tyr Gln Ile Tyr Pro Arg Ser Phe Gln Asp Thr Asn Gly Asp Gly Leu
 65                  70                  75                  80

Gly Asp Leu Lys Gly Ile Thr Ser Arg Leu Asp Tyr Leu Ala Asp Leu
                 85                  90                  95

Gly Val Asp Val Leu Trp Leu Ser Pro Val Tyr Arg Ser Pro Gln Asp
            100                 105                 110

Asp Asn Gly Tyr Asp Ile Ser Asp Tyr Arg Asp Ile Asp Pro Leu Phe
            115                 120                 125

Gly Thr Leu Asp Asp Met Asp Glu Leu Leu Ala Glu Ala His Lys Arg
            130                 135                 140

Gly Leu Lys Ile Val Met Asp Leu Val Val Asn His Thr Ser Asp Glu
145                 150                 155                 160

His Ala Trp Phe Glu Ala Ser Lys Asp Lys Asp Pro His Ala Asp
                165                 170                 175

Trp Tyr Trp Trp Arg Pro Ala Arg Pro Gly His Glu Pro Gly Thr Pro
                180                 185                 190

Gly Ala Glu Pro Asn Gln Trp Gly Ser Tyr Phe Gly Gly Ser Ala Trp
            195                 200                 205

Glu Tyr Ser Pro Glu Arg Gly Glu Tyr Tyr Leu His Gln Phe Ser Lys
210                 215                 220

Lys Gln Pro Asp Leu Asn Trp Glu Asn Pro Ala Val Arg Arg Ala Val
225                 230                 235                 240

Tyr Asp Met Met Asn Trp Trp Leu Asp Arg Gly Ile Asp Gly Phe Arg
                245                 250                 255

Met Asp Val Ile Thr Leu Ile Ser Lys Arg Thr Asp Pro Asn Gly Arg
                260                 265                 270

Leu Pro Gly Glu Thr Gly Ser Glu Leu Gln Asp Leu Pro Val Gly Glu
            275                 280                 285

Glu Gly Tyr Ser Ser Pro Asn Pro Phe Cys Ala Asp Gly Pro Arg Gln
            290                 295                 300

Asp Glu Phe Leu Ala Glu Met Arg Arg Glu Val Phe Asp Gly Arg Asp
305                 310                 315                 320

Gly Phe Leu Thr Val Gly Glu Ala Pro Gly Ile Thr Ala Glu Arg Asn
                325                 330                 335

Glu His Ile Thr Asp Pro Ala Asn Gly Glu Leu Asp Met Leu Phe Leu
                340                 345                 350

Phe Glu His Met Gly Val Asp Gln Thr Pro Glu Ser Lys Trp Asp Asp
                355                 360                 365

Lys Pro Trp Thr Pro Ala Asp Leu Glu Thr Lys Leu Ala Glu Gln Gln
            370                 375                 380

Asp Ala Ile Ala Arg Arg Gly Trp Ala Ser Leu Phe Leu Asp Asn His
385                 390                 395                 400

Asp Gln Pro Arg Val Val Ser Arg Trp Gly Asp Asp Thr Ser Lys Thr
                405                 410                 415

Gly Arg Ile Arg Ser Ala Lys Ala Leu Ala Leu Leu His Met His
                420                 425                 430

Arg Gly Thr Pro Tyr Val Tyr Gln Gly Glu Glu Leu Gly Met Thr Asn
            435                 440                 445

Ala His Phe Thr Ser Leu Asp Gln Tyr Arg Asp Leu Glu Ser Ile Asn
            450                 455                 460

Ala Tyr His Gln Arg Val Glu Glu Thr Gly Ile Arg Thr Ser Glu Thr
465                 470                 475                 480
```

```
Met Met Arg Ser Leu Ala Arg Tyr Gly Arg Asp Asn Ala Arg Thr Pro
            485                 490                 495

Met Gln Trp Asp Asp Ser Thr Tyr Ala Gly Phe Thr Met Pro Asp Ala
        500                 505                 510

Pro Val Glu Pro Trp Ile Ala Val Asn Pro Asn His Thr Glu Ile Asn
        515                 520                 525

Ala Ala Asp Glu Thr Asp Asp Pro Asp Ser Val Tyr Ser Phe His Lys
        530                 535                 540

Arg Leu Ile Ala Leu Arg His Thr Asp Pro Val Val Ala Ala Gly Asp
545                 550                 555                 560

Tyr Arg Arg Val Glu Thr Gly Asn Asp Arg Ile Ile Ala Phe Thr Arg
                565                 570                 575

Thr Leu Asp Glu Arg Thr Ile Leu Thr Val Ile Asn Leu Ser Pro Thr
        580                 585                 590

Gln Ala Ala Pro Ala Gly Glu Leu Glu Thr Met Pro Asp Gly Thr Ile
        595                 600                 605

Leu Ile Ala Asn Thr Asp Asp Pro Val Gly Asn Leu Lys Thr Thr Gly
        610                 615                 620

Thr Leu Gly Pro Trp Glu Ala Phe Ala Met Glu Thr Asp Pro Glu
625                 630                 635

<210> SEQ ID NO 11
<211> LENGTH: 1932
<212> TYPE: DNA
<213> ORGANISM: artificial sequence
<220> FEATURE:
<223> OTHER INFORMATION: gene fusion tat-agl1_cuo
<220> FEATURE:
<221> NAME/KEY: CDS
<222> LOCATION: (1)..(1929)
<223> OTHER INFORMATION: sequence coding for fusion polypeptide Tat-Agl1
<220> FEATURE:
<221> NAME/KEY: misc_signal
<222> LOCATION: (1)..(99)
<223> OTHER INFORMATION: 5' sequence of cg0955 encoding Tat-signal
      peptide of Cg0955
<220> FEATURE:
<221> NAME/KEY: misc_feature
<222> LOCATION: (1)..(101)
<223> OTHER INFORMATION: 5' sequence of cg0955
<220> FEATURE:
<221> NAME/KEY: misc_feature
<222> LOCATION: (102)..(102)
<223> OTHER INFORMATION: nucleobase adenine
<220> FEATURE:
<221> NAME/KEY: misc_feature
<222> LOCATION: (102)..(107)
<223> OTHER INFORMATION: SpeI restriction site
<220> FEATURE:
<221> NAME/KEY: misc_feature
<222> LOCATION: (108)..(108)
<223> OTHER INFORMATION: nucleobase adenine
<220> FEATURE:
<221> NAME/KEY: misc_feature
<222> LOCATION: (109)..(1929)
<223> OTHER INFORMATION: agl1_cuo
<220> FEATURE:
<221> NAME/KEY: misc_feature
<222> LOCATION: (1930)..(1932)
<223> OTHER INFORMATION: stop codon

<400> SEQUENCE: 11 atg caa ata aac cgc cga ggc ttc tta aaa gcc acc aca gga ctt gcc        48
Met Gln Ile Asn Arg Arg Gly Phe Leu Lys Ala Thr Thr Gly Leu Ala
1               5                   10                  15 act atc ggc gct gcc agc atg ttt atg cca aag gcc aac gcc ctt gga        96
```

```
                Thr Ile Gly Ala Ala Ser Met Phe Met Pro Lys Ala Asn Ala Leu Gly
                             20                  25                  30 gca ata cta gta atg atg acc acc ttc aac cgt gca atc atc cca gat       144
Ala Ile Leu Val Met Met Thr Thr Phe Asn Arg Ala Ile Ile Pro Asp
             35                  40                  45 gca atc cgc acc aac ggt gca acc cca aac cca tgg tgg tcc aac gca       192
Ala Ile Arg Thr Asn Gly Ala Thr Pro Asn Pro Trp Trp Ser Asn Ala
 50                  55                  60 gtg gtg tac cag atc tac cca cgc tcc ttc cag gat acc aac ggc gac       240
Val Val Tyr Gln Ile Tyr Pro Arg Ser Phe Gln Asp Thr Asn Gly Asp
 65                  70                  75                  80 ggc ttc ggc gat ctg aag ggc atc acc tcc cgc ttg gat tac ctg gca       288
Gly Phe Gly Asp Leu Lys Gly Ile Thr Ser Arg Leu Asp Tyr Leu Ala
                 85                  90                  95 gat ctg ggc gtg gat gtg ctg tgg ctg tcc cca gtg tac aag tcc cca       336
Asp Leu Gly Val Asp Val Leu Trp Leu Ser Pro Val Tyr Lys Ser Pro
            100                 105                 110 cag gat gat aac ggc tac gat atc tcc gat tac cag gat atc gat cca       384
Gln Asp Asp Asn Gly Tyr Asp Ile Ser Asp Tyr Gln Asp Ile Asp Pro
            115                 120                 125 ctg ttc ggc acc ctg gat gat atg gat gaa ctg ctg gca gag gca cac       432
Leu Phe Gly Thr Leu Asp Asp Met Asp Glu Leu Leu Ala Glu Ala His
        130                 135                 140 aag cgt ggc ctg aag gtg gtg atg gat ctg gtg gtg aac cac acc tcc       480
Lys Arg Gly Leu Lys Val Val Met Asp Leu Val Val Asn His Thr Ser
145                 150                 155                 160 gat gaa cac gca tgg ttc gaa gca tcc aag aac aag gat gat gaa cac       528
Asp Glu His Ala Trp Phe Glu Ala Ser Lys Asn Lys Asp Asp Glu His
                165                 170                 175 gcc gat tgg tac tgg tgg cgt cca gca cgc cca ggc acc acc cca ggt       576
Ala Asp Trp Tyr Trp Trp Arg Pro Ala Arg Pro Gly Thr Thr Pro Gly
            180                 185                 190 gaa cca ggc tcc gaa cca aac cag tgg ggc tcc tac ttc ggt ggc tcc       624
Glu Pro Gly Ser Glu Pro Asn Gln Trp Gly Ser Tyr Phe Gly Gly Ser
        195                 200                 205 gca tgg gaa tac tgc cca gaa cgc ggt gaa tac tac ctg cac cag ttc       672
Ala Trp Glu Tyr Cys Pro Glu Arg Gly Glu Tyr Tyr Leu His Gln Phe
    210                 215                 220 tcc aag aag cag cca gat ctc aac tgg gaa aac cca gca gtg cgt cgc       720
Ser Lys Lys Gln Pro Asp Leu Asn Trp Glu Asn Pro Ala Val Arg Arg
225                 230                 235                 240 gca gtg tac gat atg atg aac tgg tgg ttg gat cgc ggt atc gat ggc       768
Ala Val Tyr Asp Met Met Asn Trp Trp Leu Asp Arg Gly Ile Asp Gly
                245                 250                 255 ttc cgc atg gat gtg atc acc ctg atc tcc aag cgc acc gat gca aac       816
Phe Arg Met Asp Val Ile Thr Leu Ile Ser Lys Arg Thr Asp Ala Asn
            260                 265                 270 ggt cgc ctg cca ggt gaa tac ggc tcc gaa ctg gat gat ctg cca gtg       864
Gly Arg Leu Pro Gly Glu Tyr Gly Ser Glu Leu Asp Asp Leu Pro Val
        275                 280                 285 ggc gaa gaa ggc tac tcc aac cca aac ccg ttc tgc gca gat ggc cct       912
Gly Glu Glu Gly Tyr Ser Asn Pro Asn Pro Phe Cys Ala Asp Gly Pro
    290                 295                 300 cgc cag gat gaa ttc ctg aaa gaa atg cgt cgc gaa gtg ttc gca ggt       960
Arg Gln Asp Glu Phe Leu Lys Glu Met Arg Arg Glu Val Phe Ala Gly
305                 310                 315                 320 cgc gaa ggc ttc ctg acc gtg ggc gaa gca cca ggc atc acc cct gtg      1008
Arg Glu Gly Phe Leu Thr Val Gly Glu Ala Pro Gly Ile Thr Pro Val
                325                 330                 335
```

```
cgc aac gaa cac atc acc aac cca gca aac ggc gaa ctg gat atg ctg   1056
Arg Asn Glu His Ile Thr Asn Pro Ala Asn Gly Glu Leu Asp Met Leu
            340                 345                 350 ttc ctg ttc gat cac gtg gat ttc gat tgc gac ggc gtg aag tgg aag   1104
Phe Leu Phe Asp His Val Asp Phe Asp Cys Asp Gly Val Lys Trp Lys
        355                 360                 365 cca ctg cca ctg gat ctg cca ggc ttc aag cgc atc atg gca ggc tac   1152
Pro Leu Pro Leu Asp Leu Pro Gly Phe Lys Arg Ile Met Ala Gly Tyr
    370                 375                 380 cag acc gca gtg gaa aac gtg ggc tgg gca tcc ctg ttc acc ggc aac   1200
Gln Thr Ala Val Glu Asn Val Gly Trp Ala Ser Leu Phe Thr Gly Asn
385                 390                 395                 400 cac gat cag cca cgc gtg gtg tcc cgc tgg ggt gat gat tcc tcc gaa   1248
His Asp Gln Pro Arg Val Val Ser Arg Trp Gly Asp Asp Ser Ser Glu
                405                 410                 415 gaa tcc cgt gtg cgc tcc gca aag gca ctg ggc ctg atg ctg cac atg   1296
Glu Ser Arg Val Arg Ser Ala Lys Ala Leu Gly Leu Met Leu His Met
            420                 425                 430 cac cgt ggc acc cca tac gtg tac cag ggc gaa gaa ctg ggc atg acc   1344
His Arg Gly Thr Pro Tyr Val Tyr Gln Gly Glu Glu Leu Gly Met Thr
        435                 440                 445 aac gca cac ttc acc tcc ctg gat cag tac cgc gat ctg gaa tcc ctg   1392
Asn Ala His Phe Thr Ser Leu Asp Gln Tyr Arg Asp Leu Glu Ser Leu
    450                 455                 460 aac gca tac cgc cag cgc gtg gaa gag gca aag gtg cag tcc cca gaa   1440
Asn Ala Tyr Arg Gln Arg Val Glu Glu Ala Lys Val Gln Ser Pro Glu
465                 470                 475                 480 tcc atg ctg gca ggt atc gca gca cgc ggt cgc gat aac tcc cgc acc   1488
Ser Met Leu Ala Gly Ile Ala Ala Arg Gly Arg Asp Asn Ser Arg Thr
                485                 490                 495 cca atg cag tgg gat ggc tcc gca tac gca ggc ttc acc gca cca gat   1536
Pro Met Gln Trp Asp Gly Ser Ala Tyr Ala Gly Phe Thr Ala Pro Asp
            500                 505                 510 gca gca acc gaa cca tgg atc tcc gtg aac cca aac cac gca gaa atc   1584
Ala Ala Thr Glu Pro Trp Ile Ser Val Asn Pro Asn His Ala Glu Ile
        515                 520                 525 aac gca gca ggc gaa ttc gat gat cca gat tcc gtg tac gca ttc tac   1632
Asn Ala Ala Gly Glu Phe Asp Asp Pro Asp Ser Val Tyr Ala Phe Tyr
    530                 535                 540 aag aag ctg atc gca ctg cgc cac aac tcc tcc atc gtg gca gct ggc   1680
Lys Lys Leu Ile Ala Leu Arg His Asn Ser Ser Ile Val Ala Ala Gly
545                 550                 555                 560 gaa tgg cag ctg atc gat gca gat gat gca cac gtg tac gcc ttc acc   1728
Glu Trp Gln Leu Ile Asp Ala Asp Asp Ala His Val Tyr Ala Phe Thr
                565                 570                 575 cgc acc ctg ggc aac gaa cgc ctg ctc gtg gtg gtc aac ctg tcc ggt   1776
Arg Thr Leu Gly Asn Glu Arg Leu Leu Val Val Val Asn Leu Ser Gly
            580                 585                 590 cgc acc gtg gat ctg cca cgc gaa tcc acc gaa ctg atc gca ggc ggt   1824
Arg Thr Val Asp Leu Pro Arg Glu Ser Thr Glu Leu Ile Ala Gly Gly
        595                 600                 605 gtg acc gaa cca gat atc atc ctg tcc acc tac gat gca cca cac acc   1872
Val Thr Glu Pro Asp Ile Ile Leu Ser Thr Tyr Asp Ala Pro His Thr
    610                 615                 620 gtg gtg tcc ctg gca aac cgc gaa ctc gat cca tgg gaa gca gca gca   1920
Val Val Ser Leu Ala Asn Arg Glu Leu Asp Pro Trp Glu Ala Ala Ala
625                 630                 635                 640 gtg cag ctg taa                                                   1932
Val Gln Leu
```

```
<210> SEQ ID NO 12
<211> LENGTH: 643
<212> TYPE: PRT
<213> ORGANISM: artificial sequence
<220> FEATURE:
<223> OTHER INFORMATION: Synthetic Construct

<400> SEQUENCE: 12
```

| | | | | | | | | | | | | | | |
|---|---|---|---|---|---|---|---|---|---|---|---|---|---|---|
| Met | Gln | Ile | Asn | Arg | Arg | Gly | Phe | Leu | Lys | Ala | Thr | Thr | Gly | Leu | Ala |
| 1 | | | | 5 | | | | | 10 | | | | | 15 | |
| Thr | Ile | Gly | Ala | Ala | Ser | Met | Phe | Met | Pro | Lys | Ala | Asn | Ala | Leu | Gly |
| | | | 20 | | | | | 25 | | | | | 30 | | |
| Ala | Ile | Leu | Val | Met | Met | Thr | Thr | Phe | Asn | Arg | Ala | Ile | Ile | Pro | Asp |
| | | 35 | | | | | 40 | | | | | 45 | | | |
| Ala | Ile | Arg | Thr | Asn | Gly | Ala | Thr | Pro | Asn | Pro | Trp | Trp | Ser | Asn | Ala |
| | 50 | | | | | 55 | | | | | 60 | | | | |
| Val | Val | Tyr | Gln | Ile | Tyr | Pro | Arg | Ser | Phe | Gln | Asp | Thr | Asn | Gly | Asp |
| 65 | | | | | 70 | | | | | 75 | | | | | 80 |
| Gly | Phe | Gly | Asp | Leu | Lys | Gly | Ile | Thr | Ser | Arg | Leu | Asp | Tyr | Leu | Ala |
| | | | | 85 | | | | | 90 | | | | | 95 | |
| Asp | Leu | Gly | Val | Asp | Val | Leu | Trp | Leu | Ser | Pro | Val | Tyr | Lys | Ser | Pro |
| | | | 100 | | | | | 105 | | | | | 110 | | |
| Gln | Asp | Asp | Asn | Gly | Tyr | Asp | Ile | Ser | Asp | Tyr | Gln | Asp | Ile | Asp | Pro |
| | | 115 | | | | | 120 | | | | | 125 | | | |
| Leu | Phe | Gly | Thr | Leu | Asp | Asp | Met | Asp | Glu | Leu | Leu | Ala | Glu | Ala | His |
| | 130 | | | | | 135 | | | | | 140 | | | | |
| Lys | Arg | Gly | Leu | Lys | Val | Val | Met | Asp | Leu | Val | Val | Asn | His | Thr | Ser |
| 145 | | | | | 150 | | | | | 155 | | | | | 160 |
| Asp | Glu | His | Ala | Trp | Phe | Glu | Ala | Ser | Lys | Asn | Lys | Asp | Asp | Glu | His |
| | | | | 165 | | | | | 170 | | | | | 175 | |
| Ala | Asp | Trp | Tyr | Trp | Trp | Arg | Pro | Ala | Arg | Pro | Gly | Thr | Thr | Pro | Gly |
| | | | 180 | | | | | 185 | | | | | 190 | | |
| Glu | Pro | Gly | Ser | Glu | Pro | Asn | Gln | Trp | Gly | Ser | Tyr | Phe | Gly | Gly | Ser |
| | | 195 | | | | | 200 | | | | | 205 | | | |
| Ala | Trp | Glu | Tyr | Cys | Pro | Glu | Arg | Gly | Glu | Tyr | Tyr | Leu | His | Gln | Phe |
| | 210 | | | | | 215 | | | | | 220 | | | | |
| Ser | Lys | Lys | Gln | Pro | Asp | Leu | Asn | Trp | Glu | Asn | Pro | Ala | Val | Arg | Arg |
| 225 | | | | | 230 | | | | | 235 | | | | | 240 |
| Ala | Val | Tyr | Asp | Met | Met | Asn | Trp | Trp | Leu | Asp | Arg | Gly | Ile | Asp | Gly |
| | | | | 245 | | | | | 250 | | | | | 255 | |
| Phe | Arg | Met | Asp | Val | Ile | Thr | Leu | Ile | Ser | Lys | Arg | Thr | Asp | Ala | Asn |
| | | | 260 | | | | | 265 | | | | | 270 | | |
| Gly | Arg | Leu | Pro | Gly | Glu | Tyr | Gly | Ser | Glu | Leu | Asp | Asp | Leu | Pro | Val |
| | | 275 | | | | | 280 | | | | | 285 | | | |
| Gly | Glu | Glu | Gly | Tyr | Ser | Asn | Pro | Asn | Pro | Phe | Cys | Ala | Asp | Gly | Pro |
| | 290 | | | | | 295 | | | | | 300 | | | | |
| Arg | Gln | Asp | Glu | Phe | Leu | Lys | Glu | Met | Arg | Arg | Glu | Val | Phe | Ala | Gly |
| 305 | | | | | 310 | | | | | 315 | | | | | 320 |
| Arg | Glu | Gly | Phe | Leu | Thr | Val | Gly | Glu | Ala | Pro | Gly | Ile | Thr | Pro | Val |
| | | | | 325 | | | | | 330 | | | | | 335 | |
| Arg | Asn | Glu | His | Ile | Thr | Asn | Pro | Ala | Asn | Gly | Glu | Leu | Asp | Met | Leu |
| | | | 340 | | | | | 345 | | | | | 350 | | |
| Phe | Leu | Phe | Asp | His | Val | Asp | Phe | Asp | Cys | Asp | Gly | Val | Lys | Trp | Lys |
| | | 355 | | | | | 360 | | | | | 365 | | | |

Pro Leu Pro Leu Asp Leu Pro Gly Phe Lys Arg Ile Met Ala Gly Tyr
370                 375                 380

Gln Thr Ala Val Glu Asn Val Gly Trp Ala Ser Leu Phe Thr Gly Asn
385                 390                 395                 400

His Asp Gln Pro Arg Val Val Ser Arg Trp Gly Asp Ser Ser Glu
            405                 410                 415

Glu Ser Arg Val Arg Ser Ala Lys Ala Leu Gly Leu Met Leu His Met
            420                 425                 430

His Arg Gly Thr Pro Tyr Val Tyr Gln Gly Glu Leu Gly Met Thr
            435                 440                 445

Asn Ala His Phe Thr Ser Leu Asp Gln Tyr Arg Asp Leu Glu Ser Leu
450                 455                 460

Asn Ala Tyr Arg Gln Arg Val Glu Glu Ala Lys Val Gln Ser Pro Glu
465                 470                 475                 480

Ser Met Leu Ala Gly Ile Ala Ala Arg Gly Arg Asp Asn Ser Arg Thr
            485                 490                 495

Pro Met Gln Trp Asp Gly Ser Ala Tyr Ala Gly Phe Thr Ala Pro Asp
            500                 505                 510

Ala Ala Thr Glu Pro Trp Ile Ser Val Asn Pro Asn His Ala Glu Ile
            515                 520                 525

Asn Ala Ala Gly Glu Phe Asp Asp Pro Asp Ser Val Tyr Ala Phe Tyr
530                 535                 540

Lys Lys Leu Ile Ala Leu Arg His Asn Ser Ser Ile Val Ala Ala Gly
545                 550                 555                 560

Glu Trp Gln Leu Ile Asp Ala Asp Ala His Val Tyr Ala Phe Thr
            565                 570                 575

Arg Thr Leu Gly Asn Glu Arg Leu Leu Val Val Asn Leu Ser Gly
            580                 585                 590

Arg Thr Val Asp Leu Pro Arg Glu Ser Thr Glu Leu Ile Ala Gly Gly
            595                 600                 605

Val Thr Glu Pro Asp Ile Ile Leu Ser Thr Tyr Asp Ala Pro His Thr
            610                 615                 620

Val Val Ser Leu Ala Asn Arg Glu Leu Asp Pro Trp Glu Ala Ala Ala
625                 630                 635                 640

Val Gln Leu

<210> SEQ ID NO 13
<211> LENGTH: 38
<212> TYPE: DNA
<213> ORGANISM: Corynebacterium glutamicum
<220> FEATURE:
<221> NAME/KEY: terminator
<222> LOCATION: (1)..(38)
<223> OTHER INFORMATION: transcriptional terminator of the gap gene
      (B. J. Eikmanns 1992, Fig.3)
<220> FEATURE:
<221> NAME/KEY: misc_feature
<222> LOCATION: (3)..(38)
<223> OTHER INFORMATION: terminator sequence Tgap*

<400> SEQUENCE: 13
aatagcccgg ggtgtgcctc ggcgcacccc gggctatt                           38

<210> SEQ ID NO 14
<211> LENGTH: 85
<212> TYPE: DNA
<213> ORGANISM: artificial sequence
<220> FEATURE:
<223> OTHER INFORMATION: promoter

```
<220> FEATURE:
<221> NAME/KEY: promoter
<222> LOCATION: (1)..(85)
<223> OTHER INFORMATION: sequence labeled PtacI by De Boer et al (1983)
<220> FEATURE:
<221> NAME/KEY: promoter
<222> LOCATION: (1)..(75)
<223> OTHER INFORMATION: promoter PtacI

<400> SEQUENCE: 14
gagctgttga caattaatca tcggctcgta taatgtgtgg aattgtgagc ggataacaat      60
ttcacacagg aaacagaatt ctatg                                           85

<210> SEQ ID NO 15
<211> LENGTH: 60
<212> TYPE: DNA
<213> ORGANISM: Corynebacterium glutamicum
<220> FEATURE:
<221> NAME/KEY: promoter
<222> LOCATION: (1)..(60)
<223> OTHER INFORMATION: promoter PdapBN1

<400> SEQUENCE: 15
taggtatgga tatcagcacc ttctgaacgg gtacgggtat aatggtgggc gtttgaaaaa      60

<210> SEQ ID NO 16
<211> LENGTH: 2096
<212> TYPE: DNA
<213> ORGANISM: artificial sequence
<220> FEATURE:
<223> OTHER INFORMATION: gene fusion tat-'agl2_cuo including promotor
      and terminator
<220> FEATURE:
<221> NAME/KEY: misc_feature
<222> LOCATION: (1)..(121)
<223> OTHER INFORMATION: upstream sequence
<220> FEATURE:
<221> NAME/KEY: promoter
<222> LOCATION: (32)..(91)
<223> OTHER INFORMATION: promoter PdapBN1
<220> FEATURE:
<221> NAME/KEY: CDS
<222> LOCATION: (122)..(2038)
<223> OTHER INFORMATION: sequence coding for fusion polypeptide
      Tat-'Agl2
<220> FEATURE:
<221> NAME/KEY: misc_feature
<222> LOCATION: (2039)..(2041)
<223> OTHER INFORMATION: stop codon
<220> FEATURE:
<221> NAME/KEY: misc_feature
<222> LOCATION: (2053)..(2088)
<223> OTHER INFORMATION: terminator sequence Tgap*
```

<400> SEQUENCE: 16

```
atcgttaaca acacagacca aaacggtcag ttaggtatgg atatcagcac cttctgaacg      60
ggtacgggta atggtgggg cgtttgaaaa actcttcgcc ccacgaaaat gaaggagcat      120 a atg caa ata aac cgc cga ggc ttc tta aaa gcc acc aca gga ctt gcc    169
  Met Gln Ile Asn Arg Arg Gly Phe Leu Lys Ala Thr Thr Gly Leu Ala
  1               5                  10                  15 act atc ggc gct gcc agc atg ttt atg cca aag gcc aac gcc ctt gga      217
Thr Ile Gly Ala Ala Ser Met Phe Met Pro Lys Ala Asn Ala Leu Gly
             20                  25                  30 gca atg act agt acc tcc ttc aac cgc gaa cca ctg cca gat gca gtg      265
Ala Met Thr Ser Thr Ser Phe Asn Arg Glu Pro Leu Pro Asp Ala Val
         35                  40                  45 cgc acc aac ggt gca acc cca aac cca tgg tgg tcc aac gca gtg gtg      313
Arg Thr Asn Gly Ala Thr Pro Asn Pro Trp Trp Ser Asn Ala Val Val
```

```
              50                  55                  60
tac cag atc tac cca cgc tcc ttc cag gat acc aac ggc gac ggc ctg       361
Tyr Gln Ile Tyr Pro Arg Ser Phe Gln Asp Thr Asn Gly Asp Gly Leu
 65              70                  75                  80 ggc gat ctg aag ggc atc acc tcc cgc ttg gat tac ctg gca gat ctg       409
Gly Asp Leu Lys Gly Ile Thr Ser Arg Leu Asp Tyr Leu Ala Asp Leu
                 85                  90                  95 ggc gtg gat gtg ctg tgg ctg tcc cca gtg tac cgc tcc cca cag gat       457
Gly Val Asp Val Leu Trp Leu Ser Pro Val Tyr Arg Ser Pro Gln Asp
                100                 105                 110 gat aac ggc tac gat atc tcc gat tac cgc gat atc gat cca ctg ttc       505
Asp Asn Gly Tyr Asp Ile Ser Asp Tyr Arg Asp Ile Asp Pro Leu Phe
            115                 120                 125 ggc acc ctg gat gat atg gat gaa ctg ctg gca gag gca cac aag cgt       553
Gly Thr Leu Asp Asp Met Asp Glu Leu Leu Ala Glu Ala His Lys Arg
        130                 135                 140 ggc ctg aag atc gtg atg gat ctg gtg gtg aac cac acc tcc gat gaa       601
Gly Leu Lys Ile Val Met Asp Leu Val Val Asn His Thr Ser Asp Glu
145                 150                 155                 160 cac gca tgg ttc gaa gca tcc aag gat aag gat gat cca cac gca gat       649
His Ala Trp Phe Glu Ala Ser Lys Asp Lys Asp Asp Pro His Ala Asp
                165                 170                 175 tgg tac tgg tgg cgt cca gca cgc cca ggc cac gaa cca ggc acc cca       697
Trp Tyr Trp Trp Arg Pro Ala Arg Pro Gly His Glu Pro Gly Thr Pro
                180                 185                 190 ggc gca gaa cca aac cag tgg ggc tcc tac ttc ggt ggc tcc gca tgg       745
Gly Ala Glu Pro Asn Gln Trp Gly Ser Tyr Phe Gly Gly Ser Ala Trp
            195                 200                 205 gaa tac tcc cca gaa cgc ggt gaa tac tac ctg cac cag ttc tcc aag       793
Glu Tyr Ser Pro Glu Arg Gly Glu Tyr Tyr Leu His Gln Phe Ser Lys
        210                 215                 220 aag cag cca gat ctc aac tgg gaa aac cca gca gtg cgt cgc gca gtg       841
Lys Gln Pro Asp Leu Asn Trp Glu Asn Pro Ala Val Arg Arg Ala Val
225                 230                 235                 240 tac gat atg atg aac tgg tgg ttg gat cgc ggt atc gat ggc ttc cgc       889
Tyr Asp Met Met Asn Trp Trp Leu Asp Arg Gly Ile Asp Gly Phe Arg
                245                 250                 255 atg gat gtg atc acc ctg atc tcc aag cgc acc gat cca aac ggt cgc       937
Met Asp Val Ile Thr Leu Ile Ser Lys Arg Thr Asp Pro Asn Gly Arg
                260                 265                 270 ctg cca ggt gaa acc ggc tcc gaa ctc cag gat ctg cca gtg ggc gaa       985
Leu Pro Gly Glu Thr Gly Ser Glu Leu Gln Asp Leu Pro Val Gly Glu
            275                 280                 285 gaa ggc tac tcc tcc cca aac cct ttc tgc gca gat ggc cct cgc cag      1033
Glu Gly Tyr Ser Ser Pro Asn Pro Phe Cys Ala Asp Gly Pro Arg Gln
        290                 295                 300 gat gaa ttc ctg gca gaa atg cgt cgc gaa gtt ttc gat ggc cgt gat      1081
Asp Glu Phe Leu Ala Glu Met Arg Arg Glu Val Phe Asp Gly Arg Asp
305                 310                 315                 320 ggc ttc ctg acc gtg ggc gaa gca cca ggc atc acc gca gaa cgc aac      1129
Gly Phe Leu Thr Val Gly Glu Ala Pro Gly Ile Thr Ala Glu Arg Asn
                325                 330                 335 gaa cac atc acc gat cca gca aac ggc gaa ctg gat atg ctg ttc ctg      1177
Glu His Ile Thr Asp Pro Ala Asn Gly Glu Leu Asp Met Leu Phe Leu
            340                 345                 350 ttc gaa cac atg ggc gtg gat cag acc cca gaa tcc aag tgg gat gat      1225
Phe Glu His Met Gly Val Asp Gln Thr Pro Glu Ser Lys Trp Asp Asp
        355                 360                 365 aag cca tgg acc cca gca gat ctg gaa acc aag ctg gca gaa cag cag      1273
```

```
Lys Pro Trp Thr Pro Ala Asp Leu Glu Thr Lys Leu Ala Glu Gln Gln
        370                 375                 380 gat gca atc gca cgc cgt ggc tgg gcc tcc ctg ttc ctg gat aac cac      1321
Asp Ala Ile Ala Arg Arg Gly Trp Ala Ser Leu Phe Leu Asp Asn His
385                 390                 395                 400 gat cag cca cgc gtg gtg tcc cgc tgg ggt gat gat acc tcc aag acc      1369
Asp Gln Pro Arg Val Val Ser Arg Trp Gly Asp Asp Thr Ser Lys Thr
                405                 410                 415 ggt cgc atc cgc tcc gca aag gca ctg gca ctg ctg cac atg cac          1417
Gly Arg Ile Arg Ser Ala Lys Ala Leu Ala Leu Leu Leu His Met His
                420                 425                 430 cgt ggc acc cca tac gtg tac cag ggc gaa gaa ctg ggc atg acc aac      1465
Arg Gly Thr Pro Tyr Val Tyr Gln Gly Glu Glu Leu Gly Met Thr Asn
                435                 440                 445 gca cac ttc acc tcc ctg gat cag tac cgc gat ctg gaa tcc atc aac      1513
Ala His Phe Thr Ser Leu Asp Gln Tyr Arg Asp Leu Glu Ser Ile Asn
450                 455                 460 gca tac cac caa cgc gtg gaa gaa acc ggc atc cgc acc tcc gaa acc      1561
Ala Tyr His Gln Arg Val Glu Glu Thr Gly Ile Arg Thr Ser Glu Thr
465                 470                 475                 480 atg atg cgc tcc ctg gca cgc tac ggt cgc gat aac gca cgc acc cca      1609
Met Met Arg Ser Leu Ala Arg Tyr Gly Arg Asp Asn Ala Arg Thr Pro
                485                 490                 495 atg cag tgg gat gat tcc acc tac gca ggc ttc acc atg cca gat gcc      1657
Met Gln Trp Asp Asp Ser Thr Tyr Ala Gly Phe Thr Met Pro Asp Ala
                500                 505                 510 cca gtg gaa cca tgg atc gca gtg aac cca aac cac acc gaa atc aac      1705
Pro Val Glu Pro Trp Ile Ala Val Asn Pro Asn His Thr Glu Ile Asn
                515                 520                 525 gca gca gat gaa acc gat gat cca gat tcc gtg tac tcc ttc cac aag      1753
Ala Ala Asp Glu Thr Asp Asp Pro Asp Ser Val Tyr Ser Phe His Lys
530                 535                 540 cgc ctg atc gca ctg cgc cac acc gat cca gtg gtg gca gca ggc gat      1801
Arg Leu Ile Ala Leu Arg His Thr Asp Pro Val Val Ala Ala Gly Asp
545                 550                 555                 560 tac cgt cgc gtg gaa acc ggc aac gat cgc atc att gca ttc acc cgc      1849
Tyr Arg Arg Val Glu Thr Gly Asn Asp Arg Ile Ile Ala Phe Thr Arg
                565                 570                 575 acc ctg gac gaa cgc acc atc ctg acc gtg atc aac ctg tcc cca acc      1897
Thr Leu Asp Glu Arg Thr Ile Leu Thr Val Ile Asn Leu Ser Pro Thr
                580                 585                 590 cag gca gca cca gca ggc gaa ctg gaa acc atg cca gac ggc acc atc      1945
Gln Ala Ala Pro Ala Gly Glu Leu Glu Thr Met Pro Asp Gly Thr Ile
                595                 600                 605 ttg atc gca aac acc gat gac cca gtg ggc aac ctc aag acc acc ggc      1993
Leu Ile Ala Asn Thr Asp Asp Pro Val Gly Asn Leu Lys Thr Thr Gly
610                 615                 620 acc ctg ggt cca tgg gaa gca ttc gca atg gaa acc gat cca gaa          2038
Thr Leu Gly Pro Trp Glu Ala Phe Ala Met Glu Thr Asp Pro Glu
625                 630                 635 taagcggccg ctgttagccc ggggtgtgcc tcggcgcacc ccgggctatt tttctaga      2096
```

<210> SEQ ID NO 17
<211> LENGTH: 639
<212> TYPE: PRT
<213> ORGANISM: artificial sequence
<220> FEATURE:
<223> OTHER INFORMATION: Synthetic Construct

<400> SEQUENCE: 17

-continued

```
Met Gln Ile Asn Arg Arg Gly Phe Leu Lys Ala Thr Thr Gly Leu Ala
1               5                   10                  15

Thr Ile Gly Ala Ala Ser Met Phe Met Pro Lys Ala Asn Ala Leu Gly
                20                  25                  30

Ala Met Thr Ser Thr Ser Phe Asn Arg Glu Pro Leu Pro Asp Ala Val
            35                  40                  45

Arg Thr Asn Gly Ala Thr Pro Asn Pro Trp Trp Ser Asn Ala Val Val
    50                  55                  60

Tyr Gln Ile Tyr Pro Arg Ser Phe Gln Asp Thr Asn Gly Asp Gly Leu
65                  70                  75                  80

Gly Asp Leu Lys Gly Ile Thr Ser Arg Leu Asp Tyr Leu Ala Asp Leu
                85                  90                  95

Gly Val Asp Val Leu Trp Leu Ser Pro Val Tyr Arg Ser Pro Gln Asp
            100                 105                 110

Asp Asn Gly Tyr Asp Ile Ser Asp Tyr Arg Asp Ile Asp Pro Leu Phe
        115                 120                 125

Gly Thr Leu Asp Asp Met Asp Glu Leu Leu Ala Glu Ala His Lys Arg
    130                 135                 140

Gly Leu Lys Ile Val Met Asp Leu Val Val Asn His Thr Ser Asp Glu
145                 150                 155                 160

His Ala Trp Phe Glu Ala Ser Lys Asp Lys Asp Asp Pro His Ala Asp
                165                 170                 175

Trp Tyr Trp Trp Arg Pro Ala Arg Pro Gly His Glu Pro Gly Thr Pro
            180                 185                 190

Gly Ala Glu Pro Asn Gln Trp Gly Ser Tyr Phe Gly Gly Ser Ala Trp
        195                 200                 205

Glu Tyr Ser Pro Glu Arg Gly Glu Tyr Tyr Leu His Gln Phe Ser Lys
    210                 215                 220

Lys Gln Pro Asp Leu Asn Trp Glu Asn Pro Ala Val Arg Arg Ala Val
225                 230                 235                 240

Tyr Asp Met Met Asn Trp Trp Leu Asp Arg Gly Ile Asp Gly Phe Arg
                245                 250                 255

Met Asp Val Ile Thr Leu Ile Ser Lys Arg Thr Asp Pro Asn Gly Arg
            260                 265                 270

Leu Pro Gly Glu Thr Gly Ser Glu Leu Gln Asp Leu Pro Val Gly Glu
        275                 280                 285

Glu Gly Tyr Ser Ser Pro Asn Pro Phe Cys Ala Asp Gly Pro Arg Gln
    290                 295                 300

Asp Glu Phe Leu Ala Glu Met Arg Arg Glu Val Phe Asp Gly Arg Asp
305                 310                 315                 320

Gly Phe Leu Thr Val Gly Glu Ala Pro Gly Ile Thr Ala Glu Arg Asn
                325                 330                 335

Glu His Ile Thr Asp Pro Ala Asn Gly Glu Leu Asp Met Leu Phe Leu
            340                 345                 350

Phe Glu His Met Gly Val Asp Gln Thr Pro Glu Ser Lys Trp Asp Asp
        355                 360                 365

Lys Pro Trp Thr Pro Ala Asp Leu Glu Thr Lys Leu Ala Glu Gln Gln
    370                 375                 380

Asp Ala Ile Ala Arg Arg Gly Trp Ala Ser Leu Phe Leu Asp Asn His
385                 390                 395                 400

Asp Gln Pro Arg Val Val Ser Arg Trp Gly Asp Asp Thr Ser Lys Thr
                405                 410                 415

Gly Arg Ile Arg Ser Ala Lys Ala Leu Ala Leu Leu Leu His Met His
```

```
                420               425               430
Arg Gly Thr Pro Tyr Val Tyr Gln Gly Glu Glu Leu Gly Met Thr Asn
            435               440               445

Ala His Phe Thr Ser Leu Asp Gln Tyr Arg Asp Leu Glu Ser Ile Asn
    450               455               460

Ala Tyr His Gln Arg Val Glu Glu Thr Gly Ile Arg Thr Ser Glu Thr
465               470               475               480

Met Met Arg Ser Leu Ala Arg Tyr Gly Arg Asp Asn Ala Arg Thr Pro
            485               490               495

Met Gln Trp Asp Asp Ser Thr Tyr Ala Gly Phe Thr Met Pro Asp Ala
            500               505               510

Pro Val Glu Pro Trp Ile Ala Val Asn Pro Asn His Thr Glu Ile Asn
        515               520               525

Ala Ala Asp Glu Thr Asp Pro Asp Ser Val Tyr Ser Phe His Lys
        530               535               540

Arg Leu Ile Ala Leu Arg His Thr Asp Pro Val Val Ala Ala Gly Asp
545               550               555               560

Tyr Arg Arg Val Glu Thr Gly Asn Asp Arg Ile Ile Ala Phe Thr Arg
                565               570               575

Thr Leu Asp Glu Arg Thr Ile Leu Thr Val Ile Asn Leu Ser Pro Thr
            580               585               590

Gln Ala Ala Pro Ala Gly Glu Leu Glu Thr Met Pro Asp Gly Thr Ile
        595               600               605

Leu Ile Ala Asn Thr Asp Asp Pro Val Gly Asn Leu Lys Thr Thr Gly
    610               615               620

Thr Leu Gly Pro Trp Glu Ala Phe Ala Met Glu Thr Asp Pro Glu
625               630               635
```

<210> SEQ ID NO 18
<211> LENGTH: 2222
<212> TYPE: DNA
<213> ORGANISM: Corynebacterium glutamicum ATCC13032
<220> FEATURE:
<221> NAME/KEY: misc_feature
<222> LOCATION: (1)..(3)
<223> OTHER INFORMATION: atg start codon of NCgl2176
<220> FEATURE:
<221> NAME/KEY: misc_feature
<222> LOCATION: (1033)..(1035)
<223> OTHER INFORMATION: tga stop codon of of NCgl2176
<220> FEATURE:
<221> NAME/KEY: misc_feature
<222> LOCATION: (1594)..(1596)
<223> OTHER INFORMATION: cta codon; tag stop codon of NCgl2177 of the
    complementary strand
<220> FEATURE:
<221> NAME/KEY: misc_feature
<222> LOCATION: (2020)..(2022)
<223> OTHER INFORMATION: cat codon; atg start codon of NCgl2177 of the
    complementary strand
<220> FEATURE:
<221> NAME/KEY: misc_feature
<222> LOCATION: (2023)..(2222)
<223> OTHER INFORMATION: sequence upstream of NCgl2177

<400> SEQUENCE: 18
atggcatttg cagacattgt gcgcagcgtc gaaaaccgca ccaacgcagc gaccctcaac    60
tggtccatca aaaatggctg gaagcccgaa gtcaccggat tttccgggta cggctccggg   120
cgtcgagtgc gcgtccttgc gcgcgtgctc atgtccaacc ccgaaaattt gcttgtcgac   180
gccccctccc aatcaattac ccaacaagca cagcgcggtt ggcgccagtt cttcaccatc   240

```
caagtgccca acctgccagt aactgtcacc gttggtggga aaacagttac ctcatccacc    300
aacgacaacg gctacgttga cctcctggtg gaagaccaca accttgaccc cggctggcac    360
accatccaga tccaagccga aggttccacc cccgccgaag cccgcgtcct catcgtggaa    420
aacaccgccc gaatcggact catctccgac atcgacgaca ccatcatggt cacctggctt    480
ccccgagcac tcctcgccgc atggaactcg tgggttttgc acaccaacac ccgcaaacca    540
gtccccggaa tgaaccgctt ctacgaagaa ctcctcaaag accacccega cgcacccgtg    600
ttctacctct ccaccggcgc atggaacacc tttgaaaccc tccaagagtt catcaacaaa    660
cacgcactcc ccgacggccc catgctgctc accgactggg gaccaacccc cacaggacta    720
ttccgctcag gtcaagagca caagaaagtc caactgcgca acctgtttat cgaataccec    780
gacatgaaat ggatcctcgt cggcgacgat ggccaacacg atcccctcat ctacggcgaa    840
gcagtcgaag aacaccccaa ccgcatcgca ggcgttgcaa tccgtgagct ctcccccggc    900
gaacatgtgc tctcccacgg aacaactgcg tcactgtcca ccatcacgac caacgggggc    960
caaggagtcc cagtagttca cggccgcgat ggatatgagt tgctgcagcg ctacgagacg   1020
aagccgttcg cctgagtcct actgggtgtc tcatgaacca aaccgggtga ccagcgtcgc   1080
cttaattttg ggttcctcgg tcacctagtt tggtccttgg ttgcgttcgc gtatggcata   1140
aatgggcact gactattttt ggggcggggc cccgaggtaa aaggcgattt aagaggttga   1200
gatcccccaa taggcttttg gtatggagga cgcccgttga ggctcttaaa accgattctg   1260
agagacctcg gctttgtgac cagtgggaca gatgagattc ctgcgagctt gctgatcaag   1320
aactcaccac aattgtgtgg ccagaccgtc aaatcgaaca tattttttgca ctaactagac   1380
ccaaacttgc aaaaacccac cacaaacact gtctcgccag caatctgtgg tgaattttcg   1440
cataattgtt cgaccaagag tccgacggta atcaacacgt cacaaaccac cccacaaagt   1500
gcgccaaaaa cccgtggggc ctccctcttc ctctagagag gccccacggg ctggtctatt   1560
tacacccccgc cgagctaaag aatcactggc tttctagtca acgattcgca gctcaacttc   1620
aaaacggtat tcatcagcca gagattccag cactcctcga agtttgtcga gttcgcgtgg   1680
agttccggtg atcacctctc gacactcagt gaggccaagt tcgaatgggt cacggcgcca   1740
tgcagtgaac catcgtgcgg tgagcgggtc cctgttggag ccggacagct ccgaaggact   1800
cggaatacac acaaccattg cggattccac ggtctgacgc agttcctttg gcattccgct   1860
gatttctaga acagcggtat gcattgggag ggctacatcg tcgatggatt cttcgatggt   1920
agttttcagt tggggcaacc ccatgtcttc ccagaagtct gccgtgagca aatccgcctg   1980
atgacgggtc cggggttggca cggttaatgc attgttcgtc atgttcggtt tccttcggca   2040
acacttaact gccttcaatt cccgcacaca tatacaagta gatatgtgca gttactaaag   2100
gaagtaagac gaggttcgtc ttccccaacg gcctcgagct cgcttcaaaa tcccttgaat   2160
gactacacag gcgattgtgg ttgagtaagt ggaccccggc aaccctcaac ttaagcttta   2220
tc                                                                  2222
```

<210> SEQ ID NO 19
<211> LENGTH: 2222
<212> TYPE: DNA
<213> ORGANISM: Corynebacterium glutamicum ATCC13869
<220> FEATURE:
<221> NAME/KEY: misc_feature
<222> LOCATION: (1)..(2222)
<223> OTHER INFORMATION: sequence homologous to SEQ ID NO:18
<220> FEATURE:
<221> NAME/KEY: misc_feature

```
<222> LOCATION: (1)..(3)
<223> OTHER INFORMATION: atg start codon of BBD29_10725
<220> FEATURE:
<221> NAME/KEY: misc_feature
<222> LOCATION: (1033)..(1035)
<223> OTHER INFORMATION: tga stop codon of BBD29_10725
<220> FEATURE:
<221> NAME/KEY: misc_feature
<222> LOCATION: (1594)..(1596)
<223> OTHER INFORMATION: cta codon; tag stop codon of BBD29_10730 of the
      complementary strand
<220> FEATURE:
<221> NAME/KEY: misc_feature
<222> LOCATION: (2020)..(2022)
<223> OTHER INFORMATION: cat codon; atg start codon of BBD29_10730 of
      the complementary strand
<220> FEATURE:
<221> NAME/KEY: misc_feature
<222> LOCATION: (2023)..(2222)
<223> OTHER INFORMATION: sequence upstream of BBD29_10730

<400> SEQUENCE: 19
atggcatttg cagacattgt gcgcagcgtc gaaaaccgca ccaacgcagc gacccttaac    60
tggtccatca aaagggctg gaagcccgaa gtcaccggat tttccgggta cggctccggg    120
cgtcgagtgc gcgtccttgc gcgcgtgctc atgtccaacc cgaaaaattt gcttgtcgac    180 gcccctccc aatcaattac ccaacaagca cagcgcggtt ggcgccagtt cttcaccatc     240
caagtgccca acctgccagt aactgtcacc gttggtggga aaacagttac ctcatccacc    300
aacgacaacg gctacgttga cctcctggtg aagaccaca accttgaccc cggctggcac     360
accatccaga tccaagccga aggttccacc ccgccgaag cccgcgtcct catcgtggaa     420
aacaccgccc gaatcggact catctccgac atcgacgaca ccatcatggt cacctggctt    480
ccccgagcac tcctcgccgc atggaactcg tgggttttgc acaccaacac ccgcaaacca    540
gtccccggaa tgaaccgctt ctacgaagaa ctcctcaaag accaccccga cgcacccgtg    600
ttctacctct ccaccggcgc atggaacacc tttgaaaccc tccaagagtt catcaacaaa    660
cacgcactcc ccgacggccc catgctgctc accgactggg gaccaacccc cacaggacta    720
ttccgctcag gtcaagagca caagaaagtc caactgcgca acctgtttat cgaataccccc  780 gacatgaaat ggatcctcgt cggcgacgat ggccaacacg atccctcat ctacggcgaa    840 gcagtcgaag aacaccccaa ccgcatcgca ggcgttgcaa tcgtgagct ctcccccggc    900 gaacatgtgc tctcccacgg aacaactgcg tcactgtcca ccatcacgac aacggtggc    960 caaggagtcc cagtagttca cggccgcgat ggatatgagt tgctgcagcg ctacgagacg   1020
aagccgttcg cctgagtcct actgggtgtc tcatgaacca aaccgggtga ccagcgtcgc   1080
cttaattttg ggttcctcgg tcacctggtt tggtccttgg ttgcgttcgc gtatggcata   1140
aatgggcact gactattttt ggggcgggc cccgaggtaa aaggcgattt aagaggttga   1200
gatccccaaa taggcttttg gtatggagga cgcccgttga ggctcttaaa accgattctg   1260
agagacctcg gctttgtgac cagtgggaca gatgagattc ctgcgagctt gctgatcaag   1320
aactcaccac aatcgtgtgg ccagaccatc aaatcgaaca tattttgca ctaactagac    1380 ccaaacttgc aaaaacccac cacaaacccct gtcccgccag caatctgtgg tgaattttcg    1440
cataattgtt cgactaagcg tccgacggta atcaacacgt cacaaaccac cccaaaaagt    1500
gcgccaaaaa cccgtggggc ctccctcttc ctctagagag gccccacggg ctggtctatt    1560
tacaccccgc cgagctaaag aatcactggc tttctagtca acgattcgca gctcaacttc    1620
aaaacggtat tcatcagcca gagattccag cactcctcga agtttgtcga gttcgcgtgg   1680
```

```
agttccggtg atcacctctc ggcactcagt gaggccaagt tcgaatgggt cacggcgcca    1740
tgcagtgaac catcgtgcgg tgagcgggtc ccggttggag ccggacagct ccgaaggact    1800
cggaatacac acaaccattg cggattccac ggtctgacgc agttcctttg gcattccgct    1860
gatttctaga acagcggtat gcattgggag ggctacatcg tcgatggatt cttcaatggt    1920
agttttcagt tggggcaacc ccatgtcttc ccagaagtct gccgtgagca aatccgcctg    1980
atgacgggtc cgggttggca cggttaatgc attgttcgtc atgttcggtt tccttcggca    2040
acacttaact gccttcaatt cccgcacaca tatacaagta gatatgtgca gttactaaag    2100
gaagtaagac gaggttcgtc ttccccaacg gcctcgagct cgcttcaaaa ttccttgaat    2160
gactacacag gcgattgtgg ttgagtaagt ggaccccggc aaccctcaac ttaagcttta    2220
tc                                                                  2222
```

<210> SEQ ID NO 20
<211> LENGTH: 2222
<212> TYPE: DNA
<213> ORGANISM: Corynebacterium glutamicum ATCC14067
<220> FEATURE:
<221> NAME/KEY: misc_feature
<222> LOCATION: (1)..(2222)
<223> OTHER INFORMATION: sequence homologous to SEQ ID NO:18
<220> FEATURE:
<221> NAME/KEY: misc_feature
<222> LOCATION: (1)..(3)
<223> OTHER INFORMATION: atg start codon
<220> FEATURE:
<221> NAME/KEY: misc_feature
<222> LOCATION: (1033)..(1035)
<223> OTHER INFORMATION: tag stop codon
<220> FEATURE:
<221> NAME/KEY: misc_feature
<222> LOCATION: (1594)..(1596)
<223> OTHER INFORMATION: cta codon; tag stop codon of the complementary
      strand
<220> FEATURE:
<221> NAME/KEY: misc_feature
<222> LOCATION: (2020)..(2022)
<223> OTHER INFORMATION: cat codon; atg start codon of the complementary
      strand
<220> FEATURE:
<221> NAME/KEY: misc_feature
<222> LOCATION: (2023)..(2222)
<223> OTHER INFORMATION: sequence upstream (complementary strand) of the
      cds identified by positions 2022 to 1597

<400> SEQUENCE: 20

```
atggcatttg cagacattgt gcgcagcgtc gaaaaccgca ccaacgcagc gaccctcaac      60
tggtccatca aaaagggctg gaagcccgaa gtcaccggat tttccggtta cggctccggg     120
cgtcgagtgc gcgtccttgc gcgcgtgctc atgtccaacc ccgaaaattt gcttgtcgac     180 gcccctccc aatcaattac ccaacaagca cagcgcggtt ggcgccagtt cttcaccatc      240
caagtgccca acctgccagt aactgtcacc gttggtggga aaacagttac ctcatccacc     300
aacgacaacg gctacgttga cctcctggtg gaagaccaca accttgaccc cggctggcac     360
accatccaga tccaagccga aggttccacc cccgccgaag cccgcgtcct catcgtggaa     420
aacaccgccc gaatcggact catctccgac atcgacgaca ccatcatggt cacctggctt     480
ccccgagcac tcctcgccgc atggaactcg tgggttttgc acaccaacac ccgcaaacca     540
gtccccggaa tgaaccgctt ctacgaagaa ctcctcaaag accaccccga cgcacccgtg     600 ttctaccttct ccaccggcgc atggaacacc tttgaaaccc tccagagagtt catcaacaaa    660 cacgcactcc ccgacggccc catgttgctc accgactggg gaccaacccc cacaggacta    720
```

| | |
|---|---|
| ttccgctcag gtcaagagca caagaaagtc caactgcgca acctgtttat cgaataccc | 780 |
| gacatgaaat ggatcctcgt cggcgacgat ggccaacacg atcccctcat ctacggcgaa | 840 |
| gcagtcgaag aacaccccaa ccgcatcgca ggtgttgcaa tccgtgagct ctcccccggc | 900 |
| gaacatgtgc tctcccacgg aacaactgcg tcactgtcca ccatcacgac caacggtggc | 960 |
| caaggagtcc cagtagttca cggccgcgat ggatatgagt tgctgcagcg ctacgagacg | 1020 |
| aagccgttcg cctgagtcct actgggtgtc tcatgaacca aacgggtga ccagcgtcgc | 1080 |
| cttaactttg ggttcctcgg tcacctggtt tggtccttgg ttgcgttcgc gtatggcata | 1140 |
| aatgggcact gactattttt ggggcggggc cccgaggtaa aaggcgattt aagaggttga | 1200 |
| gatccccaaa taggcttttg gtatggagga cgcccgttga ggctcttaaa accgattctg | 1260 |
| agagacctcg gctttgtgac cagtgggaca gatgagattc ctgcgagctt gctgatcaag | 1320 |
| aactcaccac aatcgtgtgg ccagaccatc aaatcgaata gattttttgca ctaactagac | 1380 |
| ccaaacttgc aaaacccac cacaaaccct gtcccgccag caatctgtgg tgaattttcg | 1440 |
| cataattatt cgaccaatcg tccgacgta atcaacacgt cacaaaccac cccaaaaagt | 1500 |
| gcgccaaaaa cccgtggggc ctccctcttc ctctagagag gccccacggg ctggtctatt | 1560 |
| tacgccccgc cgagctaaag aatcactggc tttctagtca acgattcgca gctcaacttc | 1620 |
| aaaacggtat tcatcagcca gagattccag cactcctcga agtttgtcga gttcgcgtgg | 1680 |
| agttccggtg atcacctctc gacactcagt gaggccaagt tcgaatgggt cacggcgcca | 1740 |
| tgcagtgaac catcgtgcgg tgagcgggtc cctgttggag ccggacagct ccgaaggact | 1800 |
| cggaatacac acaaccattg cggattccac ggtctgacgc agttcctttg gcattccgct | 1860 |
| gatttctaga acagcggtat gcattgggag ggctacatcg tcgatggatt cttcgatggt | 1920 |
| agttttcagt tggggcaacc ccatgtcttc ccagaagtct gccgtgagca aatccgcctg | 1980 |
| atgacgggtc cggggttggca cggttaatgc attgttcgtc atgttcggtt tccttcggca | 2040 |
| acacttaact gccttcaatt cccgcacaca tatacaagta gatatgtgca gttactaaag | 2100 |
| gaagtaagac gaggttcgtc ttccccaacg gcctcgagct cgcttcaaaa ttccttgaat | 2160 |
| gactacacag gcgattgtgg ttgagtaagt ggaccccggc aaccctcaac ttaagcttta | 2220 |
| tc | 2222 |

```
<210> SEQ ID NO 21
<211> LENGTH: 1994
<212> TYPE: DNA
<213> ORGANISM: artificial sequence
<220> FEATURE:
<223> OTHER INFORMATION: gene fusion tat-'agl2_cuo
<220> FEATURE:
<221> NAME/KEY: misc_feature
<222> LOCATION: (1)..(6)
<223> OTHER INFORMATION: PstI restriction site
<220> FEATURE:
<221> NAME/KEY: misc_feature
<222> LOCATION: (7)..(13)
<223> OTHER INFORMATION: SexAI restriction site
<220> FEATURE:
<221> NAME/KEY: CDS
<222> LOCATION: (14)..(1930)
<223> OTHER INFORMATION: sequence coding for fusion polypeptide
      Tat-'Agl2
<220> FEATURE:
<221> NAME/KEY: misc_signal
<222> LOCATION: (14)..(112)
<223> OTHER INFORMATION: 5' sequence of cg0955 encoding Tat-signal
      peptide of Cg0955
<220> FEATURE:
<221> NAME/KEY: misc_feature
```

```
<222> LOCATION: (14)..(114)
<223> OTHER INFORMATION: 5' sequence of cg0955
<220> FEATURE:
<221> NAME/KEY: misc_feature
<222> LOCATION: (115)..(115)
<223> OTHER INFORMATION: nucleobase guanine
<220> FEATURE:
<221> NAME/KEY: misc_feature
<222> LOCATION: (116)..(121)
<223> OTHER INFORMATION: SpeI restriction site
<220> FEATURE:
<221> NAME/KEY: misc_feature
<222> LOCATION: (122)..(1930)
<223> OTHER INFORMATION: 'agl2_cuo
<220> FEATURE:
<221> NAME/KEY: misc_feature
<222> LOCATION: (155)..(162)
<223> OTHER INFORMATION: FspAI restriction site
<220> FEATURE:
<221> NAME/KEY: misc_feature
<222> LOCATION: (1931)..(1933)
<223> OTHER INFORMATION: stop codon
<220> FEATURE:
<221> NAME/KEY: misc_feature
<222> LOCATION: (1934)..(1941)
<223> OTHER INFORMATION: NotI restriction site
<220> FEATURE:
<221> NAME/KEY: misc_feature
<222> LOCATION: (1945)..(1980)
<223> OTHER INFORMATION: terminator sequence Tgap*
<220> FEATURE:
<221> NAME/KEY: misc_feature
<222> LOCATION: (1983)..(1988)
<223> OTHER INFORMATION: XbaI restriction site
<220> FEATURE:
<221> NAME/KEY: misc_feature
<222> LOCATION: (1989)..(1994)
<223> OTHER INFORMATION: BamHI restriction site

<400> SEQUENCE: 21
ctgcagacca ggt atg caa ata aac cgc cga ggc ttc tta aaa gcc acc      49
           Met Gln Ile Asn Arg Arg Gly Phe Leu Lys Ala Thr
             1               5                  10 aca gga ctt gcc act atc ggc gct gcc agc atg ttt atg cca aag gcc    97
Thr Gly Leu Ala Thr Ile Gly Ala Ala Ser Met Phe Met Pro Lys Ala
        15                  20                  25 aac gcc ctt gga gca atg act agt acc tcc ttc aac cgc gaa cca ctg   145
Asn Ala Leu Gly Ala Met Thr Ser Thr Ser Phe Asn Arg Glu Pro Leu
 30                  35                  40 cca gat gca gtg cgc acc aac ggt gca acc cca aac cca tgg tgg tcc   193
Pro Asp Ala Val Arg Thr Asn Gly Ala Thr Pro Asn Pro Trp Trp Ser
 45                  50                  55                  60 aac gca gtg gtg tac cag atc tac cca cgc tcc ttc cag gat acc aac   241
Asn Ala Val Val Tyr Gln Ile Tyr Pro Arg Ser Phe Gln Asp Thr Asn
                 65                  70                  75 ggc gac ggc ctg ggc gat ctg aag ggc atc acc tcc cgc ttg gat tac   289
Gly Asp Gly Leu Gly Asp Leu Lys Gly Ile Thr Ser Arg Leu Asp Tyr
             80                  85                  90 ctg gca gat ctg ggc gtg gat gtg ctg tgg ctg tcc cca gtg tac cgc   337
Leu Ala Asp Leu Gly Val Asp Val Leu Trp Leu Ser Pro Val Tyr Arg
         95                 100                 105 tcc cca cag gat gat aac ggc tac gat atc tcc gat tac cgc gat atc   385
Ser Pro Gln Asp Asp Asn Gly Tyr Asp Ile Ser Asp Tyr Arg Asp Ile
    110                 115                 120 gat cca ctg ttc ggc acc ctg gat gat atg gat gaa ctg ctg gca gag   433
Asp Pro Leu Phe Gly Thr Leu Asp Asp Met Asp Glu Leu Leu Ala Glu
125                 130                 135                 140 gca cac aag cgt ggc ctg aag atc gtg atg gat ctg gtg gtg aac cac   481
Ala His Lys Arg Gly Leu Lys Ile Val Met Asp Leu Val Val Asn His
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     | 145 |     |     |     | 150 |     |     |     |     | 155 |     |     |     |      |
| acc | tcc | gat | gaa | cac | gca | tgg | ttc | gaa | gca | tcc | aag | gat | aag | gat | gat | 529  |
| Thr | Ser | Asp | Glu | His | Ala | Trp | Phe | Glu | Ala | Ser | Lys | Asp | Lys | Asp | Asp |      |
|     |     |     | 160 |     |     |     | 165 |     |     |     | 170 |     |     |     |     |      |
| cca | cac | gca | gat | tgg | tac | tgg | tgg | cgt | cca | gca | cgc | cca | ggc | cac | gaa | 577  |
| Pro | His | Ala | Asp | Trp | Tyr | Trp | Trp | Arg | Pro | Ala | Arg | Pro | Gly | His | Glu |      |
|     |     | 175 |     |     |     | 180 |     |     |     |     | 185 |     |     |     |     |      |
| cca | ggc | acc | cca | ggc | gca | gaa | cca | aac | cag | tgg | ggc | tcc | tac | ttc | ggt | 625  |
| Pro | Gly | Thr | Pro | Gly | Ala | Glu | Pro | Asn | Gln | Trp | Gly | Ser | Tyr | Phe | Gly |      |
|     | 190 |     |     |     |     | 195 |     |     |     |     | 200 |     |     |     |     |      |
| ggc | tcc | gca | tgg | gaa | tac | tcc | cca | gaa | cgc | ggt | gaa | tac | tac | ctg | cac | 673  |
| Gly | Ser | Ala | Trp | Glu | Tyr | Ser | Pro | Glu | Arg | Gly | Glu | Tyr | Tyr | Leu | His |      |
| 205 |     |     |     |     | 210 |     |     |     |     | 215 |     |     |     |     | 220 |      |
| cag | ttc | tcc | aag | aag | cag | cca | gat | ctc | aac | tgg | gaa | aac | cca | gca | gtg | 721  |
| Gln | Phe | Ser | Lys | Lys | Gln | Pro | Asp | Leu | Asn | Trp | Glu | Asn | Pro | Ala | Val |      |
|     |     |     |     | 225 |     |     |     |     | 230 |     |     |     |     | 235 |     |      |
| cgt | cgc | gca | gtg | tac | gat | atg | atg | aac | tgg | tgg | ttg | gat | cgc | ggt | atc | 769  |
| Arg | Arg | Ala | Val | Tyr | Asp | Met | Met | Asn | Trp | Trp | Leu | Asp | Arg | Gly | Ile |      |
|     |     |     | 240 |     |     |     |     | 245 |     |     |     |     | 250 |     |     |      |
| gat | ggc | ttc | cgc | atg | gat | gtg | atc | acc | ctg | atc | tcc | aag | cgc | acc | gat | 817  |
| Asp | Gly | Phe | Arg | Met | Asp | Val | Ile | Thr | Leu | Ile | Ser | Lys | Arg | Thr | Asp |      |
|     |     | 255 |     |     |     |     | 260 |     |     |     |     | 265 |     |     |     |      |
| cca | aac | ggt | cgc | ctg | cca | ggt | gaa | acc | ggc | tcc | gaa | ctc | cag | gat | ctg | 865  |
| Pro | Asn | Gly | Arg | Leu | Pro | Gly | Glu | Thr | Gly | Ser | Glu | Leu | Gln | Asp | Leu |      |
|     | 270 |     |     |     |     | 275 |     |     |     |     | 280 |     |     |     |     |      |
| cca | gtg | ggc | gaa | gaa | ggc | tac | tcc | tcc | cca | aac | cct | ttc | tgc | gca | gat | 913  |
| Pro | Val | Gly | Glu | Glu | Gly | Tyr | Ser | Ser | Pro | Asn | Pro | Phe | Cys | Ala | Asp |      |
| 285 |     |     |     |     | 290 |     |     |     |     | 295 |     |     |     |     | 300 |      |
| ggc | cct | cgc | cag | gat | gaa | ttc | ctg | gca | gaa | atg | cgt | cgc | gaa | gtt | ttc | 961  |
| Gly | Pro | Arg | Gln | Asp | Glu | Phe | Leu | Ala | Glu | Met | Arg | Arg | Glu | Val | Phe |      |
|     |     |     |     | 305 |     |     |     |     | 310 |     |     |     |     | 315 |     |      |
| gat | ggc | cgt | gat | ggc | ttc | ctg | acc | gtg | ggc | gaa | gca | cca | ggc | atc | acc | 1009 |
| Asp | Gly | Arg | Asp | Gly | Phe | Leu | Thr | Val | Gly | Glu | Ala | Pro | Gly | Ile | Thr |      |
|     |     |     | 320 |     |     |     |     | 325 |     |     |     |     | 330 |     |     |      |
| gca | gaa | cgc | aac | gaa | cac | atc | acc | gat | cca | gca | aac | ggc | gaa | ctg | gat | 1057 |
| Ala | Glu | Arg | Asn | Glu | His | Ile | Thr | Asp | Pro | Ala | Asn | Gly | Glu | Leu | Asp |      |
|     |     | 335 |     |     |     |     | 340 |     |     |     |     | 345 |     |     |     |      |
| atg | ctg | ttc | ctg | ttc | gaa | cac | atg | ggc | gtg | gat | cag | acc | cca | gaa | tcc | 1105 |
| Met | Leu | Phe | Leu | Phe | Glu | His | Met | Gly | Val | Asp | Gln | Thr | Pro | Glu | Ser |      |
|     | 350 |     |     |     |     | 355 |     |     |     |     | 360 |     |     |     |     |      |
| aag | tgg | gat | gat | aag | cca | tgg | acc | cca | gca | gat | ctg | gaa | acc | aag | ctg | 1153 |
| Lys | Trp | Asp | Asp | Lys | Pro | Trp | Thr | Pro | Ala | Asp | Leu | Glu | Thr | Lys | Leu |      |
| 365 |     |     |     |     | 370 |     |     |     |     | 375 |     |     |     |     | 380 |      |
| gca | gaa | cag | cag | gat | gca | atc | gca | cgc | cgt | ggc | tgg | gcc | tcc | ctg | ttc | 1201 |
| Ala | Glu | Gln | Gln | Asp | Ala | Ile | Ala | Arg | Arg | Gly | Trp | Ala | Ser | Leu | Phe |      |
|     |     |     |     | 385 |     |     |     |     | 390 |     |     |     |     | 395 |     |      |
| ctg | gat | aac | cac | gat | cag | cca | cgc | gtg | gtg | tcc | cgc | tgg | ggt | gat | gat | 1249 |
| Leu | Asp | Asn | His | Asp | Gln | Pro | Arg | Val | Val | Ser | Arg | Trp | Gly | Asp | Asp |      |
|     |     |     | 400 |     |     |     |     | 405 |     |     |     |     | 410 |     |     |      |
| acc | tcc | aag | acc | ggt | cgc | atc | cgc | tcc | gca | aag | gca | ctg | gca | ctg | ctg | 1297 |
| Thr | Ser | Lys | Thr | Gly | Arg | Ile | Arg | Ser | Ala | Lys | Ala | Leu | Ala | Leu | Leu |      |
|     |     | 415 |     |     |     |     | 420 |     |     |     |     | 425 |     |     |     |      |
| ctg | cac | atg | cac | cgt | ggc | acc | cca | tac | gtg | tac | cag | ggc | gaa | gaa | ctg | 1345 |
| Leu | His | Met | His | Arg | Gly | Thr | Pro | Tyr | Val | Tyr | Gln | Gly | Glu | Glu | Leu |      |
|     | 430 |     |     |     |     | 435 |     |     |     |     | 440 |     |     |     |     |      |
| ggc | atg | acc | aac | gca | cac | ttc | acc | tcc | ctg | gat | cag | tac | cgc | gat | ctg | 1393 |
| Gly | Met | Thr | Asn | Ala | His | Phe | Thr | Ser | Leu | Asp | Gln | Tyr | Arg | Asp | Leu |      |
| 445 |     |     |     |     | 450 |     |     |     |     | 455 |     |     |     |     | 460 |      |
| gaa | tcc | atc | aac | gca | tac | cac | caa | cgc | gtg | gaa | gaa | acc | ggc | atc | cgc | 1441 |

```
Glu Ser Ile Asn Ala Tyr His Gln Arg Val Glu Thr Gly Ile Arg
                465                 470                 475 acc tcc gaa acc atg atg cgc tcc ctg gca cgc tac ggt cgc gat aac      1489
Thr Ser Glu Thr Met Met Arg Ser Leu Ala Arg Tyr Gly Arg Asp Asn
                480                 485                 490 gca cgc acc cca atg cag tgg gat gat tcc acc tac gca ggc ttc acc      1537
Ala Arg Thr Pro Met Gln Trp Asp Asp Ser Thr Tyr Ala Gly Phe Thr
            495                 500                 505 atg cca gat gcc cca gtg gaa cca tgg atc gca gtg aac cca aac cac      1585
Met Pro Asp Ala Pro Val Glu Pro Trp Ile Ala Val Asn Pro Asn His
        510                 515                 520 acc gaa atc aac gca gca gat gaa acc gat gat cca gat tcc gtg tac      1633
Thr Glu Ile Asn Ala Ala Asp Glu Thr Asp Asp Pro Asp Ser Val Tyr
525                 530                 535                 540 tcc ttc cac aag cgc ctg atc gca ctg cgc cac acc gat cca gtg gtg      1681
Ser Phe His Lys Arg Leu Ile Ala Leu Arg His Thr Asp Pro Val Val
                545                 550                 555 gca gca ggc gat tac cgt cgc gtg gaa acc ggc aac gat cgc atc att      1729
Ala Ala Gly Asp Tyr Arg Arg Val Glu Thr Gly Asn Asp Arg Ile Ile
            560                 565                 570 gca ttc acc cgc acc ctg gac gaa cgc acc atc ctg acc gtg atc aac      1777
Ala Phe Thr Arg Thr Leu Asp Glu Arg Thr Ile Leu Thr Val Ile Asn
        575                 580                 585 ctg tcc cca acc cag gca gca cca gca ggc gaa ctg gaa acc atg cca      1825
Leu Ser Pro Thr Gln Ala Ala Pro Ala Gly Glu Leu Glu Thr Met Pro
590                 595                 600 gac ggc acc atc ttg atc gca aac acc gat gac cca gtg ggc aac ctc      1873
Asp Gly Thr Ile Leu Ile Ala Asn Thr Asp Asp Pro Val Gly Asn Leu
605                 610                 615                 620 aag acc acc ggc acc ctg ggt cca tgg gaa gca ttc gca atg gaa acc      1921
Lys Thr Thr Gly Thr Leu Gly Pro Trp Glu Ala Phe Ala Met Glu Thr
                625                 630                 635 gat cca gaa taagcggccg ctgttagccc ggggtgtgcc tcggcgcacc               1970
Asp Pro Glu ccgggctatt tttctagagg atcc                                           1994

<210> SEQ ID NO 22
<211> LENGTH: 639
<212> TYPE: PRT
<213> ORGANISM: artificial sequence
<220> FEATURE:
<223> OTHER INFORMATION: Synthetic Construct

<400> SEQUENCE: 22

Met Gln Ile Asn Arg Arg Gly Phe Leu Lys Ala Thr Thr Gly Leu Ala
1               5                   10                  15

Thr Ile Gly Ala Ala Ser Met Phe Met Pro Lys Ala Asn Ala Leu Gly
            20                  25                  30

Ala Met Thr Ser Thr Ser Phe Asn Arg Glu Pro Leu Pro Asp Ala Val
        35                  40                  45

Arg Thr Asn Gly Ala Thr Pro Asn Pro Trp Trp Ser Asn Ala Val Val
    50                  55                  60

Tyr Gln Ile Tyr Pro Arg Ser Phe Gln Asp Thr Asn Gly Asp Gly Leu
65                  70                  75                  80

Gly Asp Leu Lys Gly Ile Thr Ser Arg Leu Asp Tyr Leu Ala Asp Leu
                85                  90                  95

Gly Val Asp Val Leu Trp Leu Ser Pro Val Tyr Arg Ser Pro Gln Asp
            100                 105                 110
```

-continued

Asp Asn Gly Tyr Asp Ile Ser Asp Tyr Arg Asp Ile Asp Pro Leu Phe
            115                 120                 125

Gly Thr Leu Asp Asp Met Asp Glu Leu Leu Ala Glu Ala His Lys Arg
    130                 135                 140

Gly Leu Lys Ile Val Met Asp Leu Val Val Asn His Thr Ser Asp Glu
145                 150                 155                 160

His Ala Trp Phe Glu Ala Ser Lys Asp Lys Asp Asp Pro His Ala Asp
                165                 170                 175

Trp Tyr Trp Trp Arg Pro Ala Arg Gly His Glu Pro Gly Thr Pro
                180                 185                 190

Gly Ala Glu Pro Asn Gln Trp Gly Ser Tyr Phe Gly Gly Ser Ala Trp
    195                 200                 205

Glu Tyr Ser Pro Glu Arg Gly Glu Tyr Tyr Leu His Gln Phe Ser Lys
    210                 215                 220

Lys Gln Pro Asp Leu Asn Trp Glu Asn Pro Ala Val Arg Arg Ala Val
225                 230                 235                 240

Tyr Asp Met Met Asn Trp Trp Leu Asp Arg Gly Ile Asp Gly Phe Arg
                245                 250                 255

Met Asp Val Ile Thr Leu Ile Ser Lys Arg Thr Asp Pro Asn Gly Arg
                260                 265                 270

Leu Pro Gly Glu Thr Gly Ser Glu Leu Gln Asp Leu Pro Val Gly Glu
            275                 280                 285

Glu Gly Tyr Ser Ser Pro Asn Pro Phe Cys Ala Asp Gly Pro Arg Gln
            290                 295                 300

Asp Glu Phe Leu Ala Glu Met Arg Arg Glu Val Phe Asp Gly Arg Asp
305                 310                 315                 320

Gly Phe Leu Thr Val Gly Glu Ala Pro Gly Ile Thr Ala Glu Arg Asn
                325                 330                 335

Glu His Ile Thr Asp Pro Ala Asn Gly Glu Leu Asp Met Leu Phe Leu
            340                 345                 350

Phe Glu His Met Gly Val Asp Gln Thr Pro Glu Ser Lys Trp Asp Asp
            355                 360                 365

Lys Pro Trp Thr Pro Ala Asp Leu Glu Thr Lys Leu Ala Glu Gln Gln
    370                 375                 380

Asp Ala Ile Ala Arg Arg Gly Trp Ala Ser Leu Phe Leu Asp Asn His
385                 390                 395                 400

Asp Gln Pro Arg Val Val Ser Arg Trp Gly Asp Asp Thr Ser Lys Thr
                405                 410                 415

Gly Arg Ile Arg Ser Ala Lys Ala Leu Ala Leu Leu His Met His
                420                 425                 430

Arg Gly Thr Pro Tyr Val Tyr Gln Gly Glu Glu Leu Gly Met Thr Asn
            435                 440                 445

Ala His Phe Thr Ser Leu Asp Gln Tyr Arg Asp Leu Glu Ser Ile Asn
            450                 455                 460

Ala Tyr His Gln Arg Val Glu Glu Thr Gly Ile Arg Thr Ser Glu Thr
465                 470                 475                 480

Met Met Arg Ser Leu Ala Arg Tyr Gly Arg Asp Asn Ala Arg Thr Pro
                485                 490                 495

Met Gln Trp Asp Asp Ser Thr Tyr Ala Gly Phe Thr Met Pro Asp Ala
                500                 505                 510

Pro Val Glu Pro Trp Ile Ala Val Asn Pro Asn His Thr Glu Ile Asn
            515                 520                 525

Ala Ala Asp Glu Thr Asp Asp Pro Asp Ser Val Tyr Ser Phe His Lys

```
            530             535             540
Arg Leu Ile Ala Leu Arg His Thr Asp Pro Val Val Ala Ala Gly Asp
545                 550                 555                 560

Tyr Arg Arg Val Glu Thr Gly Asn Asp Arg Ile Ile Ala Phe Thr Arg
                565                 570                 575

Thr Leu Asp Glu Arg Thr Ile Leu Thr Val Ile Asn Leu Ser Pro Thr
            580                 585                 590

Gln Ala Ala Pro Ala Gly Glu Leu Glu Thr Met Pro Asp Gly Thr Ile
        595                 600                 605

Leu Ile Ala Asn Thr Asp Asp Pro Val Gly Asn Leu Lys Thr Thr Gly
    610                 615                 620

Thr Leu Gly Pro Trp Glu Ala Phe Ala Met Glu Thr Asp Pro Glu
625                 630                 635

<210> SEQ ID NO 23
<211> LENGTH: 2006
<212> TYPE: DNA
<213> ORGANISM: artificial sequence
<220> FEATURE:
<223> OTHER INFORMATION: gene fusion tat-agl1_cuo
<220> FEATURE:
<221> NAME/KEY: misc_feature
<222> LOCATION: (1)..(6)
<223> OTHER INFORMATION: PstI restriction site
<220> FEATURE:
<221> NAME/KEY: misc_feature
<222> LOCATION: (7)..(13)
<223> OTHER INFORMATION: SexAI restriction site
<220> FEATURE:
<221> NAME/KEY: CDS
<222> LOCATION: (14)..(1942)
<223> OTHER INFORMATION: sequence coding for fusion polypeptide
      Tat-'Agl1
<220> FEATURE:
<221> NAME/KEY: misc_signal
<222> LOCATION: (14)..(112)
<223> OTHER INFORMATION: 5' sequence of cg0955 encoding Tat-signal
      peptide of cg0955
<220> FEATURE:
<221> NAME/KEY: misc_feature
<222> LOCATION: (14)..(114)
<223> OTHER INFORMATION: 5' sequence of cg0955
<220> FEATURE:
<221> NAME/KEY: misc_feature
<222> LOCATION: (115)..(115)
<223> OTHER INFORMATION: nucleobase adenine
<220> FEATURE:
<221> NAME/KEY: misc_feature
<222> LOCATION: (115)..(120)
<223> OTHER INFORMATION: SpeI restriction site
<220> FEATURE:
<221> NAME/KEY: misc_feature
<222> LOCATION: (121)..(121)
<223> OTHER INFORMATION: nucleobase adenine
<220> FEATURE:
<221> NAME/KEY: misc_feature
<222> LOCATION: (122)..(1942)
<223> OTHER INFORMATION: agl1_cuo
<220> FEATURE:
<221> NAME/KEY: misc_feature
<222> LOCATION: (1943)..(1945)
<223> OTHER INFORMATION: stop codon
<220> FEATURE:
<221> NAME/KEY: misc_feature
<222> LOCATION: (1946)..(1953)
<223> OTHER INFORMATION: NotI restriction site
<220> FEATURE:
<221> NAME/KEY: misc_feature
<222> LOCATION: (1957)..(1992)
<223> OTHER INFORMATION: terminator sequence Tgap*
<220> FEATURE:
<221> NAME/KEY: misc_feature
```

```
<222> LOCATION: (1995)..(2000)
<223> OTHER INFORMATION: XbaI restriction site
<220> FEATURE:
<221> NAME/KEY: misc_feature
<222> LOCATION: (2001)..(2006)
<223> OTHER INFORMATION: BamHI restriction site

<400> SEQUENCE: 23
```

| | | | | | | | | | | | | | | |
|---|---|---|---|---|---|---|---|---|---|---|---|---|---|---|
| ctgcagacca | ggt | atg | caa | ata | aac | cgc | cga | ggc | ttc | tta | aaa | gcc | acc | 49 |
| | | Met | Gln | Ile | Asn | Arg | Arg | Gly | Phe | Leu | Lys | Ala | Thr | |
| | | 1 | | 5 | | | | | | 10 | | | | |
| aca | gga | ctt | gcc | act | atc | ggc | gct | gcc | agc | atg | ttt | atg | cca | aag | gcc | 97 |
| Thr | Gly | Leu | Ala | Thr | Ile | Gly | Ala | Ala | Ser | Met | Phe | Met | Pro | Lys | Ala | |
| | | 15 | | | | | 20 | | | | | 25 | | | | |
| aac | gcc | ctt | gga | gca | ata | cta | gta | atg | atg | acc | acc | ttc | aac | cgt | gca | 145 |
| Asn | Ala | Leu | Gly | Ala | Ile | Leu | Val | Met | Met | Thr | Thr | Phe | Asn | Arg | Ala | |
| | 30 | | | | | 35 | | | | | 40 | | | | | |
| atc | atc | cca | gat | gca | atc | cgc | acc | aac | ggt | gca | acc | cca | aac | cca | tgg | 193 |
| Ile | Ile | Pro | Asp | Ala | Ile | Arg | Thr | Asn | Gly | Ala | Thr | Pro | Asn | Pro | Trp | |
| 45 | | | | | 50 | | | | | 55 | | | | | 60 | |
| tgg | tcc | aac | gca | gtg | gtg | tac | cag | atc | tac | cca | cgc | tcc | ttc | cag | gat | 241 |
| Trp | Ser | Asn | Ala | Val | Val | Tyr | Gln | Ile | Tyr | Pro | Arg | Ser | Phe | Gln | Asp | |
| | | | | 65 | | | | | 70 | | | | | 75 | | |
| acc | aac | ggc | gac | ggc | ttc | ggc | gat | ctg | aag | ggc | atc | acc | tcc | cgc | ttg | 289 |
| Thr | Asn | Gly | Asp | Gly | Phe | Gly | Asp | Leu | Lys | Gly | Ile | Thr | Ser | Arg | Leu | |
| | | | 80 | | | | | 85 | | | | | 90 | | | |
| gat | tac | ctg | gca | gat | ctg | ggc | gtg | gat | gtg | ctg | tgg | ctg | tcc | cca | gtg | 337 |
| Asp | Tyr | Leu | Ala | Asp | Leu | Gly | Val | Asp | Val | Leu | Trp | Leu | Ser | Pro | Val | |
| | | 95 | | | | | 100 | | | | | 105 | | | | |
| tac | aag | tcc | cca | cag | gat | gat | aac | ggc | tac | gat | atc | tcc | gat | tac | cag | 385 |
| Tyr | Lys | Ser | Pro | Gln | Asp | Asp | Asn | Gly | Tyr | Asp | Ile | Ser | Asp | Tyr | Gln | |
| | 110 | | | | | 115 | | | | | 120 | | | | | |
| gat | atc | gat | cca | ctg | ttc | ggc | acc | ctg | gat | gat | atg | gat | gaa | ctg | ctg | 433 |
| Asp | Ile | Asp | Pro | Leu | Phe | Gly | Thr | Leu | Asp | Asp | Met | Asp | Glu | Leu | Leu | |
| 125 | | | | | 130 | | | | | 135 | | | | | 140 | |
| gca | gag | gca | cac | aag | cgt | ggc | ctg | aag | gtg | gtg | atg | gat | ctg | gtg | gtg | 481 |
| Ala | Glu | Ala | His | Lys | Arg | Gly | Leu | Lys | Val | Val | Met | Asp | Leu | Val | Val | |
| | | | | 145 | | | | | 150 | | | | | 155 | | |
| aac | cac | acc | tcc | gat | gaa | cac | gca | tgg | ttc | gaa | gca | tcc | aag | aac | aag | 529 |
| Asn | His | Thr | Ser | Asp | Glu | His | Ala | Trp | Phe | Glu | Ala | Ser | Lys | Asn | Lys | |
| | | | 160 | | | | | 165 | | | | | 170 | | | |
| gat | gat | gaa | cac | gcc | gat | tgg | tac | tgg | tgg | cgt | cca | gca | cgc | cca | ggc | 577 |
| Asp | Asp | Glu | His | Ala | Asp | Trp | Tyr | Trp | Trp | Arg | Pro | Ala | Arg | Pro | Gly | |
| | | 175 | | | | | 180 | | | | | 185 | | | | |
| acc | acc | cca | ggt | gaa | cca | ggc | tcc | gaa | cca | aac | cag | tgg | ggc | tcc | tac | 625 |
| Thr | Thr | Pro | Gly | Glu | Pro | Gly | Ser | Glu | Pro | Asn | Gln | Trp | Gly | Ser | Tyr | |
| | 190 | | | | | 195 | | | | | 200 | | | | | |
| ttc | ggt | ggc | tcc | gca | tgg | gaa | tac | tgc | cca | gaa | cgc | ggt | gaa | tac | tac | 673 |
| Phe | Gly | Gly | Ser | Ala | Trp | Glu | Tyr | Cys | Pro | Glu | Arg | Gly | Glu | Tyr | Tyr | |
| 205 | | | | | 210 | | | | | 215 | | | | | 220 | |
| ctg | cac | cag | ttc | tcc | aag | aag | cag | cca | gat | ctc | aac | tgg | gaa | aac | cca | 721 |
| Leu | His | Gln | Phe | Ser | Lys | Lys | Gln | Pro | Asp | Leu | Asn | Trp | Glu | Asn | Pro | |
| | | | | 225 | | | | | 230 | | | | | 235 | | |
| gca | gtg | cgt | cgc | gca | gtg | tac | gat | atg | atg | aac | tgg | tgg | ttg | gat | cgc | 769 |
| Ala | Val | Arg | Arg | Ala | Val | Tyr | Asp | Met | Met | Asn | Trp | Trp | Leu | Asp | Arg | |
| | | | 240 | | | | | 245 | | | | | 250 | | | |
| ggt | atc | gat | ggc | ttc | cgc | atg | gat | gtg | atc | acc | ctg | atc | tcc | aag | cgc | 817 |
| Gly | Ile | Asp | Gly | Phe | Arg | Met | Asp | Val | Ile | Thr | Leu | Ile | Ser | Lys | Arg | |
| | | 255 | | | | | 260 | | | | | 265 | | | | |
| acc | gat | gca | aac | ggt | cgc | ctg | cca | ggt | gaa | tac | ggc | tcc | gaa | ctg | gat | 865 |
| Thr | Asp | Ala | Asn | Gly | Arg | Leu | Pro | Gly | Glu | Tyr | Gly | Ser | Glu | Leu | Asp | |

-continued

```
            270                 275                 280
gat ctg cca gtg ggc gaa gaa ggc tac tcc aac cca aac ccg ttc tgc      913
Asp Leu Pro Val Gly Glu Glu Gly Tyr Ser Asn Pro Asn Pro Phe Cys
285                 290                 295                 300 gca gat ggc cct cgc cag gat gaa ttc ctg aaa gaa atg cgt cgc gaa      961
Ala Asp Gly Pro Arg Gln Asp Glu Phe Leu Lys Glu Met Arg Arg Glu
                305                 310                 315 gtg ttc gca ggt cgc gaa ggc ttc ctg acc gtg ggc gaa gca cca ggc     1009
Val Phe Ala Gly Arg Glu Gly Phe Leu Thr Val Gly Glu Ala Pro Gly
            320                 325                 330 atc acc cct gtg cgc aac gaa cac atc acc aac cca gca aac ggc gaa     1057
Ile Thr Pro Val Arg Asn Glu His Ile Thr Asn Pro Ala Asn Gly Glu
335                 340                 345 ctg gat atg ctg ttc ctg ttc gat cac gtg gat ttc gat tgc gac ggc     1105
Leu Asp Met Leu Phe Leu Phe Asp His Val Asp Phe Asp Cys Asp Gly
        350                 355                 360 gtg aag tgg aag cca ctg cca ctg gat ctg cca ggc ttc aag cgc atc     1153
Val Lys Trp Lys Pro Leu Pro Leu Asp Leu Pro Gly Phe Lys Arg Ile
365                 370                 375                 380 atg gca ggc tac cag acc gca gtg gaa aac gtg ggc tgg gca tcc ctg     1201
Met Ala Gly Tyr Gln Thr Ala Val Glu Asn Val Gly Trp Ala Ser Leu
                385                 390                 395 ttc acc ggc aac cac gat cag cca cgc gtg gtg tcc cgc tgg ggt gat     1249
Phe Thr Gly Asn His Asp Gln Pro Arg Val Val Ser Arg Trp Gly Asp
            400                 405                 410 gat tcc tcc gaa gaa tcc cgt gtg cgc tcc gca aag gca ctg ggc ctg     1297
Asp Ser Ser Glu Glu Ser Arg Val Arg Ser Ala Lys Ala Leu Gly Leu
                415                 420                 425 atg ctg cac atg cac cgt ggc acc cca tac gtg tac cag ggc gaa gaa     1345
Met Leu His Met His Arg Gly Thr Pro Tyr Val Tyr Gln Gly Glu Glu
430                 435                 440 ctg ggc atg acc aac gca cac ttc acc tcc ctg gat cag tac cgc gat     1393
Leu Gly Met Thr Asn Ala His Phe Thr Ser Leu Asp Gln Tyr Arg Asp
445                 450                 455                 460 ctg gaa tcc ctg aac gca tac cgc cag cgc gtg gaa gag gca aag gtg     1441
Leu Glu Ser Leu Asn Ala Tyr Arg Gln Arg Val Glu Glu Ala Lys Val
                465                 470                 475 cag tcc cca gaa tcc atg ctg gca ggt atc gca gca cgc ggt cgc gat     1489
Gln Ser Pro Glu Ser Met Leu Ala Gly Ile Ala Ala Arg Gly Arg Asp
            480                 485                 490 aac tcc cgc acc cca atg cag tgg gat ggc tcc gca tac gca ggc ttc     1537
Asn Ser Arg Thr Pro Met Gln Trp Asp Gly Ser Ala Tyr Ala Gly Phe
                495                 500                 505 acc gca cca gat gca gca acc gaa cca tgg atc tcc gtg aac cca aac     1585
Thr Ala Pro Asp Ala Ala Thr Glu Pro Trp Ile Ser Val Asn Pro Asn
510                 515                 520 cac gca gaa atc aac gca gca ggc gaa ttc gat gat cca gat tcc gtg     1633
His Ala Glu Ile Asn Ala Ala Gly Glu Phe Asp Asp Pro Asp Ser Val
525                 530                 535                 540 tac gca ttc tac aag aag ctg atc gca ctg cgc cac aac tcc tcc atc     1681
Tyr Ala Phe Tyr Lys Lys Leu Ile Ala Leu Arg His Asn Ser Ser Ile
                545                 550                 555 gtg gca gct ggc gaa tgg cag ctg atc gat gca gat gat gca cac gtg     1729
Val Ala Ala Gly Glu Trp Gln Leu Ile Asp Ala Asp Asp Ala His Val
            560                 565                 570 tac gcc ttc acc cgc acc ctg ggc aac gaa cgc ctg ctc gtg gtg gtc     1777
Tyr Ala Phe Thr Arg Thr Leu Gly Asn Glu Arg Leu Leu Val Val Val
                575                 580                 585 aac ctg tcc ggt cgc acc gtg gat ctg cca cgc gaa tcc acc gaa ctg     1825
Asn Leu Ser Gly Arg Thr Val Asp Leu Pro Arg Glu Ser Thr Glu Leu
```

```
                Asn Leu Ser Gly Arg Thr Val Asp Leu Pro Arg Glu Ser Thr Glu Leu
                    590                 595                 600 atc gca ggc ggt gtg acc gaa cca gat atc atc ctg tcc acc tac gat         1873
Ile Ala Gly Gly Val Thr Glu Pro Asp Ile Ile Leu Ser Thr Tyr Asp
605                 610                 615                 620 gca cca cac acc gtg gtg tcc ctg gca aac cgc gaa ctc gat cca tgg         1921
Ala Pro His Thr Val Val Ser Leu Ala Asn Arg Glu Leu Asp Pro Trp
                625                 630                 635 gaa gca gca gca gtg cag ctg taagcggccg ctgttagccc ggggtgtgcc            1972
Glu Ala Ala Ala Val Gln Leu
                640 tcggcgcacc ccgggctatt tttctagagg atcc                                   2006

<210> SEQ ID NO 24
<211> LENGTH: 643
<212> TYPE: PRT
<213> ORGANISM: artificial sequence
<220> FEATURE:
<223> OTHER INFORMATION: Synthetic Construct

<400> SEQUENCE: 24

Met Gln Ile Asn Arg Arg Gly Phe Leu Lys Ala Thr Thr Gly Leu Ala
1               5                   10                  15

Thr Ile Gly Ala Ala Ser Met Phe Met Pro Lys Ala Asn Ala Leu Gly
            20                  25                  30

Ala Ile Leu Val Met Met Thr Thr Phe Asn Arg Ala Ile Ile Pro Asp
        35                  40                  45

Ala Ile Arg Thr Asn Gly Ala Thr Pro Asn Pro Trp Trp Ser Asn Ala
    50                  55                  60

Val Val Tyr Gln Ile Tyr Pro Arg Ser Phe Gln Asp Thr Asn Gly Asp
65                  70                  75                  80

Gly Phe Gly Asp Leu Lys Gly Ile Thr Ser Arg Leu Asp Tyr Leu Ala
                85                  90                  95

Asp Leu Gly Val Asp Val Leu Trp Leu Ser Pro Val Tyr Lys Ser Pro
            100                 105                 110

Gln Asp Asp Asn Gly Tyr Asp Ile Ser Asp Tyr Gln Asp Ile Asp Pro
        115                 120                 125

Leu Phe Gly Thr Leu Asp Asp Met Asp Glu Leu Leu Ala Glu Ala His
    130                 135                 140

Lys Arg Gly Leu Lys Val Val Met Asp Leu Val Val Asn His Thr Ser
145                 150                 155                 160

Asp Glu His Ala Trp Phe Glu Ala Ser Lys Asn Lys Asp Asp Glu His
                165                 170                 175

Ala Asp Trp Tyr Trp Trp Arg Pro Ala Arg Pro Gly Thr Thr Pro Gly
            180                 185                 190

Glu Pro Gly Ser Glu Pro Asn Gln Trp Gly Ser Tyr Phe Gly Gly Ser
        195                 200                 205

Ala Trp Glu Tyr Cys Pro Glu Arg Gly Glu Tyr Tyr Leu His Gln Phe
    210                 215                 220

Ser Lys Lys Gln Pro Asp Leu Asn Trp Glu Asn Pro Ala Val Arg Arg
225                 230                 235                 240

Ala Val Tyr Asp Met Met Asn Trp Trp Leu Asp Arg Gly Ile Asp Gly
                245                 250                 255

Phe Arg Met Asp Val Ile Thr Leu Ile Ser Lys Arg Thr Asp Ala Asn
            260                 265                 270

Gly Arg Leu Pro Gly Glu Tyr Gly Ser Glu Leu Asp Asp Leu Pro Val
```

```
            275                 280                 285
Gly Glu Glu Gly Tyr Ser Asn Pro Asn Pro Phe Cys Ala Asp Gly Pro
290                 295                 300

Arg Gln Asp Glu Phe Leu Lys Glu Met Arg Arg Val Phe Ala Gly
305                 310                 315                 320

Arg Glu Gly Phe Leu Thr Val Gly Glu Ala Pro Gly Ile Thr Pro Val
                325                 330                 335

Arg Asn Glu His Ile Thr Asn Pro Ala Asn Gly Glu Leu Asp Met Leu
            340                 345                 350

Phe Leu Phe Asp His Val Asp Phe Asp Cys Asp Gly Val Lys Trp Lys
                355                 360                 365

Pro Leu Pro Leu Asp Leu Pro Gly Phe Lys Arg Ile Met Ala Gly Tyr
        370                 375                 380

Gln Thr Ala Val Glu Asn Val Gly Trp Ala Ser Leu Phe Thr Gly Asn
385                 390                 395                 400

His Asp Gln Pro Arg Val Val Ser Arg Trp Gly Asp Ser Ser Glu
                405                 410                 415

Glu Ser Arg Val Arg Ser Ala Lys Ala Leu Gly Leu Met Leu His Met
                420                 425                 430

His Arg Gly Thr Pro Tyr Val Tyr Gln Gly Glu Glu Leu Gly Met Thr
            435                 440                 445

Asn Ala His Phe Thr Ser Leu Asp Gln Tyr Arg Asp Leu Glu Ser Leu
        450                 455                 460

Asn Ala Tyr Arg Gln Arg Val Glu Glu Ala Lys Val Gln Ser Pro Glu
465                 470                 475                 480

Ser Met Leu Ala Gly Ile Ala Ala Arg Gly Arg Asp Asn Ser Arg Thr
                485                 490                 495

Pro Met Gln Trp Asp Gly Ser Ala Tyr Ala Gly Phe Thr Ala Pro Asp
                500                 505                 510

Ala Ala Thr Glu Pro Trp Ile Ser Val Asn Pro Asn His Ala Glu Ile
            515                 520                 525

Asn Ala Ala Gly Glu Phe Asp Asp Pro Asp Ser Val Tyr Ala Phe Tyr
530                 535                 540

Lys Lys Leu Ile Ala Leu Arg His Asn Ser Ser Ile Val Ala Ala Gly
545                 550                 555                 560

Glu Trp Gln Leu Ile Asp Ala Asp Ala His Val Tyr Ala Phe Thr
                565                 570                 575

Arg Thr Leu Gly Asn Glu Arg Leu Leu Val Val Asn Leu Ser Gly
                580                 585                 590

Arg Thr Val Asp Leu Pro Arg Glu Ser Thr Glu Leu Ile Ala Gly Gly
                595                 600                 605

Val Thr Glu Pro Asp Ile Ile Leu Ser Thr Tyr Asp Ala Pro His Thr
            610                 615                 620

Val Val Ser Leu Ala Asn Arg Glu Leu Asp Pro Trp Glu Ala Ala Ala
625                 630                 635                 640

Val Gln Leu

<210> SEQ ID NO 25
<211> LENGTH: 1949
<212> TYPE: DNA
<213> ORGANISM: artificial sequence
<220> FEATURE:
<223> OTHER INFORMATION: gene fusion tat-'IMA1_cuo
<220> FEATURE:
<221> NAME/KEY: misc_feature
```

```
<222> LOCATION: (1)..(6)
<223> OTHER INFORMATION: PstI restriction site
<220> FEATURE:
<221> NAME/KEY: misc_feature
<222> LOCATION: (7)..(13)
<223> OTHER INFORMATION: SexAI restriction site
<220> FEATURE:
<221> NAME/KEY: CDS
<222> LOCATION: (14)..(1885)
<223> OTHER INFORMATION: sequence coding for fusion polypeptide
      Tat-'IMA1
<220> FEATURE:
<221> NAME/KEY: misc_signal
<222> LOCATION: (14)..(112)
<223> OTHER INFORMATION: 5' sequence of cg0955 encoding Tat-signal
      peptide of cg0955
<220> FEATURE:
<221> NAME/KEY: misc_feature
<222> LOCATION: (14)..(114)
<223> OTHER INFORMATION: 5' sequence of cg0955
<220> FEATURE:
<221> NAME/KEY: misc_feature
<222> LOCATION: (115)..(115)
<223> OTHER INFORMATION: nucleobase adenine
<220> FEATURE:
<221> NAME/KEY: misc_feature
<222> LOCATION: (115)..(120)
<223> OTHER INFORMATION: SpeI restriction site
<220> FEATURE:
<221> NAME/KEY: misc_feature
<222> LOCATION: (121)..(121)
<223> OTHER INFORMATION: nucleobase adenine
<220> FEATURE:
<221> NAME/KEY: misc_feature
<222> LOCATION: (122)..(1885)
<223> OTHER INFORMATION: 'IMA1_cuo
<220> FEATURE:
<221> NAME/KEY: misc_feature
<222> LOCATION: (1886)..(1888)
<223> OTHER INFORMATION: stop codon
<220> FEATURE:
<221> NAME/KEY: misc_feature
<222> LOCATION: (1889)..(1896)
<223> OTHER INFORMATION: NotI restriction site
<220> FEATURE:
<221> NAME/KEY: misc_feature
<222> LOCATION: (1900)..(1935)
<223> OTHER INFORMATION: terminator sequence Tgap*
<220> FEATURE:
<221> NAME/KEY: misc_feature
<222> LOCATION: (1938)..(1943)
<223> OTHER INFORMATION: XbaI restriction site
<220> FEATURE:
<221> NAME/KEY: misc_feature
<222> LOCATION: (1944)..(1949)
<223> OTHER INFORMATION: BamHI restriction site

<400> SEQUENCE: 25
ctgcagacct ggt atg caa ata aac cgc cga ggc ttc tta aaa gcc acc        49
           Met Gln Ile Asn Arg Arg Gly Phe Leu Lys Ala Thr
            1               5                  10 aca gga ctt gcc act atc ggc gct gcc agc atg ttt atg cca aag gcc        97
Thr Gly Leu Ala Thr Ile Gly Ala Ala Ser Met Phe Met Pro Lys Ala
        15                  20                  25 aac gcc ctt gga gca ata cta gta acc atc tcc tcc gca cac cca gaa       145
Asn Ala Leu Gly Ala Ile Leu Val Thr Ile Ser Ser Ala His Pro Glu
    30                  35                  40 acc gaa cca aag tgg tgg aaa gaa gca acc ttc tac cag atc tac cca       193
Thr Glu Pro Lys Trp Trp Lys Glu Ala Thr Phe Tyr Gln Ile Tyr Pro
45                  50                  55                  60 gca tcc ttc aag gat tcc aac gat gat ggc tgg ggt gat atg aag ggt       241
Ala Ser Phe Lys Asp Ser Asn Asp Asp Gly Trp Gly Asp Met Lys Gly
                65                  70                  75
```

```
atc gca tcc aag ctg gaa tac atc aaa gaa ctg ggt gca gat gca atc      289
Ile Ala Ser Lys Leu Glu Tyr Ile Lys Glu Leu Gly Ala Asp Ala Ile
            80                  85                  90 tgg atc tcc cca ttc tac gat tcc cca cag gat gat atg ggc tac gat      337
Trp Ile Ser Pro Phe Tyr Asp Ser Pro Gln Asp Asp Met Gly Tyr Asp
        95                 100                 105 atc gca aac tac gaa aag gtg tgg cca acc tac ggc acc aac gaa gat      385
Ile Ala Asn Tyr Glu Lys Val Trp Pro Thr Tyr Gly Thr Asn Glu Asp
    110                 115                 120 tgc ttc gca ctg atc gaa aag acc cac aag ctg ggc atg aag ttc atc      433
Cys Phe Ala Leu Ile Glu Lys Thr His Lys Leu Gly Met Lys Phe Ile
125                 130                 135                 140 acc gat ctg gtg atc aac cac tgc tcc tcc gaa cac gaa tgg ttc aaa      481
Thr Asp Leu Val Ile Asn His Cys Ser Ser Glu His Glu Trp Phe Lys
                145                 150                 155 gaa tcc cgc tcc tcc aag acc aac cca aag cgc gat tgg ttc ttc tgg      529
Glu Ser Arg Ser Ser Lys Thr Asn Pro Lys Arg Asp Trp Phe Phe Trp
            160                 165                 170 cgt cca cca aag ggc tac gat gca gaa ggc aag cca atc cca cca aac      577
Arg Pro Pro Lys Gly Tyr Asp Ala Glu Gly Lys Pro Ile Pro Pro Asn
        175                 180                 185 aac tgg aag tcc tac ttc ggt ggc tcc gca tgg acc ttc gat gaa aag      625
Asn Trp Lys Ser Tyr Phe Gly Gly Ser Ala Trp Thr Phe Asp Glu Lys
    190                 195                 200 acc caa gaa ttc tac ctg cgc ctg ttc tgc tcc acc cag cca gat ctc      673
Thr Gln Glu Phe Tyr Leu Arg Leu Phe Cys Ser Thr Gln Pro Asp Leu
205                 210                 215                 220 aac tgg gaa aac gag gat tgc cgc aag gca atc tac gaa tcc gca gtg      721
Asn Trp Glu Asn Glu Asp Cys Arg Lys Ala Ile Tyr Glu Ser Ala Val
                225                 230                 235 ggc tac tgg ctg gat cac ggc gtg gat ggc ttc cgc atc gat gtg ggc      769
Gly Tyr Trp Leu Asp His Gly Val Asp Gly Phe Arg Ile Asp Val Gly
            240                 245                 250 tcc ctg tac tcc aag gtg gtg ggc ctg cca gat gca cca gtg gtg gat      817
Ser Leu Tyr Ser Lys Val Val Gly Leu Pro Asp Ala Pro Val Val Asp
        255                 260                 265 aag aac tcc acc tgg cag tcc tcc gat cca tac acc ctg aac ggt cca      865
Lys Asn Ser Thr Trp Gln Ser Ser Asp Pro Tyr Thr Leu Asn Gly Pro
    270                 275                 280 cgc atc cac gaa ttc cac caa gaa atg aac cag ttt atc cgc aac cgc      913
Arg Ile His Glu Phe His Gln Glu Met Asn Gln Phe Ile Arg Asn Arg
285                 290                 295                 300 gtg aag gat ggt cgc gaa atc atg acc gtg ggc gaa atg cag cac gca      961
Val Lys Asp Gly Arg Glu Ile Met Thr Val Gly Glu Met Gln His Ala
                305                 310                 315 tcc gat gaa acc aag cgc ctg tac acc tcc gca tcc cgt cac gaa ctg     1009
Ser Asp Glu Thr Lys Arg Leu Tyr Thr Ser Ala Ser Arg His Glu Leu
            320                 325                 330 tcc gaa ctg ttc aac ttc tcc cac acc gat gtg ggc acc tcc cca ctg     1057
Ser Glu Leu Phe Asn Phe Ser His Thr Asp Val Gly Thr Ser Pro Leu
        335                 340                 345 ttc cgc tac aac ctc gtg cca ttc gaa ctg aag gat tgg aag atc gca     1105
Phe Arg Tyr Asn Leu Val Pro Phe Glu Leu Lys Asp Trp Lys Ile Ala
    350                 355                 360 ctg gca gaa ctc ttc cgc tac atc aac ggc acc gat tgc tgg tcc acc     1153
Leu Ala Glu Leu Phe Arg Tyr Ile Asn Gly Thr Asp Cys Trp Ser Thr
365                 370                 375                 380 atc tac ctg gaa aac cac gat cag cca cgc tcc atc acc cgc ttc ggc     1201
Ile Tyr Leu Glu Asn His Asp Gln Pro Arg Ser Ile Thr Arg Phe Gly
                385                 390                 395
```

```
gac gat tcc cca aag aac cgc gtg atc tcc ggc aag ctg ctg tcc gtg   1249
Asp Asp Ser Pro Lys Asn Arg Val Ile Ser Gly Lys Leu Leu Ser Val
            400                 405                 410 ctg ctg tcc gca ctg acc ggc acc ctg tac gtg tac cag ggc caa gaa   1297
Leu Leu Ser Ala Leu Thr Gly Thr Leu Tyr Val Tyr Gln Gly Gln Glu
            415                 420                 425 ctg ggc cag atc aac ttc aag aac tgg cca gtg gaa aag tac gaa gat   1345
Leu Gly Gln Ile Asn Phe Lys Asn Trp Pro Val Glu Lys Tyr Glu Asp
        430                 435                 440 gtg gaa atc cgc aac aac tac aac gca atc aaa gaa gaa cac ggc gaa   1393
Val Glu Ile Arg Asn Asn Tyr Asn Ala Ile Lys Glu Glu His Gly Glu
445                 450                 455                 460 aac tcc gaa gag atg aag aag ttt ctg gaa gca atc gca ctg atc tcc   1441
Asn Ser Glu Glu Met Lys Lys Phe Leu Glu Ala Ile Ala Leu Ile Ser
                465                 470                 475 cgt gat cac gca cgc acc cca atg cag tgg tcc cgt gaa gaa cca aac   1489
Arg Asp His Ala Arg Thr Pro Met Gln Trp Ser Arg Glu Glu Pro Asn
            480                 485                 490 gca ggc ttc tcc ggt cca tcc gca aag cca tgg ttc tac ctg aac gat   1537
Ala Gly Phe Ser Gly Pro Ser Ala Lys Pro Trp Phe Tyr Leu Asn Asp
            495                 500                 505 tcc ttc cgc gaa ggc atc aac gtg gaa gat gaa atc aag gac cca aac   1585
Ser Phe Arg Glu Gly Ile Asn Val Glu Asp Glu Ile Lys Asp Pro Asn
        510                 515                 520 tcc gtg ctg aac ttc tgg aaa gaa gcc ctg aag ttc cgc aag gca cac   1633
Ser Val Leu Asn Phe Trp Lys Glu Ala Leu Lys Phe Arg Lys Ala His
525                 530                 535                 540 aag gat atc acc gtg tac ggc tac gat ttc gaa ttc atc gat ctg gat   1681
Lys Asp Ile Thr Val Tyr Gly Tyr Asp Phe Glu Phe Ile Asp Leu Asp
                545                 550                 555 aac aaa aag ctg ttc tcc ttc acc aag aag tac aac aac aag acc ctg   1729
Asn Lys Lys Leu Phe Ser Phe Thr Lys Lys Tyr Asn Asn Lys Thr Leu
            560                 565                 570 ttc gca gcc ctg aac ttc tcc tcc gat gca acc gat ttc aag atc cca   1777
Phe Ala Ala Leu Asn Phe Ser Ser Asp Ala Thr Asp Phe Lys Ile Pro
            575                 580                 585 aac gat gat tcc tcc ttc aag ctg gaa ttc ggc aac tac cca aag aaa   1825
Asn Asp Asp Ser Ser Phe Lys Leu Glu Phe Gly Asn Tyr Pro Lys Lys
590                 595                 600 gaa gtg gac gca tcc tcc cgc acc ctg aag cca tgg gaa ggt cgc atc   1873
Glu Val Asp Ala Ser Ser Arg Thr Leu Lys Pro Trp Glu Gly Arg Ile
605                 610                 615                 620 tac atc tcc gaa taagcggccg ctgttagccc ggggtgtgcc tcggcgcacc        1925
Tyr Ile Ser Glu ccgggctatt tttctagagg atcc                                        1949

<210> SEQ ID NO 26
<211> LENGTH: 624
<212> TYPE: PRT
<213> ORGANISM: artificial sequence
<220> FEATURE:
<223> OTHER INFORMATION: Synthetic Construct

<400> SEQUENCE: 26

Met Gln Ile Asn Arg Arg Gly Phe Leu Lys Ala Thr Gly Leu Ala
1               5                   10                  15

Thr Ile Gly Ala Ala Ser Met Phe Met Pro Lys Ala Asn Ala Leu Gly
            20                  25                  30

Ala Ile Leu Val Thr Ile Ser Ser Ala His Pro Glu Thr Glu Pro Lys
```

-continued

```
                35                  40                  45
Trp Trp Lys Glu Ala Thr Phe Tyr Gln Ile Tyr Pro Ala Ser Phe Lys
 50                  55                  60

Asp Ser Asn Asp Asp Gly Trp Gly Asp Met Lys Gly Ile Ala Ser Lys
 65                  70                  75                  80

Leu Glu Tyr Ile Lys Glu Leu Gly Ala Asp Ala Ile Trp Ile Ser Pro
                     85                  90                  95

Phe Tyr Asp Ser Pro Gln Asp Asp Met Gly Tyr Asp Ile Ala Asn Tyr
             100                 105                 110

Glu Lys Val Trp Pro Thr Tyr Gly Thr Asn Glu Asp Cys Phe Ala Leu
             115                 120                 125

Ile Glu Lys Thr His Lys Leu Gly Met Lys Phe Ile Thr Asp Leu Val
             130                 135                 140

Ile Asn His Cys Ser Ser Glu His Glu Trp Phe Lys Glu Ser Arg Ser
145                 150                 155                 160

Ser Lys Thr Asn Pro Lys Arg Asp Trp Phe Phe Trp Arg Pro Pro Lys
                 165                 170                 175

Gly Tyr Asp Ala Glu Gly Lys Pro Ile Pro Pro Asn Asn Trp Lys Ser
             180                 185                 190

Tyr Phe Gly Gly Ser Ala Trp Thr Phe Asp Glu Lys Thr Gln Glu Phe
             195                 200                 205

Tyr Leu Arg Leu Phe Cys Ser Thr Gln Pro Asp Leu Asn Trp Glu Asn
 210                 215                 220

Glu Asp Cys Arg Lys Ala Ile Tyr Glu Ser Ala Val Gly Tyr Trp Leu
225                 230                 235                 240

Asp His Gly Val Asp Gly Phe Arg Ile Asp Val Gly Ser Leu Tyr Ser
                 245                 250                 255

Lys Val Val Gly Leu Pro Asp Ala Pro Val Val Asp Lys Asn Ser Thr
             260                 265                 270

Trp Gln Ser Ser Asp Pro Tyr Thr Leu Asn Gly Pro Arg Ile His Glu
             275                 280                 285

Phe His Gln Glu Met Asn Gln Phe Ile Arg Asn Arg Val Lys Asp Gly
 290                 295                 300

Arg Glu Ile Met Thr Val Gly Glu Met Gln His Ala Ser Asp Glu Thr
305                 310                 315                 320

Lys Arg Leu Tyr Thr Ser Ala Ser Arg His Glu Leu Ser Glu Leu Phe
                 325                 330                 335

Asn Phe Ser His Thr Asp Val Gly Thr Ser Pro Leu Phe Arg Tyr Asn
             340                 345                 350

Leu Val Pro Phe Glu Leu Lys Asp Trp Lys Ile Ala Leu Ala Glu Leu
             355                 360                 365

Phe Arg Tyr Ile Asn Gly Thr Asp Cys Trp Ser Thr Ile Tyr Leu Glu
             370                 375                 380

Asn His Asp Gln Pro Arg Ser Ile Thr Arg Phe Gly Asp Asp Ser Pro
385                 390                 395                 400

Lys Asn Arg Val Ile Ser Gly Lys Leu Leu Ser Val Leu Leu Ser Ala
                 405                 410                 415

Leu Thr Gly Thr Leu Tyr Val Tyr Gln Gly Gln Glu Leu Gly Gln Ile
             420                 425                 430

Asn Phe Lys Asn Trp Pro Val Glu Lys Tyr Glu Asp Val Glu Ile Arg
             435                 440                 445

Asn Asn Tyr Asn Ala Ile Lys Glu Glu His Gly Glu Asn Ser Glu Glu
450                 455                 460
```

```
Met Lys Lys Phe Leu Glu Ala Ile Ala Leu Ile Ser Arg Asp His Ala
465                 470                 475                 480

Arg Thr Pro Met Gln Trp Ser Arg Glu Pro Asn Ala Gly Phe Ser
            485                 490                 495

Gly Pro Ser Ala Lys Pro Trp Phe Tyr Leu Asn Asp Ser Phe Arg Glu
        500                 505                 510

Gly Ile Asn Val Glu Asp Glu Ile Lys Asp Pro Asn Ser Val Leu Asn
        515                 520                 525

Phe Trp Lys Glu Ala Leu Lys Phe Arg Lys Ala His Lys Asp Ile Thr
    530                 535                 540

Val Tyr Gly Tyr Asp Phe Glu Phe Ile Asp Leu Asp Asn Lys Lys Leu
545                 550                 555                 560

Phe Ser Phe Thr Lys Lys Tyr Asn Asn Lys Thr Leu Phe Ala Ala Leu
                565                 570                 575

Asn Phe Ser Ser Asp Ala Thr Asp Phe Lys Ile Pro Asn Asp Asp Ser
            580                 585                 590

Ser Phe Lys Leu Glu Phe Gly Asn Tyr Pro Lys Lys Glu Val Asp Ala
        595                 600                 605

Ser Ser Arg Thr Leu Lys Pro Trp Glu Gly Arg Ile Tyr Ile Ser Glu
        610                 615                 620

<210> SEQ ID NO 27
<211> LENGTH: 1865
<212> TYPE: DNA
<213> ORGANISM: artificial sequence
<220> FEATURE:
<223> OTHER INFORMATION: gene fusion tat-'AY008307_cuo
<220> FEATURE:
<221> NAME/KEY: misc_feature
<222> LOCATION: (1)..(6)
<223> OTHER INFORMATION: PstI restriction site
<220> FEATURE:
<221> NAME/KEY: misc_feature
<222> LOCATION: (7)..(13)
<223> OTHER INFORMATION: SexAI restriction site
<220> FEATURE:
<221> NAME/KEY: CDS
<222> LOCATION: (14)..(1801)
<223> OTHER INFORMATION: sequence coding for fusion polypeptide
      Tat-'AY008307
<220> FEATURE:
<221> NAME/KEY: misc_signal
<222> LOCATION: (14)..(112)
<223> OTHER INFORMATION: 5' sequence of cg0955 encoding Tat-signal
      peptide
<220> FEATURE:
<221> NAME/KEY: misc_feature
<222> LOCATION: (14)..(114)
<223> OTHER INFORMATION: 5' sequence of cg0955
<220> FEATURE:
<221> NAME/KEY: misc_feature
<222> LOCATION: (115)..(115)
<223> OTHER INFORMATION: nucleobase adenine
<220> FEATURE:
<221> NAME/KEY: misc_feature
<222> LOCATION: (115)..(120)
<223> OTHER INFORMATION: SpeI restriction site
<220> FEATURE:
<221> NAME/KEY: misc_feature
<222> LOCATION: (121)..(121)
<223> OTHER INFORMATION: nucleobase adenine
<220> FEATURE:
<221> NAME/KEY: misc_feature
<222> LOCATION: (122)..(1801)
<223> OTHER INFORMATION: 'AY008307_cuo
<220> FEATURE:
<221> NAME/KEY: misc_feature
<222> LOCATION: (1802)..(1804)
```

```
<223> OTHER INFORMATION: stop codon
<220> FEATURE:
<221> NAME/KEY: misc_feature
<222> LOCATION: (1805)..(1812)
<223> OTHER INFORMATION: NotI restriction site
<220> FEATURE:
<221> NAME/KEY: misc_feature
<222> LOCATION: (1816)..(1851)
<223> OTHER INFORMATION: terminator sequence Tgap*
<220> FEATURE:
<221> NAME/KEY: misc_feature
<222> LOCATION: (1854)..(1859)
<223> OTHER INFORMATION: XbaI restriction site
<220> FEATURE:
<221> NAME/KEY: misc_feature
<222> LOCATION: (1860)..(1865)
<223> OTHER INFORMATION: BamHI restriction site

<400> SEQUENCE: 27
ctgcagacct ggt atg caa ata aac cgc cga ggc ttc tta aaa gcc acc       49
            Met Gln Ile Asn Arg Arg Gly Phe Leu Lys Ala Thr
             1               5                  10 aca gga ctt gcc act atc ggc gct gcc agc atg ttt atg cca aag gcc     97
Thr Gly Leu Ala Thr Ile Gly Ala Ala Ser Met Phe Met Pro Lys Ala
         15                  20                  25 aac gcc ctt gga gca ata cta gta tcc gaa tgg tgg aaa gaa gca gtg    145
Asn Ala Leu Gly Ala Ile Leu Val Ser Glu Trp Trp Lys Glu Ala Val
 30                  35                  40 gtc tac cag atc tac cca cgc tcc ttc tac gat gca aac ggc gac ggc    193
Val Tyr Gln Ile Tyr Pro Arg Ser Phe Tyr Asp Ala Asn Gly Asp Gly
 45                  50                  55                  60 ttc ggc gat ctc cag ggc gtg atc cag aag ctg gat tac atc aag aac    241
Phe Gly Asp Leu Gln Gly Val Ile Gln Lys Leu Asp Tyr Ile Lys Asn
                 65                  70                  75 ctg ggt gca gat gtg atc tgg ctg tcc cca gtg ttc gat tcc cca cag    289
Leu Gly Ala Asp Val Ile Trp Leu Ser Pro Val Phe Asp Ser Pro Gln
             80                  85                  90 gat gat aac ggc tac gat atc tcc gat tac aag aac atg tac gaa aag    337
Asp Asp Asn Gly Tyr Asp Ile Ser Asp Tyr Lys Asn Met Tyr Glu Lys
         95                 100                 105 ttc ggc acc aac gaa gat atg ttc cag ctg atc gat gaa gca cac aag    385
Phe Gly Thr Asn Glu Asp Met Phe Gln Leu Ile Asp Glu Ala His Lys
110                 115                 120 cgt ggc atg aag atc gtg atg cac ctc gtg gtg aac cac acc tcc gat    433
Arg Gly Met Lys Ile Val Met His Leu Val Val Asn His Thr Ser Asp
125                 130                 135                 140 gaa cac gca tgg ttc gca gaa tcc cgc aag tcc aag gat aac cct tac    481
Glu His Ala Trp Phe Ala Glu Ser Arg Lys Ser Lys Asp Asn Pro Tyr
                145                 150                 155 cgc gat tac tac ttc tgg aag gac cca aag tcc gat ggc tcc gaa cca    529
Arg Asp Tyr Tyr Phe Trp Lys Asp Pro Lys Ser Asp Gly Ser Glu Pro
            160                 165                 170 aac aac tgg ggc tcc atc ttc tcc ggc tcc gca tgg acc tac gat gaa    577
Asn Asn Trp Gly Ser Ile Phe Ser Gly Ser Ala Trp Thr Tyr Asp Glu
        175                 180                 185 ggc acc ggt cag tac tac ctg cac tac ttc tcc aag aag cag cca gat    625
Gly Thr Gly Gln Tyr Tyr Leu His Tyr Phe Ser Lys Lys Gln Pro Asp
    190                 195                 200 ctc aac tgg gaa aac gaa gca gtg cgt cgc gaa gtg tac gat gtg atg    673
Leu Asn Trp Glu Asn Glu Ala Val Arg Arg Glu Val Tyr Asp Val Met
205                 210                 215                 220 cgc ttc tgg atg gat cgc ggt gtg gat ggc tgg cgc atg gat gtg atc    721
Arg Phe Trp Met Asp Arg Gly Val Asp Gly Trp Arg Met Asp Val Ile
                225                 230                 235
```

```
ggc tcc atc tcc aag tac acc gat ttc cca gat tac gaa acc gat cac    769
Gly Ser Ile Ser Lys Tyr Thr Asp Phe Pro Asp Tyr Glu Thr Asp His
            240                 245                 250 tcc cgc tcc tac atc gtg ggt cgc tac cac tcc aac ggt cca cgc ctg    817
Ser Arg Ser Tyr Ile Val Gly Arg Tyr His Ser Asn Gly Pro Arg Leu
            255                 260                 265 cac gat ttc atc caa gaa atg aac cgc gaa gtg ctg tcc cac tac gat    865
His Asp Phe Ile Gln Glu Met Asn Arg Glu Val Leu Ser His Tyr Asp
            270                 275                 280 tgc atg acc gtg ggc gaa gca aac ggc tcc gat atc gaa gaa gca aag    913
Cys Met Thr Val Gly Glu Ala Asn Gly Ser Asp Ile Glu Glu Ala Lys
285                 290                 295                 300 aag tac acc gac gca tcc cgt caa gaa ctg aac atg atc ttc acc ttc    961
Lys Tyr Thr Asp Ala Ser Arg Gln Glu Leu Asn Met Ile Phe Thr Phe
                    305                 310                 315 gaa cac atg gat atc gat acc gaa cag aac tcc cca aac ggc aag tgg   1009
Glu His Met Asp Ile Asp Thr Glu Gln Asn Ser Pro Asn Gly Lys Trp
                320                 325                 330 cag atc aag cca ttc gat ctg atc gca ctg aag aaa acc atg acc cgc   1057
Gln Ile Lys Pro Phe Asp Leu Ile Ala Leu Lys Lys Thr Met Thr Arg
            335                 340                 345 tgg cag acc ggc ttg atg aac gtg ggc tgg aac acc ctg tac ttc gaa   1105
Trp Gln Thr Gly Leu Met Asn Val Gly Trp Asn Thr Leu Tyr Phe Glu
350                 355                 360 aac cac gat cag cca cgc gtg atc tcc cgc tgg ggc aac gat ggc aag   1153
Asn His Asp Gln Pro Arg Val Ile Ser Arg Trp Gly Asn Asp Gly Lys
365                 370                 375                 380 ctg cgc aaa gaa tgc gca aag gca ttc gca acc gat ctg gat ggc atg   1201
Leu Arg Lys Glu Cys Ala Lys Ala Phe Ala Thr Asp Leu Asp Gly Met
                385                 390                 395 aag ggc acc cca ttc atc tac cag ggc gaa gaa atc ggc atg gtg aac   1249
Lys Gly Thr Pro Phe Ile Tyr Gln Gly Glu Glu Ile Gly Met Val Asn
            400                 405                 410 cgc gat atg cca ctg gaa atg tac gat gat ctg gaa atc aag aac gca   1297
Arg Asp Met Pro Leu Glu Met Tyr Asp Asp Leu Glu Ile Lys Asn Ala
            415                 420                 425 tac cgc gaa ctg gtg gtg gaa aac aag acc atg tcc gaa aaa gaa ttc   1345
Tyr Arg Glu Leu Val Val Glu Asn Lys Thr Met Ser Glu Lys Glu Phe
            430                 435                 440 gtg aag gca gtg atg atc aag ggt cgc gat cac gca cgc acc cca atg   1393
Val Lys Ala Val Met Ile Lys Gly Arg Asp His Ala Arg Thr Pro Met
445                 450                 455                 460 cag tgg gat gca ggc aag cac gca ggc ctg acc gca ggc gac cca tgg   1441
Gln Trp Asp Ala Gly Lys His Ala Gly Leu Thr Ala Gly Asp Pro Trp
                465                 470                 475 att cca gtg aac tcc cgc tac cag gat atc aac gtg aaa gaa tcc ctg   1489
Ile Pro Val Asn Ser Arg Tyr Gln Asp Ile Asn Val Lys Glu Ser Leu
            480                 485                 490 gaa gat cag gat tcc atc ttc ttc tac tac cag aag ctg atc cag ctg   1537
Glu Asp Gln Asp Ser Ile Phe Phe Tyr Tyr Gln Lys Leu Ile Gln Leu
                495                 500                 505 cgc aag cag tac aaa atc atg atc tac ggc gat tac cag ctg ctg caa   1585
Arg Lys Gln Tyr Lys Ile Met Ile Tyr Gly Asp Tyr Gln Leu Leu Gln
            510                 515                 520 gaa aac gat cct cag gtg ttc tcc tac ctg cgc gaa tac cgt ggc gaa   1633
Glu Asn Asp Pro Gln Val Phe Ser Tyr Leu Arg Glu Tyr Arg Gly Glu
525                 530                 535                 540 aag ctg ctc gtg gtg gtc aac ctg tcc gaa gaa aag gca ctg ttc gaa   1681
Lys Leu Leu Val Val Val Asn Leu Ser Glu Glu Lys Ala Leu Phe Glu
```

-continued

```
                      545                 550                 555
gca cca cca gaa ctc atc cac gaa cgc tgg aag gtg ctg atc tcc aac      1729
Ala Pro Pro Glu Leu Ile His Glu Arg Trp Lys Val Leu Ile Ser Asn
        560                 565                 570 tac cca caa gaa cgc gca gat ctg aag tcc atc tcc ctg aag cca tac      1777
Tyr Pro Gln Glu Arg Ala Asp Leu Lys Ser Ile Ser Leu Lys Pro Tyr
    575                 580                 585 gaa gca gtg atg ggc atc tcc att taagcggccg ctgttagccc ggggtgtgcc     1831
Glu Ala Val Met Gly Ile Ser Ile
590                 595 tcggcgcacc ccgggctatt tttctagagg atcc                                1865

<210> SEQ ID NO 28
<211> LENGTH: 596
<212> TYPE: PRT
<213> ORGANISM: artificial sequence
<220> FEATURE:
<223> OTHER INFORMATION: Synthetic Construct

<400> SEQUENCE: 28

Met Gln Ile Asn Arg Arg Gly Phe Leu Lys Ala Thr Thr Gly Leu Ala
1               5                   10                  15

Thr Ile Gly Ala Ala Ser Met Phe Met Pro Lys Ala Asn Ala Leu Gly
            20                  25                  30

Ala Ile Leu Val Ser Glu Trp Trp Lys Glu Ala Val Val Tyr Gln Ile
        35                  40                  45

Tyr Pro Arg Ser Phe Tyr Asp Ala Asn Gly Asp Gly Phe Gly Asp Leu
    50                  55                  60

Gln Gly Val Ile Gln Lys Leu Asp Tyr Ile Lys Asn Leu Gly Ala Asp
65                  70                  75                  80

Val Ile Trp Leu Ser Pro Val Phe Asp Ser Pro Gln Asp Asp Asn Gly
                85                  90                  95

Tyr Asp Ile Ser Asp Tyr Lys Asn Met Tyr Glu Lys Phe Gly Thr Asn
            100                 105                 110

Glu Asp Met Phe Gln Leu Ile Asp Glu Ala His Lys Arg Gly Met Lys
        115                 120                 125

Ile Val Met His Leu Val Val Asn His Thr Ser Asp Glu His Ala Trp
    130                 135                 140

Phe Ala Glu Ser Arg Lys Ser Lys Asp Asn Pro Tyr Arg Asp Tyr Tyr
145                 150                 155                 160

Phe Trp Lys Asp Pro Lys Ser Asp Gly Ser Glu Pro Asn Asn Trp Gly
                165                 170                 175

Ser Ile Phe Ser Gly Ser Ala Trp Thr Tyr Asp Glu Gly Thr Gly Gln
            180                 185                 190

Tyr Tyr Leu His Tyr Phe Ser Lys Lys Gln Pro Asp Leu Asn Trp Glu
        195                 200                 205

Asn Glu Ala Val Arg Arg Glu Val Tyr Asp Val Met Arg Phe Trp Met
    210                 215                 220

Asp Arg Gly Val Asp Gly Trp Arg Met Asp Val Ile Gly Ser Ile Ser
225                 230                 235                 240

Lys Tyr Thr Asp Phe Pro Asp Tyr Glu Thr Asp His Ser Arg Ser Tyr
                245                 250                 255

Ile Val Gly Arg Tyr His Ser Asn Gly Pro Arg Leu His Asp Phe Ile
            260                 265                 270

Gln Glu Met Asn Arg Glu Val Leu Ser His Tyr Asp Cys Met Thr Val
        275                 280                 285
```

-continued

```
Gly Glu Ala Asn Gly Ser Asp Ile Glu Glu Ala Lys Lys Tyr Thr Asp
            290                 295                 300

Ala Ser Arg Gln Glu Leu Asn Met Ile Phe Thr Phe Glu His Met Asp
305                 310                 315                 320

Ile Asp Thr Glu Gln Asn Ser Pro Asn Gly Lys Trp Gln Ile Lys Pro
                325                 330                 335

Phe Asp Leu Ile Ala Leu Lys Lys Thr Met Thr Arg Trp Gln Thr Gly
            340                 345                 350

Leu Met Asn Val Gly Trp Asn Thr Leu Tyr Phe Glu Asn His Asp Gln
        355                 360                 365

Pro Arg Val Ile Ser Arg Trp Gly Asn Asp Gly Lys Leu Arg Lys Glu
    370                 375                 380

Cys Ala Lys Ala Phe Ala Thr Asp Leu Asp Gly Met Lys Gly Thr Pro
385                 390                 395                 400

Phe Ile Tyr Gln Gly Glu Glu Ile Gly Met Val Asn Arg Asp Met Pro
                405                 410                 415

Leu Glu Met Tyr Asp Asp Leu Glu Ile Lys Asn Ala Tyr Arg Glu Leu
            420                 425                 430

Val Val Glu Asn Lys Thr Met Ser Glu Lys Glu Phe Val Lys Ala Val
        435                 440                 445

Met Ile Lys Gly Arg Asp His Ala Arg Thr Pro Met Gln Trp Asp Ala
    450                 455                 460

Gly Lys His Ala Gly Leu Thr Ala Gly Asp Pro Trp Ile Pro Val Asn
465                 470                 475                 480

Ser Arg Tyr Gln Asp Ile Asn Val Lys Glu Ser Leu Glu Asp Gln Asp
                485                 490                 495

Ser Ile Phe Phe Tyr Tyr Gln Lys Leu Ile Gln Leu Arg Lys Gln Tyr
            500                 505                 510

Lys Ile Met Ile Tyr Gly Asp Tyr Gln Leu Leu Gln Glu Asn Asp Pro
        515                 520                 525

Gln Val Phe Ser Tyr Leu Arg Glu Tyr Arg Gly Glu Lys Leu Leu Val
    530                 535                 540

Val Val Asn Leu Ser Glu Glu Lys Ala Leu Phe Glu Ala Pro Pro Glu
545                 550                 555                 560

Leu Ile His Glu Arg Trp Lys Val Leu Ile Ser Asn Tyr Pro Gln Glu
                565                 570                 575

Arg Ala Asp Leu Lys Ser Ile Ser Leu Lys Pro Tyr Glu Ala Val Met
            580                 585                 590

Gly Ile Ser Ile
        595

<210> SEQ ID NO 29
<211> LENGTH: 1889
<212> TYPE: DNA
<213> ORGANISM: artificial sequence
<220> FEATURE:
<223> OTHER INFORMATION: agl2 of Bifidobacterium breve UCC2003 optimized
      for the codon usage of Corynebacterium glutamicum
<220> FEATURE:
<221> NAME/KEY: misc_feature
<222> LOCATION: (1)..(6)
<223> OTHER INFORMATION: PstI restriction site
<220> FEATURE:
<221> NAME/KEY: misc_feature
<222> LOCATION: (7)..(13)
<223> OTHER INFORMATION: SexAI restriction site
<220> FEATURE:
<221> NAME/KEY: CDS
```

```
<222> LOCATION: (14)..(1825)
<223> OTHER INFORMATION: agl2_cuo (sequence encoding Agl2 of
      Bifidobacterium breve UCC2003 optimized for the codon usage of
      Corynebacterium glutamicum)
<220> FEATURE:
<221> NAME/KEY: misc_feature
<222> LOCATION: (50)..(57)
<223> OTHER INFORMATION: FspAI restriction site
<220> FEATURE:
<221> NAME/KEY: misc_feature
<222> LOCATION: (1826)..(1828)
<223> OTHER INFORMATION: stop codon
<220> FEATURE:
<221> NAME/KEY: misc_feature
<222> LOCATION: (1829)..(1836)
<223> OTHER INFORMATION: NotI restriction site
<220> FEATURE:
<221> NAME/KEY: misc_feature
<222> LOCATION: (1840)..(1875)
<223> OTHER INFORMATION: terminator sequence Tgap*
<220> FEATURE:
<221> NAME/KEY: misc_feature
<222> LOCATION: (1884)..(1889)
<223> OTHER INFORMATION: restriction site BamHI

<400> SEQUENCE: 29
ctgcagacca ggt atg acc tcc ttc aac cgc gaa cca ctg cca gat gca         49
           Met Thr Ser Phe Asn Arg Glu Pro Leu Pro Asp Ala
            1               5                  10 gtg cgc acc aac ggt gca acc cca aac cca tgg tgg tcc aac gca gtg        97
Val Arg Thr Asn Gly Ala Thr Pro Asn Pro Trp Trp Ser Asn Ala Val
         15                  20                  25 gtg tac cag atc tac cca cgc tcc ttc cag gat acc aac ggc gac ggc       145
Val Tyr Gln Ile Tyr Pro Arg Ser Phe Gln Asp Thr Asn Gly Asp Gly
     30                  35                  40 ctg ggc gat ctg aag ggc atc acc tcc cgc ttg gat tac ctg gca gat       193
Leu Gly Asp Leu Lys Gly Ile Thr Ser Arg Leu Asp Tyr Leu Ala Asp
 45                  50                  55                  60 ctg ggc gtg gat gtg ctg tgg ctg tcc cca gtg tac cgc tcc cca cag       241
Leu Gly Val Asp Val Leu Trp Leu Ser Pro Val Tyr Arg Ser Pro Gln
                 65                  70                  75 gat gat aac ggc tac gat atc tcc gat tac cgc gat atc gat cca ctg       289
Asp Asp Asn Gly Tyr Asp Ile Ser Asp Tyr Arg Asp Ile Asp Pro Leu
             80                  85                  90 ttc ggc acc ctg gat gat atg gat gaa ctg ctg gca gag gca cac aag       337
Phe Gly Thr Leu Asp Asp Met Asp Glu Leu Leu Ala Glu Ala His Lys
         95                 100                 105 cgt ggc ctg aag atc gtg atg gat ctg gtg gtg aac cac acc tcc gat       385
Arg Gly Leu Lys Ile Val Met Asp Leu Val Val Asn His Thr Ser Asp
    110                 115                 120 gaa cac gca tgg ttc gaa gca tcc aag gat aag gat gat cca cac gca       433
Glu His Ala Trp Phe Glu Ala Ser Lys Asp Lys Asp Asp Pro His Ala
125                 130                 135                 140 gat tgg tac tgg tgg cgt cca gca cgc cca ggc cac gaa cca ggc acc       481
Asp Trp Tyr Trp Trp Arg Pro Ala Arg Pro Gly His Glu Pro Gly Thr
                145                 150                 155 cca ggc gca gaa cca aac cag tgg ggc tcc tac ttc ggt ggc tcc gca       529
Pro Gly Ala Glu Pro Asn Gln Trp Gly Ser Tyr Phe Gly Gly Ser Ala
            160                 165                 170 tgg gaa tac tcc cca gaa cgc ggt gaa tac tac ctg cac cag ttc tcc       577
Trp Glu Tyr Ser Pro Glu Arg Gly Glu Tyr Tyr Leu His Gln Phe Ser
        175                 180                 185 aag aag cag cca gat ctc aac tgg gaa aac cca gca gtg cgt cgc gca       625
Lys Lys Gln Pro Asp Leu Asn Trp Glu Asn Pro Ala Val Arg Arg Ala
    190                 195                 200
```

-continued

| | | |
|---|---|---|
| gtg tac gat atg atg aac tgg tgg ttg gat cgc ggt atc gat ggc ttc<br>Val Tyr Asp Met Met Asn Trp Trp Leu Asp Arg Gly Ile Asp Gly Phe<br>205                    210                   215                   220 | 673 |
| cgc atg gat gtg atc acc ctg atc tcc aag cgc acc gat cca aac ggt<br>Arg Met Asp Val Ile Thr Leu Ile Ser Lys Arg Thr Asp Pro Asn Gly<br>                    225                   230                   235 | 721 |
| cgc ctg cca ggt gaa acc ggc tcc gaa ctc cag gat ctg cca gtg ggc<br>Arg Leu Pro Gly Glu Thr Gly Ser Glu Leu Gln Asp Leu Pro Val Gly<br>                    240                   245                   250 | 769 |
| gaa gaa ggc tac tcc tcc cca aac cct ttc tgc gca gat ggc cct cgc<br>Glu Glu Gly Tyr Ser Ser Pro Asn Pro Phe Cys Ala Asp Gly Pro Arg<br>             255                   260                   265 | 817 |
| cag gat gaa ttc ctg gca gaa atg cgt cgc gaa gtt ttc gat ggc cgt<br>Gln Asp Glu Phe Leu Ala Glu Met Arg Arg Glu Val Phe Asp Gly Arg<br>270                    275                   280 | 865 |
| gat ggc ttc ctg acc gtg ggc gaa gca cca ggc atc acc gca gaa cgc<br>Asp Gly Phe Leu Thr Val Gly Glu Ala Pro Gly Ile Thr Ala Glu Arg<br>285                    290                   295                   300 | 913 |
| aac gaa cac atc acc gat cca gca aac ggc gaa ctg gat atg ctg ttc<br>Asn Glu His Ile Thr Asp Pro Ala Asn Gly Glu Leu Asp Met Leu Phe<br>                    305                   310                   315 | 961 |
| ctg ttc gaa cac atg ggc gtg gat cag acc cca gaa tcc aag tgg gat<br>Leu Phe Glu His Met Gly Val Asp Gln Thr Pro Glu Ser Lys Trp Asp<br>             320                   325                   330 | 1009 |
| gat aag cca tgg acc cca gca gat ctg gaa acc aag ctg gca gaa cag<br>Asp Lys Pro Trp Thr Pro Ala Asp Leu Glu Thr Lys Leu Ala Glu Gln<br>335                    340                   345 | 1057 |
| cag gat gca atc gca cgc cgt ggc tgg gcc tcc ctg ttc ctg gat aac<br>Gln Asp Ala Ile Ala Arg Arg Gly Trp Ala Ser Leu Phe Leu Asp Asn<br>350                    355                   360 | 1105 |
| cac gat cag cca cgc gtg gtg tcc cgc tgg ggt gat gat acc tcc aag<br>His Asp Gln Pro Arg Val Val Ser Arg Trp Gly Asp Asp Thr Ser Lys<br>365                    370                   375                   380 | 1153 |
| acc ggt cgc atc cgc tcc gca aag gca ctg gca ctg ctg ctg cac atg<br>Thr Gly Arg Ile Arg Ser Ala Lys Ala Leu Ala Leu Leu Leu His Met<br>                    385                   390                   395 | 1201 |
| cac cgt ggc acc cca tac gtg tac cag ggc gaa gaa ctg ggc atg acc<br>His Arg Gly Thr Pro Tyr Val Tyr Gln Gly Glu Glu Leu Gly Met Thr<br>             400                   405                   410 | 1249 |
| aac gca cac ttc acc tcc ctg gat cag tac cgc gat ctg gaa tcc atc<br>Asn Ala His Phe Thr Ser Leu Asp Gln Tyr Arg Asp Leu Glu Ser Ile<br>415                    420                   425 | 1297 |
| aac gca tac cac caa cgc gtg gaa gaa acc ggc atc cgc acc tcc gaa<br>Asn Ala Tyr His Gln Arg Val Glu Glu Thr Gly Ile Arg Thr Ser Glu<br>430                    435                   440 | 1345 |
| acc atg atg cgc tcc ctg gca cgc tac ggt cgc gat aac gca cgc acc<br>Thr Met Met Arg Ser Leu Ala Arg Tyr Gly Arg Asp Asn Ala Arg Thr<br>445                    450                   455                   460 | 1393 |
| cca atg cag tgg gat gat tcc acc tac gca ggc ttc acc atg cca gat<br>Pro Met Gln Trp Asp Asp Ser Thr Tyr Ala Gly Phe Thr Met Pro Asp<br>                    465                   470                   475 | 1441 |
| gcc cca gtg gaa cca tgg atc gca gtg aac cca aac cac acc gaa atc<br>Ala Pro Val Glu Pro Trp Ile Ala Val Asn Pro Asn His Thr Glu Ile<br>             480                   485                   490 | 1489 |
| aac gca gca gat gaa acc gat gat cca gat tcc gtg tac tcc ttc cac<br>Asn Ala Ala Asp Glu Thr Asp Asp Pro Asp Ser Val Tyr Ser Phe His<br>495                    500                   505 | 1537 |
| aag cgc ctg atc gca ctg cgc cac acc gat cca gtg gtg gca gca ggc<br>Lys Arg Leu Ile Ala Leu Arg His Thr Asp Pro Val Val Ala Ala Gly<br>510                    515                   520 | 1585 |

```
gat tac cgt cgc gtg gaa acc ggc aac gat cgc atc att gca ttc acc    1633
Asp Tyr Arg Arg Val Glu Thr Gly Asn Asp Arg Ile Ile Ala Phe Thr
525                 530                 535                 540 cgc acc ctg gac gaa cgc acc atc ctg acc gtg atc aac ctg tcc cca    1681
Arg Thr Leu Asp Glu Arg Thr Ile Leu Thr Val Ile Asn Leu Ser Pro
            545                 550                 555 acc cag gca gca cca gca ggc gaa ctg gaa acc atg cca gac ggc acc    1729
Thr Gln Ala Ala Pro Ala Gly Glu Leu Glu Thr Met Pro Asp Gly Thr
        560                 565                 570 atc ttg atc gca aac acc gat gac cca gtg ggc aac ctc aag acc acc    1777
Ile Leu Ile Ala Asn Thr Asp Asp Pro Val Gly Asn Leu Lys Thr Thr
    575                 580                 585 ggc acc ctg ggt cca tgg gaa gca ttc gca atg gaa acc gat cca gaa    1825
Gly Thr Leu Gly Pro Trp Glu Ala Phe Ala Met Glu Thr Asp Pro Glu
590                 595                 600 taagcggccg ctgttagccc ggggtgtgcc tcggcgcacc ccgggctatt tttctagagg   1885
atcc                                                               1889

<210> SEQ ID NO 30
<211> LENGTH: 604
<212> TYPE: PRT
<213> ORGANISM: artificial sequence
<220> FEATURE:
<223> OTHER INFORMATION: Synthetic Construct

<400> SEQUENCE: 30

Met Thr Ser Phe Asn Arg Glu Pro Leu Pro Asp Ala Val Arg Thr Asn
1               5                   10                  15

Gly Ala Thr Pro Asn Pro Trp Trp Ser Asn Ala Val Val Tyr Gln Ile
            20                  25                  30

Tyr Pro Arg Ser Phe Gln Asp Thr Asn Gly Asp Gly Leu Gly Asp Leu
        35                  40                  45

Lys Gly Ile Thr Ser Arg Leu Asp Tyr Leu Ala Asp Leu Gly Val Asp
    50                  55                  60

Val Leu Trp Leu Ser Pro Val Tyr Arg Ser Pro Gln Asp Asp Asn Gly
65                  70                  75                  80

Tyr Asp Ile Ser Asp Tyr Arg Asp Ile Asp Pro Leu Phe Gly Thr Leu
                85                  90                  95

Asp Asp Met Asp Glu Leu Leu Ala Glu Ala His Lys Arg Gly Leu Lys
            100                 105                 110

Ile Val Met Asp Leu Val Val Asn His Thr Ser Asp Glu His Ala Trp
        115                 120                 125

Phe Glu Ala Ser Lys Asp Lys Asp Pro His Ala Asp Trp Tyr Trp
    130                 135                 140

Trp Arg Pro Ala Arg Pro Gly His Glu Pro Gly Thr Pro Gly Ala Glu
145                 150                 155                 160

Pro Asn Gln Trp Gly Ser Tyr Phe Gly Gly Ser Ala Trp Glu Tyr Ser
                165                 170                 175

Pro Glu Arg Gly Glu Tyr Tyr Leu His Gln Phe Ser Lys Lys Gln Pro
            180                 185                 190

Asp Leu Asn Trp Glu Asn Pro Ala Val Arg Ala Val Tyr Asp Met
        195                 200                 205

Met Asn Trp Trp Leu Asp Arg Gly Ile Asp Gly Phe Arg Met Asp Val
    210                 215                 220

Ile Thr Leu Ile Ser Lys Arg Thr Asp Pro Asn Gly Arg Leu Pro Gly
225                 230                 235                 240
```

```
Glu Thr Gly Ser Glu Leu Gln Asp Leu Pro Val Gly Glu Gly Tyr
            245                 250                 255

Ser Ser Pro Asn Pro Phe Cys Ala Asp Gly Pro Arg Gln Asp Glu Phe
            260                 265                 270

Leu Ala Glu Met Arg Arg Glu Val Phe Asp Gly Arg Asp Gly Phe Leu
            275                 280                 285

Thr Val Gly Glu Ala Pro Gly Ile Thr Ala Glu Arg Asn Glu His Ile
            290                 295                 300

Thr Asp Pro Ala Asn Gly Glu Leu Asp Met Leu Phe Leu Phe Glu His
305                 310                 315                 320

Met Gly Val Asp Gln Thr Pro Glu Ser Lys Trp Asp Asp Lys Pro Trp
            325                 330                 335

Thr Pro Ala Asp Leu Glu Thr Lys Leu Ala Glu Gln Gln Asp Ala Ile
            340                 345                 350

Ala Arg Arg Gly Trp Ala Ser Leu Phe Leu Asp Asn His Asp Gln Pro
            355                 360                 365

Arg Val Val Ser Arg Trp Gly Asp Asp Thr Ser Lys Thr Gly Arg Ile
            370                 375                 380

Arg Ser Ala Lys Ala Leu Ala Leu Leu Leu His Met His Arg Gly Thr
385                 390                 395                 400

Pro Tyr Val Tyr Gln Gly Glu Glu Leu Gly Met Thr Asn Ala His Phe
            405                 410                 415

Thr Ser Leu Asp Gln Tyr Arg Asp Leu Glu Ser Ile Asn Ala Tyr His
            420                 425                 430

Gln Arg Val Glu Glu Thr Gly Ile Arg Thr Ser Glu Thr Met Met Arg
            435                 440                 445

Ser Leu Ala Arg Tyr Gly Arg Asp Asn Ala Arg Thr Pro Met Gln Trp
            450                 455                 460

Asp Asp Ser Thr Tyr Ala Gly Phe Thr Met Pro Asp Ala Pro Val Glu
465                 470                 475                 480

Pro Trp Ile Ala Val Asn Pro Asn His Thr Glu Ile Asn Ala Ala Asp
            485                 490                 495

Glu Thr Asp Asp Pro Asp Ser Val Tyr Ser Phe His Lys Arg Leu Ile
            500                 505                 510

Ala Leu Arg His Thr Asp Pro Val Val Ala Ala Gly Asp Tyr Arg Arg
            515                 520                 525

Val Glu Thr Gly Asn Asp Arg Ile Ile Ala Phe Thr Arg Thr Leu Asp
            530                 535                 540

Glu Arg Thr Ile Leu Thr Val Ile Asn Leu Ser Pro Thr Gln Ala Ala
545                 550                 555                 560

Pro Ala Gly Glu Leu Glu Thr Met Pro Asp Gly Thr Ile Leu Ile Ala
            565                 570                 575

Asn Thr Asp Asp Pro Val Gly Asn Leu Lys Thr Thr Gly Thr Leu Gly
            580                 585                 590

Pro Trp Glu Ala Phe Ala Met Glu Thr Asp Pro Glu
            595                 600

<210> SEQ ID NO 31
<211> LENGTH: 414
<212> TYPE: DNA
<213> ORGANISM: artificial sequence
<220> FEATURE:
<223> OTHER INFORMATION: polynucleotide Wo_tat
<220> FEATURE:
<221> NAME/KEY: misc_feature
```

```
<222> LOCATION: (21)..(28)
<223> OTHER INFORMATION: MauBI restriction site
<220> FEATURE:
<221> NAME/KEY: misc_feature
<222> LOCATION: (222)..(296)
<223> OTHER INFORMATION: promoter PtacI
<220> FEATURE:
<221> NAME/KEY: misc_feature
<222> LOCATION: (338)..(343)
<223> OTHER INFORMATION: PstI restriction site
<220> FEATURE:
<221> NAME/KEY: misc_feature
<222> LOCATION: (344)..(350)
<223> OTHER INFORMATION: SexAI restriction site
<220> FEATURE:
<221> NAME/KEY: CDS
<222> LOCATION: (351)..(413)
<223> OTHER INFORMATION: cds of the 5'-end of agl2_cuo
<220> FEATURE:
<221> NAME/KEY: misc_feature
<222> LOCATION: (387)..(394)
<223> OTHER INFORMATION: FspAI restriction site

<400> SEQUENCE: 31
aatgcatgcc gcttcgcctt cgcgcgcgaa ttgcaagctg atccgggctt atcgactgca      60
cggtgcacca atgcttctgg cgtcaggcag ccatcggaag ctgtggtatg gctgtgcagg     120
tcgtaaatca ctgcataatt cgtgtcgctc aaggcgcact cccgttctgg ataatgtttt     180
ttgcgccgac atcataacgg ttctggcaaa tattctgaaa tgagctgttg acaattaatc     240
atcggctcgt ataatgtgtg gaattgtgag cggataacaa tttcacacag gaaacagaat     300
taaaagatat gaccatgatt acgccaagct tgcatgcctg cagaccaggt atg acc       356
                                                          Met Thr
                                                           1 tcc ttc aac cgc gaa cca ctg cca gat gca gtg cgc acc aac ggt gca       404
Ser Phe Asn Arg Glu Pro Leu Pro Asp Ala Val Arg Thr Asn Gly Ala
      5                  10                  15 acc cca aac c                                                         414
Thr Pro Asn
   20

<210> SEQ ID NO 32
<211> LENGTH: 21
<212> TYPE: PRT
<213> ORGANISM: artificial sequence
<220> FEATURE:
<223> OTHER INFORMATION: Synthetic Construct

<400> SEQUENCE: 32

Met Thr Ser Phe Asn Arg Glu Pro Leu Pro Asp Ala Val Arg Thr Asn
1               5                   10                  15

Gly Ala Thr Pro Asn
            20

<210> SEQ ID NO 33
<211> LENGTH: 23
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(23)
<223> OTHER INFORMATION: primer pVW_1

<400> SEQUENCE: 33
gtgagcggat aacaatttca cac                                             23
```

```
<210> SEQ ID NO 34
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer pVW_2

<400> SEQUENCE: 34
tttgcgccga catcataacg                                               20

<210> SEQ ID NO 35
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer pVW_3

<400> SEQUENCE: 35
tactgccgcc aggcaaattc                                               20

<210> SEQ ID NO 36
<211> LENGTH: 23
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(23)
<223> OTHER INFORMATION: primer gluc_rev

<400> SEQUENCE: 36
gtgagcggat aacaatttca cac                                           23

<210> SEQ ID NO 37
<211> LENGTH: 23
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(23)
<223> OTHER INFORMATION: primer gluc2_rev

<400> SEQUENCE: 37
tgctccaagg gcgttggcct ttg                                           23

<210> SEQ ID NO 38
<211> LENGTH: 202
<212> TYPE: DNA
<213> ORGANISM: artificial sequence
<220> FEATURE:
<223> OTHER INFORMATION: sequence coding for signal peptide of CgR_0079
<220> FEATURE:
<221> NAME/KEY: misc_feature
<222> LOCATION: (1)..(25)
<223> OTHER INFORMATION: 5'-overlap for Gibson Assembly
<220> FEATURE:
<221> NAME/KEY: CDS
<222> LOCATION: (26)..(202)
<220> FEATURE:
```

```
<221> NAME/KEY: misc_feature
<222> LOCATION: (26)..(178)
<223> OTHER INFORMATION: sequence coding for signal peptide of CgR0079
<220> FEATURE:
<221> NAME/KEY: misc_feature
<222> LOCATION: (179)..(202)
<223> OTHER INFORMATION: 3'-overlap for Gibson Assembly

<400> SEQUENCE: 38
aagcttgcat gcctgcagac caggt atg cct agc ttt aaa tct gct cga tgg        52
                           Met Pro Ser Phe Lys Ser Ala Arg Trp
                           1               5 agg atg aac aga cgc ctc ttc cta gga act tcc gca gct atc atc gct       100
Arg Met Asn Arg Arg Leu Phe Leu Gly Thr Ser Ala Ala Ile Ile Ala
 10              15                  20                  25 gtc ggt ggc gtg ctc ggt gga gtg cag gtt gta cct tat att tcc tct       148
Val Gly Gly Val Leu Gly Gly Val Gln Val Val Pro Tyr Ile Ser Ser
                 30                  35                  40 ggt gaa atc caa acg tca gca tca tcg act atg act agt acc tcc ttc       196
Gly Glu Ile Gln Thr Ser Ala Ser Ser Thr Met Thr Ser Thr Ser Phe
         45                  50                  55 aac cgc                                                                202
Asn Arg <210> SEQ ID NO 39
<211> LENGTH: 59
<212> TYPE: PRT
<213> ORGANISM: artificial sequence
<220> FEATURE:
<223> OTHER INFORMATION: Synthetic Construct

<400> SEQUENCE: 39

Met Pro Ser Phe Lys Ser Ala Arg Trp Arg Met Asn Arg Arg Leu Phe
1               5                  10                  15

Leu Gly Thr Ser Ala Ala Ile Ile Ala Val Gly Gly Val Leu Gly Gly
             20                  25                  30

Val Gln Val Val Pro Tyr Ile Ser Ser Gly Glu Ile Gln Thr Ser Ala
         35                  40                  45

Ser Ser Thr Met Thr Ser Thr Ser Phe Asn Arg
     50                  55

<210> SEQ ID NO 40
<211> LENGTH: 213
<212> TYPE: DNA
<213> ORGANISM: artificial sequence
<220> FEATURE:
<223> OTHER INFORMATION: sequence coding for signal peptide of CgR_0120
<220> FEATURE:
<221> NAME/KEY: misc_feature
<222> LOCATION: (1)..(45)
<223> OTHER INFORMATION: 5'-overlap for Gibson Assembly
<220> FEATURE:
<221> NAME/KEY: CDS
<222> LOCATION: (46)..(213)
<220> FEATURE:
<221> NAME/KEY: misc_feature
<222> LOCATION: (46)..(159)
<223> OTHER INFORMATION: sequence coding for signal peptide of CgR0120
<220> FEATURE:
<221> NAME/KEY: misc_feature
<222> LOCATION: (160)..(213)
<223> OTHER INFORMATION: 3'-overlap for Gibson Assembly

<400> SEQUENCE: 40
gatatgacca tgattacgcc aagcttgcat gcctgcagac caggt atg aca agt agt      57
                                                  Met Thr Ser Ser
                                                  1
```

```
ttt tcc cgg cga cag ttt ctg ctc ggc ggg ctc gta ctc gcc ggc acc        105
Phe Ser Arg Arg Gln Phe Leu Leu Gly Gly Leu Val Leu Ala Gly Thr
 5                  10                  15                  20 ggg gcc gtg gcc gcc tgc acc agc gac cct gga ccc gct gcc tcg gca        153
Gly Ala Val Ala Ala Cys Thr Ser Asp Pro Gly Pro Ala Ala Ser Ala
                 25                  30                  35 cca ggt atg act agt acc tcc ttc aac cgc gaa cca ctg cca gat gca        201
Pro Gly Met Thr Ser Thr Ser Phe Asn Arg Glu Pro Leu Pro Asp Ala
         40                  45                  50 gtg cgc acc aac                                                        213
Val Arg Thr Asn
        55

<210> SEQ ID NO 41
<211> LENGTH: 56
<212> TYPE: PRT
<213> ORGANISM: artificial sequence
<220> FEATURE:
<223> OTHER INFORMATION: Synthetic Construct

<400> SEQUENCE: 41

Met Thr Ser Ser Phe Ser Arg Arg Gln Phe Leu Leu Gly Gly Leu Val
 1               5                  10                  15

Leu Ala Gly Thr Gly Ala Val Ala Ala Cys Thr Ser Asp Pro Gly Pro
             20                  25                  30

Ala Ala Ser Ala Pro Gly Met Thr Ser Thr Ser Phe Asn Arg Glu Pro
         35                  40                  45

Leu Pro Asp Ala Val Arg Thr Asn
     50                  55

<210> SEQ ID NO 42
<211> LENGTH: 133
<212> TYPE: DNA
<213> ORGANISM: artificial sequence
<220> FEATURE:
<223> OTHER INFORMATION: sequence coding for signal peptide of CgR_0124
<220> FEATURE:
<221> NAME/KEY: misc_feature
<222> LOCATION: (2)..(10)
<223> OTHER INFORMATION: SexAI restriction site
<220> FEATURE:
<221> NAME/KEY: CDS
<222> LOCATION: (9)..(131)
<220> FEATURE:
<221> NAME/KEY: misc_feature
<222> LOCATION: (9)..(122)
<223> OTHER INFORMATION: sequence coding for signal peptide of CgR_0124
<220> FEATURE:
<221> NAME/KEY: misc_feature
<222> LOCATION: (126)..(131)
<223> OTHER INFORMATION: SpeI restriction site

<400> SEQUENCE: 42 gaccaggt atg acc acc ccg act tcc ccc ttg ctg ccg ctg gcc tcc gac       50
        Met Thr Thr Pro Thr Ser Pro Leu Leu Pro Leu Ala Ser Asp
         1               5                  10 ggt tgt gga tgc tgc gcg ccc tct acg ccg tcc gcg acc gtc tcc gcc        98
Gly Cys Gly Cys Cys Ala Pro Ser Thr Pro Ser Ala Thr Val Ser Ala
 15                  20                  25                  30 ccg gcc gtg gcc gcg gca acc gac atg act agt ac                         133
Pro Ala Val Ala Ala Ala Thr Asp Met Thr Ser
                 35                  40

<210> SEQ ID NO 43
<211> LENGTH: 41
```

-continued

```
<212> TYPE: PRT
<213> ORGANISM: artificial sequence
<220> FEATURE:
<223> OTHER INFORMATION: Synthetic Construct

<400> SEQUENCE: 43

Met Thr Thr Pro Thr Ser Pro Leu Leu Pro Leu Ala Ser Asp Gly Cys
1               5                   10                  15

Gly Cys Cys Ala Pro Ser Thr Pro Ser Ala Thr Val Ser Ala Pro Ala
                20                  25                  30

Val Ala Ala Ala Thr Asp Met Thr Ser
            35                  40

<210> SEQ ID NO 44
<211> LENGTH: 149
<212> TYPE: DNA
<213> ORGANISM: artificial sequence
<220> FEATURE:
<223> OTHER INFORMATION: sequence coding for signal peptide of CgR_0900
<220> FEATURE:
<221> NAME/KEY: misc_feature
<222> LOCATION: (1)..(25)
<223> OTHER INFORMATION: 5'-overlap for Gibson Assembly
<220> FEATURE:
<221> NAME/KEY: CDS
<222> LOCATION: (26)..(148)
<220> FEATURE:
<221> NAME/KEY: misc_feature
<222> LOCATION: (26)..(121)
<223> OTHER INFORMATION: sequence coding for signal peptide of CgR0900
<220> FEATURE:
<221> NAME/KEY: misc_feature
<222> LOCATION: (122)..(149)
<223> OTHER INFORMATION: 3'-overlap for Gibson Assembly

<400> SEQUENCE: 44
aagcttgcat gcctgcagac caggt atg cgc aga ccg gtc tca cgc cgc gcc        52
                            Met Arg Arg Pro Val Ser Arg Arg Ala
                            1               5 att ttt gca aca tct gtt ttg gtt gcg ggg gtg agc atc atg tca cct       100
Ile Phe Ala Thr Ser Val Leu Val Ala Gly Val Ser Ile Met Ser Pro
10              15                  20                  25 tcg gcc aac gca gct gag gct atg act agt acc tcc ttc aac cgc aac       149
Ser Ala Asn Ala Ala Glu Ala Met Thr Ser Thr Ser Phe Asn Arg Asn
                30                  35                  40

<210> SEQ ID NO 45
<211> LENGTH: 41
<212> TYPE: PRT
<213> ORGANISM: artificial sequence
<220> FEATURE:
<223> OTHER INFORMATION: Synthetic Construct

<400> SEQUENCE: 45

Met Arg Arg Pro Val Ser Arg Arg Ala Ile Phe Ala Thr Ser Val Leu
1               5                   10                  15

Val Ala Gly Val Ser Ile Met Ser Pro Ser Ala Asn Ala Ala Glu Ala
                20                  25                  30

Met Thr Ser Thr Ser Phe Asn Arg Asn
            35                  40

<210> SEQ ID NO 46
<211> LENGTH: 149
<212> TYPE: DNA
<213> ORGANISM: artificial Sequence
<220> FEATURE:
<223> OTHER INFORMATION: sequence coding for signal peptide of CgR_0949
```

```
<220> FEATURE:
<221> NAME/KEY: misc_feature
<222> LOCATION: (1)..(25)
<223> OTHER INFORMATION: 5'-overlap for Gibson Assembly
<220> FEATURE:
<221> NAME/KEY: CDS
<222> LOCATION: (26)..(148)
<220> FEATURE:
<221> NAME/KEY: misc_feature
<222> LOCATION: (26)..(124)
<223> OTHER INFORMATION: sequence coding for signal peptide of CgR0949
<220> FEATURE:
<221> NAME/KEY: misc_feature
<222> LOCATION: (125)..(149)
<223> OTHER INFORMATION: 3'-overlap for Gibson Assembly

<400> SEQUENCE: 46
aagcttgcat gcctgcagac caggt atg caa ata aac cgc cga ggc ttc tta       52
                            Met Gln Ile Asn Arg Arg Gly Phe Leu
                             1               5 aaa gcc acc gca gga ctt gcc act atc ggc gct gcc agc atg ttt atg      100
Lys Ala Thr Ala Gly Leu Ala Thr Ile Gly Ala Ala Ser Met Phe Met
 10              15                  20                  25 cca aag gcc aac gcc ctt gga gca atg act agt acc tcc ttc aac cgc a    149
Pro Lys Ala Asn Ala Leu Gly Ala Met Thr Ser Thr Ser Phe Asn Arg
             30                  35                  40

<210> SEQ ID NO 47
<211> LENGTH: 41
<212> TYPE: PRT
<213> ORGANISM: artificial Sequence
<220> FEATURE:
<223> OTHER INFORMATION: Synthetic Construct

<400> SEQUENCE: 47

Met Gln Ile Asn Arg Arg Gly Phe Leu Lys Ala Thr Ala Gly Leu Ala
 1               5                  10                  15

Thr Ile Gly Ala Ala Ser Met Phe Met Pro Lys Ala Asn Ala Leu Gly
             20                  25                  30

Ala Met Thr Ser Thr Ser Phe Asn Arg
             35                  40

<210> SEQ ID NO 48
<211> LENGTH: 151
<212> TYPE: DNA
<213> ORGANISM: artificial sequence
<220> FEATURE:
<223> OTHER INFORMATION: sequence coding for signal peptide of CgR_1023
<220> FEATURE:
<221> NAME/KEY: misc_feature
<222> LOCATION: (1)..(25)
<223> OTHER INFORMATION: 5'-overlap for Gibson Assembly
<220> FEATURE:
<221> NAME/KEY: CDS
<222> LOCATION: (26)..(151)
<220> FEATURE:
<221> NAME/KEY: misc_feature
<222> LOCATION: (26)..(127)
<223> OTHER INFORMATION: sequence coding for signal peptide of CgR1023
<220> FEATURE:
<221> NAME/KEY: misc_feature
<222> LOCATION: (128)..(151)
<223> OTHER INFORMATION: 3'-overlap for Gibson Assembly

<400> SEQUENCE: 48
aagcttgcat gcctgcagac caggt gtg cgt aaa gga att tcc cgc gtc ctc      52
                            Val Arg Lys Gly Ile Ser Arg Val Leu
                             1               5 tcg gta gcg gtt gct agt tca atc gga ttc gga act gta ctg aca ggc     100
```

```
Ser Val Ala Val Ala Ser Ser Ile Gly Phe Gly Thr Val Leu Thr Gly
 10              15                  20                  25 acc ggc atc gca gca gct caa gac tct atg act agt acc tcc ttc aac    148
Thr Gly Ile Ala Ala Ala Gln Asp Ser Met Thr Ser Thr Ser Phe Asn
             30                  35                  40 cgc                                                                151
Arg

<210> SEQ ID NO 49
<211> LENGTH: 42
<212> TYPE: PRT
<213> ORGANISM: artificial sequence
<220> FEATURE:
<223> OTHER INFORMATION: Synthetic Construct

<400> SEQUENCE: 49

Val Arg Lys Gly Ile Ser Arg Val Leu Ser Val Ala Val Ala Ser Ser
 1               5                  10                  15

Ile Gly Phe Gly Thr Val Leu Thr Gly Thr Gly Ile Ala Ala Gln
             20                  25                  30

Asp Ser Met Thr Ser Thr Ser Phe Asn Arg
         35                  40

<210> SEQ ID NO 50
<211> LENGTH: 163
<212> TYPE: DNA
<213> ORGANISM: artificial sequence
<220> FEATURE:
<223> OTHER INFORMATION: sequence coding for signal peptide of CgR_1448
<220> FEATURE:
<221> NAME/KEY: misc_feature
<222> LOCATION: (1)..(25)
<223> OTHER INFORMATION: 5'-overlap for Gibson Assembly
<220> FEATURE:
<221> NAME/KEY: CDS
<222> LOCATION: (26)..(163)
<220> FEATURE:
<221> NAME/KEY: misc_feature
<222> LOCATION: (26)..(139)
<223> OTHER INFORMATION: sequence coding for signal peptide of CgR1448
<220> FEATURE:
<221> NAME/KEY: misc_feature
<222> LOCATION: (140)..(163)
<223> OTHER INFORMATION: 3'-overlap for Gibson Assembly

<400> SEQUENCE: 50
aagcttgcat gcctgcagac caggt atg gct cag att tct cgt cgt cac ttc    52
                            Met Ala Gln Ile Ser Arg Arg His Phe
                             1               5 ctg gct gca gca act gtt gca ggc gca ggc gca act ttg gca gca tgt    100
Leu Ala Ala Ala Thr Val Ala Gly Ala Gly Ala Thr Leu Ala Ala Cys
 10              15                  20                  25 gcg ggt acc ggt gga agc act tct tcc tcc agc gat tct atg act agt    148
Ala Gly Thr Gly Gly Ser Thr Ser Ser Ser Ser Asp Ser Met Thr Ser
             30                  35                  40 acc tcc ttc aac cgc                                                163
Thr Ser Phe Asn Arg
             45

<210> SEQ ID NO 51
<211> LENGTH: 46
<212> TYPE: PRT
<213> ORGANISM: artificial sequence
<220> FEATURE:
<223> OTHER INFORMATION: Synthetic Construct

<400> SEQUENCE: 51
```

Met Ala Gln Ile Ser Arg Arg His Phe Leu Ala Ala Ala Thr Val Ala
1               5                   10                  15

Gly Ala Gly Ala Thr Leu Ala Ala Cys Ala Gly Thr Gly Gly Ser Thr
                20                  25                  30

Ser Ser Ser Ser Asp Ser Met Thr Ser Thr Ser Phe Asn Arg
        35                  40                  45

<210> SEQ ID NO 52
<211> LENGTH: 149
<212> TYPE: DNA
<213> ORGANISM: artificial sequence
<220> FEATURE:
<223> OTHER INFORMATION: sequence coding for signal peptide of CgR_2137
<220> FEATURE:
<221> NAME/KEY: misc_feature
<222> LOCATION: (1)..(25)
<223> OTHER INFORMATION: 5'-overlap for Gibson Assembly
<220> FEATURE:
<221> NAME/KEY: CDS
<222> LOCATION: (26)..(148)
<220> FEATURE:
<221> NAME/KEY: misc_feature
<222> LOCATION: (26)..(121)
<223> OTHER INFORMATION: sequence coding for signal peptide of CgR2137
<220> FEATURE:
<221> NAME/KEY: misc_feature
<222> LOCATION: (122)..(149)
<223> OTHER INFORMATION: 3'-overlap for Gibson Assembly

<400> SEQUENCE: 52
aagcttgcat gcctgcagac caggt atg cca cag tta agc aga cgc cag ttc      52
                           Met Pro Gln Leu Ser Arg Arg Gln Phe
                           1               5 ttg cag aca acc gcc gtt act gca ggt cta gcc act ttt ttg ggc aca     100
Leu Gln Thr Thr Ala Val Thr Ala Gly Leu Ala Thr Phe Leu Gly Thr
10              15                  20                  25 cct gca cgc gct gaa gaa cgc atg act agt acc tcc ttc aac cgc aac c   149
Pro Ala Arg Ala Glu Glu Arg Met Thr Ser Thr Ser Phe Asn Arg Asn
            30                  35                  40

<210> SEQ ID NO 53
<211> LENGTH: 41
<212> TYPE: PRT
<213> ORGANISM: artificial sequence
<220> FEATURE:
<223> OTHER INFORMATION: Synthetic Construct

<400> SEQUENCE: 53

Met Pro Gln Leu Ser Arg Arg Gln Phe Leu Gln Thr Thr Ala Val Thr
1               5                   10                  15

Ala Gly Leu Ala Thr Phe Leu Gly Thr Pro Ala Arg Ala Glu Glu Arg
                20                  25                  30

Met Thr Ser Thr Ser Phe Asn Arg Asn
        35                  40

<210> SEQ ID NO 54
<211> LENGTH: 178
<212> TYPE: DNA
<213> ORGANISM: artificial sequence
<220> FEATURE:
<223> OTHER INFORMATION: sequence coding for signal peptide of CgR_2627
<220> FEATURE:
<221> NAME/KEY: misc_feature
<222> LOCATION: (1)..(25)
<223> OTHER INFORMATION: 5'-overlap for Gibson Assembly
<220> FEATURE:
<221> NAME/KEY: CDS

```
<222> LOCATION: (26)..(178)
<220> FEATURE:
<221> NAME/KEY: misc_feature
<222> LOCATION: (26)..(154)
<223> OTHER INFORMATION: sequence coding for signal peptide of CgR2627
<220> FEATURE:
<221> NAME/KEY: misc_feature
<222> LOCATION: (155)..(178)
<223> OTHER INFORMATION: 3'-overlap for Gibson Assembly

<400> SEQUENCE: 54
aagcttgcat gcctgcagac caggt atg gtg aac acg ttg aac tct aaa acc         52
                           Met Val Asn Thr Leu Asn Ser Lys Thr
                           1               5 gtg aat gta ccc cgt ttt gcc aga ggc gtt gtt gct gca gcc aca gcg        100
Val Asn Val Pro Arg Phe Ala Arg Gly Val Val Ala Ala Ala Thr Ala
 10              15                  20                  25 cta ttt ttt ggc gct ttg gta agc ctc gcg cct agt gcg ttg gcg cag        148
Leu Phe Phe Gly Ala Leu Val Ser Leu Ala Pro Ser Ala Leu Ala Gln
                 30                  35                  40 gaa cca atg act agt acc tcc ttc aac cgc                                178
Glu Pro Met Thr Ser Thr Ser Phe Asn Arg
             45                  50

<210> SEQ ID NO 55
<211> LENGTH: 51
<212> TYPE: PRT
<213> ORGANISM: artificial sequence
<220> FEATURE:
<223> OTHER INFORMATION: Synthetic Construct

<400> SEQUENCE: 55

Met Val Asn Thr Leu Asn Ser Lys Thr Val Asn Val Pro Arg Phe Ala
1               5                   10                  15

Arg Gly Val Val Ala Ala Ala Thr Ala Leu Phe Phe Gly Ala Leu Val
            20                  25                  30

Ser Leu Ala Pro Ser Ala Leu Ala Gln Glu Pro Met Thr Ser Thr Ser
        35                  40                  45

Phe Asn Arg
    50

<210> SEQ ID NO 56
<211> LENGTH: 172
<212> TYPE: DNA
<213> ORGANISM: artificial sequence
<220> FEATURE:
<223> OTHER INFORMATION: sequence coding for signal peptide of CgR_2926
<220> FEATURE:
<221> NAME/KEY: misc_feature
<222> LOCATION: (1)..(25)
<223> OTHER INFORMATION: 5'-overlap for Gibson Assembly
<220> FEATURE:
<221> NAME/KEY: CDS
<222> LOCATION: (26)..(172)
<220> FEATURE:
<221> NAME/KEY: misc_feature
<222> LOCATION: (26)..(148)
<223> OTHER INFORMATION: sequence coding for signal peptide of CgR2926
<220> FEATURE:
<221> NAME/KEY: misc_feature
<222> LOCATION: (149)..(172)
<223> OTHER INFORMATION: 3'-overlap for Gibson Assembly

<400> SEQUENCE: 56
aagcttgcat gcctgcagac caggt atg act caa cca gcc ccc atg tgt agc         52
                           Met Thr Gln Pro Ala Pro Met Cys Ser
                           1               5
```

```
cgc cgc atg ttt ctt ctt gga aca gca aca acc ttc gca ggt gct ttt      100
Arg Arg Met Phe Leu Leu Gly Thr Ala Thr Thr Phe Ala Gly Ala Phe
 10              15                  20                  25 ctt gca gcc tgt ggt act gaa cca gat cag gag gta gcg gct act gaa      148
Leu Ala Ala Cys Gly Thr Glu Pro Asp Gln Glu Val Ala Ala Thr Glu
             30                  35                  40 atg act agt acc tcc ttc aac cgc                                      172
Met Thr Ser Thr Ser Phe Asn Arg
             45
```

<210> SEQ ID NO 57
<211> LENGTH: 49
<212> TYPE: PRT
<213> ORGANISM: artificial sequence
<220> FEATURE:
<223> OTHER INFORMATION: Synthetic Construct

<400> SEQUENCE: 57

```
Met Thr Gln Pro Ala Pro Met Cys Ser Arg Arg Met Phe Leu Leu Gly
 1               5                  10                  15

Thr Ala Thr Thr Phe Ala Gly Ala Phe Leu Ala Ala Cys Gly Thr Glu
             20                  25                  30

Pro Asp Gln Glu Val Ala Ala Thr Glu Met Thr Ser Thr Ser Phe Asn
             35                  40                  45

Arg
```

<210> SEQ ID NO 58
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer pVW_4

<400> SEQUENCE: 58
tttgcgccga catcataacg                                                 20

<210> SEQ ID NO 59
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat1_agl2_rev

<400> SEQUENCE: 59
gccaccgaca gcgatgatag                                                 20

<210> SEQ ID NO 60
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat2_agl2_rev

<400> SEQUENCE: 60
actgtcgccg ggaaaaacta                                              20

<210> SEQ ID NO 61
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat3a_agl2

<400> SEQUENCE: 61
gtcgcggacg gcgtagaggg                                              20

<210> SEQ ID NO 62
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat4_agl2_rev

<400> SEQUENCE: 62
ggccgaaggt gacatgatgc                                              20

<210> SEQ ID NO 63
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat5a_agl2

<400> SEQUENCE: 63
agcgccgata gtggcaagtc                                              20

<210> SEQ ID NO 64
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat6_agl2_rev

<400> SEQUENCE: 64
ggtgcctgtc agtacagttc                                              20

<210> SEQ ID NO 65
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat7_agl2_rev

<400> SEQUENCE: 65
acccgcacat gctgccaaag                                                    20

<210> SEQ ID NO 66
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat8a_agl2

<400> SEQUENCE: 66
gtggctagac ctgcagtaac                                                    20

<210> SEQ ID NO 67
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat9_agl2_rev

<400> SEQUENCE: 67
tgcagcaaca acgcctctgg                                                    20

<210> SEQ ID NO 68
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer Wtat10_agl2

<400> SEQUENCE: 68
agcacctgcg aaggttgttg                                                    20

<210> SEQ ID NO 69
<211> LENGTH: 1492
<212> TYPE: DNA
<213> ORGANISM: artificial sequence
<220> FEATURE:
<223> OTHER INFORMATION: polynucleotide (DNA molecule) INT
<220> FEATURE:
<221> NAME/KEY: misc_feature
<222> LOCATION: (1)..(6)
<223> OTHER INFORMATION: EcoRI restriction site
<220> FEATURE:
<221> NAME/KEY: misc_feature
<222> LOCATION: (7)..(401)
<223> OTHER INFORMATION: 3'-end of the nucleotide sequence of locus tag
      NCgl2176
<220> FEATURE:
<221> NAME/KEY: misc_feature
<222> LOCATION: (398)..(401)
<223> OTHER INFORMATION: tga stop codon of NCgl2176
<220> FEATURE:
<221> NAME/KEY: misc_feature
<222> LOCATION: (402)..(959)
<223> OTHER INFORMATION: intergenic region between NCgl2176 and NCgl2177
      modiified by nucleotide exchanges to give restriction sites for
      EcoRV, AvRII and SmaI
<220> FEATURE:
<221> NAME/KEY: misc_feature

```
<222> LOCATION: (725)..(730)
<223> OTHER INFORMATION: EcoRV restriction site
<220> FEATURE:
<221> NAME/KEY: misc_feature
<222> LOCATION: (736)..(741)
<223> OTHER INFORMATION: AvRII restriction site
<220> FEATURE:
<221> NAME/KEY: misc_feature
<222> LOCATION: (746)..(751)
<223> OTHER INFORMATION: SmaII restriction site
<220> FEATURE:
<221> NAME/KEY: misc_feature
<222> LOCATION: (960)..(962)
<223> OTHER INFORMATION: cta codon: tag stop codon of NCgl2177 of the
      complementary strand
<220> FEATURE:
<221> NAME/KEY: misc_feature
<222> LOCATION: (960)..(1388)
<223> OTHER INFORMATION: nucleotide sequence complementary to NCgl2177
<220> FEATURE:
<221> NAME/KEY: misc_feature
<222> LOCATION: (1386)..(1388)
<223> OTHER INFORMATION: cat codon; atg start codon of NCgl2177 of the
      complementary strand
<220> FEATURE:
<221> NAME/KEY: misc_feature
<222> LOCATION: (1389)..(1486)
<223> OTHER INFORMATION: sequence upstream of NCgl2177
<220> FEATURE:
<221> NAME/KEY: misc_feature
<222> LOCATION: (1487)..(1492)
<223> OTHER INFORMATION: HindIII restriction site

<400> SEQUENCE: 69
```

| | | | | | |
|---|---|---|---|---|---|
| gaattctcca | agagttcatc | aacaaacacg | cactccccga | cggccccatg | ctgctcaccg | 60 |
| actggggacc | aaccccaca | ggactattcc | gctcaggtca | agagcacaag | aaagtccaac | 120 |
| tgcgcaacct | gtttatcgaa | taccccgaca | tgaaatggat | cctcgtcggc | gacgatggcc | 180 |
| aacacgatcc | cctcatctac | ggcgaagcag | tcgaagaaca | ccccaaccgc | atcgcaggcg | 240 |
| ttgcaatccg | tgagctctcc | cccggcgaac | atgtgctctc | ccacggaaca | actgcgtcac | 300 |
| tgtccaccat | cacgaccaac | gggggccaag | gagtcccagt | agttcacggc | cgcgatggat | 360 |
| atgagttgct | gcagcgctac | gagacgaagc | cgttcgcctg | agtcctactg | ggtgtctcat | 420 |
| gaaccaaacc | gggtgaccag | cgtcgcctta | atttgggtt | cctcggtcac | ctagtttggt | 480 |
| ccttggttgc | gttcgcgtat | ggcataaatg | ggcactgact | attttgggg | cggggccccg | 540 |
| aggtaaaagg | cgatttaaga | ggttgagatc | cccaaatagg | cttttggtat | ggaggacgcc | 600 |
| cgttgaggct | cttaaaaccg | attctgagag | acctcggctt | tgtgaccagt | gggacagatg | 660 |
| agattcctgc | gagcttgctg | atcaagaact | caccacaatt | gtgtggccag | accgtcaaat | 720 |
| cgaagatatc | tttgccctag | gtagacccgg | gcttgcaaaa | acccaccaca | aacactgtct | 780 |
| cgccagcaat | ctgtggtgaa | ttttcgcata | attgttcgac | caagagtccg | acggtaatca | 840 |
| acacgtcaca | aaccacccca | caaagtgcgc | caaaaaccg | tggggcctcc | ctcttcctct | 900 |
| agagaggccc | cacgggctgg | tctatttaca | ccccgccgag | ctaaagaatc | actggctttc | 960 |
| tagtcaacga | ttcgcagctc | aacttcaaaa | cggtattcat | cagccagaga | ttccagcact | 1020 |
| cctcgaagtt | tgtcgagttc | gcgtggagtt | ccggtgatca | cctctcgaca | ctcagtgagg | 1080 |
| ccaagttcga | atgggtcacg | gcgccatgca | gtgaaccatc | gtgcggtgag | cgggtccctg | 1140 |
| ttggagccgg | acagctccga | aggactcgga | atacacacaa | ccattgcgga | ttccacggtc | 1200 |
| tgacgcagtt | cctttggcat | tccgctgatt | tctagaacag | cggtatgcat | tgggagggct | 1260 |
| acatcgtcga | tggattcttc | gatggtagtt | ttcagttggg | gcaaccccat | gtcttcccag | 1320 |

-continued

```
aagtctgccg tgagcaaatc cgcctgatga cgggtccggg ttggcacggt taatgcattg    1380
ttcgtcatgt tcggtttcct tcggcaacac ttaactgcct tcaattcccg cacacatata    1440
caagtagata tgtgcagtta ctaaaggaag taagacgagg ttcgtcaagc tt            1492
```

<210> SEQ ID NO 70
<211> LENGTH: 2125
<212> TYPE: DNA
<213> ORGANISM: artificial sequence
<220> FEATURE:
<223> OTHER INFORMATION: gene fusion tat-'agl2_cuo including promoter and terminator
<220> FEATURE:
<221> NAME/KEY: misc_feature
<222> LOCATION: (1)..(20)
<223> OTHER INFORMATION: 20 nucleotides
<220> FEATURE:
<221> NAME/KEY: misc_feature
<222> LOCATION: (4)..(9)
<223> OTHER INFORMATION: XbaI restriction site
<220> FEATURE:
<221> NAME/KEY: promoter
<222> LOCATION: (52)..(111)
<223> OTHER INFORMATION: promoter PdapBN1
<220> FEATURE:
<221> NAME/KEY: misc_feature
<222> LOCATION: (142)..(2058)
<223> OTHER INFORMATION: sequence coding for fusion polypeptide Tat-'Agl2
<220> FEATURE:
<221> NAME/KEY: misc_feature
<222> LOCATION: (2059)..(2061)
<223> OTHER INFORMATION: stop codon
<220> FEATURE:
<221> NAME/KEY: misc_feature
<222> LOCATION: (2062)..(2069)
<223> OTHER INFORMATION: NotI restriction site
<220> FEATURE:
<221> NAME/KEY: misc_feature
<222> LOCATION: (2073)..(2108)
<223> OTHER INFORMATION: terminator Tgap*
<220> FEATURE:
<221> NAME/KEY: misc_feature
<222> LOCATION: (2111)..(2116)
<223> OTHER INFORMATION: XbaI restriction site
<220> FEATURE:
<221> NAME/KEY: misc_feature
<222> LOCATION: (2117)..(2125)
<223> OTHER INFORMATION: 9 nucleotides

<400> SEQUENCE: 70

```
gcgtctagaa ctgatgaaca atcgttaaca acacagacca aaacggtcag ttaggtatgg     60
atatcagcac cttctgaacg ggtacgggta taatggtggg cgtttgaaaa actcttcgcc    120
ccacgaaaat gaaggagcat aatgcaaata aaccgccgag gcttcttaaa agccaccaca    180
ggacttgcca ctatcggcgc tgccagcatg tttatgccaa aggccaacgc ccttggagca    240
atgactagta cctccttcaa ccgcgaacca ctgccagatg cagtgcgcac caacggtgca    300 acccccaaacc catggtggtc caacgcagtg gtgtaccaga tctacccacg ctccttccag    360
gataccaacg gcgacggcct gggcgatctg aagggcatca cctcccgctt ggattacctg    420
gcagatctgg gcgtggatgt gctgtggctg tccccagtgt accgctcccc acaggatgat    480
aacggctacg atatctccga ttaccgcgat atcgatccac tgttcggcac cctggatgat    540
atggatgaac tgctggcaga ggcacacaag cgtggcctga agatcgtgat ggatctggtg    600
gtgaaccaca cctccgatga acacgcatgg ttcgaagcat ccaaggataa ggatgatcca    660
cacgcagatt ggtactggtg gcgtccagca cgcccaggcc acgaaccagg caccccaggc    720
gcagaaccaa accagtgggg ctcctacttc ggtggctccg catgggaata ctccccagaa    780
```

-continued

```
cgcggtgaat actacctgca ccagttctcc aagaagcagc cagatctcaa ctgggaaaac      840
ccagcagtgc gtcgcgcagt gtacgatatg atgaactggt ggttggatcg cggtatcgat      900
ggcttccgca tggatgtgat caccctgatc tccaagcgca ccgatccaaa cggtcgcctg      960
ccaggtgaaa ccggctccga actccaggat ctgccagtgg gcgaagaagg ctactcctcc     1020
ccaaacccct tctgcgcaga tggccctcgc caggatgaat tcctggcaga aatgcgtcgc     1080
gaagttttcg atggccgtga tggcttcctg accgtgggcg aagcaccagg catcaccgca     1140
gaacgcaacg aacacatcac cgatccagca acggcgaac tggatatgct gttcctgttc      1200
gaacacatgg gcgtggatca gaccccagaa tccaagtggg atgataagcc atggacccca     1260
gcagatctgg aaaccaagct ggcagaacag caggatgcaa tcgcacgccg tggctgggcc     1320
tccctgttcc tggataacca cgatcagcca cgcgtggtgt cccgctgggg tgatgatacc     1380
tccaagaccg gtcgcatccg ctccgcaaag gcactggcac tgctgctgca catgcaccgt     1440
ggcaccccat acgtgtacca gggcgaagaa ctgggcatga ccaacgcaca cttcacctcc     1500
ctggatcagt accgcgatct ggaatccatc aacgcatacc accaacgcgt ggaagaaacc     1560
ggcatccgca cctccgaaac catgatgcgc tccctggcac gctacggtcg cgataacgca     1620
cgcaccccaa tgcagtggga tgattccacc tacgcaggct tcaccatgcc agatgcccca     1680
gtggaaccat ggatcgcagt gaacccaaac cacaccgaaa tcaacgcagc agatgaaacc     1740
gatgatccag attccgtgta ctccttccac aagcgcctga tcgcactgcg ccacaccgat     1800
ccagtggtgg cagcaggcga ttaccgtcgc gtggaaaccg gcaacgatcg catcattgca     1860
ttcacccgca ccctggacga acgcaccatc ctgaccgtga tcaacctgtc cccaacccag     1920
gcagcaccag caggcgaact ggaaaccatg ccagacggca ccatcttgat cgcaaacacc     1980
gatgacccag tgggcaacct caagaccacc ggcaccctgg gtccatggga agcattcgca     2040
atggaaaccg atccagaata agcggccgct gttagcccgg ggtgtgcctc ggcgcacccc     2100
gggctatttt tctagaggat ccgcg                                            2125
```

<210> SEQ ID NO 71
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer IR_1

<400> SEQUENCE: 71

```
gacctcggct ttgtgaccag                                                    20
```

<210> SEQ ID NO 72
<211> LENGTH: 20
<212> TYPE: DNA
<213> ORGANISM: artificial sequence
<220> FEATURE:
<223> OTHER INFORMATION: primer
<220> FEATURE:
<221> NAME/KEY: misc_feature
<222> LOCATION: (1)..(20)
<223> OTHER INFORMATION: primer IR_2

<400> SEQUENCE: 72

```
ctcaccgcac gatggttcac                                                    20
```

METHOD FOR THE PRODUCTION OF FINE CHEMICALS USING A *CORYNEBACTERIUM* SECRETING MODIFIED α-1,6-GLUCOSIDASES

CROSS REFERENCE TO RELATED APPLICATIONS

The present application claims priority under 35 USC § 119 to European application, EP 17175992.1, filed on Jun. 14, 2017, the contents of which is incorporated herein by reference in its entirety.

FIELD OF THE INVENTION

The present invention relates to polynucleotides encoding novel fusion polypeptides essentially composed of a signal peptide for membrane translocation and a polypeptide providing α-1,6-glucosidase activity and to bacteria containing said polynucleotides. The invention further relates to methods for producing fine chemicals using media containing isomaltose and/or panose as carbon source.

BACKGROUND OF THE INVENTION

Strains of the genus *Corynebacterium*, in particular the species *Corynebacterium glutamicum*, are known producers of L-amino acids, such as proteinogenic amino acids, e.g. L-lysine, L-threonine, L-valine or L-isoleucine, and of other fine chemicals, such as vitamins, nucleosides and nucleotides. Because of the great economic importance of these chemicals work is continually being done on improving the production methods. Improvements may relate to the genetic constitution of the microorganism, to the fermentation technology applied or to the working-up to the desired product form. The methods used for improving the genetic constitution are those of mutagenesis, selection and choice of mutants. Methods of recombinant DNA technology have likewise been used for a number of years for strain improvement of this group of bacteria. Background summaries concerning *Corynebacterium*, in particular *Corynebacterium glutamicum*, may be found in L. Eggeling and M. Bott (Handbook of *Corynebacterium glutamicum*, CRC Press, 2005), A. Burkovski (Corynebacteria Genomics and Molecular Biology, Caister Academic Press, 2008) or H. Yukawa and M. Inui (*Corynebacterium glutamicum* Biology and Biotechnology, Springer Verlag, 2013).

One of the main carbon sources used for propagation of this group of bacteria and for formation of a desired chemical is glucose. Glucose used in the fermentation industry is typically produced from starch by enzymatic hydrolysis. Starch is a mixture of two different polysaccharides each consisting of chains of linked, repeated glucose units. The mixture mainly consists of two separate polysaccharides, amylose and amylopectin. Amylose is an almost linear polysaccharide with glucose units connected almost exclusively through α-1,4 glycosidic linkages. Glucose units in amylopectin are additionally linked through α-1,6 glycosidic linkages. The content of amylose in starch in plant species like maize, wheat or rice is about 20 to 30% and the amylopectin content about 80 to 70%. Detailed information about starch may be found in J. Bemiller and R. Whistler (Starch: Chemistry and Technology, 3. ed., Elsevier, 2009).

Enzymatic starch hydrolysis to glucose involves two main steps. In the first step, also referred to as liquefaction, starch is treated with α-amylase (4-α-D-glucan glucanohydrolase; EC 3.2.1.1). The products of this reaction are α-1,4 linked oligomers of glucose, also referred to as maltodextrin, comprising molecules like maltotriose (O-α-D-Glcp-(1→4)-O-α-D-Glcp-(1→4)-D-Glcp) and maltohexaose (the respective α-(1→4)-linked D-glucose hexamer), and oligomers of glucose containing an α-1,6 linkage also referred to as limit dextrin. In the second step, also referred to as saccharification, this mixture is treated with glucoamylase, also referred to as amyloglucosidase in the art (4-α-D-glucan glucohydrolase; EC 3.2.1.3). This enzyme hydrolyzes the α-1,4 linkage rapidly. It also hydrolyzes the α-1,6 linkage but at a slower rate. The art also describes the use of pullulanase (pullulan 6-α-glucanohydrolase) in order to hydrolyze the α-1,6 linkage contained in the limit dextrins. The product of this second step is a glucose solution containing amongst others residual maltose (4-O-(α-D-Glucopyranosyl)-D-Glucopyranose), isomaltose (6-O-(α-D-Glucopyranosyl)-D-Glucopyranose) and panose (O-α-D-Glcp-(1→6)-O-α-D-Glcp-(1→4)-D-Glcp) as side products. These side products are the result of reverse enzymatic reactions due to the high glucose concentration accumulating during the saccharification step. The reverse reaction of glucoamylase yields maltose and isomaltose. As commercial enzyme preparations may contain transglucosidase (1,4-α-glucan 6-α-glucosyltransferase; EC 2.4.1.24) the presence of this enzyme also contributes to the formation of isomaltose and panose. Many variations of this basic procedure exist due to the enzymes available, mixtures thereof and reaction conditions.

Summaries concerning the enzymatic hydrolysis of starch to glucose and the side products formed may be found in P. H. Blanchard (Technology of Corn Wet Milling and Associated Processes, Elsevier, 1992), M. W. Kearsley and S. Z. Dziedzic: Handbook of Starch Hydrolysis Products and their Derivatives, Chapmann & Hall, 1995), B. H. Lee (Fundamentals of Food Biotechnology, VCH Publishers, 1996) or H. Uhlig (Industrial Enzymes and their Application, John Wiley & Sons 1998). Data concerning the composition of starch hydrolysates thus manufactured may be found in A. Converti (starch/starke 46 (7), 260-265, 1994), M. Chaplin and C. Bucke (Enzyme Technolgy, Cambridge University Press, 1990), Amarakone, P. et al (Journal of the Japanese Society of Starch Science, 31(1), 1-7, 1984), WO9927124 A1 and WO2005100583 A2. The glucose content of such starch hydrolysates is approximately 85 to 97% (based on dry matter content).

For industrial fermentative production of commodity fine chemicals like L-amino acids, e.g. L-lysine, it is not economical to first purify glucose from starch hydrolysate and then use it in the fermentation process. Instead starch hydrolysate itself is used as a low cost, glucose containing feedstock.

*Corynebacterium glutamicum* is unable to use isomaltose or panose as a carbon source. Accordingly these compounds accumulate in the fermentation broth during a production process when said starch hydrolysate is used as feedstock. The presence of these sugars in turn is unfavourable because they are an additional load to the plants waste water. Further they may generate product losses during the processing steps for manufacturing the final product. For example it is known that the reducing end of a sugar molecule may react with the amino group of L-amino acids, e.g. L-lysine, to give Maillard reaction products (M. W. Kearsley and S. Z. Dziedzic: Handbook of Starch Hydrolysis Products and their Derivatives, Chapmann & Hall, 1995).

In order to avoid these disadvantages methods were developed to convert isomaltose and/or panose to glucose during a fermentation process. WO2005100583 A2, WO2014093312 A1 and WO2015061289 A1 describe the addition of transglucosidase to the fermentation broth containing starch hydrolysate or sugar syrup as carbon source. This approach has the disadvantage that the enzyme must be produced separately thus adding to the production costs.

A different approach was followed by EP2241632 A1. It is suggested to impart a microorganism with an isomaltase activity. As microorganisms Enterobacteriaceae including *E. coli* and coryneform bacteria, including specific examples of this group of bacteria are presented. EP2241632 A1 further teaches that an intracellular or an extracellular isomaltase can be used. In case an intracellular isomaltase is imparted and the cell does not possess an activity to take up isomaltose it is preferred to impart both the intracellular isomaltase activity and the activity to take up isomaltose into the cell. As examples for an isomaltase gene the genes malL and glvA of *Bacillus subtilis* and homologues thereof are shown. As isomaltose transporter genes the glvC gene of *Bacillus subtilis* and other genes fulfilling a similar function of various origin are shown. During examination proceedings an experimental example was presented in which the glvA and the glvC gene of *Bacillus subtilis* were expressed in an L-lysine excreting strain of *C. glutamicum*. The strain constructed showed favorable isomaltose consumption and L-lysine formation as compared to the reference. However, EP2241632 A1 is silent whether this system will enable a *C. glutamicum* cell to consume panose.

EP2241632 A1 further generally proposes that an extracellular isomaltase gene may be obtained by ligating the coding region of the isomaltase gene with a sequence coding for a signal peptide for secreting the protein into a cell surface layer or out of the cell. As signal peptide the protein A of *Staphylococcus aureus* is suggested. A technical example is given for *E. coli* by fusing said signal peptide of protein A to the MalL isomaltase of *Bacillus subtilis*. The document is silent whether this secreted isomaltase also attacks panose. Furthermore, the document is silent about suitable signal peptides for *Corynebacterium glutamicum* or how to elect an appropriate signal peptide fitting to the isomaltase.

EP2241632 A1 also presents two lists of putative isomaltase genes from various microorganisms. Table 1 of EP2241632 A1 presents potential isomaltases as homologues of MalL having the function of amongst others oligosaccharide-producing multifunctional G-amylase, oligo-1,6-glucosidase, alpha amylase catalytic region or trehalose-6-phosphate hydrolase. Table 2 presents potential isomaltase genes as homologues having the function of maltose-6'-phosphate glucosidase or 6-phospho-alpha glucosidase.

Similarly, S. Jiang and L. Ma disclosed the nucleotide sequence of an oligo-1,6-glucosidase gene of *Bacillus subtilis* strain HB002 (available at the National Center for Biotechnology Information (NCBI) under GenBank accession number AY008307.1). The entry is silent about the activity of the encoded protein towards isomaltose and panose.

The art teaches various intracellular α-1,6-glucosidases (EC 3.2.1.10) having the ability to attack the α-1,6 linkage of isomaltose and/or panose.

The nucleotide sequence of the IMA1 gene of *Saccharomyces cerevisiae* strain S288c encoding an oligo-1,6-glucosidase is available at the NCBI under GenBank accession number NC_001139 having the locus_tag YGR287C. The entry discloses the encoded protein as an isomaltase. The entry is silent about its activity towards panose.

The dexB gene of *Streptococcus mutans* encodes an intracellular glucan 1,6-alpha-glucosidase (Whiting et al, Journal of General Microbiology 139, 2019-2026, 1993) having the ability to hydrolize the α-1,6 linkage in isomaltose and panose.

WO2004018645 A2 relates to the sequencing of the genome of *Bifidobacterium breve* ATCC 15700 and in particular to the identification of genes encoding enzymes having the ability to hydrolyze the α-1,6 linkage in isomaltose and panose.

Pokusaeva et al (Applied and Environmental Microbiology 75, 1135-1143, 2009) describe two genes agl1 and agl2 of *Bifidobacterium breve* UCC2003 encoding the enzymes Agl1 and Agl2, both having the activity of α-1,6-glucosidases. The enzymes were able to hydrolyze the α-1,6 linkage in panose and isomaltose. Pokusaeva et al. make no explicit statement about the intra- or extracellular location of the two enzymes. However in a review article by Pokusaeva et al. (Genes and Nutrition 6, 285-306, 2011) the two enzymes Agl1 and Agl2 are classified as "cytoplasmic enzymes" (see page 299-300).

In *C. glutamicum* two pathways for the secretion of proteins exist. One is referred to as Sec-pathway and mediates translocation of preproteins in an unfolded state through the membrane. The other is referred to as Tat-pathway and mediates transfer of preproteins in their folded state. The signal peptide of the preprotein is cleaved of from the preprotein by a peptidase during the secretion process and the mature protein is released into the culture medium. Summaries concerning protein secretion in *Corynebacterium glutamicum* were presented by A. A. Vertes contained in H. Yukawa and M. Inui (*Corynebacterium glutamicum* Biology and Biotechnolgy, Springer Verlag, 2013) and Liu et al (Critical Reviews in Biotechnology 1-11, 2016).

There are a number of reports for successful secretion of different proteins from different species or origin in *C. glutamicum*. However most of these proteins are secreted by their natural hosts indicating that these proteins have an intrinsic ability of being secretable.

Liebl et al. (Journal of Bacteriology 174, 1854-1861, 1992) reported on the successful expression and secretion of a staphylococcal nuclease, an extracellular enzyme of *Staphylococcus aureus* in *C. glutamicum* using the signal peptide of the original host.

Billman-Jacobe et al. (Applied and Environmental Microbiology 61, 1610-1613, 1995) report on expression and secretion of the basic protease of *Dichelobacter nodosus* and the subtilisin of *Bacillus subtilis* in *C. glutamicum*. While the secretion of subtilisin was directed by its own signal peptide the natural signal peptide of the basic protease did not facilitate secretion. After replacement of the natural signal sequence by the subtilisin signal sequence the basic protease was secreted by *C. glutamicum*.

Salim et al. (Applied and Environmental Microbiology 63, 4392-4400, 1997) report on the expression and secretion of antigen 85 protein of *Mycobacterium tuberculosis* in *C. glutamicum*. This protein is naturally found in the culture filtrates of *M. tuberculosis*.

EP1375664 A1 relates to the production and secretion of heterologous proteins such as the pro-transglutaminase of *Streptoverticillium mobarense* or the human epidermal growth factor (hEGF) in *Corynebacterium glutamicum* by fusing said proteins with signal peptide sequences of cell surface proteins of *C. glutamicum* or *C. ammoniagenes*. The pro-transglutaminase of *Streptoverticillum mobarense* is an enzyme which is secreted by its natural host (Pasternack et al; European Journal of Biochemistry 257, 570-576, 1998).

The human epidermal growth factor is a secreted peptide originally found in human urine by Cohen, S. and Carpenter, G. (Proceedings of National Academy of Sciences USA 72(4), 1317-1321, 1975).

EP1748077 A1 relates to the production and secretion of heterologous proteins in coryneform bacteria making use of a Tat system-dependent signal peptide region. In particular isomalto-dextranase of *Arthrobacter globiformis* (a 6-α-D-glucan isomaltohydrolase) was secreted by *C. glutamicum* using the signal sequence of the isomalto-dextranase or the signal sequence of the cell surface layer protein SIpA of *C. ammoniagenes*. Protein glutaminase of *Chryseobacterium proteolyticum* was secreted by *C. glutamicum* using the isomaltodextranase signal sequence of *A. globiformis*, the SIpA signal sequence of *C. ammoniagenes* or the TorA signal sequence of *Escherichia coli*. The isomalto-dextranase of *Arthrobacter globiformis* is an enzyme which is secreted by its natural host (Iwai et al; Journal of Bacteriology 176, 7730-7734, 1994). The protein glutaminase of *Chryseobacterium proteolyticum* is also an enzyme which is secreted into the culture medium by its natural host (Kikuchi et al; Applied Microbiology and Biotechnology 78, 67-74, 2008).

Watanabe et al. (Microbiology 155, 741-750, 2009) identified the N-terminus of the CgR0949 gene product and other gene products of *C. glutamicum* R as signal peptides addressing the Tat secretory pathway for proteins. The CgR0949 signal sequences comprises a sequence of 30 amino acid residues. After addition of this signal amino acid sequence to the α-amylase of *Geobacillus stearothermophilus* from which the natural signal peptide was removed the enzyme was secreted by the *C. glutamicum* host into the culture medium. The α-amylase of *Geobacillus stearothermophilus* is an enzyme which is secreted by its natural host (Fincan and Enez, Starch 66, 182-189, 2014).

Breitinger, K. J. (Dissertation/Ph.D. Thesis Ulm University 2013) disclosed the expression of a fusion polypeptide composed of the putative signal sequence of the protein encoded by gene cg0955 of *C. glutamicum* ATCC 13032 and the pullulanase PulA of *Klebsiella pneumoniae* UNF5023 in an L-lysine producing strain of *C. glutamicum*. Pullulanase activity was detected in the cell lysate and in the membrane fraction of said *C. glutamicum* cells but not in the culture supernatant of said strain. The pullulanase PulA of *Klebsiella pneumoniae* UNF5023 is an enzyme which is secreted by its natural host (Kornacker and Pugsley, Molecular Microbiology 4, 73-85, 1990). Breitinger, K. J. further stated that the 5'-terminus of gene Cg0955 of *C. glutamicum* ATCC 13032 shows a 95% homology to the signal sequence of gene cgR0949 of *C. glutamicum* R. The signal sequence of the protein encoded by gene cgR0949 was classified as a Tat-type signal sequence by Watanabe et al. (Microbiology 155, 741-750, 2009).

Hyeon et al (Enzyme and Microbial Technology 48, 371-377, 2011) constructed vector pMT1s designed for secretion of gene products into the culture medium using the cg0955 nucleotide sequence encoding the Tat signal peptide. Thus they were able to achieve secretion of the CbpA scaffolding protein of *Cellulomonas celluvorans* and the endoglucanase CelE of *Clostridium thermocellum* in *C. glutamicum* to form minicellulosomes. These proteins are secreted and displayed on the cell surface in their natural hosts.

Kim et al (Enzyme and Microbial Technology 66, 67-73, 2014) similarly expressed and secreted the endoglucanase CelE and the β-glucosidase BglA of *C. thermocellum* in *C. glutamicum* to display them on the cell surface. In their natural host these enzymes are constituents of cellulosomes located on the cell surface of its host.

Matano et al (BMC Microbiology 16, 177, 2016) studied the expression and secretion of N-acetylglucosaminidase from different microorganisms. A gene termed nagA2 was identified in the chromosome of *C. glutamicum*. After its expression enzyme activity was detected in the cytoplasmic fraction and culture supernatant. After replacement of the putative signal peptide of NagA2 with different Tat-type signal sequences including SP0955 (another term for the signal peptide encoded by cg0955) secretion efficiency was improved.

Matano et al. further achieved secretion of the exochitinase ChiB of *Serratia marcescens* by fusing the sequence encoding the Tat secretion signal peptide from the *C. glutamicum* gene cg0955 to chiB. It is noted that the exochitinase ChiB of *Serratia marcescens* is an enzyme which is exported into the periplasm by its natural host (Brurberg et al, Microbiology 142, 1581-1589 (1996)). Matano et al. further investigated the secretion of the *Bacillus subtilis* N-acetylglucosaminidase encoded by nagZ in *C. glutamicum*. This enzyme is inefficiently secreted by its natural host. NagZ N-acetylglucosaminidase was also expressed with various *C. glutamicum* signal peptides to increase the amount of enzyme in the supernatant. However, fusion to these signal peptides including the signal peptide from Cg0955 had no effect on the amount of enzyme secreted into the culture supernatant. In particular it is noted that fusion to the signal peptide from Cg0955 drastically increased the amount of intracellular enzyme activity.

Yim et al. (Applied Microbiology and Biotechnology 98, 273-284, 2014) report on the secretion of a recombinant single-chain variable antibody fragment against anthrax toxin in *C. glutamicum*. The use of the TorA signal peptide addressing the Tat pathway resulted in negligible secretion whereas the use of the PorB signal peptide addressing the Sec pathway resulted in measurable secretion. The authors also stated that the use of a codon optimized gene sequence was one of the components for high production of the protein.

WO2008049782 A1 relates to increasing gene expression in *C. glutamicum* by adjusting the codon usage of genes to that of abundant proteins in the host cell.

The green fluorescent protein (GFP) has attracted much interest in molecular biology as a model protein easy to monitor due to its fluorescence. It is found in jellyfish like *Aequora victoria*, where it is localized in specialized photocytes (J. M. Kendall and M. N. Badminton, Tibtech, 216-224, 1998). Meissner et al. (Applied Microbiology and Biotechnology 76, 633-642, 2007) investigated protein secretion using the green fluorescent protein in three different Gram-positive bacteria *Staphylococcus carnosus, Bacillus subtilis* and *Corynebacterium glutamicum*. In all three microorganisms fusion of a Tat-signal peptide to GFP resulted in its translocation through the cytoplasmic membrane. However, in *S. carnosus* GFP was trapped entirely in the cell wall and not released into the supernatant. In *Bacillus subtilis* GFP was secreted into the supernatant in an inactive form. In *C. glutamicum* different Tat signal peptides were used. The TorA signal peptide from *E. coli*, the PhoD signal sequence of *C. glutamicum* and the PhoD signal sequence of *Bacillus subtilis*. Although GFP was secreted in all three cases the amount of secreted protein was significantly different. Strikingly the PhoD signal sequence from *B. subtilis* gave the best result.

Teramoto et al. (Applied Microbiology and Biotechnoogy 91, 677-687, 2011) used the signal peptide of CgR0949 to achieve high yield secretion of GFP in *C. glutamicum*.

It is noted that Hemmerich et al. (Microbial Cell Factory 15(1), 208, 2016) after a search for a suitable signal peptide for the secretion of the cutinase of *Fusarium solani pisi* in *Corynebacterium glutamicum* concluded that the best signal peptide for a specific target protein has to be evaluated each time from scratch.

Isomaltose and/or panose are contained in starch hydrolysate in comparably small amounts. Accordingly, for a research program aiming at a *C. glutamicum* strain producing a fine chemical, e. g. L-lysine, at high yield and using the comparatively low amounts of these sugars as additional carbon source, it is not desirable to produce and secrete an enzyme, hydrolyzing the α-1,6 glycosidic linkage of these sugars, at high yield. Both compounds, the fine chemical and the enzyme, would compete for the same carbon source(s) and thus the yield of the compound of commercial interest, which is the fine chemical, would be negatively affected. The enzyme produced and secreted would then be a metabolic burden for the producer of the fine chemical.

Hitherto, directing an intracellular enzyme of a microorganism having the ability to hydrolyse the α-1,6 glycosidic linkage of isomaltose and/or panose, to the extracellular matrix, i. e. the culture supernatant, has not been demonstrated for *Corynebacterium glutamicum*.

However, it is desirable to provide a fermentative process for a fine chemical based on a low cost fermentation raw material containing panose and/or isomaltose such as starch hydrolysate using a *Corynebacterium*, in particular a *Corynebacterium glutamicum*, having the ability to hydrolyse the α-1,6 glycosidic linkage of panose and/or isomaltose thus making available these glucose oligomers for propagation and fine chemical formation.

SUMMARY OF THE INVENTION

It is an object of the present invention to provide a polynucleotide encoding a polypeptide having α-1,6 glucosidase activity and which polypeptide can be secreted by a *Corynebacterium*, preferably by *Corynebacterium glutamicum*.

A further object of the present invention is the provision of a *Corynebacterium*, preferably *Corynebacterium glutamicum* comprising said polynucleotide.

Furthermore, it is an object of the present invention to provide a method for producing a fine chemical, such as L-amino acids, vitamins, nucleosides and nucleotides, from a carbon source comprising oligosaccharides consisting of least two α-1-6-glycosidically linked glucose monomers, such as panose (O-α-D-Glcp-(1→6)-O-α-D-Glcp-(1→4)-D-Glcp) or isomaltose (O-α-D-Glcp-(1→6)-O-α-D-Glcp), by using said *Corynebacterium*.

To achieve the object outlined above the present invention makes available polynucleotides encoding novel fusion polypeptides essentially comprising the Tat-signal peptide of CgR0949 or Cg0955 and the polypeptides Agl2 or Agl1 of *Bifidobacterium breve* UCC2003 and variants thereof providing α-1,6-glucosidase activity.

The present invention further makes available bacteria of the genus *Corynebacterium* and *Escherichia* carrying said polynucleotides and methods for the producing the fine chemicals from oligosaccharides consisting of least two α-1-6-glycosidically linked glucose monomers, such as panose and/or isomaltose using said bacteria.

BRIEF DESCRIPTION OF THE DRAWINGS

FIG. 1: FIG. 1 is a map of plasmid pVWEx1.

FIG. 2: FIG. 2 is a map of plasmid pVWEx1_tat-'agl2_cuo.

FIG. 3: FIG. 3 is a map of plasmid pVWEx1_agl2_cuo.

FIG. 4: FIG. 4 is a graph showing the growth rate of the strains DM1933/pVWEx1 and DM1933/pVWEx1_tat-'agl2_cuo using glucose as carbon source.

FIG. 5: FIG. 5 is a map of expression unit PBN1-tat-'agl2_cuo.

FIG. 6: FIG. 6 is a map of the INT::PBN1-tat-'agl2_cuo unit.

FIG. 7: FIG. 7 is a map of plasmid pK18mobsacB_INT::PBN1-tat-'agl2_cuo containing the pK18mobsacB unit and the PBN1-tat-'agl2_cuo unit.

DETAILED DESCRIPTION OF THE INVENTION

The objects underlying the present invention were solved by an isolated polynucleotide, preferably deoxyribo-polynucleotide, encoding a fusion polypeptide comprising amino acid sequences a), b) and c) with a) being an N-terminal Tat-signal peptide consisting of an amino acid sequence selected from
  a1) positions 1 to 33 of SEQ ID NO:10 or positions 1 to 33 of SEQ ID NO:12 and
  a2) positions 1 to 33 of SEQ ID NO:10 with Ala at position 13 or positions 1 to 33 of SEQ ID NO:12 with Ala at position 13;

b) being a C-terminal polypeptide having α-1,6-glucosidase activity consisting of an amino acid sequence selected from
  b1) at least (≥) 95% identical, preferably ≥99% identical, to the sequence from positions 37 to 639 of SEQ ID NO:10 and
  b2) at least (≥) 95% identical, preferably ≥99% identical, to the sequence from positions 37 to 643 of SEQ ID NO:12, and c) being 0 to maximally 10 amino acid residues, preferably 1 to 3 amino acid residues, particularly preferred 3 amino acid residues, between a) and b).

In case that the amino acid sequence c) consists of 3 amino acid residues it is preferred that these 3 amino acids have the sequence Met Thr Ser.

It could be shown that the inventive polynucleotide combining the coding sequence for the specific Tat-signal peptide according to a1) or a2) with the specific α-1,6-glucosidase according to b1) or b2) enables the breakdown of panose and isomaltose when expressed in a fine chemical producing bacterium of the genus *Corynebacterium* or *Escherichia*. The expression of the polynucleotide according to the invention does not put a metabolic burden on the production of said fine chemical. Expression of the polynucleotide according to the invention further improves the yield of a fine chemical produced by the fine chemical producing bacterium by making available panose and isomaltose as carbon source.

The inventive polynucleotide according to the invention thus solves the following problems:

Providing an α-1,6-glucosidase with a specificity that allows depolymerization of isomaltose and panose under conditions of a fermentation.

Expressing the α-1,6-glucosidase in a fine chemical producing bacterium without becoming a metabolic burden for the production of the fine chemical.

Achieving secretion of the α-1,6-glucosidase into the surrounding medium of the fine chemical producing bacterium by combining the coding sequence of the α-1,6-glucosidase with a suitable signal peptide that is compatible with the specific α-1,6-glucosidase.

Providing additional metabolizable carbon source for the production of the fine chemical and increasing the overall yield of the fine chemical produced by the bacterium by accomplishing that the expression of the secreted α-1,6-glucosidase is not competing with the production of the fine chemical for carbon source.

In case the amino acid sequence of a) is directly adjoined or connected resp. to the amino acid sequence of b) the number of amino acid residues of c) is 0 (zero).

In case the number of amino acid residues of c) is 3 (three) it is preferred that the sequence of said amino acid residues is Met Thr Ser or Ile Leu Val.

It is preferred that the N-terminal Tat-signal peptide of a) consists of the amino acid sequence of a1) which is the amino acid sequence of positions 1 to 33 of SEQ ID NO:10 or positions 1 to 33 of SEQ ID NO:12.

Further it is preferred that the amino acid sequence of the C-terminal polypeptide of b1) is selected from positions 37 to 639 of SEQ ID NO:10 and from positions 37 to 639 of SEQ ID NO:10 plus an additional Met in front of position 37 as shown in SEQ ID NO:6, particularly preferred is the amino acid sequence from positions 37 to 639 of SEQ ID NO:10.

The term "an additional Met in front of position 37 as shown in SEQ ID NO:6" means that the amino acid Met is inserted in the amino acid sequence of SEQ ID NO:10 between positions 36 and 37.

Further it is preferred that the C-terminal polypeptide of b2) is selected from positions 39 to 643 of SEQ ID NO:12, positions 38 to 643 of SEQ ID NO:12 and positions 37 to 643 of SEQ ID NO:12, particularly preferred is the amino acid sequence from positions 37 to 643 of SEQ ID NO:12.

Details regarding the biochemistry and chemical structure of polynucleotides and polypeptides as present in living things such as bacteria like *Corynebacterium* or *Escherichia*, for example, can be found inter alia in the text book "Biochemie" by Berg et al (Spektrum Akademischer Verlag Heidelberg, Berlin, Germany, 2003; ISBN 3-8274-1303-6).

Polynucleotides consisting of deoxyribonucleotide monomers containing the nucleobases or bases resp. adenine (a), guanine (g), cytosine (c) and thymine (t) are referred to as deoxyribopolynucleotides or deoxyribonucleic acid (DNA). Polynucleotides consisting of ribonucleotide monomers containing the nucleobases or bases adenine (a), guanine (g), cytosine (c) and uracil (u) are referred to as ribo-polynucleotides or ribonucleic acid (RNA). The monomers in said polynucleotides are covalently linked to one another by a 3',5'-phosphodiester bond. By convention single strand polynucleotides are written from 5'- to 3'-direction. Accordingly a polynucleotide has a 5'-end and 3'-end. For the purpose of this invention deoxyribopolynucleotides are preferred. In bacteria, for example *Corynebacterium* or *Escherichia*, the DNA is typically present in double stranded form. Accordingly the length of a DNA molecule is typically given in base pairs (bp).

Polypeptides consist of L-amino acid monomers joined by peptide bonds. For abbreviation of L-amino acids the one letter code and three letter code of IUPAC is used. Due to the nature of polypeptide biosynthesis polypeptides have an amino terminal end and a carboxyl terminal end also referred to as N-terminal end and C-terminal end. Polypeptides are also referred to as proteins.

Fusion polypeptides also referred to as fusion proteins or chimeric proteins in the art are polypeptides created through the joining of two or more genes that originally coded for separate polypeptides. Translation of such fusion gene results in a polypeptide with functional properties from each of the original polypeptides.

During the work for the present invention a portion comprising the 5'-end of the nucleotide sequence of various genes coding for the N-terminal portion of polypeptides having the ability to be translocated through the cytoplasmic membrane of a bacterium were fused to nucleotide sequences of genes or parts thereof coding for polypeptides having α-1,6-glucosidase enzyme activity, said polypeptides thus constituting the C-terminal portion or C-terminal polypeptide resp. within the fusion polypeptide.

In bacteria such as *Corynebacterium* and *Escherichia* two major pathways exist to secrete proteins or polypeptides resp. across the cytoplasmic membrane. One is called the general Secretion route or Sec-pathway and the other is called the Twin-arginine translocation pathway or Tat-pathway. A general review of these two translocation pathways was presented by Natale et al (Biochimica et Biophysica Acta 1778, 1735-1756, 2008) and a review specific for *Corynebacterium glutamicum* was given by Liu et al (Critical Reviews in Biotechnology 2016) and Freudl (Journal of Biotechnology http://dx.doi.org/10.1016/j.jbiotec.2017.02.023).

A functional analysis of the Twin-arginine translocation pathway in *Corynebacterium glutamicum* was presented by Kikuchi et al (Applied and Environmental Microbiology 72, 7183-7192, 2006).

The nucleotide sequence of the coding region (cds) of cgR0949 of *Corynebacterium glutamicum* strain R is shown in SEQ ID NO:3 and the amino acid sequence of the encoded CgR0949 polypeptide is shown in SEQ ID NO:4 of the sequence protocol. The nucleotide sequence of the coding region of cgR0949 can also be found at the NCBI under locus tag CGR_RS04950 of the genome sequence accessible under NC_009342. The amino acid sequence of CgR0949, also designated CgR_0949 in the art, can be found under GenBank accession number BAF53923.1.

Watanabe et al (Microbiology 155, 741-750, 2009) identified the amino acid sequence from position 1 to 30 of SEQ ID NO:4 as a signal sequence or signal peptide, resp. adressing the Tat-pathway and the sequence Leu Gly Ala shown in positions 31 to 33 of SEQ ID NO:4 as a putative cleavage site.

The nucleotide sequence of the coding region (cds) of cg0955 of *Corynebacterium glutamicum* strain ATCC13032 is shown in SEQ ID NO:1 and the amino acid sequence of the encoded Cg0955 polypeptide is shown in SEQ ID NO:2 of the sequence protocol. The nucleotide sequence of the coding region of cg0955 can also be found at the NCBI under locus tag NCgl0801 of the genome sequence accessible under NC_003450. The amino acid sequence of Cg0955 can be found under accession number NP_600064.1.

Within this invention the term signal peptide of CgR0949 or Tat-signal peptide of CgR0949 or signal peptide of Cg0955 or Tat-signal peptide of Cg0955 comprises the amino acid sequence of the signal sequence and the putative cleavage site Leu Gly Ala as defined by Watanabe et al (see FIG. 3 on page 745 of Watanabe et al).

The amino acid sequence from position 1 to 33 of SEQ ID NO:2 is identical with the amino acid sequence from position 1 to 33 of SEQ ID NO:4 with the exception of position 13. The amino acid at position 13 of of SEQ ID NO:2 is Thr and the amino acid at position 13 of SEQ ID NO:4 is Ala.

The amino acid sequence from positions 1 to 33 of SEQ ID NO:2 is fully identical with the amino acid sequence from positions 1 to 33 of SEQ ID NO:10 and fully identical with the amino acid sequence of SEQ ID NO:12.

The term α-1,6-glucosidase designates an enzyme which has the activity of hydrolyzing the α-1,6 linkage in some oligo-saccharides produced from starch or glycogen. For the purpose of this invention the enzyme has at least the ability to hydrolyze the α-1,6 linkage contained in isomaltose and/or panose. According to the Nomenclature Committee of the International Union of Biochemistry and Molecular Biology (NC-IUBMB) the accepted name for the enzyme is "oligo-1,6-glucosidase" and the systematic name "oligosaccharide α-1,6-glucohydrolase". The EC number of the enzyme is EC 3.2.1.10. Instructions for measuring said enzyme activity may be found in Pokusaeva et al (Applied and Environmental Microbiology 75, 1135-1143, 2009). The activity of the enzyme may also be assessed by using a chromogenic substrate like para-nitrophenyl-α-glucoside as for example described by Deng et al (FEBS Open Bio 4, 200-212, 2014).

In one set of preferred embodiments according to the invention the C-terminal polypeptide portion or C-terminal polypeptide resp. of the fusion polypeptide is the Agl2 α-1,6-glucosidase of *Bifidobacterium breve* strain UCC2003 (see Pokusaeva et al) and variants thereof. This group of C-terminal polypeptides is also referred to as Agl2-type C-terminal polypeptides hereafter. The amino acid sequence of the encoded Agl2 α-1,6-glucosidase polypeptide of *Bifidobacterium breve* strain UCC2003 is publicly available in the GenBank database of the NCBI (National Center for Biotechnology Information, U.S. National Library of Medicine 8600 Rockville Pike, Bethesda Md., 20894 USA) under accession number FJ386390. It is also shown in SEQ ID NO:6 of the sequence protocol. The amino acid sequence from positions 2 to 604 of SEQ ID NO:6 is identical to the amino acid sequence from position 37 to 639 of SEQ ID NO:10. The amino acid sequence from positions 37 to 639 of SEQ ID NO:10 represents the C-terminal polypeptide of the encoded fusion polypeptide shown in SEQ ID NO:10.

According to the invention variants of said C-terminal polypeptide may be used which have an amino acid sequence ≥95% identical, preferably ≥99%, particularly preferred 100% identical to the amino acid sequence from positions 37 to 639 of SEQ ID NO:10. An example of a C-terminal polypeptide having an amino acid sequence ≥99% identical to that from positions 37 to 639 of SEQ ID NO:10 is shown in SEQ ID NO:6.

It was found that connecting the Tat-signal peptide of Cg0955 to said Agl2 α-1,6-glucosidases achieved the object of the invention in an efficient manner.

These Agl2-type C-terminal polypeptides are preferably connected to the Tat-signal peptide of Cg0955 shown in the amino acid sequence of SEQ ID NO:2 from positions 1 to 33. The amino acid sequence from positions 1 to 33 of SEQ ID NO:2 is identical with the amino acid sequence from positions 1 to 33 of SEQ ID NO:10. They may be directly connected or by a sequence of maximally 10 amino acids, preferably 1 to 3, particularly preferred 3 amino acids. It is preferred that these 3 amino acids have the sequence Met Thr Ser.

Accordingly, the invention provides an isolated polynucleotide encoding a fusion polypeptide comprising, preferably consisting of, the amino acid sequence of SEQ ID NO:10 and having α-1,6-glucosidase activity. The encoded fusion polypeptide shown in SEQ ID NO:10 was designated Tat-'Agl2.

The amino acid sequence of the C-terminal polypeptide of the fusion polypeptide shown in SEQ ID NO:10, which is the amino acid sequence from positions 37 to 639 of SEQ ID NO:10 may be encoded by the nucleotide sequence from positions 4 to 1812 of SEQ ID NO:5, which is the nucleotide sequence of the coding region of the agl2 gene contained in *Bifidobacterium breve* UCC2003 without the atg start codon. The nucleotide sequence from positions 4 to 1812 of SEQ ID NO:5 is also referred to as 'agl2.

It is known in the art that the genetic code is degenerated which means that a certain amino acid may be encoded by a number of different triplets. The term codon usage refers to the observation that a certain organism will typically not use every possible codon for a certain amino acid with the same frequency. Instead an organism will typically show certain preferences for specific codons meaning that these codons are found more frequently in the coding sequence of transcribed genes of an organism. If a certain gene foreign to its future host, i. e. from a different species, should be expressed in the future host organism the coding sequence of said gene should then be adjusted to the codon usage of said future host organism. In the present invention said gene foreign to its future host is agl2 of *Bifidobacterium breve* UCC2003 or variants thereof and said future host is *Corynebacterium*, preferably *Corynebacterium glutamicum*. Teachings concerning codon usage optimization may be found in Fath et al (PLos ONE, 6(3), e17596, 2011) and WO2008049782.

According to a further embodiment of the invention said amino acid sequence from positions 37 to 639 of SEQ ID NO:10 is encoded by an isolated polynucleotide having a nucleotide sequence optimized for the codon usage of *Corynebacterium glutamicum* said nucleotide sequence being ≥99,0%, particularly preferred ≥99,5%, more particularly preferred 100% identical to the nucleotide sequence from position 109 to 1917 of SEQ ID NO:9.

The nucleotide sequence from position 109 to 1917 of SEQ ID NO:9 being codon usage optimized (cuo) for *Corynebacterium glutamicum* is also referred to as "'agl2_cuo" in this invention.

According to the invention the isolated polynucleotide encoding a fusion polypeptide comprising the amino acid sequence from positions 1 to 33 of SEQ ID NO:10, directly followed by a sequence of three amino acids, preferably the amino acid sequence from positions 34 to 36 of SEQ ID NO:10, directly followed by the amino acid sequence from positions 37 to 639 of SEQ ID NO:10 may be encoded by nucleotide sequence comprising nucleotides 1 to 1917 of SEQ ID NO:9, preferably comprising SEQ ID NO:9. More specifically said nucleotide sequence may consist of nucleotides 1 to 1917 of SEQ ID NO:9 or SEQ ID NO:9.

In another set of embodiments according to the invention the C-terminal polypeptide portion or C-terminal polypeptide resp. of the fusion polypeptide is the Agl1 α-1,6-glucosidase of *Bifidobacterium breve* strain UCC2003 (see Pokusaeva et al) and variants thereof. This group of C-terminal polypeptides is also referred to as Agl1-type C-terminal polypeptides hereafter. The amino acid sequence of the encoded Agl1 α-1,6-glucosidase polypeptide of *Bifidobacterium breve* strain UCC2003 is publicly available in the GenBank database of the NCBI (National Center for Biotechnology Information, U.S. National Library of Medicine 8600 Rockville Pike, Bethesda Md., 20894 USA) under accession number FJ386389. It is also shown in SEQ ID NO:8 of the sequence protocol. The amino acid sequence from positions 1 to 607 of SEQ ID NO:8 is identical to the amino acid sequence from position 37 to 643 of SEQ ID NO: 12. The amino acid sequence from positions 37 to 643 of SEQ ID NO:12 represents the C-terminal polypeptide of the encoded fusion polypeptide shown in SEQ ID NO:12. According to the invention variants of said C-terminal polypeptide may be used which have an amino acid sequence ≥95% identical, preferably ≥99%, particularly preferred 100% identical to the amino acid sequence from positions 37 to 643 of SEQ ID NO:12. Examples of C-terminal polypeptides having an amino acid sequence ≥99% identical to that from positions 37 to 643 of SEQ ID NO:12 are C-terminal polypeptides having the amino acid sequence from 38 to 643 of SEQ ID NO:12 or from 39 to 643 of SEQ ID NO:12.

These Agl1-type C-terminal polypeptides are preferably connected to the Tat-signal peptide of Cg0955 shown in the amino acid sequence of SEQ ID NO:2 from positions 1 to 33. The amino acid sequence from positions 1 to 33 of SEQ ID NO:2 is identical with the amino acid sequence from positions 1 to 33 of SEQ ID NO:12. They may be directly connected or by a sequence of maximally 10 amino acids, preferably 1 to 3, particularly preferred 3 amino acids. It is preferred that these 3 amino acids have the sequence Ile Leu Val.

Accordingly the invention provides an isolated polynucleotide encoding a fusion polypeptide comprising, preferably consisting of, the amino acid sequence of SEQ ID NO:12 and having α-1,6-glucosidase activity. The encoded fusion polypeptide shown in SEQ ID NO:12 was designated Tat-Agl1.

The amino acid sequence of the C-terminal polypeptide of the fusion polypeptide shown in SEQ ID NO:12, which is the amino acid sequence from positions 37 to 643 of SEQ ID NO:12 may be encoded by the nucleotide sequence from positions 1 to 1821 of SEQ ID NO:7, which is the nucleotide sequence of the coding region of the agl1 gene contained in *Bifidobacterium breve* UCC2003.

It is known in the art that the genetic code is degenerate which means that a certain amino acid may be encoded by a number of different triplets. The term codon usage refers to the observation that a certain organism will typically not use every possible codon for a certain amino acid with the same frequency. Instead an organism will typically show certain preferences for specific codons meaning that these codons are found more frequently in the coding sequence of transcribed genes of an organism. If a certain gene foreign to its future host, i. e. from a different species, should be expressed in the future host organism the coding sequence of said gene should then be adjusted to the codon usage of said future host organism. In the present invention said gene foreign to its future host is agl1 of *Bifidobacterium breve* UCC2003 or variants thereof and said future host is *Corynebacterium*, preferably *Corynebacterium glutamicum*.

According to the invention it is preferred that said amino acid sequence from positions 37 to 643 of SEQ ID NO:12 is encoded by an isolated polynucleotide having a nucleotide sequence optimized for the codon usage of *Corynebacterium glutamicum* said nucleotide sequence being ≥99,0%, particularly preferred ≥99,5%, more particularly preferred 100% identical to the nucleotide sequence from position 109 to 1929 of SEQ ID NO:11.

The nucleotide sequence from position 109 to 1929 of SEQ ID NO:11 being codon usage optimized (cuo) for *Corynebacterium glutamicum* is also referred to as "agl1_cuo" in this invention.

According to the invention it is furthermore preferred that the isolated polynucleotide encoding a fusion polypeptide comprising the amino acid sequence from positions 1 to 33 of SEQ ID NO:12, directly followed by a sequence of three amino acids, preferably the amino acid sequence from positions 34 to 36 of SEQ ID NO:12, directly followed by the amino acid sequence from positions 37 to 643 of SEQ ID NO:12 is encoded by the nucleotide sequence comprising nucleotides 1 to 1929 of SEQ ID NO:11, preferably comprising SEQ ID NO:11. More specifically it is preferred that said nucleotide sequence consists of nucleotides 1 to 1929 of SEQ ID NO:11 or SEQ ID NO:11.

Due to the double-stranded structure of DNA, the strand complementary to the strand shown in the sequence protocol e. g. SEQ ID NO:9 or SEQ ID NO:11 is likewise subject of the invention. In order to achieve expression of the polynucleotides of the present invention said polynucleotides are functionally linked to a promotor.

Accordingly the invention provides an isolated polynucleotide encoding a fusion polypeptide of the invention functionally linked to a promotor.

A promotor denotes a polynucleotide, preferably deoxyribo-polynucleotide, which is functionally linked to a polynucleotide to be transcribed and determines the point and frequency of initiation of transcription of the poly-nucleotide thus enabling expression of the polynucleotide.

The term "functionally linked" denotes in this context the sequential arrangement of the promotor with a polynucleotide to be expressed resulting in transcription of said polynucleotide. In these arrangements the distance between the 3'-end of the promoter and the 5'-end of the coding sequence typically is ≤300 base pairs, preferred ≤200 base pairs, particularly preferred ≤100 base pairs, more particularly preferred ≤60 base pairs. In the context of the present invention said polynucleotide to be expressed encodes a fusion polypeptide according to the invention as for example shown in SEQ ID NO:10 or SEQ ID NO:12.

The term "transcription" means the process by which a complementary RNA molecule is produced starting from a DNA template. This process involves specific proteins e.g. RNA polymerase. The synthesized RNA (messenger RNA) then serves as template in the process of translation which yields the polypeptide or protein resp. Transcription typically ends at a nucleotide sequence referred to as transcriptional terminator. An example of a transcriptional terminator is the transcriptional terminator of the gap gene of *Corynebacterium glutamicum* identified by Eikmanns, B. J. (Journal of Bacteriology 174(19), 6067-6068, 1992) and shown in SEQ ID NO:13 of the sequence listing.

Further details concerning gene expression, DNA biosynthesis, RNA biosynthesis can be found in textbooks of biochemistry and molecular genetics as known in the art.

Promoters for *Corynebacterium*, preferably *Corynebacterium glutamicum*, are well known in the art. See e.g. M. Patek (Regulation of gene expression, in: L. Eggeling and M. Bott (Handbook of *Corynebacterium glutamicum*, CRC Press, 2005)) or Patek et al (Microbial Biotechnology 6, 103-117, 2013).

Suitable promoters include the promoters described in WO2002040679, preferably the promoters shown in SEQ ID NO:4 to 22 thereof, the tac promoters described by De Boer et al (Proceedings of the National Academy of Sciences USA 80, 21-25, 1983; see also: Morinaga et al (Journal of Biotechnology 5, 305-312, 1987)), preferably the promoters PtacI or PtacII, particularly preferred PtacI as defined by the nucleotide sequence from positions 1 to 75 of SEQ ID NO:14 of the sequence listing, the promoter Pef-tu of the protein translation elongation factor TU described in WO2005059093, preferably the promoter shown in SEQ ID NO:1 thereof, the promoter Pgro as described in WO2005059143, preferably the promoter shown in SEQ ID NO:1 thereof, the promoter Psod described in WO2005059144, preferably the promoter shown in SEQ ID NO:1 thereof, the promoter variants of the gap gene as described in WO 2013000827, preferably the promoters Pgap3 shown in SEQ ID NO:3 and Pg3N3 shown SEQ ID NO:34 thereof, and the promotor variants of the dapB gene as described in U.S. Pat. No. 8,637,295, preferably the promoter PdapBN1 shown in SEQ ID NO:13 thereof.

Preferred promoters are the tac promotors, the PdapBN1 promoter, the Pgap3 promoter and the Pg3N3 promoter.

In particular preferred are the PtacI promoter shown in SEQ ID NO:14 positions 1 to 75 and the PdapBN1 promoter shown in SEQ ID NO:15 of the sequence listing of the present invention. Said promoters are joined to the polynucleotide encoding the fusion polypeptide of the invention by constructing an expression unit, which is an isolated polynucleotide, comprising a promoter, preferably a promoter as elaborated above, particularly preferred the promotor PdapBN1, and functionally linked to said promoter the nucleotide sequence encoding the fusion polypeptide according to the present invention.

It is preferred that said expression unit, which is an isolated polynucleotide, comprises the promoter PdapBN1 as shown in SEQ ID NO:16 positions 32 to 91 of the sequence protocol and functionally linked to said promotor, preferably directly by the nucleotide sequence from positions 92 to 121 of SEQ ID NO:16, a nucleotide sequence encoding the fusion polypeptide of SEQ ID NO:17, preferably the nucleotide sequence from position 122 to 2038 of SEQ ID NO:16.

It is particularly preferred that said expression unit, which is an isolated polynucleotide, comprises the nucleotide sequence from position 32 to 2038 of SEQ ID NO:16, more particularly preferred the nucleotide sequence from positions 32 to 2041 of SEQ ID NO:16.

In a further embodiment the expression unit, which is an isolated polynucleotide, comprises the nucleotide sequence from 32 to 2088 of SEQ ID NO:16, preferably SEQ ID NO:16. The nucleotide sequence from positions 2053 to 2088 of SEQ ID NO:16 is identical to the nucleotide sequence from positions 3 to 38 of SEQ ID NO:13, SEQ ID NO:13 being the transcriptional terminator of the gap gene as described by B. J. Eickmanns (Journal of Bacteriology 174(19), 6076-6086, 1992). For the work of the present invention a transcriptional terminator named Tgap* having the nucleotide sequence of positions 3 to 38 of SEQ ID NO:13 was used.

Said expression unit can be inserted into a suitable plasmid vector. Likewise said expression unit can be created by insertion of an isolated polynucleotide encoding a fusion polypeptide according to the invention downstream of a promotor provided by an expression vector available in the art as outlined below.

Suitable plasmid vectors for *Corynebacterium glutamicum* are well known in the art. A summary of suitable plasmid vectors, including native plasmids, cloning vectors, expression vectors and plamid vectors enabling chromosomal integration is given by M. Patek and J. Nesvera: Promoters and Plasmid Vectors of *Corynebacterium gluta-micum* (H. Yukawa and M. Inui: *Corynebacterium glutamicum* Biology and Biotechnolgy, Springer Verlag, 2013) and L. Eggeling and O. Reyes: Experiments (L. Eggeling and M. Bott: Handbook of *Corynebacterium glutamicum*, CRC Press 2005).

An example of a suitable plasmid vector, preferably expression vector, is pVWEx1 described by Peters-Wendisch et al (Journal of Molecular Microbiology and Biotechnology 3, 295-300, 2001). The nucleotide sequence of pVWEx1 is available at the GenBank database under accession number MF034723. Plasmid vector pVWEx1 has the ability to be autonomously replicated by *Corynebacterium glutamicum* and by *Escherichia coli*. It is therefore also called a shuttle vector. It provides the PtacI promoter and suitable cloning sites, e.g. PstI and BamHI restriction site, at the 3' end or downstream resp. of said PtacI promoter. Further elements and details concerning this expression vector can be found in Peters-Wendisch et al. After insertion of a nucleotide sequence coding for the fusion polypeptide of the present invention, e.g. the polynucleotide shown in SEQ ID NO:21, into said cloning sites it is functionally linked to said PtacI promoter and its expression is controlled by said PtacI promoter accordingly. Thus the resulting plasmid vector contains an expression unit as described above.

Another example of suitable plasmid vectors, preferably plasmid vectors enabling chromosomal integration, are pK*mob and pK*mobsacB, particularly preferred pK18mobsacB, described by Schäfer et al (Gene 145, 69-73, 1994). The nucleotide sequence of pk18mobsacB is availaible at the NCBI under accession number FJ437239. These plasmid vectors are capable of autonomous replication in *Escherichia coli* but not in *Corynebacterium*. However due to their mobilizable nature they can be transferred from *Escherichia coli* to *Corynebacterium glutamicum* by conjugation. Due to the presence of the sacB gene selection system, conferring sucrose sensitivity to its host, plamid vector pK18mobsacB provides the means to select for double recombination events after homologous recombination. It thus enables the isolation of strains carrying the gene of interest integrated in a target site of their chromosomes. Similar plasmid vectors are described in e. g. WO2002070685 and WO2003014362. In the context of the present invention the term gene of interest means the isolated polynucleotides of the present invention.

A target site in this context is a nucleotide sequence which is dispensable for growth and formation of the fine chemical by the *Corynebacterium* strain. A list of suitable target sites being coding sequences dispensable for L-lysine formation, e.g. the aecD gene encoding a C-S lyase (Rossol and Pühler, Journal of Bacteriology 174(9), 2968-2977, 1992) by *Corynebacterium glutamicum* is shown in table 3 of WO2003040373. The target sites further include nucleotide sequences coding for phages or phage components, for example those shown in table 13 of WO2004069996. The target sites furthermore include intergenic regions. An intergenic region is a nucleotide sequence located between two coding sequences and has no function. A list of suitable intergenic regions is for example shown in table 12 of WO2004069996.

During the work for the present invention a novel, suitable target site was identified.

A preferred target site is the intergenic region between the coding sequences identified by locus tag NCgl2176 and locus tag NCgl2177 of the chromosome of *Corynebacterium glutamicum* ATCC13032, preferably SEQ ID NO:18 from position 1036 to 1593 and the corresponding (homologous)

target site in different strains of the species. The nucleotide sequence of the chromosome of *Corynebacterium glutamicum* ATCC13032 is available at the NCBI under accession number NC_003450.

It is known in the art that homologous nucleotide sequences, or alleles resp. in the chromosome of the species *Corynebacterium glutamicum* vary between different wild type strains and mutants obtained therefrom.

The corresponding (homologous) sequence to SEQ ID NO:18 in strain ATCC13869 is shown in SEQ ID NO:19. The corresponding intergenic region is located between the coding sequences identified by locus tag BBD29_10725 and locus tag BBD29_1730, preferably SEQ ID NO:19 from position 1036 to 1593. SEQ ID NO:19 from position 1036 to 1593 is >98% identical to SEQ ID NO:18 from position 1036 to 1593. The nucleotide sequence of the chromosome of *Corynebacterium glutamicum* ATCC13869 is available at the NCBI under accession number NZ_CP016335.1.

The corresponding (homologous) sequence to SEQ ID NO:18 in strain ATCC14067 is shown in SEQ ID NO:20. The intergenic region preferably is located from position 1036 to 1593 of SEQ ID NO:20. SEQ ID NO:20 from position 1036 to 1593 is >97% identical to SEQ ID NO:18 from position 1036 to 1593.

Accordingly a preferred target site is >95%, preferably >97%, particular preferred >98%, very particular preferred >99% identical, most particular preferred 100% identical to SEQ ID NO:18 from position 1036 to 1593.

To accomplish integration of the isolated polynucleotides of the invention, preferably those functionally linked to a promoter, into a target site by homologous recombination their 5'-end and their 3'-end are linked to polynucleotides comprising nucleotide sequences upstream and downstream of the target site. The art also refers to these sequences as flanking sequences, in particular as 5'-flanking sequence and 3'-flanking sequence. A flanking sequence typically has a length of ≥200 to ≤2.000 base pairs.

A plasmid vector for accomplishing integration of a desired polynucleotide into the chromosome of a desired *Corynebacterium* contains a polynucleotide comprising from 5'- to 3'-direction: a 5'-flanking sequence, the desired polynucleotide and a 3'-flanking sequence.

Accordingly a plasmid vector for accomplishing integration of a polynucleotide of the invention into the chromosome of a suitable *Corynebacterium* contains a polynucleotide comprising from 5'- to 3'-direction: a 5'-flanking sequence, a polynucleotide according to the invention and a 3'-flanking sequence.

After two events of homologous recombination comprising a recombination event within the 5'-flanking sequence provided by the plasmid vector with the homologous sequence of the *Corynebacterium* chromosome and a recombination event within the 3'-flanking sequence provided by the plasmid vector with the homologous sequence of the *Corynebacterium* chromosome the polynucleotide of the invention is integrated in the Coryne-bacterium chromosome.

An event of homologous recombination may also be referred to as crossing over.

In a preferred embodiment said flanking sequences are chosen from nucleotide sequences contained in SEQ ID NO:18, which contains the intergenic region between locus tag NCgI2176 and locus tag NCgI2177 or from nucleotide sequences >95%, preferably >97%, particular preferred >98%, very particular preferred >99% identical to SEQ ID NO:18.

Likewise said flanking sequences may be chosen from nucleotide sequences contained in SEQ ID NO:19 or SEQ ID NO:20, which both have an identity of >99% to to SEQ ID NO:18. Accordingly the invention provides plasmid vectors containing the isolated polynucleotides of the present invention.

Teachings and information concerning the synthesis, analysis and handling of polynucleotides may be found inter alia in the book of P. Fu and S. Panke (Systems Biology and Synthetic Biology, Wiley, 2009), the book of S. Narang (Synthesis and Applications of DNA and RNA Academic Press, 1987), the handbook of J. Sambrook et al (Molecular Cloning, A Laboratory Manual, Cold Spring Harbor Laboratory Press, 1989), the textbook of C. R. Newton and A. Graham (PCR, Spektrum Akademischer Verlag, 1994) and the handbook of D. Rickwood and B. D. Hames (Gel electrophoresis of nucleic acids, a practical approach, IRL Press, 1982).

Sequence analysis of polynucleotides and polypeptides, e.g. sequence alignments, can be made using public software such as the CLC Genomics Workbench (Qiagen, Hilden, Germany) or the program MUSCLE provided by the European Bioinformatics Institute (EMBL-EBI, Hinxton, UK).

The isolated polynucleotides of the invention are transferred into strains of *Corynebacterium*, preferably *Corynebacterium glutamicum*, or *Escherichia*, preferably *Escherichia coli*, by means of transformation using physico-chemical methods or by conjugation using plasmid vectors containing said polynucleotides. For physico-chemical transformation of *Corynebacterium* the electroporation methods of Dunican and Shivnan (Bio/Technology 7, 1067-1070, 1989) or Ruan et al (Biotechnology letters, 2015, DOI 10.1007/510529-015-1934-x) or the spheroplast or protoplast transformation method of Thierbach et al (Applied Microbiology and Biotechnology 29, 356-362, 1988) can be used. For conjugational transfer or conjugation resp. from *Escherichia coli* to *Corynebacterium* the method of Schäfer et al (Journal of Bacteriology 172, 1663-1666, 1990) can be used. For selection of *Corynebacterium* strains carrying the polynucleotide of the invention in a target site of the chromosome after two events of homologous recombination the method of Schäfer et al can be used. Technical details for various target sites can be found for example in WO2003040373 and WO2004069996. Further details can also be found in the article "Experiments" by L. Eggeling and O. Reyes contained in L. Eggeling and M. Bott (Handbook of *Corynebacterium glutamicum*, CRC Press, 2005).

For the purpose of the present invention the terms transformation and conjugation may be summarized under the term transformation.

Transfer of the polynucleotides of the invention can be confirmed by Southern hybridization using a probe complementary to the polynucleotide of the invention or a part thereof, by polymerase chain amplification (PCR) of the polynucleotide of the invention or a part thereof, preferably followed by nucleotide sequence analysis of the amplification product, or by measuring the α-1,6-glucosidase activity.

During the work of the present invention it was found that after transformation of bacteria of the genus *Corynebacterium*, preferably bacteria of the species *Corynebacterium glutamicum*, with the isolated polynucleotide encoding a polypeptide according to the invention, preferably linked to a promoter, the transformants obtained had the ability to secrete a polypeptide having α-1,6-glucosidase activity into a medium.

It was further found that the encoded polypeptide Tat-Agl2 shown in SEQ ID NO:10 after being secreted into the medium by said *Corynebacterium glutamicum*, had the amino acid sequence of positions 31 to 639 of SEQ ID NO:10 or the amino acid sequence of positions 38 to 639 of SEQ ID NO:10.

Said polypeptide or polypeptides resp. secreted into the medium by said *Corynebacterium* hydrolyzes isomaltose to give glucose and hydrolyzes panose to give glucose and maltose. Thus said *Corynebacterium* has the ability to use panose and/or isomaltose as carbon source.

Accordingly the present invention provides a bacterium selected from the genus *Corynebacterium*, preferably *Corynebacterium glutamicum*, or *Escherichia*, preferably *Escherichia coli*, comprising the isolated polynucleotide encoding a polypeptide according to the invention, preferably linked to a promoter, wherein said bacterium has the ability to secrete a polypeptide having α-1,6-glucosidase activity encoded by said isolated polynucleotide.

Accordingly the present invention further provides a *Corynebacterium*, preferably *Corynebacterium glutamicum*, having the ability to secrete a polypeptide having α-1,6-glucosidase activity and having the amino acid sequence of positions 31 to 639 of SEQ ID NO:10 or the amino acid sequence of positions 38 to 639 of SEQ ID NO:10.

The isolated polynucleotides of the invention may be contained in a plasmid vector autonomously replicating in the *Corynebacterium* or may be contained in the chromosome of the *Corynebacterium*. In case the isolated polynucleotide of the invention is contained in the chromosome it is replicated as part of the chromosome. It is preferred that said isolated polynucleotide is contained in the chromosome of the bacterium. It is particularly preferred that said isolated polynucleotide is contained in a sequence of the chromosome (target site) being >95% identical to SEQ ID NO:18 from position 1036 to 1593 as outlined above.

The number of copies (copies per *Corynebacterium* cell) of an expression unit comprising the isolated polynucleotide of the invention linked to a promoter typically does not exceed 40. It is preferred that said number of copies is ≤10, particularly preferred ≤5, very particularly preferred ≤2, most particularly preferred 1.

A description of the genus *Corynebacterium* and the species comprised by this genus can be found in the article "*Corynebacterium*" by K. A. Bernard and G. Funke in Bergey's Manual of Systematics of Archaea and Bacteria (Bergey's Manual Trust, 2012).

Within the genus *Corynebacterium* the species *Corynebacterium glutamicum* is preferred. Suitable strains are for example strains ATCC13032, ATCC14067 and ATCC13869, strains also referred to as wild type strains in the art, and fine chemical excreting strains obtained therefrom. Strain ATCC13032 (also available as DSM20300) is the taxonomic type strain of the species *Corynebacterium glutamicum*. Strain ATCC14067 (also available as DSM20411) is also known under the outdated designation *Brevibacterium flavum*. Strain ATCC13869 (also available as DSM1412) is also known under the outdated designation *Brevibacterium lactofermentum*. A taxonomic study of this group of bacteria based on DNA-DNA hybridization was done by Liebl et al (International Journal of Systematic Bacteriology 41(2), 255-260, 1991). A comparative analysis of various strains of the species *Corynebacterium glutamicum* based on genome sequence analysis was provided by Yang and Yang (BMC Genomics 18(1):940).

A multitude of fine chemical excreting strains of the genus *Corynebacterium* were obtained in the art during the past decades starting from strains like ATCC13032, ATCC14067, ATCC13869 and the like. They were obtained as a result of strain development programs using inter alia methods like classical mutagenesis, selection for antimetabolite resistance as well as amplification and promotor modification of genes of the biosynthetic pathway of the fine chemical in question by genetic engineering methods. Summaries may be found in L. Eggeling and M. Bott (Handbook of *Corynebacterium glutamicum*, CRC Press, 2005) or H. Yukawa and M. Inui (*Corynebacterium glutamicum* Biology and Biotechnolgy, Springer Verlag, 2013).

Strains of *Corynebacterium*, preferably *Corynebacterium glutamicum*, suitable for the measures of the present invention have a functional Tat-(twin-arginine translocation) pathway for protein secretion. The proteins of the Tat-pathway of *Corynebacterium glutamicum* are encoded by genes tatA, tatB, tatC and tatE and described by Kikuchi et al (Applied and Environmental Microbiology 72(11), 7183-7192, 2006).

The term fine chemical includes L-amino acids, vitamins, nucleosides and nucleotides with L-amino acids being preferred.

The term "vitamin" includes riboflavin.

The term "L-amino acid" includes the proteinogenic L-amino acids and also L-ornithine and L-homoserine. Proteinogenic L-amino acids are to be understood to mean the L-amino acids present in natural proteins, that is in proteins of microorganisms, plants, animals and humans. Proteinogenic L-amino acids comprise L-aspartic acid, L-asparagine, L-threonine, L-serine, L-glutamic acid, L-glutamine, L-glycine, L-alanine, L-cysteine, L-valine, L-methionine, L-isoleucine, L-leucine, L-tyrosine, L-phenylalanine, L-histidine, L-lysine, L-tryptophan, L-arginine, L-proline and in some cases L-selenocysteine and L-pyrrolysine.

The fine chemical is preferably selected from the group consisting of proteinogenic L-amino acid, L-ornithine and L-homoserine. Particular preference is given to the proteinogenic L-amino acids selected from L-lysine, L-threonine, L-valine and L-isoleucine with L-lysine being very particularly preferred.

The term L-amino acids, where mentioned herein in the context of product formation, also comprises their salts, for example L-lysine monohydrochloride or L-lysine sulphate in the case of the L-amino acid L-lysine.

L-lysine excreting strains of the species *Corynebacterium glutamicum* are widely known in the art and can be used for the purpose of the present invention. For example Blombach et al (Applied and Environmental Microbiology 75(2), 419-427, 2009) describe strain DM1933, which is deposited under accession DSM25442; WO2008033001 describes strain KFCC10881-014, which is deposited under accession number KCCM10770P and EP0841395 refers to strain AJ11082, which is deposited under accession number NRRL B-1147. Furthermore L-lysine excreting *Corynebacterium glutamicum* strain DM2031, deposited according to the Budapest Treaty as DSM32514 may be used. Strain DM2031 is a further developed derivative of DM1933 having enhanced L-lysine excretion ability.

Summaries concerning the breeding of L-lysine excreting strains of *Corynebacterium glutamicum* may be found inter alia in L. Eggeling and M. Bott (Handbook of *Corynebacterium glutamicum*, CRC Press, 2005), V. F. Wendisch (Amino Acid Biosynthesis-Pathways, Regulation and Metabolic Engineering, Springer Verlag, 2007), H. Yukawa and M. Inui (*Corynebacterium glutamicum* Biology and Biotechnolgy, Springer Verlag, 2013), and Eggeling and Bott (Applied Microbiology and Biotechnology 99 (9), 3387-3394, 2015).

L-threonine excreting strains of the species *Corynebacterium glutamicum* are known in the art and can be used for the purpose of the present invention. For example EP0385940 describes strain DM368-2, which is deposited under DSM5399.

L-valine excreting strains of the species *Corynebacterium glutamicum* are known in the art and can be used for the purpose of the present invention. For example U.S. Pat. No. 5,188,948 describes strain AJ12341, which is deposited under FERM BP-1763 and EP2811028 describes strain ATCC14067_PprpD2-ilvBN.

L-isoleucine excreting strains of the species *Corynebacterium glutamicum* are known in the art and can be used for the purpose of the present invention. For example U.S. Pat. No. 4,656,135 describes strain AJ12152, which is deposited under Ferm BP-760.

Riboflavin excreting strains of the species *Corynebacterium glutamicum* are described in EP2787082.

The term DSM denotes the depository Deutsche Sammlung für Mikroorganismen and Zellkulturen located in Braunschweig, Germany. The term KCCM denotes the depository Korean Culture Center of Microorganisms located in Seoul, Korea. The term NRRL denotes the depository Agricultural Research Service Culture Collection located in Peoria, Ill., US. The term ATCC denotes the depository American Type Culture Collection located in Manasass, Va., US. The term FERM denotes the depository National Institute of Technology and Evaluation (NITE) located in Tokyo, Japan.

To obtain a fine chemical excreting bacterium of the genus *Corynebacterium*, preferably *Corynebacterium glutamicum* having the ability to secrete a polypeptide having $\alpha$-1,6-glucosidase activity encoded by the isolated polynucleotide of the invention a fine chemical excreting bacterium of the genus *Corynebacterium* is transformed with an isolated polynucleotide of the invention, preferably an isolated polynucleotide linked to a promotor (expression unit).

Thus a fine chemical excreting bacterium of the genus *Corynebacterium*, preferably *Corynebacterium glutamicum* having the ability to use panose and/or isomaltose as a carbon source for growth and fine chemical excretion is obtained.

Likewise it is possible to obtain a fine chemical excreting bacterium according to the invention by first transforming a wild type strain of the genus *Corynebacterium*, preferably *Corynebacterium glutamicum*, like e. g. ATCC13032, ATCC13869 or ATCC14067 with the polynucleotide of the invention and then to use the transformant obtained as starting point for a strain development program aiming at the desired fine chemical.

Accordingly the present invention provides a fine chemical excreting *Corynebacterium*, preferably *Corynebacterium glutamicum*, comprising an isolated polynucleotide of the invention thus having the ability to use panose and/or isomaltose for growth and fine chemical excretion and production. The invention further provides a fermentative process for producing a fine chemical using the *Corynebacterium* according to the present invention.

The fermentative process may be a continuous process or a discontinuous process like a batch process or a fed batch process. A summary concerning the general nature of fermentation processes is available in the textbook by H. Chmiel (Bioprozesstechnik, Spektrum Akademischer Verlag, 2011), in the textbook of C. Ratledge and B. Kristiansen (Basic Biotechnology, Cambridge University Press, 2006) or in the textbook of V. C. Hass and R. Pörtner (Praxis der Bioprozesstechnik Spektrum Akademischer Verlag, 2011).

Within the fermentative process the *Corynebacterium* of the invention is cultured in a suitable medium.

A suitable medium used for the production of a fine chemical by a fermentative process contains a carbon source, a nitrogen source, a phosphorus source, inorganic ions and other organic compounds as required. The components employed in the fermentative process are also referred to as input materials in the art.

In a fermentative process according to the invention a *Corynebacterium*, preferably *Corynebacterium glutamicum*, comprising the isolated polynucleotide of the invention and having the ability to excrete a fine chemical is cultured in a suitable medium to produce and accumulate said fine chemical using a carbon source comprising at least one oligomer of $\alpha$-D-glucose consisting of least two $\alpha$-1-6-glycosidically linked glucose monomers, such as isomaltose and panose, preferably containing glucose and at least one oligomer of glucose selected from isomaltose and panose.

In further embodiments of the invention said carbon source contains glucose and isomaltose or contains glucose and panose or contains glucose, isomaltose and panose.

According to the economic needs a carbon source may further contain other compounds, apart from glucose, isomaltose and panose, which are used by *Corynebacterium*, preferably *Corynebacterium glutamicum*, for growth and fine chemical excretion and production. These compounds include sugars like maltose, sucrose or fructose or organic acids like lactic acid. The isomaltose content in said carbon source is $\geq 0.1\%$, preferably $\geq 0.2\%$ per dry matter. The isomaltose content in said carbon source does not exceed ($\leq$) 50% per dry matter, does not exceed ($\leq$) 40% per dry matter, does not exceed ($\leq$) 30% per dry matter, does not exceed ($\leq$) 20% per dry matter or does not exceed ($\leq$) 10% per dry matter when mixtures of compounds serving as carbon source are fed.

The panose content in said carbon source is 0.1%, preferably 0.2% per dry matter. The panose content in said carbon source does not exceed ($\leq$) 50% per dry matter, does not exceed ($\leq$) 40% per dry matter, does not exceed ($\leq$) 30% per dry matter, does not exceed ($\leq$) 20% per dry matter or does not exceed ($\leq$) 10% per dry matter when mixtures of compounds serving as carbon source are fed.

The glucose content in said carbon source is $\geq 30\%$, preferably $\geq 40\%$ per dry matter, particularly preferred $\geq 50\%$ per dry matter. The glucose content in said carbon source does not exceed ($\leq$) 99.9% per dry matter, does not exceed ($\leq$) 99.8% per dry matter, does not exceed ($\leq$) 99.6% per dry matter or does not exceed ($\leq$) 99% per dry matter when mixtures of compounds serving as carbon sources are fed.

It is obvious for a person of ordinary skill in the art that the sum of all components in the dry matter serving as carbon source does not exceed 100%.

An example of a carbon source containing glucose and an oligomer of glucose selected from isomaltose and panose are starch hydrolysates.

Starch hydrolysates are obtained by hydrolysis of starch typically manufactured from the grains of corn, wheat, barley or rice or from the tubers of potato or roots of cassava. Owing to the regimen of starch hydrolysis various products typically with a main component e. g. glucose or maltose and different side components e. g. maltose, isomaltose, panose or maltotriose are obtained.

For the purpose of this invention a starch hydrolysate is defined as product obtained by hydrolysis, preferably enzymatic hydrolysis, of starch manufactured from the grains of corn, wheat, barley or rice or from the tubers of potato or roots of cassava, preferably from the grains of corn, wheat or rice and having the following composition in dry matter (weight per weight): glucose $\geq 80\%$, preferably $\geq 90\%$, not exceeding (≤) 99% or not exceeding (≤) 98%; isomaltose ≥0.1%, preferably ≥0.2%, not exceeding (≤) 4%; panose ≥0.1%, preferably ≥0.2%, not exceeding (≤) 3%. The starch hydrolysate used for the purpose of the present invention typically further contains maltose at ≥0.1% or ≥0.2% not exceeding (≤) 5% per dry matter. Furthermore the starch hydrolysate used for the purpose of the present invention may contain further oligomers of glucose as well as inorganic ions and proteins. It is obvious for a person of ordinary skill in the art that the sum of all components in the dry matter does not exceed 100%. The dry matter of commercial liquid starch hydrolysates is usually in the range of 55 to 75% (weight per weight). Teachings concerning the analysis of starch hydrolysates can be found in M. W. Kearsley and S. Z. Dziedzic (Handbook of Starch Hydrolysis Products and their Derivatives, Chapmann & Hall, 1995).

As nitrogen source organic nitrogen-containing compounds such as peptones, meat extract, soy bean hydrolysates or urea, or inorganic compounds such as ammonium sulfate, ammonium chloride, ammonium phosphate, ammonium carbonate, ammonium nitrate, ammonium gas or aqueous ammonia can be used.

As phosphorus source, phosphoric acid, potassium dihydrogen phosphate or dipotassium hydrogen phosphate or the corresponding sodium-containing salts can be used.

Inorganic ions like potassium, sodium, magnesium, calcium, iron and further trace elements etc. are supplied as salts of sulfuric acid, phosphoric acid or hydrochloric acid.

Other organic compounds means essential growth factors like vitamins e. g. thiamine or biotin or L-amino acids e. g. L-homoserine.

The media components may be added to the culture in form of a single batch or be fed in during the cultivation in a suitable manner.

During the fermentative process the pH of the culture can be controlled by employing basic compounds such as sodium hydroxide, potassium hydroxide, ammonia or aqueous ammonia, or acidic compounds such as phosphoric acid or sulfuric acid in a suitable manner. The pH is generally adjusted to a value of from 6.0 to 8.5, preferably 6.5 to 8.0. To control foaming, it is possible to employ antifoam agents such as, for example, fatty acid polyglycol esters. To maintain the stability of plasmids, it is possible to add to the medium suitable selective substances such as, for example, antibiotics. The fermentative process is preferably carried out under aerobic conditions. In order to maintain these conditions, oxygen or oxygen-containing gas mixtures such as, for example air are introduced into the culture. The fermentative process is carried out, where appropriate, at elevated pressure, for example at an elevated pressure of 0.03 to 0.2 MPa. The temperature of the culture is normally from 25° C. to 40° C., preferably from 30° C. to 37° C. In a discontinuous process, the cultivation is continued until an amount of the desired fine chemical sufficient for being recovered has been formed. The cultivation is then completed. This aim is normally achieved within 10 hours to 160 hours. In continuous processes, longer cultivation times are possible.

Examples of suitable media and culture conditions can be found inter alia in L. Eggeling and M. Bott (Handbook of Corynebacterium glutamicum, CRC Press, 2005) and the patent documents U.S. Pat. Nos. 5,770,409, 5,990,350, 5,275,940, 5,763,230 and 6,025,169.

Due to the ability of the Corynebacterium of the invention to excrete and produce the fine chemical into the medium during the fermentative process the concentration of the fine chemical increases and accumulates in the medium.

Thus the fermentative process results in a fermentation broth which contains the desired fine chemical, preferably L-amino acid. A product containing the fine chemical is then recovered in liquid or solid form.

A "fermentation broth" means a medium in which a Corynebacterium of the invention has been cultivated for a certain time and under certain conditions.

When the fermentative process is completed, the resulting fermentation broth accordingly comprises:
a) the biomass (cell mass) of the Corynebacterium of the invention, said biomass having been produced due to propagation of the cells of said Corynebacterium,
b) the desired fine chemical accumulated during the fermentative process,
c) the organic by-products accumulated during the fermentative process, and
d) the components of the medium employed which have not been consumed in the fermentative process.

The organic by-products include compounds which may be formed by the Corynebacterium of the invention during the fermentative process in addition to production of the desired fine chemical.

The fermentation broth is removed from the culture vessel or fermentation tank, collected where appropriate, and used for providing a product containing the fine chemical, preferably an L-amino acid-containing product, in liquid or solid form. The expression "recovering the fine chemical-containing product" is also used for this. In the simplest case, the fine chemical-containing fermentation broth itself, which has been removed from the fermentation tank, constitutes the recovered product.

The fermentation broth can subsequently be subjected to one or more of the measures selected from the group consisting of:
a) partial (>0% to <80%) to complete (100%) or virtually complete (≥80%, ≥90%, ≥95%, ≥96%, ≥97%, ≥98%, ≥99%) removal of the water,
b) partial (>0% to <80%) to complete (100%) or virtually complete (≥80%, ≥90%, ≥95%, ≥96%, ≥97%, ≥98%, ≥99%) removal of the biomass, the latter being optionally inactivated before removal,
c) partial (>0% to <80%) to complete (100%) or virtually complete (≥80%, ≥90%, ≥95%, ≥96%, ≥97%, ≥98%, ≥99%, ≥99.3%, ≥99.7%) removal of the organic by-products formed during the fermentative process, and
d) partial (>0%) to complete (100%) or virtually complete (≥80%, ≥90%, ≥95%, ≥96%, ≥97%, ≥98%, ≥99%, ≥99.3%, ≥99.7%) removal of the residual components of the medium employed or of the residual input materials resp., which have not been consumed in the fermentative process.

An abundance of technical instructions for measures a), b), c) and d) are available in the art.

Removal of water (measure a)) can be achieved inter alia by evaporation, using e.g. a falling film evaporator, by reverse osmosis or nanofiltration. The concentrates thus obtained can be further worked up by spray drying or spray granulation. It is likewise possible to dry the fermentation broth directly using spray drying or spray granulation.

Removal of the biomass (measure b)) can be achieved inter alia by centrifugation, filtration or decantation or a combination thereof.

Removal of the organic by-products (measure c)) or removal of residual components of the medium (measure d) can be achieved inter alia by chromatography, e.g. ion exchange chromatography, treatment with activated carbon or crystallization. In case the organic by-products or residual components of the medium are present in the fermentation broth as solids they can be removed by measure b).

General instructions on separation, purification and granulation methods can be found inter alia in the book of R. Ghosh "Principles of Bioseperation Engineering" (World Scientific Publishing, 2006), the book of F. J. Dechow "Seperation and Purification Techniques in Biotechnology" (Noyes Publications, 1989), the article "Bioseparation" of Shaeiwitz et al (Ullmann's Encyclopedia of Industrial Chemistry, Wiley-VCH, 2012) and the book of P. Serno et al "Granulieren" (Editio Cantor Verlag, 2007).

A downstream processing scheme for L-lysine products can be found in the article "L-lysine Production" of R. Kelle et al (L. Eggeling and M. Bott (Handbook of *Corynebacterium glutamicum*, CRC Press, 2005)). U.S. Pat. No. 5,279, 744 teaches the manufacturing of a purified L-lysine product by ion exchange chromatography. U.S. Pat. No. 4,956,471 teaches the manufacturing of a purified L-valine product by ion exchange chromatography. U.S. Pat. No. 5,431,933 teaches the manufacturing of dry L-amino acid products, e. g. an L-lysine product or an L-valine product, containing most of the constituents of the fermentation broth.

Thus a concentration or purification of the desired fine chemical is achieved and a product having the desired content of said fine chemical is provided.

Analysis of L-amino acids to determine the concentration at one or more time(s) during the fermentation can take place by separating the L-amino acids by means of ion exchange chromatography, preferably cation exchange chromatography, with subsequent post-column derivatization using ninhydrin, as described in Spackman et al. (Analytical Chemistry 30: 1190-1206 (1958)). It is also possible to employ ortho-phthalaldehyde rather than ninhydrin for post-column derivatization. An overview article on ion exchange chromatography can be found in Pickering (LC.GC (Magazine of Chromatographic Science 7(6):484-487 (1989)). It is likewise possible to carry out a pre-column derivatization, for example using ortho-phthalaldehyde or phenyl isothiocyanate, and to fractionate the resulting amino acid derivates by reversed-phase chromatography (RP), preferably in the form of high-performance liquid chromatography (HPLC). A method of this type is described, for example, in Lindroth et al. (Analytical Chemistry 51:1167-1174 (1979)). Detection is carried out photometrically (absorption, fluorescence) . A review regarding amino acid analysis can be found inter alia in the textbook "Bioanalytik" by Lottspeich and Zorbas (Spektrum Akademischer Verlag, Heidelberg, Germany 1998).

EXPERIMENTAL SECTION

A) Materials and Methods

The molecular biology kits, primers and chemicals used and some details of the methods applied are briefly described herewith.

1. Chemicals a. IPTG (Isopropyl β-D-1-thiogalactopyranoside) was purchased from Carl-Roth (Karlsruhe, Germany, Cat. no. 2316.4.)

b. Kanamycin solution from *Streptomyces kanamyceticus* was purchased from Sigma Aldrich (St. Louis, USA, Cat. no. K0254).

c. Nalidixic acid sodium salt was purchased from Sigma Aldrich (St. Louis, USA, Cat. no. N4382).

d. Peptone from soymeal was purchased from Merck KGaA (Darmstadt, Germany, Cat. no. 1.017212.0500).

e. Propionic acid hemicalcium salt ($C_3H_5O_2 \times ½$ Ca) was purchased from Sigma Chemical CO. (St. Louis, USA, Cat. no. P-2005).

f. SOLULYS® 048K-CORN STEEP LIQUID (CSL) with a dry substance content between 48% and 52% by weight was purchased from ROQUETTE AMERICA INC (Keokuk, Iowa, USA).

g. Starch hydrolysate Clearsweet® 95% Unrefined Liquid Dextrose Corn Syrup was purchased from Cargill, Incorporated (Minneapolis, Minn., USA). It has a total solid content of 70.5-71.5% by weight.

h. If not stated otherwise, all other chemicals were purchased analytically pure from Merck (Darmstadt, Germany), Sigma Aldrich (St. Louis, USA) or Carl-Roth (Karlsruhe, Germany).

2. Cultivation

If not stated otherwise, all cultivation/incubation procedures were performed as described in following:

a. LB broth (MILLER) from Merck (Darmstadt, Germany, Cat. no. 110285) was used to cultivate *E. coli* strains in liquid medium. The liquid cultures (10 ml liquid medium per 100 ml Erlenmeyer flask with 3 baffles) were incubated in the Infors HT Multitron standard incubator shaker from Infors AG (Bottmingen, Switzerland) at 37° C. and 200 rpm.

b. LB agar (MILLER) from Merck (Darmstadt, Germany Cat. no. 110283) was used for cultivation of *E. coli* strains on agar plate. The agar plates were incubated at 37° C. in an INCU-Line® mini incubator from VWR (Radnor, USA).

c. Brain heart infusion broth (BHI) from Merck (Darmstadt, Germany; Cat. no. 110493) was used to cultivate *C. glutamicum* strains in liquid medium. The liquid cultures (10 ml liquid medium per 100 ml Erlenmeyer flask with 3 baffles) were incubated in the Infors HT Multitron standard incubator shaker from Infors AG (Bottmingen, Switzerland) at 33° C. and 200 rpm.

d. Brain heart agar (BHI-agar) from Merck (Darmstadt, Germany; Cat. no. 113825) was used for cultivation of *C. glutamicum* strains on agar plates. The agar plates were incubated at 33° C. in an incubator from Heraeus Instruments with Kelvitron® temperature controller (Hanau, Germany).

3. Determining optical density a. The optical density of bacterial suspensions in shake flask cultures was determined at 600 nm (OD600) using the BioPhotometer from Eppendorf AG (Hamburg, Germany).

b. The optical density of bacterial suspensions produced in the micro fermentation system BioLector® (48-Well FlowerPlate®) was determined at 660 nm (OD660) with the GENios™ plate reader from Tecan Group AG (Mannedorf, Switzerland).

4. Centrifugation a. Benchtop centrifuge for reaction tubes with a volume of up to 2 ml Bacterial suspensions with a maximum volume of 2 ml were caused to sediment using 1 ml or 2 ml reaction tubes (e.g. Eppendorf Tubes® 3810X) using an Eppendorf 5417 R centrifuge for 5 min. at 13.000 rpm.

b. Benchtop centrifuge for tubes with a volume of up to 50 ml Bacterial suspensions with a maximum volume of 50 ml were caused to sediment using 15 ml or 50 ml centrifuge tubes (e.g. Falcon™ 50 ml Conical Centrifuge Tubes) using an Eppendorf 5810 R centrifuge for 10 min. at 4.000 rpm.

5. DNA isolation a. Plasmid DNA was isolated from *E. coli* cells using the QIAprep Spin Miniprep Kit from Qiagen (Hilden, Germany, Cat. No. 27106) following the instructions of the manufacturer.

b. Plasmid isolation from *C. glutamicum* was carried out with the same kit described in section a. but cells were pre-incubated in 600 µl buffer P1 supplemented with 12.5 mg lysozyme and 10 U mutanolysin (from *Streptomyces globisporus* ATCC 21553, Sigma Aldrich, St. Louis, USA, Cat. no. M4782) for 2 h at 37° C.

c. Total DNA from *C. glutamicum* was isolated using the method of Eikmanns et al. (Microbiology 140, 1817-1828, 1994).

6. Gene synthesis

DNA molecules were synthesized by the company GeneArt (Thermo Fisher Scientific GENEART GmbH, Regensburg, Germany) using their proprietary GeneAssemble process. The method comprises de novo oligonucleotide synthesis and self assembly of the overlapping complementary oligonucleotides with subsequent PCR amplification. The method is summarized in the article "Rationales of Gene Design and De Novo Gene Construction" by Graf et al. in: Systems Biology and Synthetic Biology by P. Fu and S. Panke eds. (John Wiley, 411-438, 2009).

7. Polymerase chain reaction (PCR)

a. Taq PCR Core Kit (Taq Kit) from Qiagen (Hilden, Germany, Cat. No. 201203) was used to amplify a desired segment of DNA in order to confirm its presence or for sequence verification by the method of Sanger. The kit was used according to the instructions of the manufacturer (see table 1).

TABLE 1

Thermocycling conditions for PCR with Taq PCR Core Kit (Taq Kit) from Qiagen. PCR-program

| Step | Time [min.] | T [° C.] | Description |
|---|---|---|---|
| 1 | 05:00 | 94 | Initial denaturation step |
| 2 | 00:30 | 94 | Denaturation step |
| 3 | 00:30 | 50-57 | Annealing step Approximately 5° C. below $T_m$ of primers |
| 4 | 00:30 | 72 | Elongation step 1 min. per kb DNA Repeat step 2 to 4: 30 x |
| 5 | 04:00 | 72 | Final Elongation step |
| 6 | Hold | 4 | Cooling step | b. SapphireAmp® Fast PCR Master Mix (Sapphire Mix) from Takara Bio Inc (Takara Bio Europe S.A.S., Saint-Germain-en-Laye, France; Cat. No. RR350A/B) was used as an alternative to confirm the presence of a desired segment of DNA in cells taken from *E. coli* or *C. glutamicum* colonies according to the instructions of the manufacturer (see table 2).

TABLE 2

Thermocycling conditions for PCR with SapphireAmp® Fast PCR Master Mix (Sapphire Mix) from Takara Bio Inc. PCR-program

| Step | Time [min.] | T [° C.] | Description |
|---|---|---|---|
| 1 | 01:00 | 94 | Initial denaturation step |
| 2 | 00:05 | 98 | Denaturation step |
| 3 | 00:05 | 55 | Annealing step |
| 4 | 00:05-00:30 | 72 | Elongation step: 10 sec. per kb DNA Repeat step 2 to 4: 30 x |

TABLE 2-continued

Thermocycling conditions for PCR with SapphireAmp® Fast PCR Master Mix (Sapphire Mix) from Takara Bio Inc. PCR-program

| Step | Time [min.] | T [° C.] | Description |
|---|---|---|---|
| 5 | 04:00 | 72 | Final Elongation step |
| 6 | Hold | 4 | Cooling step | c. Primer

The oligonucleotides used were synthesized by eurofins genomics GmbH (Ebersberg, Germany) using the phosphoramidite method described by McBride and Caruthers (Tetrahedron Lett. 24, 245-248, 1983).

d. Template

As PCR template either a suitably diluted solution of isolated plasmid DNA or the total DNA contained in a colony was used (colony PCR). For said colony PCR the template was prepared by taking cell material with a toothpick from a colony on an agar plate and placing the cell material direct in the PCR reaction tube. The cell material was heated for 10 sec. with 800 W in a microwave oven type Mikrowave & Grill from SEVERIN Elektrogerate GmbH (Sundern, Germany) and then the PCR mastermix from Takara Bio Inc was added to the template in the PCR reaction tube.

e. PCR Cycler

PCR's were carried out in PCR cyclers type Mastercycler or Mastercycler nexus gradient from Eppendorf AG (Hamburg, Germany).

8. Restriction enzyme digestion of DNA

The FastDigest restriction endonucleases (FD) and the associated buffer from ThermoFisher Scientific (Waltham, USA) were used for restriction digestion of plasmid DNA. The reactions were carried out according to the instructions of the manufacturer's manual.

9. Ligation of DNA fragments

For ligation of restricted vector DNA with desired DNA fragments the Ready-To-Go T4 DNA Ligase from Amersham Biosciences Corp (purchased from GE Healthcare, Chalfont St Giles, Great Britain, Cat. No. 27036101) was used according to the manufacturer's instructions.

10. Determining the size of DNA fragments

Depending on the number and the size of the DNA fragments to be investigated, automated capillary or agarose gel electrophoresis was used:

a. Capillary electrophoresis

The size of DNA fragments was determined by automatic capillary electrophoresis using the QIAxcel from Qiagen (Hilden, Germany).

b. Agarose gel electrophoresis

To separate DNA fragments after restriction digestion or PCR, agarose gels with 0.8% agarose (Biozym LE Agarose, Hess. Oldendorf, Germany) in 1×TAE (Tris-Acetate-EDTA buffer; Stock-Solution: 50×TAE buffer (Applichem, Darmstadt, Germany)) were used. The separation was carried out with Mini-sub Cell GT electrophoresis equipment from BioRad (Bio-Rad Laboratories GmbH, Munich, Germany) at 100 V for 45 min. The O'GeneRuler 1 kb DNA Ladder (Thermo scientific, Schwerte, Germany) was used as a reference to determine the fragment size. After 20 min. incubation of the gel in a colour bath containing GelRed™ nucleic acid stain from Biotrend (Cologne, Germany. Dilution according to the producer: 1:10000) the DNA fragments were visualised through UV radiation using a Gel iX20 Imager from Intas (Göttingen, Germany).

11. Purification of PCR amplificates and restriction fragments

PCR amplificates and restriction fragments were cleaned up using the QIAquick PCR Purification Kit from Qiagen (Hilden, Germany, Cat. No. 28106), according to the manufacturer's instructions.

After gel electrophoresis and excision of the desired DNA fragment, the Qiagen MinElute Gel Extraction Kit (Hilden, Germany, Cat. No. 28604) was used according to the manufacturer's instructions.

12. Determining DNA concentration

DNA concentration was measured using the NanoDrop Spectrophotometer ND-1000 from PEQLAB Biotechnologie GmbH, since 2015 VWR brand (Erlangen, Germany).

13. Gibson Assembly

Expression- and integration-vectors were made using the method of Gibson et al. (Science 319, 1215-20, 2008). The Gibson Assembly Kit from New England BioLabs Inc. (Ipswich, USA, Cat. No. E2611) was used for this purpose. The reaction mix, containing the restricted vector and at least one DNA insert, was incubated at 50° C. for 60 min. 0.5 µl of the Assembly mixture was used for a transformation experiment.

14. Chemical transformation of E. coli a. Chemically competent E. coli Stellar™ cells were purchased from Clontech Laboratories Inc. (Mountain View, USA, Cat. No. 636763) and transformed according to the manufacturers protocol (PT5055-2).

These cells were used as transformation hosts for reaction mixtures after Gibson Assembly. The transformation batches were cultivated overnight for approximately 18 h at 37° C. and the transformants containing plasmids selected on LB agar supplemented with 50 mg/l kanamycin.

b. E. coli K-12 strain S17-1 was used as donor for conjugational transfer of plasmids based on pK18mobsacB from E. coli to C. glutamicum. Strain S17-1 is described by Simon, R. et al. (Bio/Technology 1, 784-794, 1983). It is available from the American Type Culture Collection under the access number ATCC47055.

Chemically competent E. coli S17-1 cells were made as follows: A preculture of 10 ml LB medium (10 ml liquid medium per 100 ml Erlenmeyer flask with 3 baffles) was inoculated with 100 µl bacterial suspension of strain S17-1 and the culture was incubated overnight for about 18 h at 37° C. and 250 rpm. The main culture (70 ml LB contained in a 250 ml Erlenmeyer flask with 3 baffles) was inoculated with 300 µl of the preculture and incubated up to an OD600 of 0.5-0.8 at 37° C. The culture was centrifuged for 6 min. at 4° C. and 4000 rpm and the supernatant was discarded. The cell pellet was resuspended in 20 ml sterile, ice-cold 50 mM CaCl2 solution and incubated on ice for 30 min. After another centrifugation step, the pellet was resuspended in 5 ml ice-cold 50 mM CaCl2 solution and the suspension incubated on ice for 30 min. The cell suspension was then adjusted to a final concentration of 20% glycerol (v/v) with 85% sterile ice-cold glycerol. The suspension was divided into 50 µl aliquots and stored at −80° C.

To transform S17-1 cells, the protocol according to Tang et al. (Nucleic Acids Res. 22(14), 2857-2858, 1994) with a heat shock of 45 sec. was used.

15. Transformation of C. glutamicum by electroporation

Plasmid vectors based on pVWEx1 were transferred into cells of C. glutamicum using a modified electroporation method by Van der Rest et al. (Appl Microbiol Biotechnol 52, 541-545, 1999).

To produce competent C. glutamicum cells the strains were propagated in BHIS medium (37 g/l BHI, 91 g/l sorbitol (Sigma Aldrich, St. Louis, USA)) by a preculture and a subsequent main culture. The preculture consisted of 10 ml BHIS medium contained in a 100 ml Erlenmeyer flask with 3 baffles. It was inoculated with 100 µl of a glycerol stock culture and incubated overnight for about 18 h at 33° C. and 200 rpm. The main culture consisted of 250 ml BHIS medium contained in a 1 l Erlenmeyer flask with 4 baffles. It was inoculated with 5 ml of the preculture and incubated for 4 h at 33° C. and 150 rpm to an OD600 of approx. 1.8.

The following working steps were carried out on ice using sterile, ice cold buffers or solutions resp. The main culture was centrifuged for 20 min. at 4° C. and 4000 rpm. The supernatant was discarded, the cell pellet resuspended in 2 ml TG buffer (1 mM Tris(hydroxymethyl)-aminomethane, 10% glycerol, adjusted to pH 7.5 with HCl) and another 20 ml TG buffer added to the cell suspension. This washing step was repeated twice. Said washing steps were followed by two further washing steps in which the TG buffer was replaced by a 10% (v/v) glycerol solution. After the final centrifugation step 2 ml 10% (v/v) glycerol were added to the cell pellet. The cell suspension obtained was then aliquoted in 100 µl portions and stored at −80° C.

The electroporation of the C. glutamicum strains was carried out as described by Van der Rest et al. Deviating from this procedure the cultivation temperature was 33° C. and the medium for agar plate cultures was BHI agar. Transformants were selected on BHI agar plates supplemented with 25 mg/l kanamycin.

16. Conjugation of C. glutamicum

The pK18mobsacB plasmid system described by Schäfer et al. (Gene 145, 69-73, 1994) was used to integrate desired DNA fragments into the chromosome of C. glutamicum. A modified conjugation method of Schäfer et al. (Journal of Bacteriology 172, 1663-1666, 1990) was used to transfer the respective plasmid into the desired C. glutamicum recipient strain.

Liquid cultures of the C. glutamicum strains were carried out in BHI medium at 33° C. The heat shock was carried out at 48.5° C. for 9 min. Transconjugants resulting from a first recombination event were selected by plating the conjugation batch on EM8 agar (Table 3), which was supplemented with 25 mg/l kanamycin and 50 mg/l nalidixic acid. The EM8 agar plates were incubated for 72 h at 33° C.

TABLE 3

Composition of the EM8 agar.

| Components | Concentration (g/l) |
| --- | --- |
| Glucose (sterile-filtered) | 23 |
| CSL (corn steep liquor) | 30 |
| Peptone from soymeal (Merck, Germany) | 40 |
| $(NH_4)_2SO_4$ | 8 |
| Urea | 3 |
| $KH_2PO_4$ | 4 |
| $MgSO_4 \cdot 7\ H_2O$ | 0.5 |
| $FeSO_4 \cdot 7\ H_2O$ | 0.01 |
| $CuSO_4 \cdot 5\ H_2O$ | 0.001 |
| $ZnSO_4 \cdot 7\ H_2O$ | 0.01 |
| Calcium pantothenate, D(+) | 0.01 |
| Thiamine | 0.001 |
| Inositol | 0.1 |
| Nicotinic acid | 0.001 |
| Biotin (sterile-filtered) | 0.005 |
| $CaCO_3$ (autoclaved separately) | 1.6 |
| Agar-Agar (Merck, Germany) | 14 |

Sterile toothpicks were used to transfer the transconjugants onto BHI agar, which was supplemented with 25 mg/l kanamycin and 50 mg/l nalidixic acid. The agar plates were incubated for 20 h at 33° C. The cultures of the respective transconjugants produced in this manner were then propagated further for 24 h at 33° C. in 10 ml BHI medium contained in 100 ml Erlenmeyer flasks with 3 baffles. To isolate clones having encountered a second recombination event an aliquot was taken from the liquid culture, suitably diluted and plated (typically 100 to 200 µl) on BHI agar which was supplemented with 10% saccharose. The agar plates were incubated for 48 h at 33° C. The colonies growing on the saccharose containing agar plates were then examined for the phenotype kanamycin sensitivity. To do so a toothpick was used to remove cell material from the colony and to transfer it onto BHI agar containing 25 mg/l kanamycin and onto BHI agar containing 10% saccharose. The agar plates were incubated for 60 h at 33° C. Transconjugant clones that proved to be sensitive to kanamycin and resistant to saccharose were examined for integration of the desired DNA fragment into the chromosome by means of PCR.

17. Determining nucleotide sequences

Nucleotide sequences of DNA molecules were determined by eurofins genomics GmbH (Ebersberg, Germany) by cycle sequencing, using the dideoxy chain termination method of Sanger et al. (Proceedings of the National Academy of Sciences USA 74, 5463-5467, 1977), on Applied Biosystems® (Carlsbad, Calif., USA) 3730xl DNA Analyzers. Clonemanager Professional 9 software from Scientific & Educational Software (Denver, USA) was used to visualise and evaluate the sequences.

18. Glycerol stocks of *E. coli* and *C. glutamicum* strains

For long time storage of *E. coli*- and *C. glutamicum* strains glycerol stocks were prepared. Selected *E. coli* clones were cultivated in 10 ml LB medium supplemented with 2 g/l glucose. Selected *C. glutamicum* clones were cultivated in two fold concentrated BHI medium supplemented with 2 g/l glucose. Cultures of plasmid containing *E. coli* strains were supplemented with 50 mg/l kanamycin. Cultures of plasmid containing *C. glutamicum* strains were supplemented with 25 mg/l kanamycin. The medium was contained in 100 ml Erlenmeyer flasks with 3 baffles. It was inoculated with a loop of cells taken from a colony and the culture incubated for about 18 h at 37° C. and 200 rpm in the case of *E. coli* and 33° C. and 200 rpm in the case of *C. glutamicum*. After said incubation period 1.2 ml 85% (v/v) sterile glycerol were added to the culture. The obtained glycerol containing cell suspension was then aliquoted in 2 ml portions and stored at −80° C.

19. Cultivation system BioLector®

The micro fermentation system BioLector® (m2p labs GmbH, Baseweiler, Germany) was used to investigate the performance of the *C. glutamicum* strains constructed.

For this purpose a 48 Well FlowerPlate® (m2p labs GmbH, Baseweiler, Germany, Cat. no. MTP-48-BO) filled with 1 ml medium per well was used. The wells of the FlowerPlate® are equipped with an optode to analyze the dissolved oxygen content of the liquid. The BioLector® is further equipped with an optical device to measure the intensity of scattered light caused by the cell particles of a microbial culture contained in a well of a FlowerPlate®. This so called backscatter signal (Samorski et al., Biotechnol Bioeng. 92(1):61-8, 2005) correlates with the concentration of the cell particles. It allows non invasive on line tracking of the growth of a microbial culture.

Precultures of the strains were done in 10 ml two fold concentrated BHI medium. In case of plasmid (pVWEx1 and derivatives thereof) containing strains the medium was supplemented with 25 mg/l kanamycin. The medium was contained in a 100 ml Erlenmeyer flask with 3 baffles. It was inoculated with 100 µl of a glycerol stock culture and the culture incubated for 24 h at 33° C. and 200 rpm.

After said incubation period the optical densities OD600 of the precultures were determined.

The main cultures were done by inoculating the 1 ml medium containing wells of the 48 Well FlowerPlate® with an aliquot of the preculture to give an optical density OD600 of 0.1.

As medium for the main culture modifications of the CGXII medium described by Keilhauer et al. (J. Bacteriol. 1993 September; 175(17): 5595-5603) were used. For convenience the composition of the CGXII medium is shown in table 4.

TABLE 4

Composition of Keilhauer's CGXII medium.

| Components | Concentration (g/l) |
|---|---|
| MOPS (3-(N-Morpholino)propanesulfonic acid) | 42 |
| $(NH_4)_2SO_4$ | 20 |
| Urea | 5 |
| $KH_2PO_4$ | 1 |
| $K_2HPO_4$ | 1 |
| $MgSO_4 \cdot 7\ H_2O$ | 0.25 |
| $CaCl_2$ | 0.01 |
| $FeSO_4 \cdot 7\ H_2O$ | 0.01 |
| $MnSO_4\ H_2O$ | 0.01 |
| $ZnSO_4 \cdot 7\ H_2O$ | 0.001 |
| $CuSO_4 \cdot 5\ H_2O$ | 0.0002 |
| $NiCl_2\ 6\ H_2O$ | 0.00002 |
| Biotin (sterile-filtered) | 0.0002 |
| Protocatechuic acid (sterile-filtered) | 0.03 |
| Carbon source (sterile-filtered) | variable |
| adjust the pH to 7 with NaOH | |

The medium referred to as CGXII_CSL additionally contains cornsteep liquor at a concentration of 7.5 g/l. The medium referred to as CGXII_YE additionally contains yeast extract at a concentration of 7.5 g/l.

In case of plasmid (pVWEx1 and derivatives thereof) containing strains the medium was further supplemented with 25 mg/l kanamycin and 0.3 mM IPTG to induce expression by the PtacI promotor.

These main cultures were incubated for up to 48 h at 33° C. and 800 rpm in the BioLector® system until complete consumption of glucose.

The glucose concentration in the suspension was analysed with the blood glucose-meter OneTouch Vita® from LifeScan (Johnson & Johnson Medical GmbH, Neuss, Germany).

After cultivation the culture suspensions were transferred to a deep well microplate. A part of the culture suspension was suitably diluted to measure the OD600. Another part of the culture was centrifuged and the concentration of L-amino acids, e.g. L-lysine or L-valine, and residual carbon source like panose was analysed in the supernatant.

20. Cultivation in 2 l flasks

L-lysine production using starch hydrolysate as carbon source was done in 2 l flasks as follows:

Precultures of the *C. glutamicum* strains were done in 10 ml two fold concentrated BHI medium. The medium was contained in 100 ml Erlenmeyer flasks with 3 baffles. It was inoculated with 100 µl of a glycerol stock culture. The culture was then incubated for 24 h at 33° C. and 200 rpm. After said incubation period the optical densities OD600 of the precultures were determined.

The main cultures were done by inoculating 200 ml medium containing starch hydrolysate (sterilized separately in a continuous sterilizer) as carbon source contained in 2 l Erlenmeyer flasks having 4 baffles with an aliquot of the preculture to give an optical density OD600 of 0.5. The cultures were incubated for 57 h at 33° C. and 150 rpm.

21. Amino acid analyser

The concentration of L-lysine and other L-amino acids, e.g. L-valine, in the culture supernatants was determined by ion exchange chromatography using a SYKAM S433 amino acid analyser from SYKAM Vertriebs GmbH (Fürstenfeldbruck, Germany). As solid phase a column with spherical, polystyrene-based cation exchanger (Peek LCA N04/Na, dimension 150×4.6 mm) from SYKAM was used. Depending on the L-amino acid the separation takes place in an isocratic run using a mixture of buffers A and B for elution or by gradient elution using said buffers. As buffer A an aquous solution containing in 20 l 263 g trisodium citrate, 120 g citric acid, 1100 ml methanol, 100 ml 37% HCl and 2 ml octanoic acid (final pH 3.5) was used. As buffer B an aquous solution containing in 20 l 392 g trisodium citrate, 100 g boric acidand 2 ml octanoic acid (final pH 10.2) was used. The free amino acids were coloured with ninhydrin through post-column derivatization and detected photometrically at 570 nm.

22. Glucose determination with continuous flow system (CFS)

A SANplus multi-channel continuous flow analyser from SKALAR analytic GmbH (Erkelenz, Germany) was used to determine the concentration of glucose in the supernatant. Glucose was detected with a coupled-enzyme assay (Hexokinase/Glucose-6-Phosphate-Dehydrogenase) via NADH formation.

23. Analysis of panose and isomaltose

A HPLC (high pressure liquid chromatography) compact system from Thermo Fisher Scientific Inc. (Waltham, Mass., USA) was used to determine the concentration of panose and isomaltose in the supernatant of a culture. The separation is carried out by partition chromatography on an amino-modified silica gel with ion exchange character (YMC Polyamine II S-5 µm Amino Column 250*4.6 mm; Thermo Fisher Scientific Inc., Waltham, Mass., USA) with an eluent composed of 30% water and 70% acetonitrile (v/v). The detection takes place via an RI (refractive index) detector (Thermo Fisher Scientific Inc., Waltham, Mass., USA).

24. Preparation of a culture supernatant for analysis of the secreted α-1,6-glucosidase fusion protein Preculture of the C. glutamicum strain was done in 10 ml two fold concentrated BHI medium supplemented with 25 mg/l kanamycin. The medium was contained in a 100 ml Erlenmeyer flask with 3 baffles. It was inoculated with 100 µl of a glycerol stock culture. The culture was then incubated for 24 h at 33° C. and 200 rpm.

After said incubation period the optical density OD600 of the preculture was determined.

The main cultures consisted of 2×50 ml CGXII_CSL medium (see table 5), supplemented with 25 mg/l kanamycin and 0.3 mM IPTG contained in 500 ml Erlenmeyer flasks with 4 baffles. It was inoculated with an aliquot of the preculture to give an optical density OD600 of 0.8 and incubated for 24 h at 33° C. and 150 rpm.

After said incubation period the optical densities OD600 of the main cultures were 41. The cultures were centrifuged for 10 min. at 4.000 rpm. The supernatant obtained was filtrated with a Minisart® High Flow Syringe Filter (0.22 µm) from Sartorius (Göttingen, Germany, Cat. No. 16532). The filtrate was concentrated via an Amicon Ultra-15 Centrifugal Filter unit (30K) from Merck Millipore Ltd. (Cork, Ireland, Cat. No. UFC903024) in order to increase the protein content. For this the supernatant (max. 12 ml) was pippeted onto the filter device and put in the provided centrifuge tube. The centrifugal filter unit was centrifuged for 45 min. at 10° C. and 4000 rpm. After centrifugation the supernatant in the filter unit was pippeted into a separate tube.

The protein content of the concentrate was determined according to Bradford (Anal. Biochem. 72, 248-254, 1976) using the Bio-Rad Protein Assay Dye Reagent from BioRad (Bio-Rad Laboratories GmbH, Munich, Germany, Cat. No. 5000006) according to the instructions of the manufacturer. As standard bovine serum albumin was used. The protein concentration in the concentrate was 0.8 mg/ml.

25. Detection of the cleavage site of fusion protein

The supernatant of a fusion polypeptid expressing cell culture was investigated by LC-MS (liquid chromatography coupled to mass spectrometry) using electrospray ionization (ESI). As instrument an Accela 1250 UPLC coupled with Orbitrap elite from Thermo Fisher (Scientific Inc., Waltham, USA) with a Poroshell SB300-C18, 75×2.1 mm column from Agilent (Santa Clara, USA) was used. As eluent A an aquous solution of 0.1% TFA (trifluoroacetic acid) and as eluent B 0.1% TFA dissolved in Acetonitrile/1-Propanol (60/40) was used. For separation the gradient shown in table 5 was used with a flow rate of 0.3 ml/min at 70° C. Before measurement the sample was diluted 1:20 in aquous 50 mM Tris buffer (pH 7.5). The injection volume of the sample was 15 µl.

TABLE 5

| Elution gradient. | | |
|---|---|---|
| Time [min.] | % eluent A | % eluent B |
| 0 | 100 | 0 |
| 1 | 100 | 0 |
| 2 | 80 | 20 |
| 17 | 35 | 65 |
| 20 | 5 | 95 |
| 25 | 5 | 95 |
| 26 | 100 | 0 |
| 35 | 100 | 0 |

Using ESI method proteins are ionized as multiply protonated molecular ions [M+nH]n+. This allows the detection of even large molecular weight compounds in a limited mass range window. The molecular weight of the uncharged protein can be recalculated by the charge deconvolution software Promass 2.8 for Xcalibur from Novatia, LLC (New Jersey, USA). The protein fractions elute in the retention time area between 8 and 12 min.

26. Measuring α-1,6-glucosidase enzyme activity

α-1,6-glucosidase activity in culture supernatants was determined using para-nitrophenyl-α-glucoside as chromogenic substrate as described by Deng et al. (FEBS Open Bio 4, 200-212, 2014).

The culture supernatants used for the assay were prepared by centrifugation of the cultures and subsequent filtration of the supernatants using a Minisart® High Flow Syringe Filter (0.22 µm) from Sartorius (Göttingen, Germany, Cat. No. 16532).

The assay was carried out at 34° C. in a reaction mixture having a final volume of 1500 µl. 750 µl of 100 mM potassium phosphate buffer (pH 7), 150 µl of 10 mg/ml BSA (bovine serum albumin) and 150 µl of 40 mM para-nitrophenyl-α-glucoside were pipetted into a reaction tube and the reaction started by addition of 450 µl culture supernatant. After 2, 4, 6 and 8 minutes samples of 200 µl were removed from the reaction mixture and pipetted onto 800 µl of a 1 M sodium carbonate solution. The concentration of p-nitrophenol was determined at 405 nm using a U-3200 spectrophotometer from Hitachi Scientific Instruments (Nissel Sangyo GmbH, Düsseldorf, Germany). The molar extinction coefficient for p-nitrophenol was determined as ε=17.6 cm2/ mmol at 405 nm in a 0.8 M sodium carbonate solution having pH 11 and at 34° C. One unit (U) is defined as the amount of enzyme that catalyzes the conversion of 1 μmol of substrate per min.

B) Experimental Results

Example 1

Identification of a Suitable α-1,6-glucosidase

Example 1.1

Experimental Design

Genes of different origin encoding glucosidases reported to hydrolyze α-1,6 linkages in glucose oligomers were tested for their ability to confer the feature of panose degradation to *C. glutamicum*. Bibliographic details of the genes are summarized in table 6.

TABLE 6

Origin of α-1,6-glucosidase functions tested and Tat-signal peptide used.

| origin | gene/cds designation | NCBI accession | other reference | description |
|---|---|---|---|---|
| *Bifidobacterium breve* UCC2003 | agl2 | FJ386390 | Pokusaeva et al. [1] | α-1,6-glucosidase |
| *Bifidobacterium breve* UCC2003 | agl1 | FJ386389 | Pokusaeva et al. [1] | α-1,6-glucosidase |
| *Saccharomyces cerevisiae* S288c | IMA1 | NC_001139; locus_tag: YGR287C | — | oligo-1,6-glucosidase IMA1 |
| *Bacillus subtilis* HB002 | — | AY008307.1 | — | oligo-1,6-glucosidase |
| *Corynebacterium glutamicum* ATCC13032 | cg0955 | NC_006958.1; old_locus_tag: cg0955 [3] | Breitinger[2] | Cg0955 |

[1] (Applied and Environmental Microbiology 75, 1135-1143, 2009)
[2] (Dissertation Ulm University 2013)
[3] (locus_tag: CGTRNA_RS04205); under accession number NC_003450.3; the same cds is available under locus_tag NCgl0801)

In essence the coding sequences of the genes listed in table 6 encoding polypeptides providing the enzyme function were adapted to the codon usage of *Corynebacterium glutamicum* (cuo=codon usage optimized) and fused to the nucleotide sequence encoding the Tat-signal peptide of Cg0955 described by Breitinger (Dissertation Ulm University 2013). The amino acid sequence of the Tat-signal peptide of Cg0955 and the nucleotide sequence encoding it are shown in SEQ ID NO:2 and SEQ ID NO:1 of the sequence listing. The polynucleotides encoding the resulting fusion polypeptides were cloned into the expression vector pVWEx1 described by Peters-Wendisch et al. (Journal of Molecular Microbiology and Biotechnology 3, 295-300, 2001). The nucleotide sequence of pVWEx1 is available at the GenBank database under accession number MF034723. A map of plasmid pVWEx1 is shown in FIG. 1.

An L-lysine producing strain of *Corynebacterium glutamicum* was transformed with the expression vectors constructed and the resulting transformants tested for their ability to degrade panose.

Example 1.2

Design and Synthesis of the Gene Fusions

The polynucleotides encoding the fusion polypeptides were designed and synthesized with a PstI endonuclease restriction site (CTGCAG) at the 5'-end and the transcriptional terminator Tgap* (see SEQ ID NO:13) and a BamHI endonuclease restriction site (GGATCC) at the 3'-end of the nucleotide sequence. The PstI and BamHI restriction sites allow for cloning into the *E. coli-C. glutamicum* shuttle vector pVWEx1.

Gene Fusion tat-'agl2_cuo:

The nucleotide sequence of the polynucleotide synthesized and containing the coding sequence of the gene fusion tat-'agl2_cuo is shown in SEQ ID NO:21. The amino acid sequence of the fusion polypeptide Tat-'Agl2 is shown in SEQ ID NO:22. The amino acid sequence of the fusion polypeptide from positions 1 to 33 is identical with the amino acid sequence of Cg0955 shown in SEQ ID NO:2 from position 1-33. This part of the amino acid sequence of the fusion polypeptide is also referred to as N-terminal Tat-signal peptide.

The amino acid sequence of the fusion polypeptide from positions 37 to 639 of SEQ ID NO:22 is identical to the amino acid sequence of the Agl2 polypeptide shown in SEQ ID NO:6 from position 2-604. The absence of the starting amino acid methionine (Met) of Agl2 in the fusion polypeptide is indicated by the "'" in the designation of the fusion polypeptide.

The G+C content of the nucleotide sequence coding for the C-terminal polypeptide of the fusion polypeptide ('agl2_cuo) shown in SEQ ID NO:21 position 122 to 1930 is 58.2%. The G+C content of the nucleotide sequence coding for the Agl2 polypeptide of *Bifidobacterium breve* UCC2003 lacking the atg start codon ('agl2) shown in SEQ ID NO:5 position 4 to 1812 is 65.6%.

The polynucleotide tat-'agl2_cuo shown in SEQ ID NO:21 was cloned into the shuttle vector pVWEx1. For this purpose the polynucleotide shown in SEQ ID NO:21 was cut with the restriction endonucleases PstI and BamHI and ligated into the vector treated with the restriction endonucleases PstI and BamHI. The obtained plasmid was named pVWEx1_tat-'agl2_cuo. A map of plasmid pVWEx1_tat-'agl2_cuo is shown in FIG. 2.

Gene Fusion tat-agl1_cuo:

The nucleotide sequence of the polynucleotide synthesized and containing the coding sequence of the gene fusion tat-agl1_cuo is shown in SEQ ID NO:23. The amino acid sequence of the fusion polypeptide Tat-Agl1 is shown in SEQ ID NO:24. The amino acid sequence of the fusion polypeptide from positions 1 to 33 is identical with the amino acid sequence of Cg0955 shown in SEQ ID NO:2 from position 1-33. This part of the amino acid sequence of the fusion polypeptide is also referred to as N-terminal Tat-signal peptide.

The amino acid sequence of the fusion polypeptide from positions 37 to 643 of SEQ ID NO:24 is identical to the amino acid sequence of the Agl1 polypeptide shown in SEQ ID NO:8.

The G+C content of the nucleotide sequence coding for the C-terminal polypeptide of the fusion polypeptide (agl1_cuo) shown in SEQ ID NO:23 position 122 to 1942 is 58.1%. The G+C content of the nucleotide sequence coding for the Agl1 polypeptide of *Bifidobacterium breve* UCC2003 (agl1) shown in SEQ ID NO:7 position 1 to 1821 is 58.6%.

The polynucleotide tat-agl1_cuo shown in SEQ ID NO:23 was cloned into the shuttle vector pVWEx1. For this purpose the polynucleotide shown in SEQ ID NO:23 was cut with the restriction endonucleases PstI and BamHI and ligated into the vector treated with the restriction endonucleases PstI and BamHI. The obtained plasmid was named pVWEx1_tat-agl1_cuo.

Gene Fusion tat-IMA1_cuo:

The nucleotide sequence of the polynucleotide synthesized and containing the coding sequence of the gene fusion tat-IMA1_cuo is shown in SEQ ID NO:25. The amino acid sequence of the fusion polypeptide Tat-IMA1 is shown in SEQ ID NO:26. The amino acid sequence of the fusion polypeptide from positions 1 to 33 is identical with the amino acid sequence of Cg0955 shown in SEQ ID NO:2 from position 1-33. This part of the amino acid sequence of the fusion polypeptide is also referred to as N-terminal Tat-signal peptide.

The amino acid sequence of the fusion polypeptide from positions 37 to 624 of SEQ ID NO:26 is identical to the amino acid sequence of the IMA1 polypeptide shown under accession number NP_11803 from position 2-589. The absence of the starting amino acid methionine (Met) of IMA1 in the fusion polypeptide is indicated by the in the designation of the fusion polypeptide.

The G+C content of the nucleotide sequence coding for the C-terminal polypeptide of the fusion polypeptide ('IMA1_cuo) shown in SEQ ID NO:25 position 122 to 1885 is 53.2%. The G+C content of the nucleotide sequence coding for the IMA1 polypeptide of *Saccharomyces cerevisiae* S288c lacking the atg startcodon ('IMA1) is 42.4%.

The polynucleotide tat-'IMA1_cuo shown in SEQ ID NO:25 was cloned into the shuttle vector pVWEx1. For this purpose the polynucleotide shown in SEQ ID NO:25 was cut with the restriction endonucleases PstI and BamHI and ligated into the vector treated with the restriction endonucleases PstI and BamHI. The obtained plasmid was named pVWEx1_tat-'IMA1_cuo.

Gene Fusion tat-'AY008307_cuo:

The nucleotide sequence of the polynucleotide synthesized and containing the coding sequence of the gene fusion tat-'AY008307_cuo is shown in SEQ ID NO:27. The amino acid sequence of the fusion polypeptide Tat-'AY008307 is shown in SEQ ID NO:28. The amino acid sequence of the fusion polypeptide from positions 1 to 33 is identical with the amino acid sequence of Cg0955 shown in SEQ ID NO:2 from position 1-33. This part of the amino acid sequence of the fusion polypeptide is also referred to as N-terminal Tat-signal peptide.

The amino acid sequence of the fusion polypeptide from positions 37 to 596 of SEQ ID NO:28 is identical to the amino acid sequence of the oligo-1,6-glucosidase polypeptide shown under accession number AAG23399 from position 2-561. The absence of the starting amino acid methionine (Met) in the fusion polypeptide is indicated by the in the designation of the fusion polypeptide.

The G+C content of the nucleotide sequence coding for the C-terminal polypeptide of the fusion polypeptide ('AY008307_cuo) shown in SEQ ID NO:27 position 122 to 1801 is 53.1%. The G+C content of the nucleotide sequence coding for the AY008307 polypeptide of *Bacillus subtilis* HB002 lacking the atg startcodon ('AY008307) is 44.0%.

The polynucleotide tat-'AY008307_cuo shown in SEQ ID NO:27 was cloned into the shuttle vector pVWEx1. For this end the polynucleotide shown in SEQ ID NO:27 was cut with the restriction endonucleases PstI and BamHI and ligated into the vector treated with the restriction endonucleases PstI and BamHI. The obtained plasmid was named pVWEx1_tat-'AY008307_cuo.

Gene agl2_cuo:

The nucleotide sequence of the polynucleotide containing the coding sequence of the gene agl2_cuo is shown in SEQ ID NO:29 and the encoded amino acid sequence of the polypeptide Agl2 shown in SEQ ID NO:30. The amino acid sequence of the polypeptide from positions 1 to 604 is identical with the amino acid sequence of Agl2 shown in SEQ ID NO:6 from position 1 to 604. The amino acid sequence of the polypeptide shown in SEQ ID NO:30 from positions 2 to 604 is identical with the amino acid sequence of the fusion protein Tat-Agl2 shown in SEQ ID NO:10 from position 37 to 639.

To show the effect of the Tat-signal peptide on enzyme secretion or panose degradation resp. a control plasmid containing the complete coding sequence of the gene agl2_cuo but lacking a nucleotide sequence coding for a signal peptide was designed and constructed. This control plasmid was called pVWEx1_agl2_cuo.

For this purpose the polynucleotide Wo_tat shown in SEQ ID NO:31 was designed and synthesized.

Wo_tat contains from 5'- to 3'-end the recognition site for the endonuclease MauBI, the PtacI promoter, recognition sites for the endonucleases PstI and SexAI and the 5'-end of the coding sequence of agl2_cuo including the recognition site for the endonuclease FspAI (see SEQ ID NO:21). Said 5'-end of the coding sequence of agl2_cuo consists of the nucleotide sequence from position 14 to 77 of SEQ ID NO:29 encoding the first 21 N-terminal amino acids of the Agl2 polypeptide including the starting amino acid methionine.

Plasmid pVWEx1_agl2_cuo was constructed as follows: Plasmid pVWEx1_tat-'agl2_cuo (see FIG. 2) was digested with the restriction endonucleases MauBI and FspI. Thus two DNA fragments were obtained. One DNA fragment of 473 bps length comprising the PtacI promoter and the 5'-end of the gene fusion tat-'agl2_cuo essentialy encoding the Tat-signal peptide (marked as tat in FIG. 2) and a second DNA fragment of 10116 bps length comprising pVWEx1 sequence and the 3'-end of the gene fusion tat-'agl2_cuo essentially encoding the Agl2 α-1,6 glucosidase (marked as 'agl2_cuo in FIG. 2). The two DNA fragments were separated by agarose gel electrophoresis. The 473 bps DNA fragment was discarded and the 10116 bps DNA fragment isolated from the agarose gel and purified. The polynucleotide Wo_tat was also treated with the restriction endonucleases MauBI and FspAI and purified. The two DNA fragments thus prepared were ligated and the ligation mixture used to transform chemically competent E. coli Stellar™ cells. The nucleotide sequence of agl2_cuo (also shown in SEQ ID NO:29) in the isolated plasmid of a transformant was confirmed using the Sanger sequencing method.

Thus the plasmid pVWEx1_agl2_cuo was obtained. Its map is shown in FIG. 3.

Example 1.3

Strain Construction

As host for assessing the ability of the constructed gene fusions to confer the ability of panose degradation to the species C. glutamicum strain DM1933 was chosen.

Strain DM1933 is an L-lysine producer described by Blombach et al. (Applied and Environmental Microbiology 75(2), 419-427, 2009). It is deposited according to the Budapest treaty under accession number DSM25442.

Strain DM1933 was transformed with isolated plasmid DNA of pVWEx1, pVWEx1_tat-'agl2_cuo, pVWEx1_tat-agl1_cuo, pVWEx1_tat-'IMA1_cuo, pVWEx1_tat-'AY008307_cuo and pVWEx1_agl2_cuo by electroporation. Selection for transformants, propagation of the transformants and preparation of glycerol stock cultures was done as described under materials and methods and in the presence of kanamycin.

Specific nucleotide sequences of the transformants were amplified by colony PCR in order to verify the plasmid status of the transformants. The primers used and the size of the PCR amplificates are summarized in table 7.

For PCR the Taq kit (see table 1) was used with the temperature of the annealing step (step 3) set at 53° C. and the time of the elongation step (step 4) set at 13 sec. Size determination of the amplificates was done by capillary electrophoresis.

The nucleotide sequences of the primers used are also shown in the sequence listing under SEQ ID NO:33 to SEQ ID NO:37.

The transformants thus obtained and analyzed were used for further investigation.

Example 1.4

Panose Degradation

The transformants of example 1.3 were analyzed for their ability to degrade panose by batch cultivation using the BioLector® system.

As medium CGXII_CSL containing 15 g/l glucose and 4.8 g/l panose as carbon source was used. The medium was further supplemented with kanamycin and IPTG. The cultures were incubated for ca. 20 h until complete consumption of glucose as confirmed by glucose analysis using blood glucose-meter and the optical densities of the cultures and the concentration of residual panose determined.

The result of the experiment is presented in table 8 and shows that the α-1,6-glucosidases Agl1 and Agl2 fused to the Tat-signal peptide of Cg0955, i.e. Tat-Agl1 and Tat-'Agl2, were able to confer the feature of panose degradation to C. glutamicum with Tat-'Agl2 being superior over Tat-Agl1.

TABLE 8

Degradation of panose by different transformants of DM1933 expressing different α-1,6-glucosidases fused to the signal peptide of Cg0955.

| Strain (DM1933 transformed with) | Residual panose (g/l) | Degraded panose (%) | OD660 |
| --- | --- | --- | --- |
| pVWEx1 | 4.8 | 0 | 6.4 |
| pVWEx1_tat-'agl2_cuo | 0.3 | 94 | 6.7 |
| pVWEx1_tat-agl1_cuo | 1.1 | 77 | 7.3 |

TABLE 7

List of primers used and size of amplificates during PCR analysis of transformants.

| plasmid | PCR analysis | | |
| --- | --- | --- | --- |
| | primer | sequence | size [bp] |
| pVWEX1 | pVW_2 | TTTGCGCCGACATCATAACG | 327 |
| | pVW_3 | TACTGCCGCCAGGCAAATTC | |
| pVWEx1_tat-'agl2_cuo | pVW_1 | GTGAGCGGATAACAATTTCACAC | 328 |
| | gluc_rev | GTAGCCGTTATCATCCTGTG | |
| pVWEx1_tat-agl1_cuo | pVW_1 | GTGAGCGGATAACAATTTCACAC | 439 |
| | gluc_rev | GTAGCCGTTATCATCCTGTG | |
| pVWEx1_tat-'IMA1_cuo | pVW_1 | GTGAGCGGATAACAATTTCACAC | 184 |
| | gluc2_rev | TGCTCCAAGGGCGTTGGCCTTTG | |
| pVWEx1_tat-'AY008307_cuo | pVW_1 | GTGAGCGGATAACAATTTCACAC | 376 |
| | gluc_rev | GTAGCCGTTATCATCCTGTG | |
| pVWEx1_agl2_cuo | pVW_2 | TTTGCGCCGACATCATAACG | 413 |
| | gluc_rev | GTAGCCGTTATCATCCTGTG | |

TABLE 8-continued

Degradation of panose by different transformants of DM1933 expressing different α-1,6-glucosidases fused to the signal peptide of Cg0955.

| Strain (DM1933 transformed with) | Residual panose (g/l) | Degraded panose (%) | OD660 |
|---|---|---|---|
| pVWEx1_tat-'IMA1_cuo | 4.7 | 2 | 6.4 |
| pVWEx1_tat-'AY008307_cuo | 4.6 | 4 | 6.6 |
| pVWEx1_agl2_cuo | 4.8 | 0 | 6.5 |

Example 2

Identification of a Suitable Signal Peptide

Example 2.1

Experimental Design

Tat secretion signal peptides of various secreted proteins of *C. glutamicum* were tested for their ability to direct the secretion of the Agl2 α-1,6-glucosidase into the supernatant of a *C. glutamicum* culture.

Watanabe et al. (Microbiology 155, 741-750, 2009) evaluated the efficiency of different Tat-signal peptides of *C. glutamicum* R to direct the α-amylase of *Geobacillus stearothermophilus* devoid of its natural signal peptide into the supernatant of a *C. glutamicum* R culture using an agar plate diffusion assay. See FIG. 3 on page 745 of Watanabe et al.

In a similar approach the signal peptides of polypeptides CgR0079, CgR0120, CgR0124, CgR0900, CgR0949, CgR1023, CgR1448, CgR2137, CgR2627 and CgR2926 were evaluated for their ability to direct the Agl2 α-1,6-glucosidase of *B. breve* UCC2003 into the supernatant of a *C. glutamicum* culture by measuring the panose degradation in the culture supernatant. Accordingly the nucleotide sequences coding for the signal peptides of said polypeptides were fused to the agl2 gene optimized for the codon usage of *C. glutamicum* ('agl2_cuo).

The nucleotide sequences coding for the polypeptides and the amino acid sequences of the polypeptides are available at the NCBI under GenBank accession number NC_009342 (complete genome of *C. glutamicum* R). In particular they can be identified under the old locus tags cgR_0079, cgR_0120, cgR_0124, cgR_0900, cgR_0949, cgR_1023, cgR_1448, cgR_2137, cgR_2627 and cgR_2926. The coding sequence of cgR0949 or cgR_0949 resp is also shown in SEQ ID NO:3 of the sequence listing.

Example 2.2

Design and Synthesis of the Gene Fusions

As the starting point for the construction of the different gene fusions plasmid pVWEx1_tat-'agl2_cuo was used. The nucleotide sequence coding for the tat-signal peptide of Cg0955 (current locus tag NCgl0801) contained in the plasmid was replaced by a nucleotide sequence coding for the signal peptide of CgR0079, CgR0120, CgR0124, CgR0900, CgR0949, CgR1023, CgR1448, CgR2137, CgR2627 or CgR2926.

For this purpose plasmid pVWEx1_tat-'agl2_cuo (see FIG. 2) was digested with the restriction endonucleases SexAI and SpeI. Thus two DNA fragments were obtained. One DNA fragment of 109 bps length encoding the signal peptide and a second DNA fragment of 10332 bps length essentially consisting of pVWEx1 and 'agl2_cuo DNA sequence. The two DNA fragments were separated by agarose gel electrophoresis. The 109 bps DNA fragment was discarded and the 10332 bps DNA fragment isolated from the agarose gel and purified.

The polynucleotides or DNA molecules resp. encoding the different signal peptides including the putative cleavage-site described by Watanabe et al. are shown in SEQ ID NO:38 to 57.

With the exception of the polynucleotide coding for the signal peptide of CgR0124 they were designed and synthesized to allow for cloning by Gibson Assembly. For this purpose the polynucleotides contain at their 5'-end and 3'-end sequences of 25 to 45 bps and 24 to 54 bps length, which overlap with the corresponding ends of the 10332 bps DNA fragment.

The individual Gibson Assembly mixtures of the polynucleotide encoding the signal peptide of CgR0079, CgR0120, CgR0900, CgR0949, CgR1023, CgR1448, CgR2137, CgR2627 and CgR2926 with said 10332 bps DNA fragment of pVWEx1_tat-'agl2_cuo were used to transform chemically competent *E. coli* Stellar™ cells.

The polynucleotide coding for the signal peptide of CgR0124 (See SEQ ID NO:42) was designed and synthesized to allow for cloning using DNA ligase. For this purpose the polynucleotide contains at its 5'-end a recognition site for SexAI and at its 3'-end a recognition site for SpeI. The ligation mixture comprising the polynucleotide treated with the two restriction endonucleases and said isolated 10332 bps DNA fragment of pVWEx1_tat-'agl2_cuo was used to transform chemically competent *E. coli* Stellar™ cells.

Plasmid DNA's of randomly chosen transformants obtained from the different Gibson Assembly mixtures and the ligation mixture were then analyzed. For this purpose transformants were analyzed by colony PCR using the Sapphire Mix (see table 2) with the primer pVW_4 and the "Wtat" primers as listed in table 9 followed by size determination of the amplificates by capillary electrophoresis. The primers are also shown in SEQ ID NO:58 to SEQ ID NO:68 of the sequence listing.

TABLE 9

List of primers used and size of amplificates during PCR analysis of transformants.

| detection of | name | sequence | size [bp] |
|---|---|---|---|
|  | pVW_4 | TTTGCGCCGACATCATAACG |  |
| CgR0079 | Wtat1_agl2_rev | GCCACCGACAGCGATGATAG | 255 |
| CgR0120 | Wtat2_agl2_rev | ACTGTCGCCGGGAAAAACTA | 199 |

TABLE 9-continued

List of primers used and size of amplificates during PCR analysis of transformants.

| detection of | name | sequence | size [bp] |
|---|---|---|---|
| CgR0124 | Wtat3a_agl2 | GTCGCGGACGGCGTAGAGGG | 251 |
| CgR0900 | Wtat4_agl2_rev | GGCCGAAGGTGACATGATGC | 252 |
| CgR0949 | Wtat5a_agl2 | AGCGCCGATAGTGGCAAGTC | 231 |
| CgR1023 | Wtat6_agl2_rev | GGTGCCTGTCAGTACAGTTC | 249 |
| CgR1448 | Wtat7_agl2_rev | ACCCGCACATGCTGCCAAAG | 252 |
| CgR2137 | Wtat8a_agl2 | GTGGCTAGACCTGCAGTAAC | 233 |
| CgR2627 | Wtat9_agl2_rev | TGCAGCAACAACGCCTCTGG | 237 |
| CgR2926 | Wtat10_agl2 | AGCACCTGCGAAGGTTGTTG | 243 |

Thus transformants containing plasmids bearing the desired sequence coding for the specific signal peptide linked to the Agl2 polypeptide were identified.

Despite several attempts no transformants were obtained carrying a plasmid bearing the sequence coding for the signal peptide of CgR0124.

Subsequently the nucleotide sequences of the gene fusions contained in the respective plasmids were determined. For this purpose plasmid DNA was isolated from the transformants and the nucleotide sequences of the individual gene fusions were analyzed by Sanger sequencing.

Thus pVWEx1 based plasmids bearing gene fusions of the nucleotide sequence coding for the signal peptide of CgR0079, CgR0120, CgR0900, CgR0949, CgR1023, CgR1448, CgR2137, CgR2627 and CgR2926 to the nucleotide sequence of 'agl2_cuo were identified.

Example 2.3

Strain Construction

C. glutamicum strain DM1933 was transformed with the plasmids described above by electroporation. The transformants were analyzed by colony PCR using the Sapphire Mix (see table 2) with the primers of table 9 and subsequent length analysis by capillary electrophoresis.

Glycerol stock cultures of the transformants were prepared in the presence of kanamycin and used as starting material for further investigations.

Example 2.4

Panose Degradation

The transformants carrying the different gene fusions from example 2.3 were analyzed for their ability to degrade panose by batch cultivation using the BioLector® cultivation system.

As medium CGXII_CSL containing 15 g/l glucose and 4.8 g/l panose as carbon source was used. The medium was further supplemented with kanamycin and IPTG.

The cultures were incubated for ca. 22 h until complete consumption of glucose as confirmed by glucose analysis using blood glucose-meter. The optical densities of the cultures and the concentrations of residual panose were then determined.

The result of the experiment is shown in table 10. For convenience the results of Watanabe et al. concerning the secretion of the α-amylase were incorporated into the table.

TABLE 10

Degradation of panose by different transformants of DM1933 expressing different signal peptides fused to the Agl2 α-1,6-glucosidase.

| Signal peptide of | Watanabe's Secretion efficiency[2] | Residual panose (g/l) | Degraded panose (%) | OD660 |
|---|---|---|---|---|
| none | – | 4.8 | 0 | 7.1 |
| CgR0079 | ++ | 1.1 | 77 | 9.1 |
| CgR0120 | ++++ | 4.3 | 10 | 7.2 |
| CgR0124 | + | n.t.[1] | n.t.[1] | n.t.[1] |
| CgR0900 | ++ | 0.8 | 83 | 9.1 |
| CgR0949 | ++++ | 2.6 | 46 | 8.8 |
| cg0955 | n.t.[1] by W.[2] | 0.2 | 96 | 7.6 |
| CgR1023 | ++++ | 3.8 | 21 | 9.9 |
| CgR1448 | +++ | 1.3 | 73 | 8.7 |
| CgR2137 | ++++ | 0[3] | 100 | 9.4 |
| CgR2627 | ++++ | 4.5 | 6 | 7.1 |
| CgR2926 | +++ | 4.8 | 0 | 7.2 |

[1]not tested
[2]Watanabe et al.
[3]not detectable

The best panose degradation was achieved by the strains carrying gene fusions encoding the signal peptide of CgR2137 or of Cg0955.

The strain expressing the fusion polypeptide having the signal peptide of Cg0955 is referred to as DM1933/pVWEx1_tat-'agl2_cuo (see example 1.3) and the strain expressing the fusion polypeptide having the signal peptide of CgR2137 is referred to as DM1933/pVWEx1_cgR2137-'agl2_cuo in the following.

Example 2.5

L-lysine Production by Different Transformants of Strain DM1933

Strains DM1933/pVWEx1, DM1933/pVWEx1_tat-'agl2_cuo and DM1933/pVWEx1_cgR2137-'agl2_cuo were analyzed for their ability to produce L-lysine from a mixture of glucose and panose by batch cultivation using the BioLector® system.

As medium CGXII_CSL containing 15 g/l glucose and 4.8 g/l panose as carbon source was used. The medium was further supplemented with kanamycin and IPTG. The cultures were incubated for ca. 20 h until complete consumption of glucose as confirmed by glucose analysis using blood glucose-meter and the concentrations of L-lysine, panose and optical density OD660 were determined. The result of the experiment is presented in table 11.

TABLE 11

L-lysine formation using a mixture of glucose and panose as carbon source.

| Strain | OD660 | Lys[1] (g/l) | Residual Panose (g/l) |
|---|---|---|---|
| DM1933/pVWEx1 | 7.0 | 3.7 | 4.8 |
| DM1933/pVWEx1_tat-'agl2_cuo | 7.5 | 4.6 | 0.3 |
| DM1933/pVWEx1_cgR2137-'agl2_cuo | 9.0 | 2.9 | 0[2] |

[1]L-lysine as L-lysine × HCl
[2]not detectable

The experiment showed that L-lysine formation was strongly impaired in strain DM1933/pVWEx1_cgR2137-'agl2_cuo. Accordingly the work with the gene fusion cgR2137-'agl2_cuo was no longer pursued.

The experiment further showed that strain DM1933/pVWEx1_tat-'agl2_cuo is able to produce L-lysine from panose.

Example 3

Effect of Expression of the Gene Fusion Tat-'Agl2_Cuo on Growth and Yield of L-lysine The experiments were designed to assess whether the expression of the gene fusion tat-'agl2_cuo as contained in pVWEx1_tat-'agl2_cuo negatively affects the growth rate of its host and L-lysine production.

Example 3.1

Effect on Growth Using Glucose as Carbon Source

Strains DM1933/pVWEx1 and DM1933/pVWEx1_tat-'agl2_cuo were cultivated using the BioLector® system and the formation of biomass recorded by measuring the scattered light (back scatter signal).

As medium CGXII_CSL containing 20 g/l glucose as carbon source was used. The medium was further supplemented with kanamycin and IPTG. At the end of cultivation α-1,6-glucosidase enzyme activity was measured in the culture supernatant.

The result is presented in FIG. 4 and table 12. It shows that expression of the gene fusion tat -agl2_cuo contained in an expression unit comprising the promoter PtacI as contained in strain DM1933/pVWEx1_tat-'agl2_cuo does not adversely affect the growth rate of its host strain.

TABLE 12

α-1,6-glucosidase enzyme activity in the culture supernatant of strains DM1933/pVWEx1 and DM1933/pVWEx1_tat-'agl2_cuo after growth on glucose.

| strain | activity [U/l] |
|---|---|
| DM1933/pVWEx1 | 0 |
| DM1933/pVWEx1_tat-'agl2_cuo | 119 |

Example 3.2

Effect on L-lysine Production Using Glucose as Carbon Source

Strains DM1933/pVWEx1 and DM1933/pVWEx1_tat-'agl2_cuo were cultivated using the BioLector® system and the concentration of the L-lysine formed measured at the end of cultivation.

As medium CGXII_CSL containing 20 g/l glucose as carbon source was used. The medium was further supplemented with kanamycin and IPTG. The cultures were incubated for ca. 20 h until complete consumption of glucose using blood glucose-meter as confirmed by glucose analysis and the concentration of the L-lysine formed and the optical density OD660 were measured.

The result is presented in table 13. It shows that expression of the gene fusion tat-'agl2_cuo contained in an expression unit comprising the promoter PtacI as contained in strain DM1933/pVWEx1_tat-'agl2_cuo does not adversely affect the yield of L-lysine produced.

TABLE 13

L-lysine production by strains DM1933/pVWEx1 and DM1933/pVWEx1_tat-'agl2_cuo using glucose as carbon source.

| Strain | OD660 | Lys[1] (g/l) |
|---|---|---|
| DM1933/pVWEx1 | 8.5 | 4.9 |
| DM1933/pVWEx1_tat-'agl2_cuo | 8.3 | 4.8 |

[1]L-lysine as L-lysine × HCl

Example 4

L-lysine Production Using Transformants of Strain DM2031

The L-lysine producer DM2031 C. glutamicum is a descendant of strain DM1933 characterized by an increased capability to produce L-lysine. It contains an additional copy of the lysC(T311I)asd operon expressed by the promoter Pg3N3 (WO2013000827) and inserted into the intergenic region between NCgl0038 and NCgl0039. It further contains a copy of the pyc(P458S) allele arranged tandemly at the site of pyc(P458S) as described in WO2003014330. The strain was deposited under the Budapest treaty at the DSMZ under the designation DSM32514.

Strain DM2031 was transformed with plasmids pVWEx1_tat-'agl2_cuo and pVWEx1. The strains DM2031/pVWEx1 and DM2031/pVWEx1_tat-'agl2_cuo thus obtained were cultivated using the BioLector® system and the concentration of the L-lysine formed measured at the end of cultivation.

As medium CGXII_CSL containing either 8 g/l glucose or 8 g/l glucose and 5.7 g/l panose as carbon source. The media were further supplemented with kanamycin and IPTG. The cultures were incubated for ca. 20 h until complete consumption of glucose as confirmed by glucose analysis using blood glucose-meter and the concentration of the L-lysine formed was measured.

TABLE 14

L-lysine production by transformants of strain DM2031 using glucose and a mixture of glucose and panose as carbon source.

| Carbon source:<br>Strain | Glucose<br>Lys[1]<br>(g/l) | Glucose and Panose<br>Lys[1]<br>(g/l) |
|---|---|---|
| DM2031/pVWEx1 | 3.6 | 3.7 |
| DM2031/VWEx1_tat-'agl2_cuo | 3.6 | 6.9 |

[1]L-lysine as L-lysine × HCl

The result is presented in table 14. It shows that strain DM2031/pVWEx1_tat-'agl2_cuo is able to produce L-lysine from panose.

Example 5

Chromosomal Integration and Expression of the Gene Fusion Tat-'Agl2_Cuo

An expression unit (see SEQ ID NO:16) comprising the promoter PdapBN1 (see SEQ ID NO:15), the gene fusion tat-'agl2_cuo (see SEQ ID NO:9) and the transcriptional terminator Tgap* (see SEQ ID NO:13) was designed and synthesized and integrated into the target site, which is the intergenic region between locus tag NCgl2176 and NCgl2177 (see SEQ ID NO:18), of the chromosome of the L-lysine producer DM1933.

For transfer of the expression unit into the chromosome plasmid pK18mobsacB in conjunction with *E. coli* strain S17-1 as described by Schäfer et al. (Gene 145, 69-73, 1994) was used. The nucleotide sequence of pK18mobsacB is available at the GenBank database under accession number FJ437239.

Example 5.1

Construction of the Plasmid pK18mobsacB_INT::PBN1-tat-'agl2_cuo

In first step a polynucleotide or DNA molecule resp. was designed and synthesized, in order to provide the flanking sequences required for integration of the expression unit into the target site within the chromosome of the *C. glutamicum* host by homologous recombination. The polynucleotide was called INT.

The nucleotide sequence of the polynucleotide (DNA molecule) INT is shown in SEQ ID NO:69. It comprises from its 5'-end to its 3'-end a recognition site for the restriction endonuclease EcoRI, a part (3'-end) of the gene identified by locus tag NCgl2176, the intergenic region (IR) between locus tags NCgl2176 and NCgl2177 bearing recognition sites for the restriction endonucleases EcoRV (GATATC), AvrII (CCTAGG) and SmaI (CCCGGG) artificially generated by nucleotide exchange, the nucleotide sequence of the gene identified by locus tag NCgl2177 (on the complementary strand of the DNA molecule), a sequence upstream of NCgl2177 and a recognition site for the restriction endonuclease HindIII (AAGCTT).

The two restriction sites EcoRI and HindIII at the 5'- and 3'-end of the DNA molecule were used for cloning the polynucleotide into the vector pK18mobsacB cut by restriction endonucleases EcoRI and HindIII.

As result vector pK18mobsacB containing the polynucleotide INT was obtained. This plasmid was named pK18mobsacB_INT.

In a second step a polynucleotide comprising an expression unit named PBN1-tat-'agl2_cuo was designed and synthesized. It contains the promoter PdapBN1, the gene fusion tat-'agl2_cuo and the transcriptional terminator Tgap*. Its nucleotide sequence is shown in SEQ ID NO:70. It comprises the nucleotide sequence of SEQ ID NO:16 and additionally contains 20 nucleotides (GCGTCTAGAACTGATGAACA) at the 5'-end and 9 nucleotides (GGATCCGCG) at the 3'-end. A map of the expression unit PBN1-tat-'agl2_cuo is shown in FIG. 5.

In a third step the polynucleotide PBN1-tat-'agl2_cuo was treated with restriction endonuclease XbaI and cloned into vector pK18mobsacB_INT linearized by treatment with restriction endonuclease AvrII. Chemically competent *E. coli* Stellar™ cells were used as transformation host.

Plasmid DNA was isolated from the transformants and treated with the restriction endonuclease HincII. The DNA fragments were separated by agarose gel electrophoresis (0.8% weight per volume of agarose).

Plasmids containing the desired orientation of the expression unit PBN1-tat-'agl2_cuo within the intergenic region (IR) of the INT polynucleotide, the desired orientation being 5'-'NCgl2176-PBN1-tat-'agl2_cuo-NCgl2177-3', were identified by the pattern of DNA fragments having a length of 3197 bp, 2928 bp, 2314 bp and 822 bp. One of the plasmids thus identified was named pK18mobsacB_INT::PBN1-tat-'agl2_cuo. The integrity of the INT::PBN1-tat-'agl2_cuo unit within the plasmid was confirmed by determining its nucleotide sequence using the Sanger method. A map of said INT::PBN1-tat-'agl2_cuo unit is shown in FIG. 6. In essence it consists of the features 'NCgl2176, IR', the expression unit PBN1-tat-'agl2_cuo, 'IR and NCgl2177. The segment with the features 'NCgl2176 and IR'represents the 5'-flanking sequence and the segment with the features 'IR and NCgl2177 represents the 3'-flanking sequence required for integration of the expression unit PBN1-tat-'agl2_cuo into the chromosome. A map of plasmid pK18mobsacB_INT::PBN1-tat-'agl2_cuo is shown in FIG. 7.

Example 5.2

Construction of Strain DM1933_INT::PBN1-tat-'agl2_cuo

The pK18mobsacB_INT::PBN1-tat-'agl2_cuo plasmid was used to integrate the expression unit PBN1-tat-'agl2_cuo into the chromosome of the L-lysine producer DM1933.

For this purpose *E. coli* strain S17-1 was transformed with plasmid DNA obtained in example 5.1. The modified conjugation method from Schäfer et al. (Journal of Bacteriology 172, 1663-1666, 1990) as described in materials and methods was used for conjugal transfer into strain DM1933 and selection for transconjugant clones by virtue of their saccharose resistance and kanamycin sensitivity phenotype.

Transconjugant clones were analyzed by colony PCR using the Taq Kit with the primers IR_1 and IR_2 listed in table 15 followed by size determination of the amplificates by capillary electrophoresis. The primers are also shown in SEQ ID NO:71 and SEQ ID NO:72 of the sequence listing. For PCR the Taq Kit (see table 1) was used with the temperature of the annealing step (step 3) set at 55° C. and the time of the elongation step (step 4) set at 40 sec.

TABLE 15

List of primers used and size of amplificate during PCR analysis of transconjugant clones.

| detection of | name | sequence | size [bp] |
|---|---|---|---|
| INT::PBN1-tat-agl2_cuo | IR_1 | GACCTCGGCTTTGTGACCAG | 2344 |
| | IR_2 | CTCACCGCACGATGGTTCAC | |

The nucleotide sequences of PCR products of transconjugant clones having the correct size were further analyzed by Sanger sequencing.

One of the transconjugant clones thus characterized was called DM1933_INT::PBN1-tat -'agl2_cuo. A glycerol stock culture of the transconjugant clone was prepared and used as starting material for further investigations.

Example 5.3

L-lysine Production by Strain DM1933_INT::PBN1-tat-'agl2_cuo Using Glucose and a Mixture of Glucose and Panose as Carbon Source Strains DM1933_INT::PBN1-tat-'agl2_cuo and DM1933 as a control were analyzed for their ability to produce L-lysine from glucose or from a mixture of glucose and panose by batch cultivation using the BioLector® system.

As medium CGXII_CSL containing either 20 g/l of glucose or 15 g/l of glucose or a mixture of 15 g/l of glucose and 4.8 g/l of panose was used. The cultures were incubated for ca. 20 h until complete consumption of glucose as confirmed by glucose analysis using blood glucose-meter. The optical densities OD660 and the concentrations of L-lysine and panose were then measured.

The result of the experiment is presented in table 16. It shows that the presence of the expression unit PBN1-tat-'agl2_cuo in strain DM1933_INT::PBN1-tat-'agl2_cuo does not negatively effect the L-lysine yield on glucose. It further shows that strain DM1933_INT::PBN1-tat-'agl2_cuo is able to produce L-lysine from panose.

TABLE 16

L-lysine production by strain DM1933_INT::PBN1-tat'-agl2_cuo.

| Carbon Source | | Strains | | | | | |
|---|---|---|---|---|---|---|---|
| | | DM1933 | | | DM1933_* | | |
| Glucose (g/l) | Panose (g/l) | Lys[1] (g/l) | OD660 | Panose (g/l) | Lys[1] (g/l) | OD660 | Panose (g/l) |
| 20 | 0 | 4.6 | 8.1 | n a[2] | 4.7 | 8.1 | n a[2] |
| 15 | 0 | 3.8 | 6.1 | n a[2] | 3.8 | 6.2 | n a[2] |
| 15 | 4.8 | 3.9 | 6.4 | 4.8 | 4.3 | 6.8 | 1.4 |

*INT::PBN1-tat'-agl2_cuo
[1]L-lysine as L-lysine × HCl
[2]not analyzed

Example 6

L-lysine Production by Strain DM1933_INT::PBN1-tat-'agl2_cuo Using Starch Hydrolysate as Carbon Source Strains DM1933 and DM1933_INT::PBN1-tat-'agl2_cuo were cultured in CGXII_CSL medium using starch hydrolysate as carbon source (77.3 ml starch hydrolysate Clear Sweet®/I). The medium thus prepared contained 60 g/l glucose, 0.4 g/l panose and 1.2 g/l isomaltose.

The cultivation was performed in 2 l Erlenmeyer flasks as described in materials and methods. Samples were taken from the cultures at different time points and the optical densities OD660 and the concentrations of L-lysine, isomaltose, panose and glucose were measured. The result of the experiment is summarized in table 17. It shows that strain DM1933_INT::PBN1-tat-'agl2_cuo is able to consume isomaltose and panose contained in starch hydrolysate.

TABLE 17

L-lysine production using starch hydrolysate as carbon source.

OD660

| | Time: | | | |
|---|---|---|---|---|
| Strain | 0 h | 13 h | 33 h | 57 h |

OD660

| DM1933 | 0.5 | 25.3 | 46.0 | 40.9 |
| DM1933_* | 0.5 | 22.9 | 46.7 | 43.1 |

L-lysine[2] (g/l)

| | Time: | | | |
|---|---|---|---|---|
| Strain | 0 h | 13 h | 33 h | 57 h |

L-lysine*** (g/l)

| DM1933 | n a[1] | 2.7 | 11.6 | 15.5 |
| DM1933_* | n a[1] | 2.9 | 10.5 | 16.2 |

Isomaltose (g/l)

| | Time: | | | |
|---|---|---|---|---|
| Strain | 0 h | 13 h | 33 h | 57 h |

Isomaltose (g/l)

| DM1933 | 1.1 | 1.0 | 0.8 | 0.7 |
| DM1933_* | 1.1 | 0.9 | 0[3] | 0[3] |

Panose (g/l)

| | Time: | | | |
|---|---|---|---|---|
| Strain | 0 h | 13 h | 33 h | 57 h |

Panose (g/l)

| DM1933 | 0.4 | 0.4 | 0.4 | 0.4 |
| DM1933_* | 0.4 | 0.3 | 0[3] | 0[3] |

TABLE 17-continued

L-lysine production using starch hydrolysate as carbon source.

| | Glucose (g/l) | | | |
|---|---|---|---|---|
| | Time: | | | |
| Strain | 0 h | 13 h | 33 h | 57 h |
| Glucose (g/l) | | | | |
| DM1933 | 59.9 | 35.0 | 0³ | 0³ |
| DM1933_* | 59.9 | 37.2 | 0³ | 0³ |

*INT::PBN1-tat-'agl2_cuo
¹not analyzed
²as L-lysine × HCl
³not detectable

Example 7

Determination of the Amino Acid Sequence of the Secreted α-1,6-glucosidase Fusion Protein Strain DM1933_INT::PBN1-tat-'agl2_cuo was cultivated and the culture supernatant collected, filtrated and concentrated as described in detail in materials and methods. The concentrated culture supernatant was then analyzed by liquid chromatography coupled to mass spectrometry (LC-MS).

Two species of polypeptides were found in the culture supernatant. One having a sum formula of C3031 H4582 N844 O958 S18 fitting to the amino acid sequence of SEQ ID NO:10 from positions 31 to 639. The other having a sum formula of C3004 H4535 N837 O948 S17 fitting to the amino acid sequence of SEQ ID NO:10 from positions 38 to 639. Both polypeptides were found in a ratio of approximately 1:1.

Example 8

L-valine Production

L-valine production from panose using the gene fusion tat-'agl2_cuo was investigated.

Example 8.1

Construction of an L-valine Producer Containing the Gene Fusion Tat-'Agl2_Cuo

Strain ATCC14067_PprpD2-ilvBN is an L-valine producer belonging to the species *C. glutamicum*.

The construction of the strain starting from strain ATCC14067 is described in EP2811028A1.

Strain ATCC14067_PprpD2-ilvBN was transformed with isolated plasmid DNA of pVWEx1 and pVWEx1_tat-'agl2_cuo by electroporation. Selection for transformants, propagation of the transformants and preparation of glycerol stock cultures was done as described under materials and methods and in the presence of kanamycin.

Specific nucleotide sequences of the transformants were amplified by colony PCR in order to verify the plasmid status of the transformants. The primers used and the size of the PCR amplificates are summarized in table 18.

TABLE 18

List of primers used and size of amplificates during PCR analysis of transformants.

| | | PCR analysis | | |
|---|---|---|---|---|
| plasmid | primer | sequence | | size [bp] |
| pVWEX1 | pVW_1 | GTGAGCGGATAACAATTTCACAC | | 241 |
| | pVW_3 | TACTGCCGCCAGGCAAATTC | | |
| pVWEx1_tat-'agl2_cuo | pVW_1 | GTGAGCGGATAACAATTTCACAC | | 433 |
| | gluc_rev | GTAGCCGTTATCATCCTGTG | | |

For PCR Sapphire Mix (see table 2) was used with the temperature of the annealing step (step 3) set at 53° C. and the time of the elongation step (step 4) set at 10 sec. Size determination of the amplificates was done by capillary electrophoresis.

The nucleotide sequences of the primers used are also shown in the sequence listing under SEQ ID NO:33 to SEQ ID NO:36.

The transformants ATCC14067_PprpD2-ilvBN/pVWEx1 and ATCC14067_PprpD2-ilvBN/pVWEx1_tat-'agl2_cuo thus obtained and analyzed were used for further investigation.

Example 8.2

L-valine production by strain ATCC14067_PprpD2-ilvBN/pVWEx1_tat-'agl2_cuo using glucose and a mixture of glucose and panose as carbon source.

Strains ATCC14067_PprpD2-ilvBN/pVWEx1_tat-'agl2_cuo and ATCC14067_PprpD2-ilvBN/pVWEx1 as a control were analyzed for their ability to produce L-valine from glucose or from a mixture of glucose and panose by batch cultivation using the BioLector® system.

As medium CGXII_YE containing either 15 g/l of glucose or a mixture of 15 g/l of glucose and 4.8 g/l of panose was used. The media were further supplemented with kanamycin, IPTG and propionic acid hemicalcium salt (0.75 g/l). The cultures were incubated for ca. 25 h until complete consumption of glucose as confirmed by glucose analysis using blood glucose-meter. The optical densities OD660 and the concentrations of L-valine and panose were then measured.

The result of the experiment is presented in table 19. It shows that the presence of the gene fusion tat-'agl2 contained in an expression unit comprising the promoter PtacI as contained in strain ATCC14067_PprpD2-ilvBN/pVWEx1_tat-'agl2_cuo enables the strain to produce L-valine from panose.

TABLE 19

L-valine production by strain ATCC14067_PprpD2-ilvBN/pVWEx1_tat-'agl2_cuo.

| Carbon Source | | Strains | | | | | |
|---|---|---|---|---|---|---|---|
| | | */pVWEx1 | | | */pVWEx1_tat-'agl2_cuo. | | |
| Glucose (g/l) | Panose (g/l) | Val[1] (g/l) | OD660 | Panose (g/l) | Val[1] (g/l) | OD660 | Panose (g/l) |
| 15 | 0 | 0.50 | 8.1 | n a[2] | 0.49 | 7.9 | n a[2] |
| 15 | 4.8 | 0.49 | 8.2 | 4.8 | 0.59 | 9.2 | 0[3] |

*ATCC14067_PprpD2-ilvBN
[1] L-valine
[2] not analyzed
[3] not detectable

LIST OF ABBREVIATIONS

'agl2_cuo codon usage optimized coding sequence of gene agl2 of *Bifidobacterium breve* UCC2003 lacking the ATG start codon
'IR 3'-end sequence of the intergenic region (IR) between the genes identified by locus tag Ncgl2177 and Ncgl2176
'Ncg12176 3'-end sequence of the coding sequence identified by locus tag Ncgl2176
(AvrII/XbaI) hybrid sequence obtained after ligation of sticky ends generated by restriction endonucleases AvrII and XbaI
agl2_cuo codon usage optimized coding sequence of gene agl2 of *Bifidobacterium breve* UCC2003
BamHI sequence recognized by the restriction endonuclease BamHI
EcoRI sequence recognized by the restriction endonuclease EcoRI
FspAI sequence recognized by the restriction endonuclease FspAI
h hours
HincII sequence recognized by the restriction endonuclease HincII
HindIII sequence recognized by the restriction endonuclease HindIII
IR' 5'-end sequence of the intergenic region (IR) between the genes identified by locus tag Ncgl2177 and Ncgl2176
lacI gene coding for the LacI repressor
lacZ-alpha 5'-end sequence of the lacZ gene coding for the α-peptide of the β-galactosidase
MauBI sequence recognized by the restriction endonuclease MauBI
MCS multiple cloning site
Ncgl2177 coding sequence identified by locus tag Ncgl2177
neo gene coding for aminoglycoside 3'-phosphotransferase
nptII gene coding for neomycin phosphotransferase
ori p15A origin of replication of *E. coli* plasmid p15A
ori pCG1 origin of replication of *C. glutamicum* plasmid pCG1
ori pMB1 origin of replication of *E. coli* plasmid pMB1
PBN1 sequence of promoter PdapBN1
PtacI sequence of promoter PtacI
PstI sequence recognized by the restriction endonuclease PstI
RP4-mob sequence of mob region of plasmid RP4
sacB gene coding for levan sucrase
SexAI sequence recognized by the restriction endonuclease SexAI
SpeI sequence recognized by the restriction endonuclease SpeI
tat 5'-terminus of the coding sequence cg0955 of *C. glutamicum* ATCC13032, encoding a Tat (twin-arginine translocator) signal peptide
tat-'agl2_cuo sequence of the gene fusion encoding the Tat-Agl2-fusion polypeptide
Tgap* sequence of terminator Tgap*
XbaI sequence recognized by the restriction endonuclease XbaI

What is claims is:

1. An isolated polynucleotide encoding a fusion polypeptide comprising the amino acid sequences a), b) and c) wherein:
   a) is an N-terminal Tat-signal peptide comprising the amino acid sequence of positions 1 to 33 of SEQ ID NO:10 or positions 1 to 33 of SEQ ID NO:12 or comprising the amino acid sequence of positions 1 to 33 of SEQ ID NO:10 with Ala at position 13 or positions 1 to 33 of SEQ ID NO:12 with Ala at position 13;
   b) is a C-terminal polypeptide having α-1,6-glucosidase activity comprising an amino acid sequence selected from the group consisting of:
      b1) a sequence ≥95% identical to the sequence from positions 37 to 639 of SEQ ID NO:10; and
      b2) at least (≥) 95% identical to the sequence from positions 37 to 643 of SEQ ID NO:12, and
   c) is 0 to 10 amino acid residues between a) and b).

2. The isolated polynucleotide of claim 1, wherein:
   a) the amino acid sequence of b1) is selected from: positions 37 to 639 of SEQ ID NO:10; and from positions 37 to 639 of SEQ ID NO:10 plus an additional Met at the N-terminus in front of position 37 as shown in SEQ ID NO:6; and
   b) the sequence of b2) is selected from: positions 39 to 643 of SEQ ID NO:12; positions 38 to 643 of SEQ ID NO:12; and positions 37 to 643 of SEQ ID NO:12.

3. The isolated polynucleotide of claim 1, wherein the number of amino acid residues of c) is 1 to 3.

4. The isolated polynucleotide of claim 3, wherein the number of amino acid residues of c) is 3.

5. The isolated polynucleotide of claim 4, wherein the amino acid residues between a) and b) consist of the amino acid sequence Met Thr Ser.

6. The isolated polynucleotide of claim 4, wherein the amino acid residues of c) consist of the amino acid sequence Ile Leu Val.

7. The isolated polynucleotide of claim 1, wherein said polynucleotide is functionally linked to a promotor.

8. The isolated polynucleotide of claim 7, wherein said promotor is the PtacI promotor comprising the nucleotide sequence of SEQ ID NO:14 from positions 1 to 75 or the PdapBN1 promotor comprising the nucleotide sequence of SEQ ID NO:15.

9. The isolated polynucleotide of claim 8, wherein said promotor is the PdapBN1-promotor comprising the sequence of SEQ ID NO:15.

10. A bacterium selected from the genus *Corynebacterium* and comprising the isolated polynucleotide of claim 1, wherein said bacterium has the ability to secrete a polypeptide having α-1,6-glucosidase activity encoded by said isolated polynucleotide.

11. The bacterium of claim 10, wherein said isolated polynucleotide is contained in a plasmid vector autonomously replicating in said bacterium or in the chromosome of said bacterium.

12. The bacterium of claim 10, wherein said bacterium is a *Corynebacterium glutamicum*.

13. The bacterium of claim 10, wherein said bacterium has the ability to excrete and produce a fine chemical selected from the group consisting of: L-amino acids; vitamins; nucleosides; and nucleotides.

14. The bacterium of claim 13, wherein said fine chemical is an L-amino acid.

15. The bacterium of claim 14, wherein said L-amino acid is selected from the group consisting of: L-lysine; L-threonine; L-valine; and L-isoleucine.

16. A method for producing a fine chemical selected from the group consisting of: L-amino acids; vitamins; nucleosides; and nucleotides; said method comprising culturing the fine chemical producing bacterium according to claim 10 in a suitable medium, where said medium comprises oligomers of a-D-glucose consisting of least two alpha-1-6-glycosidically linked glucose monomers as carbon source.

17. The method of claim 16, wherein said fine chemical is an L-amino acid.

18. The method of claim 17, wherein said L-amino acid is selected from the group consisting of: L-lysine; L-threonine; L-valine; and L-isoleucine.

* * * * *